(12) United States Patent
Imai et al.

(10) Patent No.: US 12,150,950 B2
(45) Date of Patent: Nov. 26, 2024

(54) ADMINISTRATION OF NICOTINAMIDE MONONUCLEOTIDE IN THE TREATMENT OF DISEASE

(71) Applicant: Washington University, St. Louis, MO (US)

(72) Inventors: Shin-Ichiro Imai, St. Louis, MO (US); Rajendra Apte, Clayton, MO (US)

(73) Assignee: Washington University, St. Louis, MO (US)

( * ) Notice: Subject to any disclaimer, the term of this patent is extended or adjusted under 35 U.S.C. 154(b) by 0 days.

(21) Appl. No.: 18/471,764

(22) Filed: Sep. 21, 2023

(65) Prior Publication Data

US 2024/0009222 A1    Jan. 11, 2024

Related U.S. Application Data

(63) Continuation of application No. 17/150,584, filed on Jan. 15, 2021, now Pat. No. 11,793,824, which is a continuation of application No. 16/290,122, filed on Mar. 1, 2019, now Pat. No. 10,925,888, which is a continuation of application No. 15/783,845, filed on Oct. 13, 2017, now Pat. No. 10,258,638, which is a continuation of application No. 14/855,293, filed on Sep. 15, 2015, now Pat. No. 9,844,561, which is a continuation of application No. PCT/US2014/030920, filed on Mar. 17, 2014.

(60) Provisional application No. 61/947,387, filed on Mar. 3, 2014, provisional application No. 61/801,188, filed on Mar. 15, 2013.

(51) Int. Cl.
*A61K 31/706* (2006.01)
*A61K 9/00* (2006.01)
*A61K 31/455* (2006.01)
*A61K 31/7064* (2006.01)

(52) U.S. Cl.
CPC .......... *A61K 31/706* (2013.01); *A61K 9/0014* (2013.01); *A61K 9/0048* (2013.01); *A61K 9/0053* (2013.01); *A61K 31/455* (2013.01); *A61K 31/7064* (2013.01)

(58) Field of Classification Search
None
See application file for complete search history.

(56) References Cited

U.S. PATENT DOCUMENTS

| | | | |
|---|---|---|---|
| 7,737,158 B2 | 6/2010 | Imai et al. | |
| 7,776,326 B2 | 8/2010 | Milbrandt et al. | |
| 8,017,634 B2 | 9/2011 | Sinclair et al. | |
| 8,268,575 B2 | 9/2012 | Imai et al. | |
| 2006/0002914 A1 | 1/2006 | Milbrandt et al. | |
| 2006/0229265 A1 | 10/2006 | Milburn et al. | |
| 2007/0014833 A1 | 1/2007 | Milburn et al. | |
| 2010/0047177 A1 | 2/2010 | Milbrandt et al. | |
| 2013/0059384 A1 | 3/2013 | Tilly et al. | |

FOREIGN PATENT DOCUMENTS

| | | |
|---|---|---|
| CN | 101601679 B | 8/2011 |
| WO | 2006/001982 A2 | 1/2006 |
| WO | 2006/105403 A2 | 10/2006 |
| WO | 2006/127987 A2 | 11/2006 |
| WO | 2009/062910 A1 | 5/2009 |
| WO | 2012/114204 A2 | 8/2012 |
| WO | 2013/002879 A1 | 1/2013 |

OTHER PUBLICATIONS

Yoshino, Jun, et al. "Nicotinamide mononucleotide, a key NAD+ intermediate, treats the pathophysiology of diet-and age-induced diabetes in mice." Cell metabolism 14.4 (2011): 528-536.*
Bai, S. and Sheline, C.T., Nad(+) maintenance attenuates light induced photoreceptor degeneration., Exp. Eye Res., 108, 76-83, 2013.
Hara, N., et al., Elevation of cellular NAD levels by nicotinic acid and involvement of nicotinic acid phosphoribosyltransferase in human cells., J. Biol. Chem., 282, 24574-24582, 2007.
Hasmann, M. and Schemainda, I., FK866, a highly specific non-competitive inhibitor of nicotinamide phosphoribosyltransferase, represents a novel mechanism for induction of tumor cell apoptosis., Cancer Research, 63, 7436-7442, 2003.
Houtkooper, R.H., et al., The secret life of NAD+: an old metabolite controlling new metabolic signaling pathways., Endocr. Rev. 31, 194-223, 2010.
Imai, S., Dissecting systemic control of metabolism and aging in the NAD World: the importance of SIRT1 and NAMPT-mediated NAD biosynthesis., FEBS Lett., 585, 1657-1662, 2011.
Imai, S., A possibility of nutriceuticals as an anti-aging intervention: Activation of sirtuins by promoting mammalian NAD biosynthesis., Pharmacol. Res., 62, 42-47, 2010.
Kawashima, M., et al., Calorie restriction: A new therapeutic intervention for age-related dry eye disease in rats., Biochem Biophys. Res. Commun., 397, 724-128, 2010.
Lau, C., et al., Isoform-specific targeting and interaction domains in human nicotinamide mononucleotide adenylyltransferases., J. Biol. Chem., 285, 18868-18876, 2010.

(Continued)

*Primary Examiner* — Patrick T Lewis
(74) *Attorney, Agent, or Firm* — Stinson LLP

(57) ABSTRACT

Disclosed are methods and compositions related to methods of treating, ameliorating, mitigating, slowing, arresting, preventing or reversing various diseases and conditions, including age-related obesity, age-related increases in blood lipid levels, age-related decreases in insulin sensitivity, age-related decreases in memory function, and age-related changes in eye function such as macular degeneration. The methods comprise administering nicotinamide mononucleotide (NMN) to a subject. In some embodiments, the administration can be oral administration. Also disclosed are pharmaceutical compositions comprising NMN.

20 Claims, 94 Drawing Sheets

(56) References Cited

OTHER PUBLICATIONS

Luo, J., et al., Negative control of p53 by Sir2alpha promotes cell survival under stress., Cell, 107, 137-148, 2001.
Ramsey, K.M., et al., Age-associated loss of Sirt1-mediated enhancement of glucose-stimulated insulin secretion in beta cell-specific Sirt1-overexpressing (BESTO) mice., Aging Cell., 7(1), 78-88, Jan. 2008.
Ramsey, K M. et al., Circadian clock feedback cycle through NAMPT-mediated NAD+ biosynthesis., Science, 324, 651-654, 2009.
Revollo, J.R., et al., The NAD biosynthesis pathway mediated by nicotinamide phosphoribosyltransferase regulates Sir2 activityin mammalian cells., The Journal of Biological Chemistry 279, 50754-50763, 2004.
Revollo, J.R., et al., NAMPT/PBEF/Visfatin regulates insulin secretion in beta cells as a systemic NAD biosynthetic enzyme., Cell Metabolism 6, 363-375, 2007.
Rongvaux, A, et al., Nicotinamide phosphoribosyl transferase/pre-B cell colony-enhancing factor/visfatin is required for lymphocyte development and cellular resistance to genotoxic stress., J. Immunol., 181, 4685-4695, 2008.
Satoh, A., et al., SIRT1 promotes the central adaptive response to diet restriction through activation of the dorsomedial and lateral nuclei of the hypothalamus., J. Neurosci., 30, 10220-10232, 2010.
Satoh, A., et al., Sirt1 extends life span and delays aging in mice through the regulation of Nk2 homeobox 1 in the DMH and LH, Cell Metab., 18, 416-430, 2013.

Tsubota, K., et al., The antiaging approach for the treatment of dry eye., Cornea, 31 Suppl 1, S1-8, 2012.
Wang, P., et al., Nicotinamide phosphoribosyltransferase protects against ischemic stroke through SIRT1-dependent adenosine monophosphate-activated kinase pathway., Annals of Neurology, 69, 360-374, 2011.
Wilhelm, F., et al., The NAD+ /NADH redox state in astrocytes: independent control of the NAD+ and NADH content., J. Neurosci. Res., 89, 1956-1964, 2011.
Artegiani, B., et al., "Age-related Cognitive Decline: Can Neural Stem Cells Help Us?," Mar. 2012, Aging, 4/3:176-186.
Falk, M.J., et al., "NMNAT1 Mutations Cause Leber Congenital Amaurosis," Sep. 2012, Nat Genet, 44/9:1040-1045.
Sepici-Dincel, Aylin et al., "Effects of in vivo antioxidant enzyme activities of myrtle oil in normoglycaemic and alloxan diabetic rabbits." Journal of ethnopharmacology 110.3 (2007), pp. 498-503.
Yoshino, Jun et al., "Nicotinamide mononucleotide, a key NAD+ intermediate, treats the pathophysiology of diet-and age-induced diabetes in mice." Cell metabolism 14.4 (2011), pp. 528-536.
Guo, Jun et al., "Impaired neural stem/progenitor cell proliferation in streptozotocin-induced and spontaneous diabetic mice." Neuroscience research 68.4 (2010), pp. 329-336.
Ghorbani, Fatemeh, "The inhibitory Effects of nucleotides." Nicotinamide Adenine Dinucleotide, Adenosine 5 (1821), pp. 182-198.
Bloom, Arnold, "Oral therapy in diabetes." Journal of the Royal College of Physicians of London 7.1 (1972): 61.

* cited by examiner

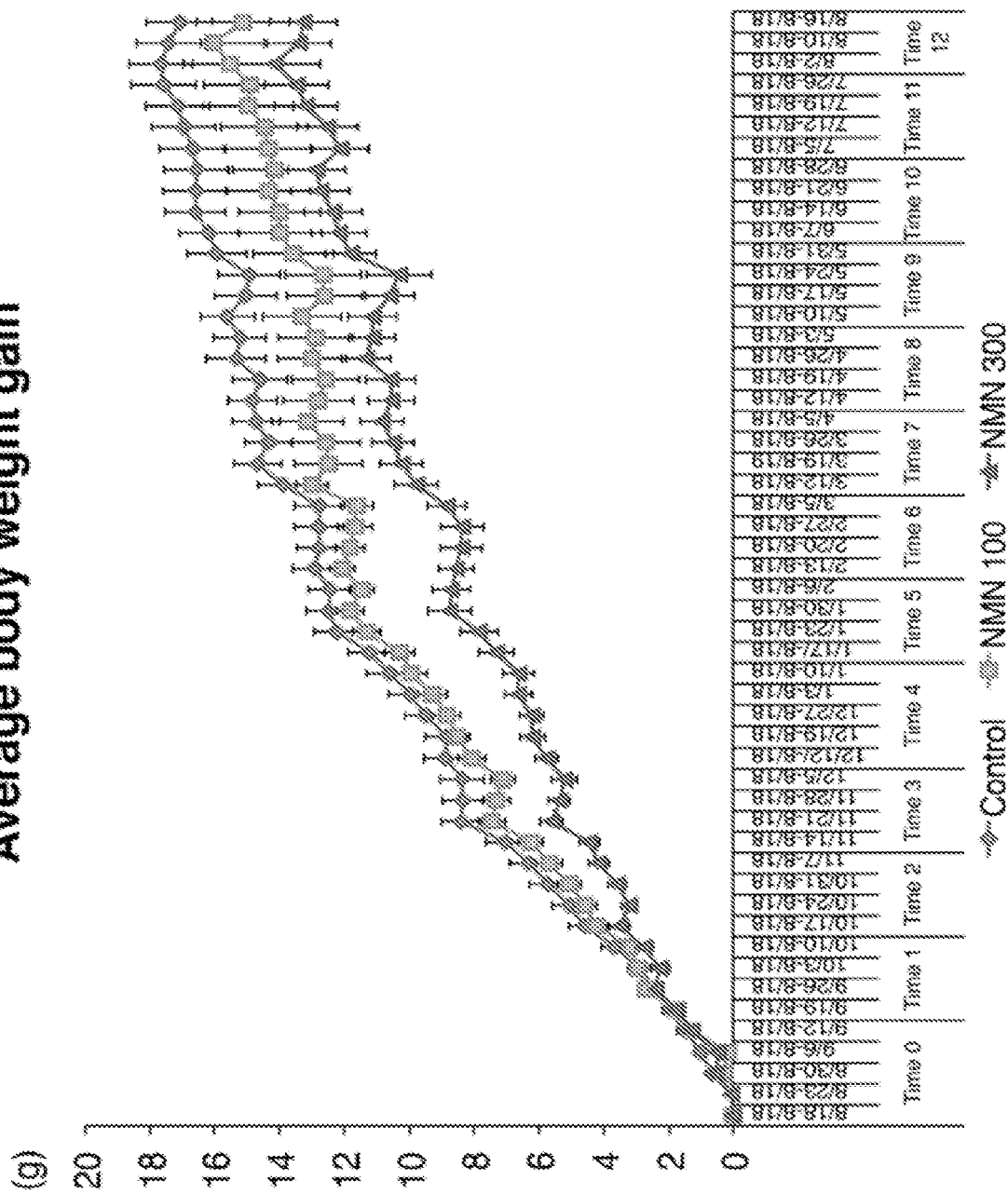

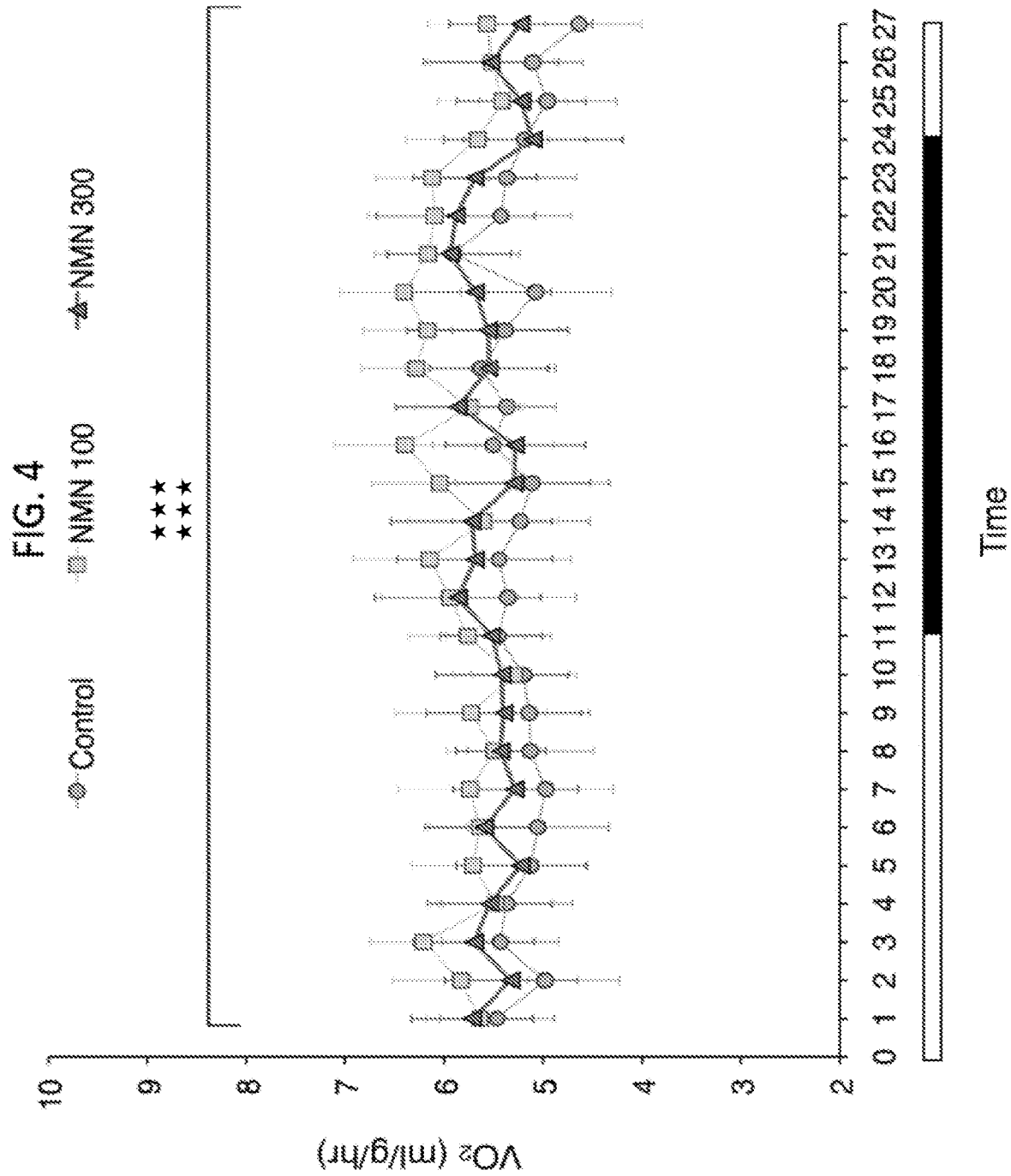

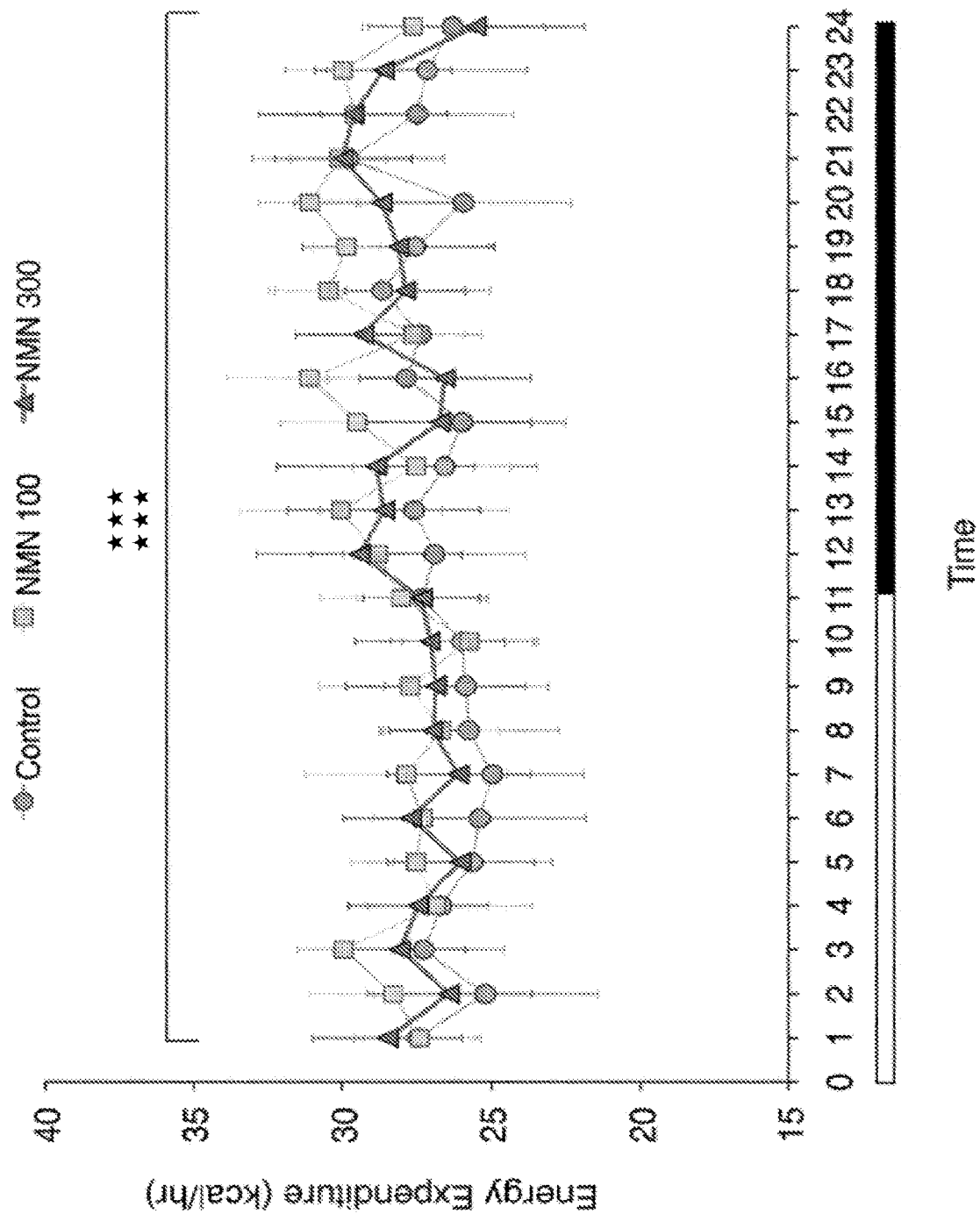

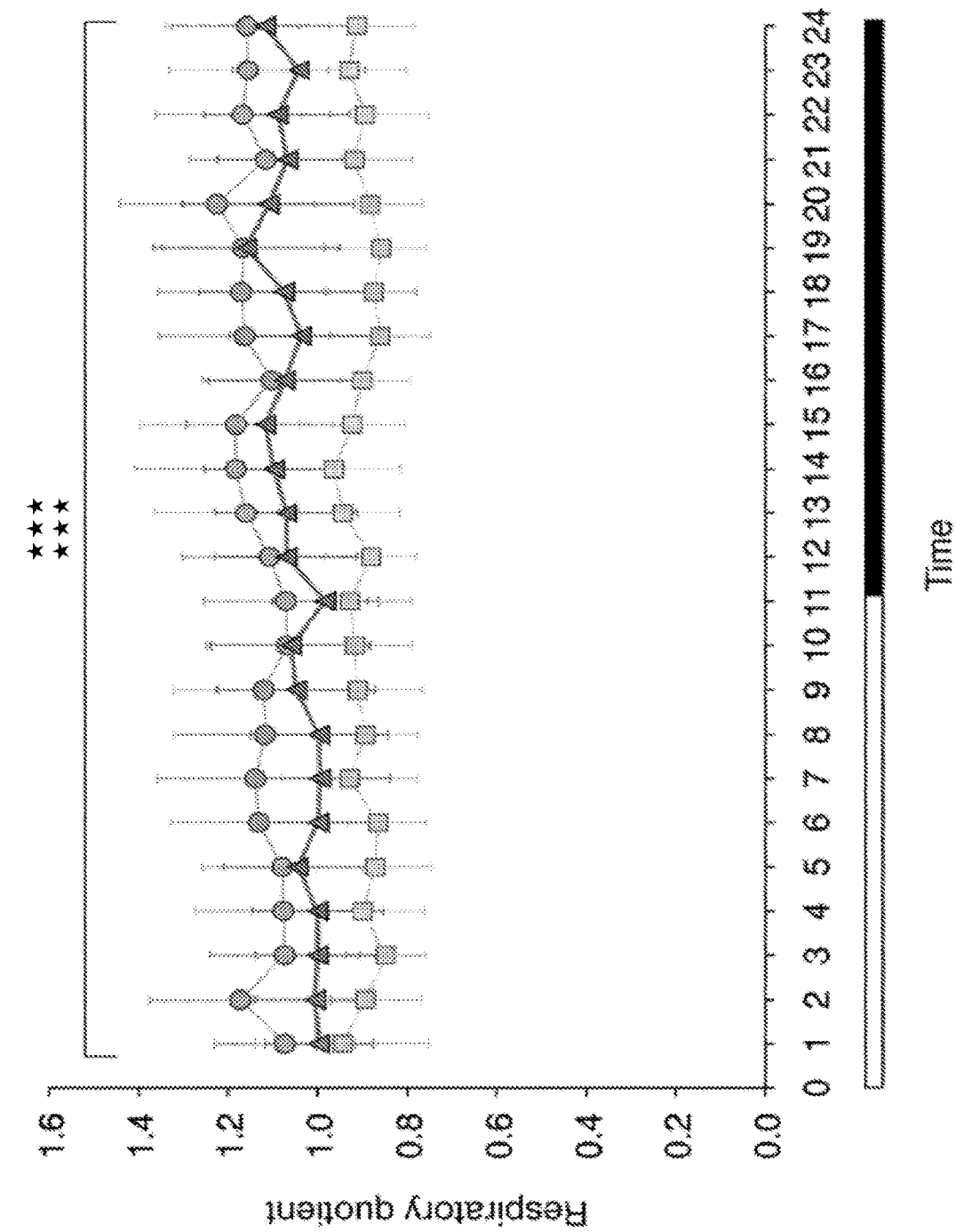

FIG. 7A
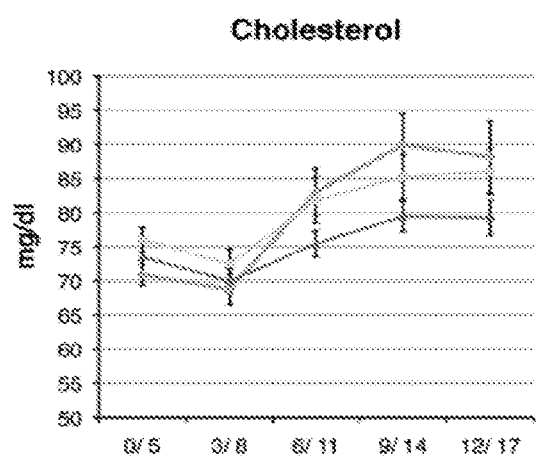
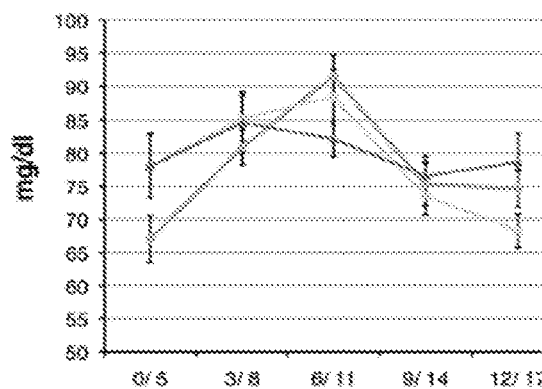
FIG. 7B
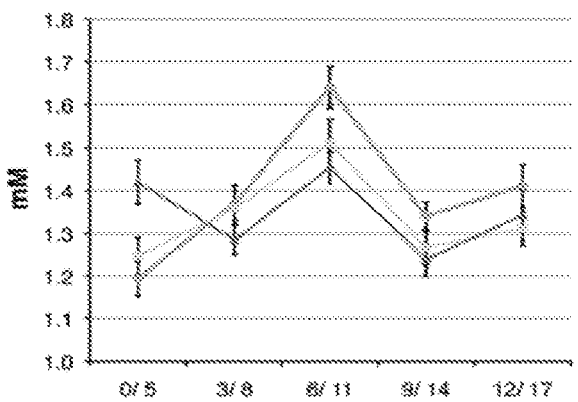
FIG. 7C

FIG. 8A
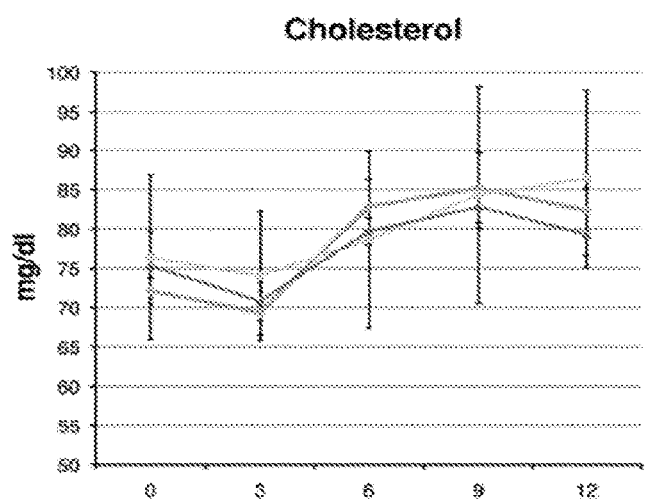
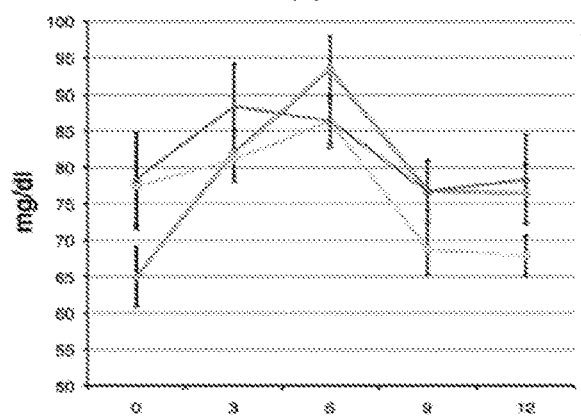
FIG. 8B
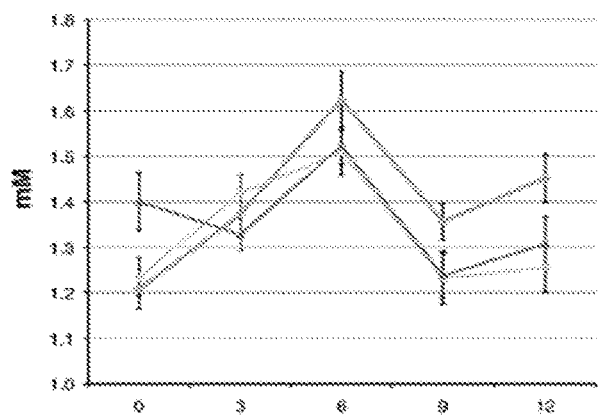
FIG. 8C

FIG. 16A
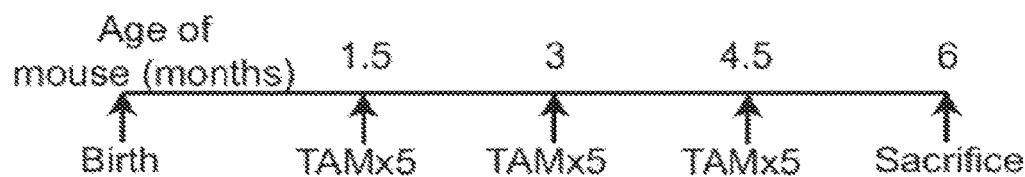
FIG. 16B
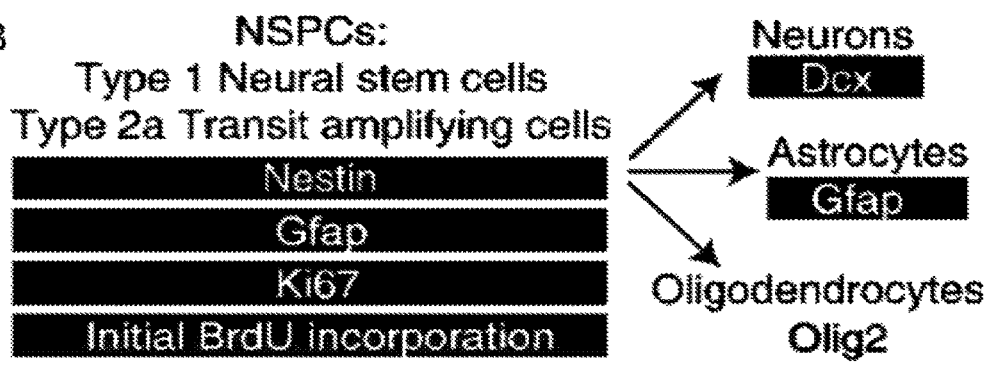
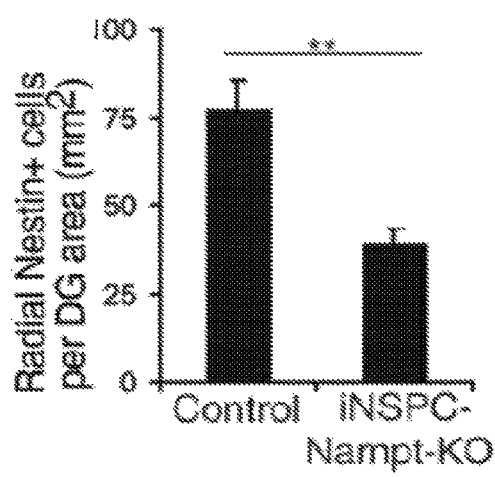
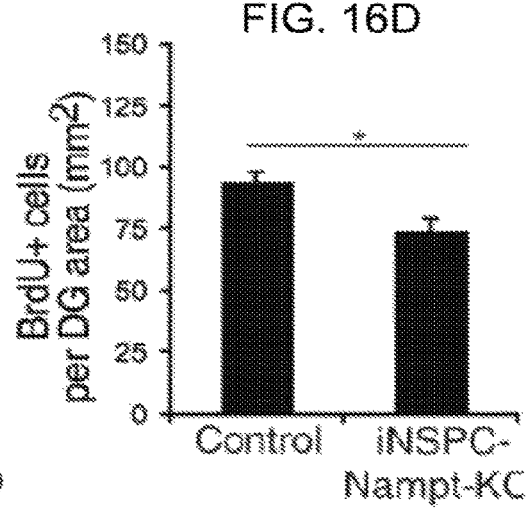

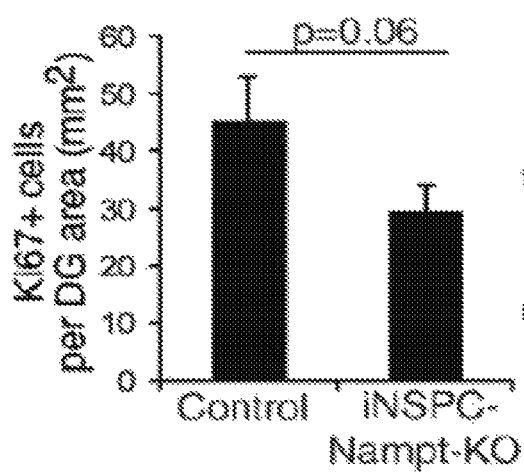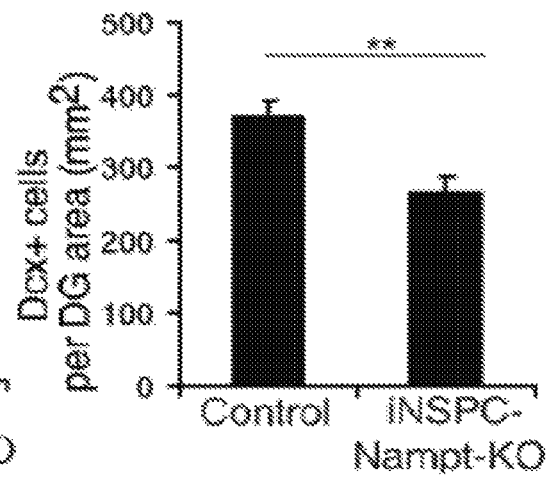

FIG. 17C
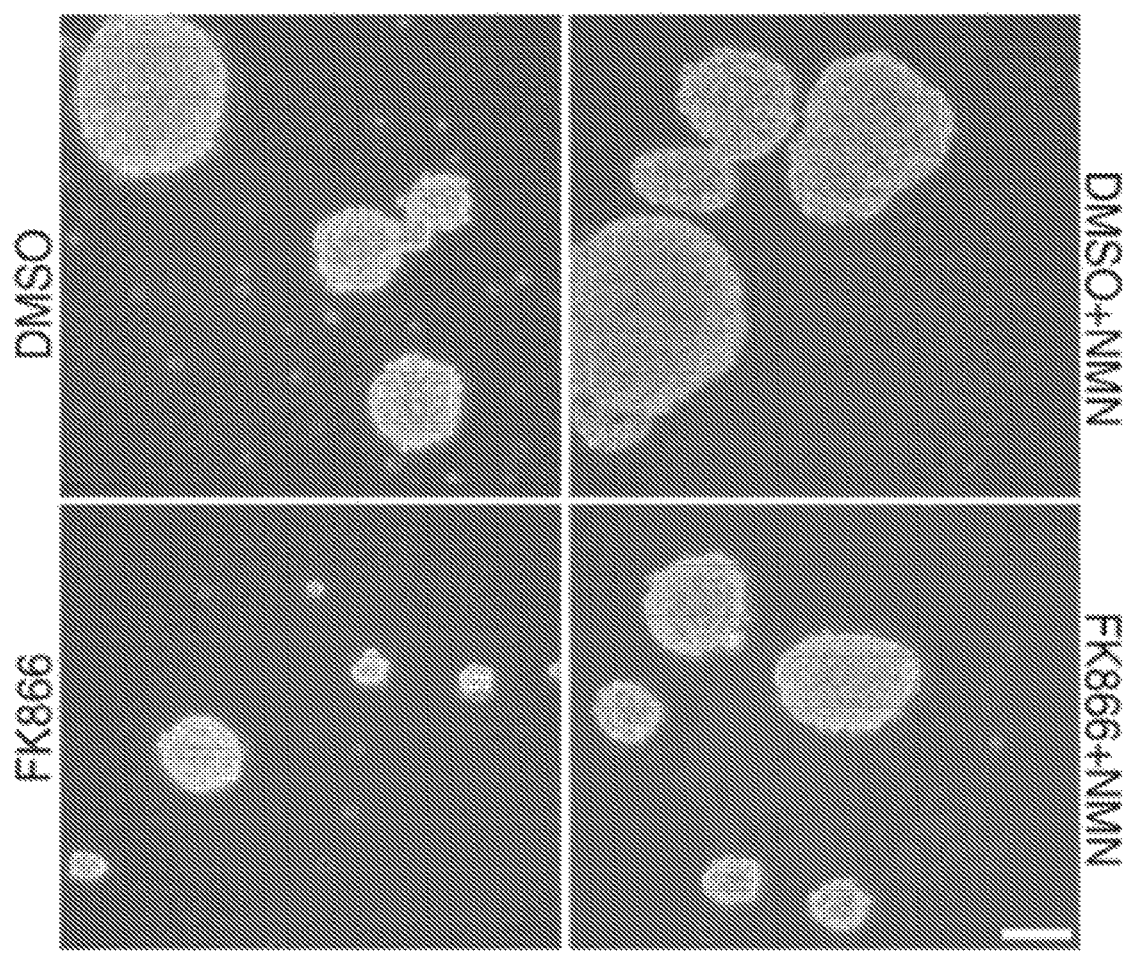
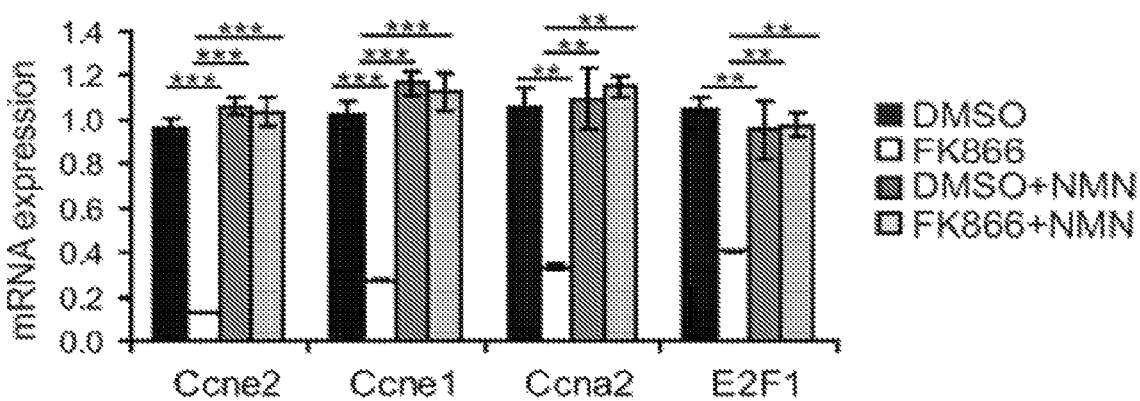
FIG. 17D

■ Nampt AD-LacZ
□ Nampt AD-Cre
▨ Nampt AD-LacZ + NMN
▨ Nampt AD-Cre + NMN

FIG. 19D
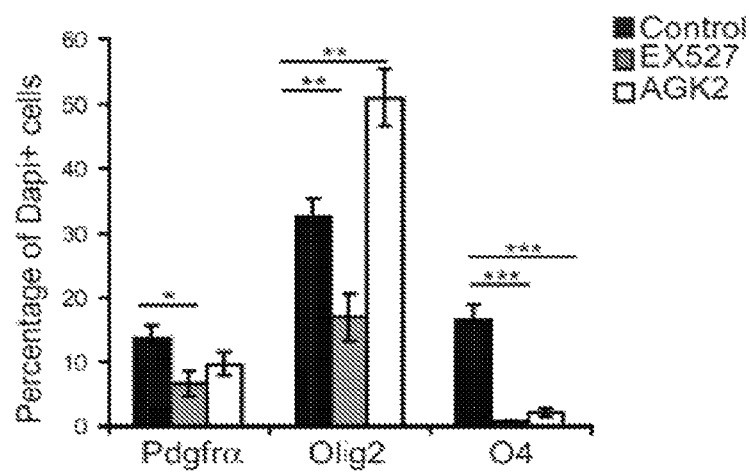
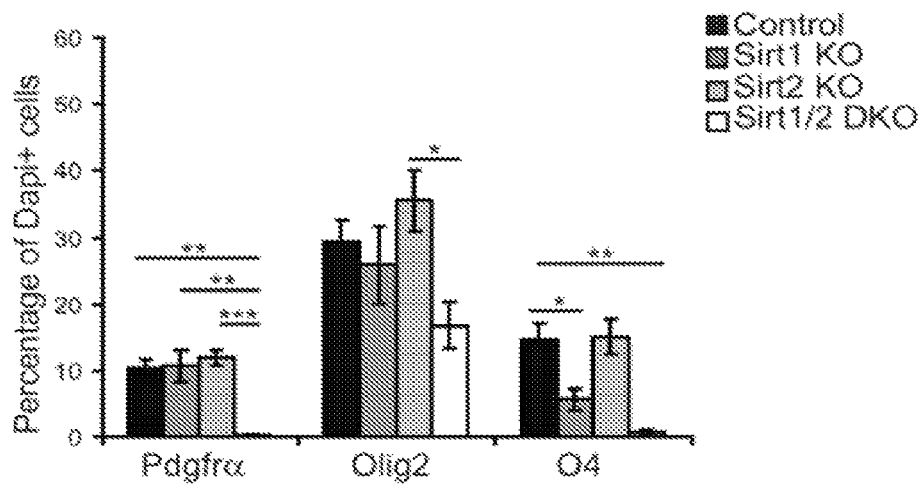
FIG. 19E

FIG. 20B
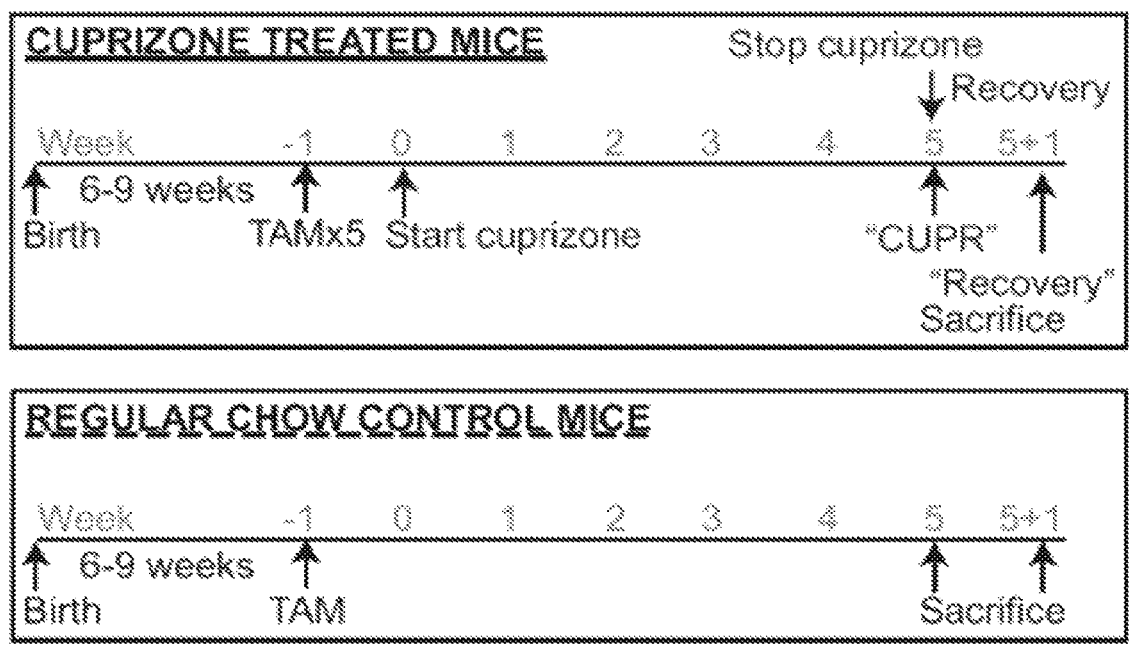
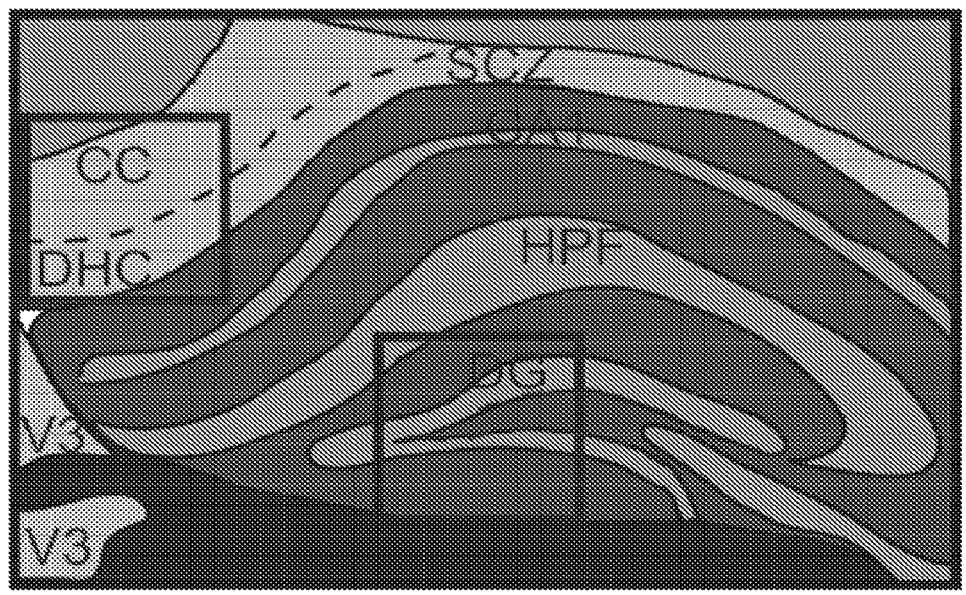
FIG. 20C

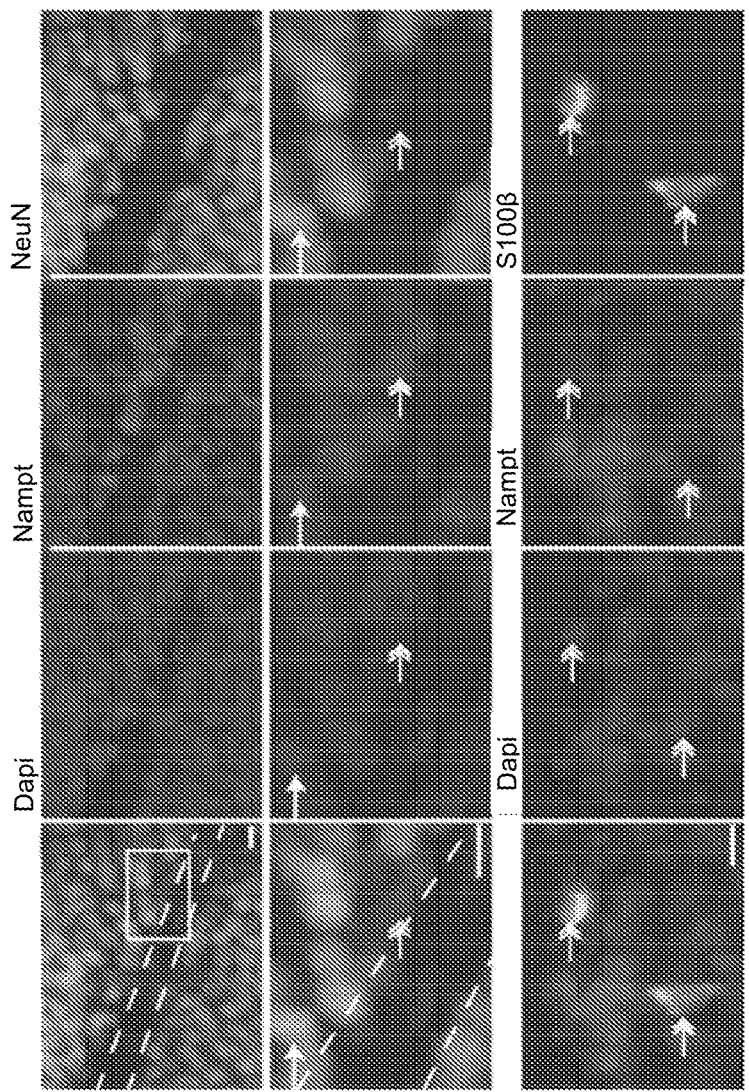

Timeline of the oligodendrocyte-directed lineage differentiation infection protocol (T-test: ** p<0.01)

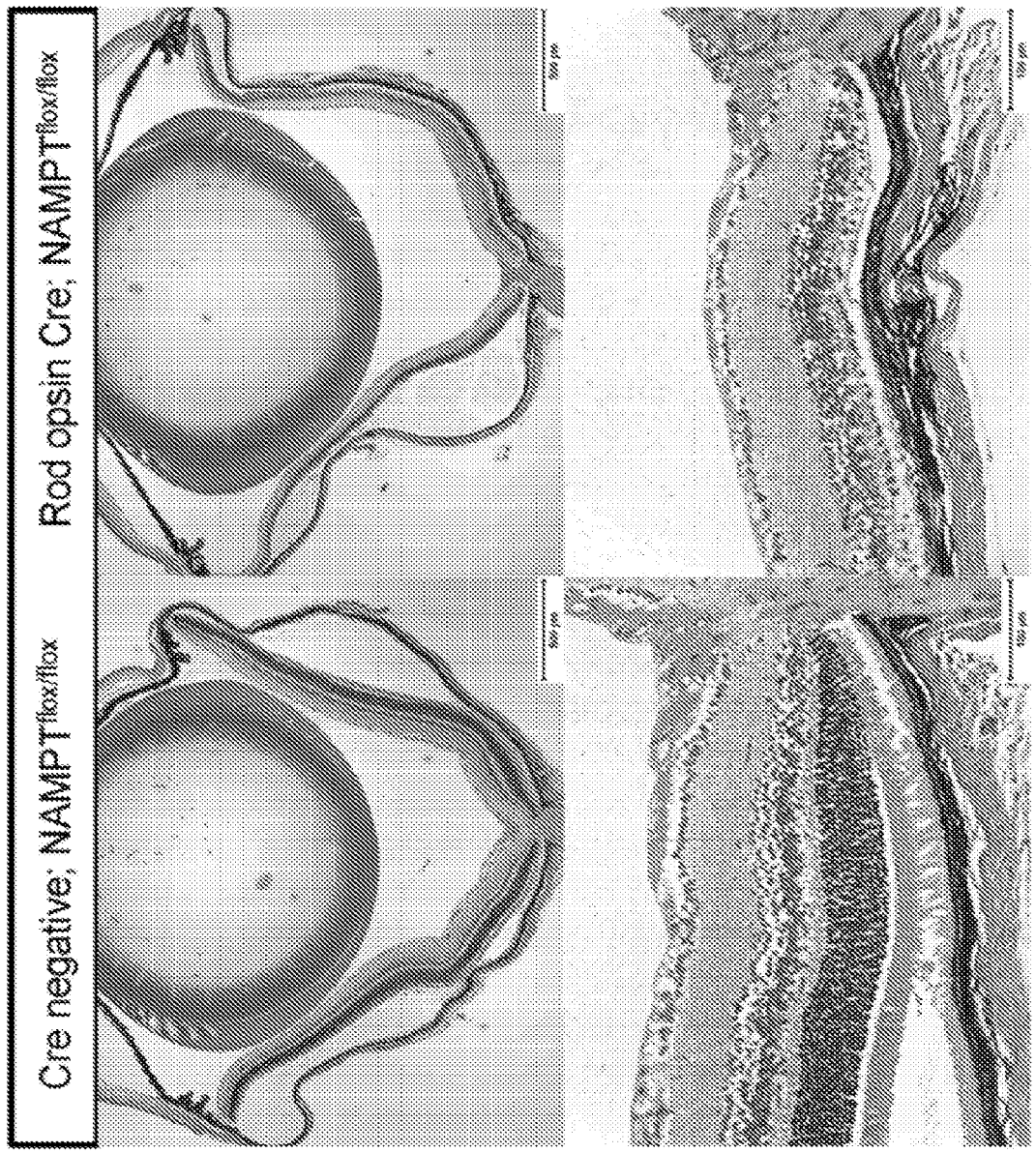

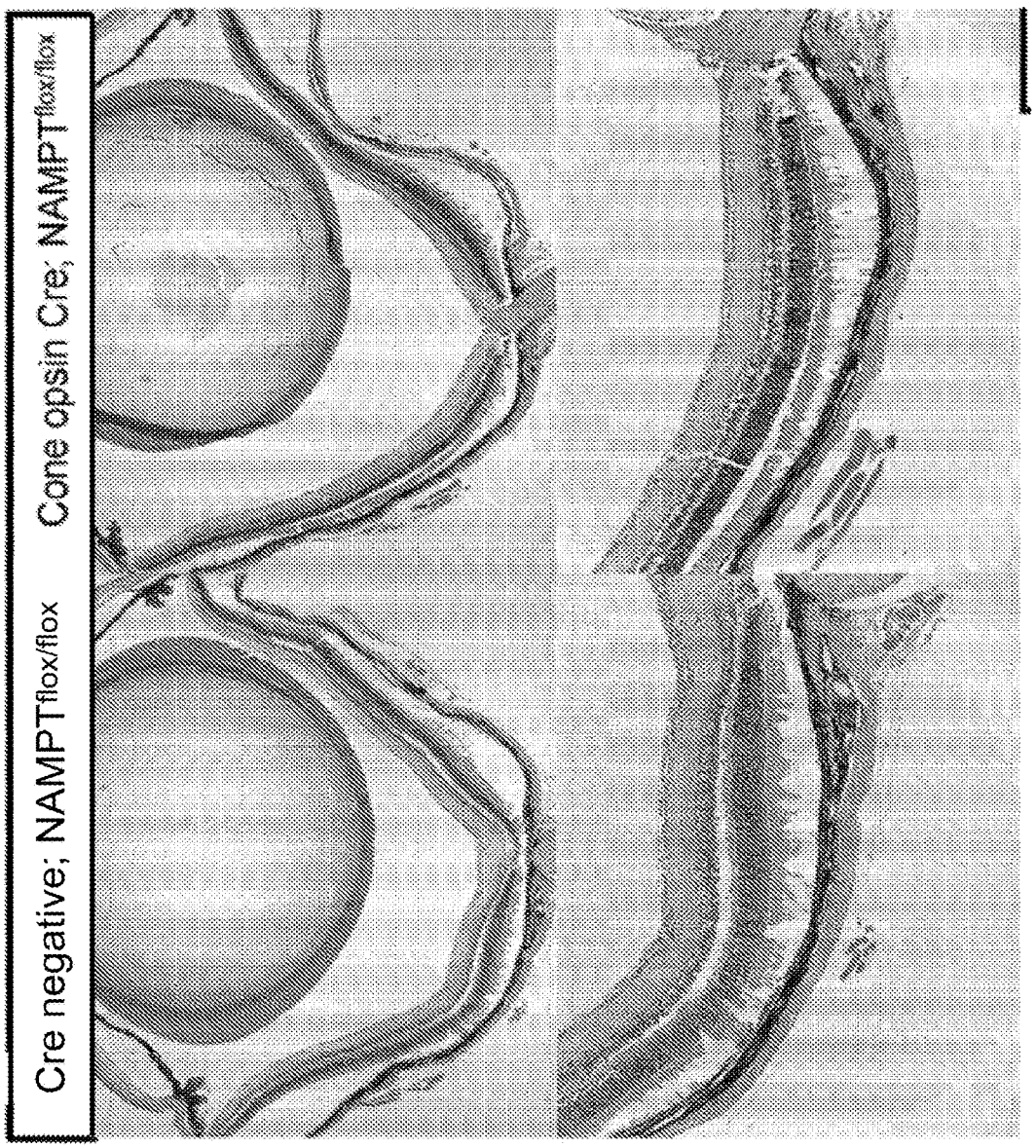

8 weeks 7 weeks 11 weeks 12-13 weeks

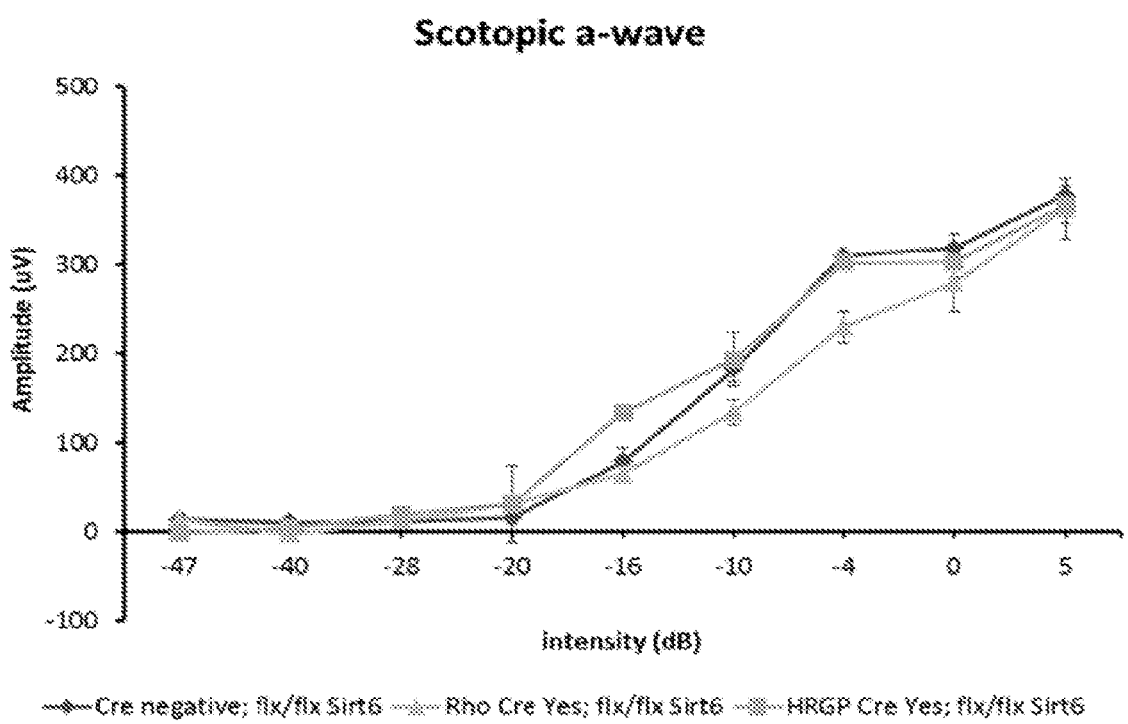

Fig. 32B

FIG. 33A
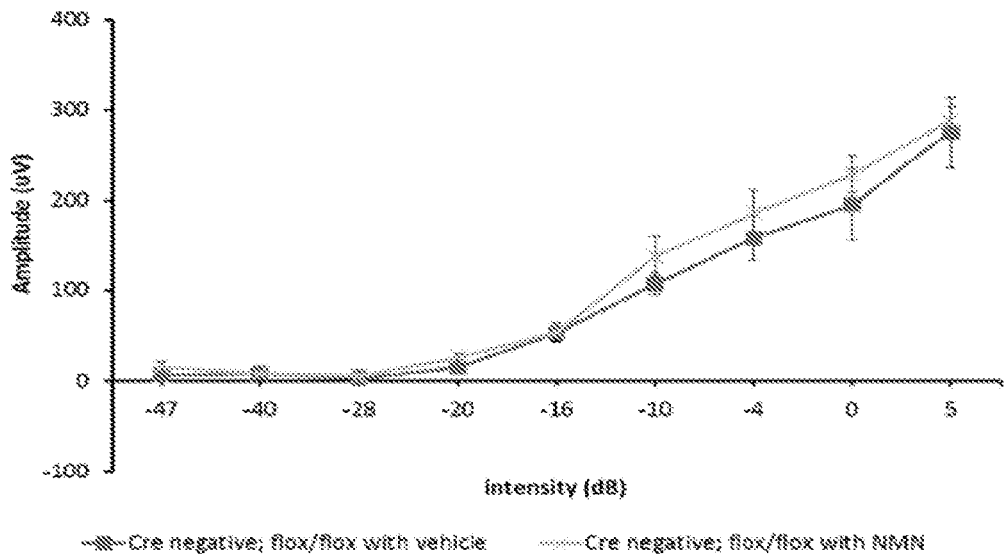
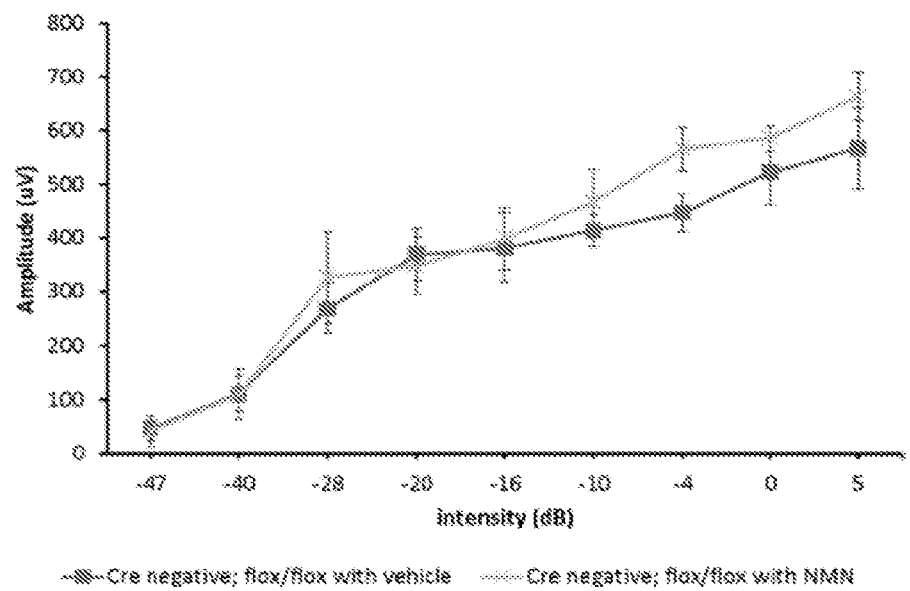

FIG. 34C
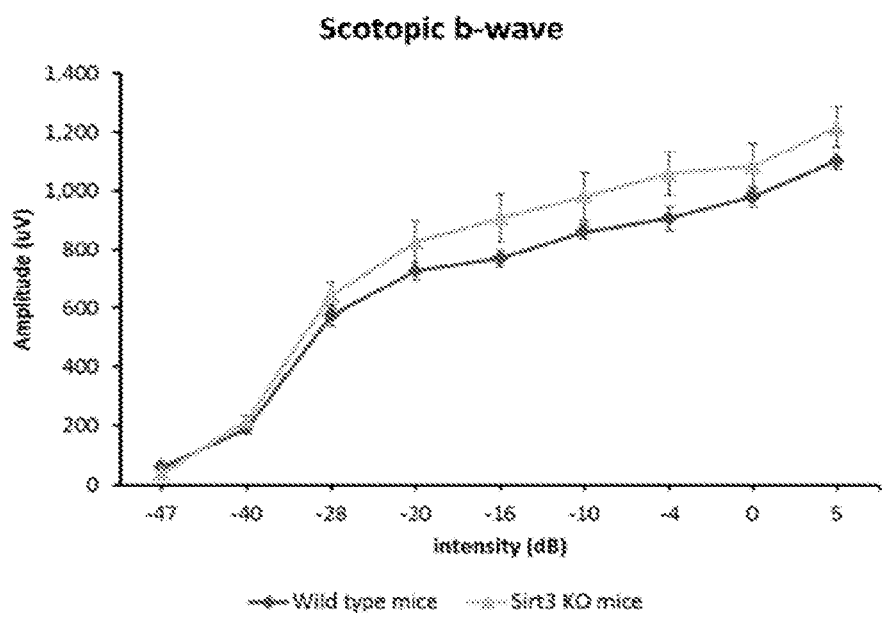
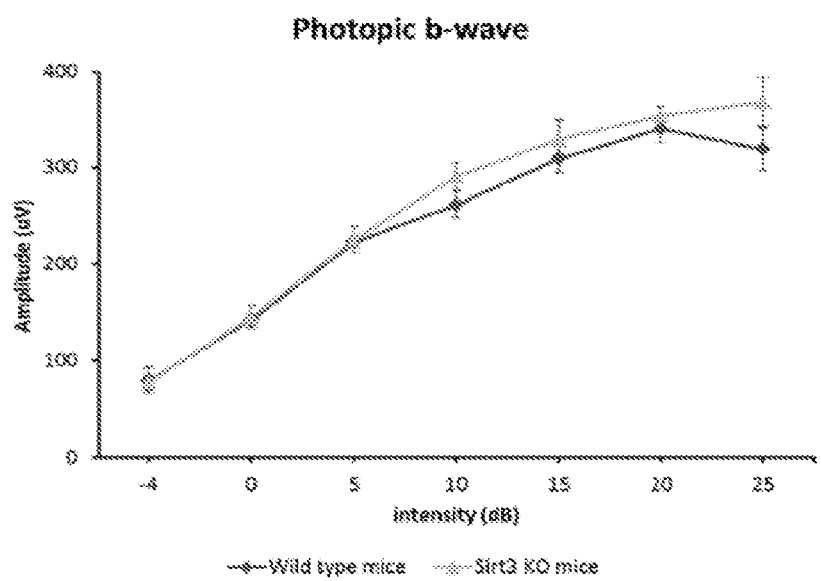

FIG. 34D
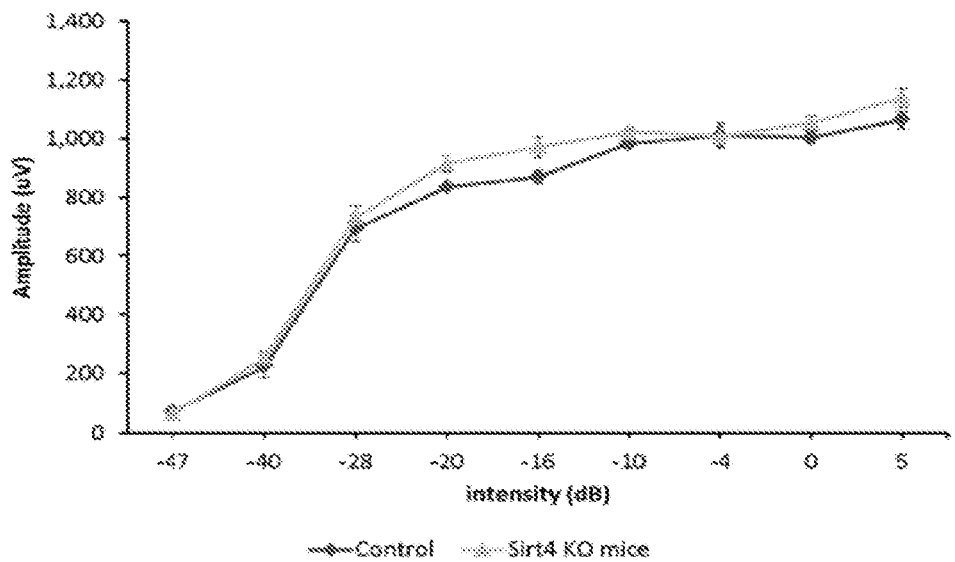
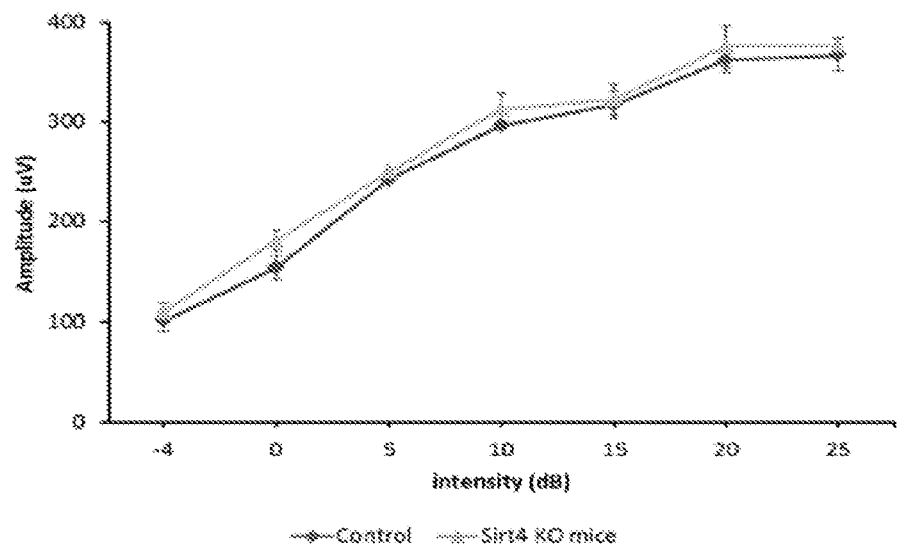

FIG. 34E
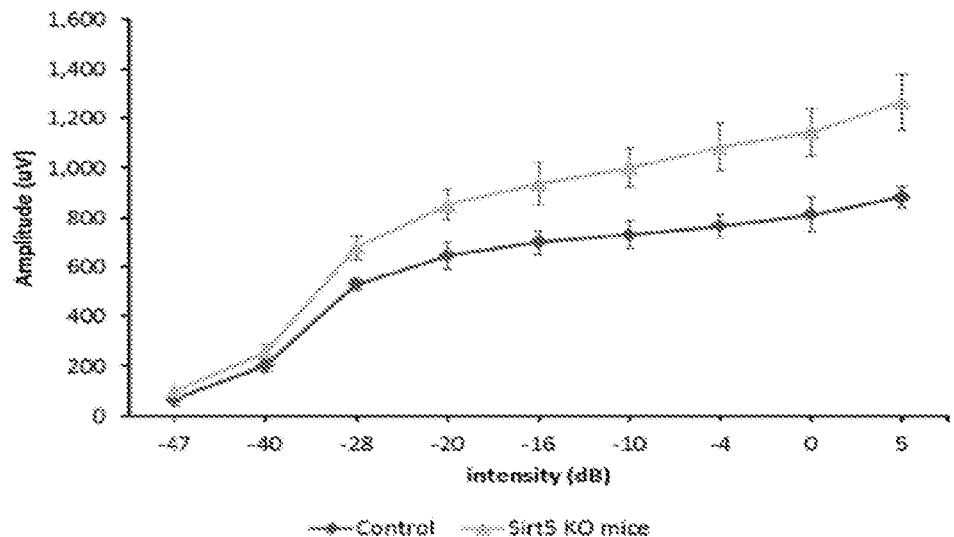
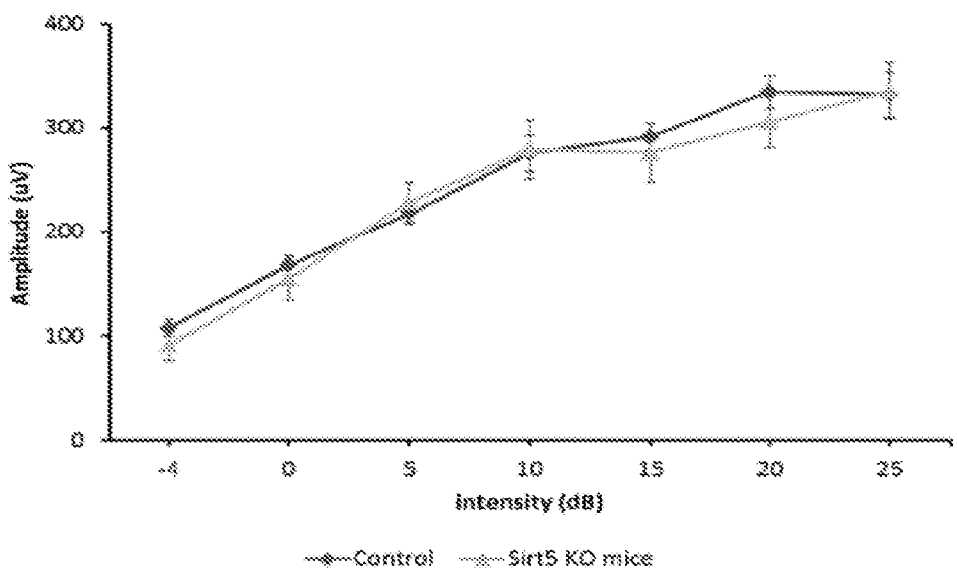

ADMINISTRATION OF NICOTINAMIDE MONONUCLEOTIDE IN THE TREATMENT OF DISEASE

CROSS-REFERENCE TO RELATED APPLICATIONS

This application is a continuation of U.S. application Ser. No. 17/150,584, filed Jan. 15, 2021 (issued U.S. Pat. No. 11,793,824), which is a continuation of U.S. application Ser. No. 16/290,122, filed Mar. 1, 2019 (issued U.S. Pat. No. 10,925,888), which is a continuation of U.S. application Ser. No. 15/783,845, filed Oct. 13, 2017 (issued U.S. Pat. No. 10,258,638), which is a continuation of U.S. application Ser. No. 14/855,293, filed Sep. 15, 2015 (issued U.S. Pat. No. 9,844,561), which is a continuation of International Application No. PCT/US14/30920, filed Mar. 17, 2014, which claims the benefit of priority to U.S. Provisional Patent Application No. 61/947,387 filed Mar. 3, 2014, and U.S. Provisional Patent Application No. 61/801,188 filed Mar. 15, 2013, each of which is incorporated herein by reference in its entirety.

GOVERNMENT LICENSE RIGHTS

This invention was made with government support under AG024150 awarded by the National Institutes of Health. The government has certain rights in the invention.

INTRODUCTION

Age-related obesity is a health-related problem for which new treatments and methods of ameliorating, mitigating, or reversing are needed. U.S. Pat. No. 8,268,575 to Imai, S., et al. asserts that "Chemical effectors for mammalian NAD biosynthesis can mediate a variety of anti-aging effects including anti-obesity, neuroprotective, and pancreatic β cell-protective effects as well as be effective to treat cancers." U.S. Pat. No. 8,017,634 to Sinclair, D. A., et al. teaches treating a cell with "an agent that increases Nrk enzyme." U.S. Patent Application Publication 2006/0229265 of Milburn, M., et al. discusses nicotinamide riboside and analogs thereof, including their use in methods of treating diseases or conditions, such as diabetes/insulin resistance, hyperlipidemia and obesity. Example 7 of Milburn, M., et al. purports to describe testing of neuroprotective effects of nicotinamide riboside and nicotinamide mononucleotide on ganglion cell survival. None of these references teach or suggest oral administration of NMN.

Age-related increases in blood lipid levels constitute another health-related problem for which new treatments and methods of ameliorating, mitigating, or reversing are needed. U.S. Pat. No. 7,737,158 of Imai, S., et al. discloses "a process for regulating the concentration of blood glucose in a mammal, the process comprising administering to the mammal a blood glucose concentration-regulating amount of nicotinamide mononucleotide (NMN) or a salt or prodrug thereof." This patent is not related to administering NMN for preventing age-associated increases in blood lipids, in particular there is no disclosure of oral administration of NMN for preventing age-associated increases in blood lipids. PCT Patent Application Publication WO2009062910 of Inufusa, H. states that an objective is to provide compositions effective in reducing blood triglyceride levels and/or cholesterol levels for the treatment and/or prophylaxis of hypertriglyceridemia, hypercholesterolemia and disease states induced thereby such as arteriosclerosis and obesity. However, this application does not disclose administering NMN for controlling age-related blood lipid increases.

Age-related decreases in insulin sensitivity constitute another health-related problem for which new treatments and methods of ameliorating, mitigating, or reversing are needed. U.S. Pat. No. 7,737,158 to Imai, S., et al. discusses "processes for regulating the concentration of blood glucose in a mammal. The processes include administering to a mammal a blood glucose concentration-regulating amount of a compound . . . useful in nicotinamide adenine dinucleotide (NAD) biosynthesis. This disclosure does not teach administering NMN, including oral administration of NMN, for improvement of insulin sensitivity in aging.

Age-related loss or decreases in memory function constitute another health-related problem for which new treatments and methods of ameliorating, mitigating, or reversing are needed. While U.S. Patent Application Publication 2006/0229265 of Milburn, M., et al. alleges, in Example 7, of "neuroprotective effects" of NMN, no data are presented. This application does not discuss using NMN to treat or prevent memory loss. U.S. Patent Application Publication 2006/0002914 of Milbrandt, J., et al. discloses administering an agent that acts by increasing NAD activity in diseased and/or injured neurons in the treatment of diseases such as Alzheimer's. There is no explicit teaching of administering NMN to improve memory function under normal aging conditions.

Age-related loss or decreases in eye function constitute another health-related problem for which new treatments and methods of ameliorating, mitigating, or reversing are needed. U.S. Patent Application Publication 2007/0014833 of Milburn, M., et al. discloses use of "sirtuin modulators" to treat vision impairment. U.S. Patent Application Publication 2006/0229265 of Milburn, M., et al. states "Conditions of the eye can be treated or prevented by, e.g., systemic, topical, intraocular injection of a sirtuin modulating compound, or by insertion of a sustained release device that releases a sirtuin-modulating compound. Neither of these publications disclose administration of NMN for the prevention of decline of eye function during aging.

Age-related dry eye constitutes another health-related problem for which new treatments and methods of ameliorating, mitigating, or reversing are needed. Dry eye is one of the most prevalent eye disorders, particularly among the elderly, and no fundamental treatments are yet available (Tsubota, K., et al. Cornea. 31 Suppl 1: S1-8, 2012). Decrease in lacrimal gland secretory function might be a possible cause of age-associated dry eye diseases (Kawashima, M., et al. Biochem Biophys. Res. Commun. 397: 724-8, 2010).

Age-related cognitive impairment constitutes another health-related problem for which new treatments and methods of ameliorating, mitigating, or reversing are needed. Aging is a negative regulator of adult neural stem and progenitor cell (NSPC) proliferation (Artegiani, B., et al.) While NSPC proliferation declines exponentially throughout life (Artegiani & Calegari, 2012), quiescent NSPCs can be reactivated in the aged murine hippocampus by multiple environmental stimuli (Decker et al, 2002; Jin et al, 2003; Lugert et al, 2010). Aging can reduce levels of the essential cofactor nicotinamide adenine dinucleotide (NAD+) in multiple peripheral tissues (Yoshino et al, 2011).

U.S.patent application Ser. No. 12/524,718 Milbrandt, J., et al. discloses experimental applications of NMN. This reference does not mention administering NMN to affect NSPCs or for oligodendrocyte proliferation.

Sasaki, Y., et al. J Neurosci. 2006 Aug. 16; 26(33):8484-91 discloses applications of NMN. This article does not disclose administration of NIVIN to affect NSPCs or promote proliferation of oligodendrocytes. U.S. Application US20130059384 A1 of Tilly, J. L., et al. discloses the use of NIVIN for enhancing female fertility.

Photoreceptor neuron dysfunction and cell death is the leading cause of blindness over the lifespan in humans. Photoreceptor neuron dysfunction constitutes another health-related problem for which new treatments and methods of ameliorating, mitigating, or reversing are needed.

PCT Application PCT/US2006/011930 (Pub No. WO2006105403) of Dipp, M., et al. disclosed methods of treating vision impairment by administration of a sirtuin modulator. In example 10 of this reference, the investigators tested neuroprotective effects of nicotinamide mononucleotide (NMN) in a retinal ganglion cell injury model. However, the retinal ganglion cells disclosed in this application not classical photoreceptors (rods and cones).

U.S. Patent Application Publication US20100047177 of Milbrandt, J., et al. discusses administering to a mammal an agent that increases NAD activity in diseased and/or injured neurons or supporting cells. The application does not specify protection or treatment of rods and cones with NMN.

U.S. Pat. No. 7,776,326 of Milbrandt, J., et al. discusses methods of treating or preventing axonal degradation in neuropathic diseases in mammals by administering an agent that can increase sirtuin activity in diseased/injured neuronal cells. The patent does not specify protection or treatment of rods and cones with NMN. This patent does not disclose administration of NMN to maintain NSPCs or promote oligodendrocyte proliferation.

"Stimulation of nicotinamide adenine dinucleotide biosynthetic pathways delays axonal degeneration after axotomy" J Neurosci. 2006 Aug. 16; 26(33):8484-8491 of Sasaki, Y., et al. discusses adding NMN to cultured neurons. This article does not disclose administration of NMN to retinal cells in vivo.

Chinese Patent CN 101601679 B "Application of nicotinamide mononucleotide" discloses applications of NMN for prevention of stroke.

PCT Application PCT/IB2012/001146 of Alvarez, C. C., et al. discloses treating a mitochondrial dysfunction with a compound that increases intracellular nicotinamide adenine dinucleotide (NAD+) in an amount sufficient to activate SIRT1 or SIRT3. The application does not disclose administration of NMN to neuronal cells. This reference does not mention NSPCs.

U.S. Pat. No. 7,737,158 of Imai, S., et al. discloses processes for regulating blood glucose concentration by administration of NMN. The patent does not teach administration of NMN to rod/cone-type photoreceptor neurons. This reference does not discuss administration of NMN to treat NSPCs or for age-related diseases or neurodegenerative diseases unrelated to glucose levels.

Revollo, J. R., et al. Cell metabolism 6, 363-375 (2007), Ramsey, K. M., et al. Aging Cell. 2008 January; 7(1):78-88, and Yoshino, J., et al. Cell Metab. 2011 Oct. 5; 14(4):528-36 do not disclose administration of NMN for treating photoreceptor degeneration, retinal degeneration, or macular degeneration. Exp Eye Res. 2013 March; 108:76-83 of Bai, S., et al. does not disclose targeting rod/cone-type photoreceptor neurons with NMN. These articles do not discuss NSPCs.

SUMMARY

The present inventors describe administration of nicotinamide mononucleotide (NMN), as illustrated in (FIG. 1), to a subject such as a vertebrate, including a human or other mammal, a bird, a reptile, a fish or other aquatic organism.

In addition, also disclosed in various embodiments are compositions comprising NMN. In various configurations, these compositions can further comprise one or more excipients. These compositions can be used for administration of NMN for the treatment, amelioration, mitigation, slowing, arrest, prevention and/or reversal of age-associated degenerative changes.

In some embodiments, any of the dosages of the present teachings of nicotinamide mononucleotide (NMN), a salt thereof and/or a prodrug thereof can be used to treat any of the diseases of the present teachings.

In various embodiments, the present teachings include a pharmaceutically acceptable composition comprising, consisting essentially of, or consisting of nicotinamide mononucleotide (NMN), a salt thereof and/or a prodrug thereof and at least one pharmaceutically acceptable excipient. In various configurations, a pharmaceutically acceptable composition can, comprise, consist essentially of, or consist of a single dosage formulation. In some configurations, a single dosage formulation can be a sustained-release formulation.

In various configurations, a pharmaceutically acceptable composition of the present teachings can be a formulation including a pill, a tablet, a caplet, a capsule, a chewable tablet, a quick dissolve tablet, a powder, an effervescent tablet, a hard gelatin capsule, a soft gelatin capsule, a non-aqueous liquid, an aqueous liquid, a granule, a capsule, a suspension, a solution, an emulsion, a syrup, a sterilized aqueous suspension or solution, a non-aqueous suspension or solution, a lyophilized formulation, or a suppository.

In some embodiments, a pharmaceutically acceptable composition of the present teachings can be a single dosage formulation. In various embodiments, a single dosage formulation can comprise an enteric coating. In some embodiments, a pharmaceutically acceptable composition of the present teachings can comprise, consist essentially of, or consist of NMN, a salt thereof and/or a prodrug thereof in an amount of about 100 mg, from 100 mg to 2000 mg, about 2000 mg, or greater. In some embodiments, a pharmaceutically acceptable composition of the present teachings can comprise, consist essentially of, or consist of NMN, a salt thereof and/or a prodrug thereof in an amount of about 100 mg, about 200 mg, about 300 mg, about 400 mg, about 500 mg, about 600 mg, about 700 mg, about 800 mg, about 900 mg, about 1000 mg, about 1100 mg, about 1200 mg, about 1300 mg, about 1400 mg, about 1500 mg, about 1600 mg, about 1700 mg, about 1800 mg, about 1900 mg, about 2000 mg, or greater. In some embodiments, a pharmaceutically acceptable composition of the present teachings can comprise, consist essentially of, or consist of NMN, a salt thereof and/or a prodrug thereof in an amount of 50-150 mg, 151-250 mg, 251-350 mg, 351-450 mg, 451-550 mg, 561-650 mg, 651-750 mg, 751-860 mg, 861-950 mg, 951-1050 mg, 1051-1150 mg, 1151-1250 mg, 1251-1350 mg, 1351-1450 mg, 1451-1550 mg, 1551-1650 mg, 1651-1750 mg, 1751-1850 mg, 1851-1950 mg, 1951-2000 mg, or greater. In some embodiments, a pharmaceutically acceptable composition of the present teachings can comprise, consist essentially of, or consist of NMN, a salt thereof and/or a prodrug thereof in an amount of at least 0.5 mg up to about 6800 mg, such as, without limitation, 0.5 mg, about 0.5 mg, 1 mg, about 1 mg, 5 mg, about 5 mg, 10 mg, about 10 mg, 20 mg, about 20 mg, 30 mg, about 30 mg, 40 mg, about 40 mg, 50 mg, about 50 mg, 60 mg, about 60 mg, 70 mg, about 70 mg, 80 mg, about 80 mg, 90 mg, about 90 mg, 100 mg, about 100 mg, 150 mg, about 150 mg, 200 mg, about 200 mg, 250 mg, about 250 mg, 300 mg, about 300 mg, 400 mg, about 400 mg, 450 mg, about 450 mg, 500 mg, about 500 mg, 600 mg, about 600 mg, 680 mg, about 680 mg, 700 mg, about 700 mg, 800 mg, about 800 mg, 900 mg, about 900 mg, 1000 mg, about 1000 mg, 1100 mg, about 1100 mg, 1130 mg, about 1130 mg, 1200 mg, about 1200 mg, 1300 mg, about 1300 mg, 1350 mg, about 1350 mg, 1360 mg, about 1360 mg, 1400 mg, about 1400 mg, 1500 mg, about 1500 mg, 1600 mg, about 1600 mg, 1700 mg, about 1700 mg, 1800 mg, about 1800 mg, 1900 mg, about 1900 mg, 2000 mg, about 2000 mg, 2040 mg, about 2040 mg, 2100 mg, about 2100 mg, 2200 mg, about 2200 mg, 2250 mg, about 2250 mg, 2300 mg, about 2300 mg, 2400 mg, about 2400 mg, 2500 mg, about 2500 mg, 2600 mg, about 2600 mg, 2700 mg, about 2700 mg, 2800 mg, about 2800 mg, 2900 mg, about 2900 mg, 3000 mg, about 3000 mg, 3100 mg, about 3100 mg, 3200 mg, about 3200 mg, 3300 mg, about 3300 mg, 3400 mg, about 3400 mg, 3500 mg, about 3500 mg, 3600 mg, about 3600 mg, 4000 mg, about 4000 mg, 4500 mg, about 4500 mg, 5000 mg, about 5000 mg, 5500 mg, about 5500 mg, 6000 mg, about 6000 mg, 6500 mg, about 6500 mg, 6800 mg, or about 6800 mg.

In some embodiments, a pharmaceutically acceptable composition of the present teachings can comprise a food product. In some embodiments, a pharmaceutically acceptable composition of the present teachings can comprise a composition suitable for oral administration, sublingual administration, parenteral administration, administration by injection, subcutaneous injection, intramuscular injection, intraperitoneal injection, intra-ocular injection, direct ocular application (eye drop) or a combination thereof.

In some embodiments, a pharmaceutically acceptable composition of the present teachings can further comprise least one excipient. In some embodiments, the at least one excipient can comprise a bulking agent, a tableting agent, a dissolution agent, a wetting agent, a lubricant, a coloring, a flavoring, a disintegrant, a coating, a binder, an antioxidant, a taste masking agent, a sweetener, or a combination thereof. In some embodiments, a bulking agent can comprise mannitol, sorbitol, sucrose, trehalose, or a combination thereof.

In some embodiment, a pharmaceutically acceptable composition of the present teachings can be formulated as an orally disintegrating capsule, tablet, pill or wafer. In some embodiment, a pharmaceutically acceptable composition of the present teachings can be formulated as a liquid, syrup, or spray.

In some embodiment, a pharmaceutically acceptable composition of the present teachings can further comprise at least one vitamin or nutrient. In some embodiments, a vitamin or nutrient can be vitamin C, vitamin D3, vitamin E, vitamin B1, vitamin B2, niacin, vitamin B6, folic acid, vitamin B12, pantothenic acid, biotin, magnesium, zinc, copper, selenium, chromium, alpha lipoic acid, b co-enzyme Q-10, lutein, lycopene, or a combination thereof. In some embodiments, a vitamin or nutrient can be an amount comprising 150 mg to about 750 mg of vitamin C, from about 315 IUs to about 1800 IUs of vitamin D3, from about IUs to about 150 IUs of vitamin E, from about 15 mg to about 35 mg of vitamin B1, from about 1.7 mg to about 5.1 mg of vitamin B2, from about 20 mg to about 50 mg of niacin, from about 20 mg to about 50 mg of vitamin B6, from about 0.5 mg to about 2.5 mg of folic acid, from about 35 mcg to about 105 mcg of vitamin B12, from about 2.5 mg to about 7.5 mg of pantothenic acid, from about 50 mcg to about 450 mcg of biotin, from about 15 mg to about 55 mg of magnesium, from about 15 mg to about 55 mg of zinc, from about 0.5 to about 1.5 mg of copper, from about 75 mcg to about 175 mcg of selenium, from about 75 mcg to about 225 mcg of chromium, from about 10 mg to about 40 mg of alpha lipoic acid, from about 20 mg to about 50 mg of co-enzyme Q-10, from about 350 mcg to about 3 mg of lutein, from about 100 mcg to about 750 mcg of lycopene, or a combination thereof.

In some embodiments, a vitamin or nutrient can be about 500 mg of ascorbic acid, about 400 IUs of cholecalciferol, about 125 IUs of d-alpha tocopherol succinate, about 35 mg of thiamine mononitrate, about 5.1 mg of riboflavin, about 50 mg of niacinamide, about 50 mg of pyridoxine HCl, about 2.5 mg of folic acid, about 105 mcg of cyanocobalamin, about 7.5 mg of d-calcium pantothenate, about 75 mcg of d-biotin, about 55 mg of dimagnesium malate, about 55 mg of zinc bisglycinate chelate, about 1.5 mg of copper amino acid chelate, about 175 mcg of selenium amino acid chelate, about 225 mcg of chromium amino acid chelate, about 10 mg of alpha lipoic acid, about 50 mg of co-enzyme Q-10, about 400 mcg of lutein, about 125 mcg of lycopene, or a combination thereof.

In some embodiments, an excipient of the present teachings can be dicalcium phosphate, microcrystalline cellulose, stearic acid, croscarmellose sodium, magnesium trisilicate, magnesium stearate, hydroxypropyl methylcellulose, hypromellose, titanium dioxide, tripotassium citrate, polyvinyl alcohol, fumed silica, citric acid, polyethylene glycol, talc, or a combination thereof. In some embodiments, an excipient of the present teachings can be about 100 mg to about 300 mg of dicalcium phosphate, from about 25 mg to about 75 mg of microcrystalline cellulose, from about 10 mg to about 30 mg of stearic acid, from about 10 mg to about 30 mg of croscarmellose sodium, from about 5 mg to about 15 mg of magnesium trisilicate, from about 5 mg to about 15 mg of magnesium stearate, from about 5 mg to about 15 mg of hydroxypropyl methylcellulose, or a combination thereof.

In some embodiments, an excipient of the present teachings can be about 200 mg of dicalcium phosphate, about 50 mg of microcrystalline cellulose, about 20 mg of stearic acid, about 20 mg of croscarmellose sodium, about 10 mg of magnesium trisilicate, about 10 mg of magnesium stearate, about 10 mg of hydroxypropyl methylcellulose, or a combination thereof.

In some embodiments, a pharmaceutically acceptable composition of the present teachings can be a sustained release formulation of nicotinamide mononucleotide for oral administration. In some embodiments, a sustained release formulation of nicotinamide mononucleotide for oral administration can comprise nicotinamide mononucleotide as an active ingredient that is released from the formulation along a pre-determined release profile, wherein the formulation comprises an extended release component and an immediate release component, wherein the extended release component is contained in at least one population of beads and releases nicotinamide mononucleotide in a continuous manner and each bead population is coated with its own release controlling coating and characterized by its own rate of release.

In some embodiments, an extended release component can release the nicotinamide mononucleotide in vivo in a continuous manner. In some embodiments, an extended release component can release the nicotinamide mononucleotide in vivo in a continuous manner and 80% of the nicotinamide mononucleotide can be released in vivo in a period of time selected from not more than 24 hours, not more than 16 hours, not more than 12 hours, not more than 8 hours or not more than 4 hours. In some embodiments, an immediate release component of the present teachings can be an enhanced immediate release (EIR) composition comprising a complexing agent, an enhancing agent, or a combination. In some embodiments, an EIR composition can exhibit an in vitro release profile such that 80% of the active ingredient is dissolved in not more than 30 min. In some embodiments, an EIR composition can exhibit an in vitro release profile selected from a group consisting of: a) a dissolution of at least 50% of the active compound in not more than 10 minutes, b) a dissolution of at least 70% of the active compound in not more than 10 minutes, c) a dissolution of at least 25% of the active compound in not more than 5 minutes, d) a dissolution of at least 40% of the active compound in not more than 5 minutes, or e) a dissolution of at least 55% of the active compound in not more than 5 minutes.

In some embodiments, a pharmaceutically acceptable composition of the present teachings can include a complexing agent. In some embodiments, a complexing agent can be hydroxypropyl-beta-cyclodextrin, beta-cyclodextrin, gamma-cyclodextrin, alpha-cyclodextrin, derivatives thereof, or a combination thereof.

In some embodiments, a pharmaceutically acceptable composition of the present teachings can include an enhancing agent. In some embodiments, an enhancing agent can be a solubility enhancing agent, a dissolution enhancing agent, an absorption enhancing agent, a penetration enhancing agent, a surface active agent, a stabilizer, an enzyme inhibitor, a p-glycoprotein inhibitor, a multidrug resistance protein inhibitor, or a combination thereof.

In some embodiments, an enhancing agent can be Vitamin E TPGS, glutamic acid, glycine, sorbitol, mannose, amylose, maltose, mannitol, lactose, sucrose, glucose, xylitose, dextrins, glycerolpolyethylene glycol oxystearate, PEG-32 glyceryl palmitostearate, sodium lauryl sulfate, polyoxyethylene sorbitan monooleate, benzyl alcohol, sorbitan monolaurate, Poloxamer 407, PEG3350, PVP K25, oleic acid, glyceryl monooleate, sodium benzoate, cetyl alcohol, sucrose stearate, crospovidone, sodium starch glycolate, croscarmellose sodium, carboxymethylcellulose, starch, pregelatinized starch, HPMC, substituted hydroxypropylcellulose, microcrystalline cellulose sodium bicarbonate, calcium citrate, sodium docusate, menthol, or any combination thereof.

In some embodiments, a pharmaceutically acceptable composition of the present teachings can include at least a part of the active ingredient in a form of micronized particles. In some embodiments, a micronized particle can have an average size of from about 2 µm to about 100 µm.

In some embodiments, a pharmaceutically acceptable composition of the present teachings can include a specific amount of each component determined according to the purpose of administration and the pre-determined release profile, and the total amount of NMN in the formulation is from 0.5 to 3000 mg.

In some embodiments, a population of beads of the present teachings can comprise an inert carrier, NMN, an optional enhancer, a release controlling coating that comprises a coating material, a pore former, an excipient, or a combination thereof. In some embodiments, an inert carrier of the present teachings can be a cellulose sphere, silicon dioxide, starch, a sugar sphere, or a combination thereof.

In some embodiments, an enhancer can be a solubility enhancer, a dissolution enhancer, a permeability enhancer, a stabilizer, a complexing agent, an enzyme inhibitor, a p-glycoprotein inhibitor, a multidrug resistance protein inhibitor, or a combination thereof.

In some embodiments, a coating material of the present teachings can be ethylcellulose, methylcellulose, hydroxypropyl cellulose, hydroxypropylmethyl cellulose, cellulose acetate, cellulose acetate phthalate, polyvinyl alcohol, polyacrylates, polymethacrylates and copolymers thereof; and/or a pore former is selected from a group consisting of glucose, fructose, mannitol, mannose, galactose, sorbitol, pullulan, dextran, water-soluble hydrophilic polymers, hydroxyalkylcelluloses, carboxyalkylcelluloses, hydroxypropylmethylcellulose, cellulose ethers, acrylic resins, polyvinylpyrrolidone, cross-linked polyvinylpyrrolidone, polyethylene oxide, Carbowaxes™ (Dow Chemical), CARBOPOL) (The Lubrizol Corp.), diols, polyols, polyhydric alcohols, polyalkylene glycols, polyethylene glycols, polypropylene glycols or block polymers thereof, polyglycols, poly(a-w)alkylenediols; inorganic compounds selected from a group consisting of alkali metal salts and alkaline earth metal salts, or combinations thereof.

In some embodiments, an amount of an individual bead population is determined according to a pre-determined release profile. In some embodiments, a pre-determined release profile can comprise a sustained rate of release after an initial immediate release. IN some embodiments, a pharmaceutically acceptable composition of the present teachings can be suitable for once a day oral administration. In some embodiments, a population of beads can comprise, consist essentially of, or consist of extended release NMN beads additionally comprising an immediate release component coated on top of the release controlling coating. In some embodiments, a formulation of a pharmaceutically acceptable composition of the present teachings can comprise an enhancer contained in a layer separate from the release controlling coating. In some embodiments, a formulation of a pharmaceutically acceptable composition of the present teachings can comprise at least one enhancing agent wherein the enhancing agent is incorporated into the formulation in the form of a powder or of a population of beads that are optionally characterized by a controlled rate of release, and wherein the enhancing agent is separated from the active ingredient.

In various configurations, a composition of the present teachings can comprise nicotinamide mononucleotide (NMN), a pharmaceutical salt of NMN, or a prodrug of NMN. In various configurations, a salt can be a pharmaceutically acceptable salt; that is, a salt prepared from pharmaceutically acceptable non-toxic acids, including inorganic acids and organic acids. Non-limiting examples of suitable non-toxic acids include inorganic and organic acids of basic residues such as amines, for example, acetic, benzenesulfonic, benzoic, amphorsulfonic, citric, ethenesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, barbaric acid, p-toluenesulfonic and the like; and alkali or organic salts of acidic residues such as carboxylic acids, for example, alkali and alkaline earth metal salts derived from the following bases: sodium hydride, sodium hydroxide, potassium hydroxide, calcium hydroxide, aluminum hydroxide, lithium hydroxide, magnesium hydroxide, zinc hydroxide, ammonia, trimethylammonia, triethylammonia, ethylenediamine, lysine, arginine, ornithine, choline, N,N"-dibenzylethylenediamine, chloroprocaine, diethanolamine, procaine, n-benzylphenethylamine, diethylamine, piperazine, tris(hydroxymethyl)-aminomethane, tetramethylammonium hydroxide, and the like. Pharmaceutically acceptable salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts can be found in Remington's Pharmaceutical Sciences, 17th ed., Mack Publishing Company, Easton, Pa., 1985, p. 1418, the disclosure of which is hereby incorporated by reference.

NMN can be delivered in prodrug form. Thus, the present teachings are intended to cover prodrugs of NMN, methods of delivering the same and compositions containing them. A "prodrug" can include any covalently bonded carriers which release an active drug in vivo when such prodrug is administered to a mammalian subject. In various configurations, a prodrug can be prepared by modifying functional groups present in the compound in such a way that the modifications are cleaved, either in routine manipulation or in vivo, to the parent compound. In various configurations, prodrugs include, without limitation, compounds of the present teachings wherein a hydroxyl or amino group can be bonded to any group that, when the prodrug is administered to a mammalian subject, cleaves to form a free hydroxyl or free amino group, respectively. Non-limiting examples of prodrugs include acetate, formate, and benzoate derivatives of alcohol and amine functional groups in the compounds and conjugates of the present teachings. Prodrugs of NMN can be, within the scope of sound medical judgment, suitable for use in contact with the tissues of humans and lower animals without undue toxicity, irritation, allergic response, and the like, commensurate with a reasonable benefit/risk ratio, and effective for their intended use, as well as the zwitterionic forms, where possible, of the compounds of the present teachings. In some configurations, prodrugs can refer to compounds that can be transformed in vivo to yield NMN, for example by hydrolysis in blood.

In some embodiments, NMN can be dispersed in a pharmaceutically acceptable carrier prior to administration to a subject. In various embodiments, a carrier, also known in the art as an excipient, vehicle, auxiliary, adjuvant, or diluent, can be a substance that is pharmaceutically inert, can confer a suitable consistency or form to the composition, and does not diminish the efficacy of the NMN. A carrier can be considered to be "pharmaceutically or pharmacologically acceptable" if it does not lead to pharmaceutically unacceptable adverse, allergic or other untoward reactions when administered to a subject, including a mammalian subject.

The selection of a pharmaceutically acceptable carrier can also, in part, be a function of the route of administration. For example, suitable routes of administration include, but are not limited to, oral, parenteral (e.g., intravenous, intraarterial, subcutaneous, rectal, subcutaneous, intramuscular, intraorbital, intracapsular, intraspinal, intraperitoneal, or intrasternal), topical (nasal, transdermal, ocular such as eyedrops, intraocular), intravesical, intrathecal, enteral, pulmonary, intralymphatic, intracavital, vaginal, transurethral, intradermal, aural, intramammary, buccal, orthotopic, intratracheal, intralesional, percutaneous, endoscopical, transmucosal, sublingual and intestinal administration.

Pharmaceutically acceptable carriers for use in the present teachings can be selected based upon a number of factors: the particular compound used, and its concentration, stability and intended bioavailability; the subject, its age, size and general condition; and the route of administration. Suitable nonaqueous, pharmaceutically-acceptable polar solvents include, but are not limited to, alcohols (e.g., α-glycerol formal, β-glycerol formal, 1,3-butyleneglycol, aliphatic or aromatic alcohols having 2-30 carbon atoms such as methanol, ethanol, propanol, isopropanol, butanol, t-butanol, hexanol, octanol, amylene hydrate, benzyl alcohol, glycerin (glycerol), glycol, hexylene glycol, tetrahydrofurfuryl alcohol, lauryl alcohol, cetyl alcohol, or stearyl alcohol, fatty acid esters of fatty alcohols such as polyalkylene glycols (e.g., polypropylene glycol, polyethylene glycol), sorbitan, sucrose and cholesterol); amides (e.g., dimethyl acetamide (DMA), benzyl benzoate DMA, dimethylformamide, N-(β-hydroxyethyl)-lactamide, N,N-dimethylacetamide amides, 2-pyrrolidinone, 1-methyl-2-pyrrolidinone, or polyvinylpyrrolidone); esters (e.g., 1-methyl-2-pyrrolidinone, 2-pyrrolidinone, acetate esters such as monoacetin, diacetin, and triacetin, aliphatic or aromatic esters such as ethyl caprylate or octanoate, alkyl oleate, benzyl benzoate, benzyl acetate, dimethylsulfoxide (DMSO), esters of glycerin such as mono, di, or tri-glyceryl citrates or tartrates, ethyl benzoate, ethyl acetate, ethyl carbonate, ethyl lactate, ethyl oleate, fatty acid esters of sorbitan, fatty acid derived PEG esters, glyceryl monostearate, glyceride esters such as mono, di, or tri-glycerides, fatty acid esters such as isopropyl myristrate, fatty acid derived PEG esters such as PEG-hydroxyoleate and PEG-hydroxystearate, N-methyl pyrrolidinone, pluronic 60, polyoxyethylene sorbitol oleic polyesters such as poly (ethoxylated) 30-60 sorbitol poly(oleate)2-4, poly(oxyethylene)15-20 monooleate, poly(oxyethylene)15-20 mono 12-hydroxystearate, and poly(oxyethylene)15-20 mono ricinoleate, polyoxyethylene sorbitan esters such as polyoxyethylene-sorbitan monooleate, polyoxyethylene-sorbitan monopalmitate, polyoxyethylene-sorbitan monolaurate, polyoxyethylene-sorbitan monostearate, and Polysorbate® 20, 40, 60 or 80 from ICI Americas, Wilmington, Del., polyvinylpyrrolidone, alkyleneoxy modified fatty acid esters such as polyoxyl 40 hydrogenated castor oil and polyoxyethylated castor oils (e.g., Cremophor® EL solution or Cremophor® RH 40 solution), saccharide fatty acid esters (i.e., the condensation product of a monosaccharide (e.g., pentoses such as ribose, ribulose, arabinose, xylose, lyxose and xylulose, hexoses such as glucose, fructose, galactose, mannose and sorbose, trioses, tetroses, heptoses, and octoses), disaccharide (e.g., sucrose, maltose, lactose and trehalose) or oligosaccharide or mixture thereof with a C4-C22 fatty acid(s) (e.g., saturated fatty acids such as caprylic acid, capric acid, lauric acid, myristic acid, palmitic acid and stearic acid, and unsaturated fatty acids such as palmitoleic acid, oleic acid, elaidic acid, erucic acid and linoleic acid)), or steroidal esters); alkyl, aryl, or cyclic ethers having 2-30 carbon atoms (e.g., diethyl ether, tetrahydrofuran, dimethyl isosorbide, diethylene glycol monoethyl ether); glycofurol (tetrahydrofurfuryl alcohol polyethylene glycol ether); ketones having 3-30 carbon atoms (e.g., acetone, methyl ethyl ketone, methyl isobutyl ketone); aliphatic, cycloaliphatic or aromatic hydrocarbons having 4-30 carbon atoms (e.g., benzene, cyclohexane, dichloromethane, dioxolanes, hexane, n-decane, n-dodecane, n-hexane, sulfolane, tetramethylenesulfon, tetramethylenesulfoxide, toluene, dimethylsulfoxide (DMSO), or tetramethylenesulfoxide); oils of mineral, vegetable, animal, essential or synthetic origin (e.g., mineral oils such as aliphatic or wax-based hydrocarbons, aromatic hydrocarbons, mixed aliphatic and aromatic based hydrocarbons, and refined paraffin oil, vegetable oils such as linseed, tung, safflower, soybean, castor, cottonseed, groundnut, rapeseed, coconut, palm, olive, corn, corn germ, sesame, persic and peanut oil and glycerides such as mono-, di- or triglycerides, animal oils such as fish, marine, sperm, cod-liver, haliver, squalene, squalane, and shark liver oil, oleic oils, and polyoxyethylated castor oil); alkyl or aryl halides having 1-30 carbon atoms and optionally more than one halogen substituent; methylene chloride; monoethanolamine; petroleum benzin; trolamine; omega-3 polyunsaturated fatty acids (e.g., alpha-linolenic acid, eicosapentaenoic acid, docosapentaenoic acid, or docosahexaenoic acid); polyglycol ester of 12-hydroxystearic acid and polyethylene glycol (Solutol® HS-15, from BASF, Ludwigshafen, Germany); polyoxyethylene glycerol; sodium laurate; sodium oleate; or sorbitan monooleate.

Other pharmaceutically acceptable solvents for use in the present teachings are well known to those of ordinary skill in the art, and are identified in The Chemotherapy Source Book (Williams & Wilkens Publishing), The Handbook of Pharmaceutical Excipients, (American Pharmaceutical Association, Washington, D.C., and The Pharmaceutical Society of Great Britain, London, England, 1968), Modern Pharmaceutics, (G. Banker et al., eds., 3d ed.)(Marcel Dekker, Inc., New York, N.Y., 1995), The Pharmacological Basis of Therapeutics, (Goodman & Gilman, McGraw Hill Publishing), Pharmaceutical Dosage Forms, (H. Lieberman et al., eds.)(Marcel Dekker, Inc., New York, N.Y., 1980), Remington's Pharmaceutical Sciences (A. Gennaro, ed., 19th ed.)(Mack Publishing, Easton, Pa., 1995), The United States Pharmacopeia 24, The National Formulary 19, (National Publishing, Philadelphia, Pa., 2000), A. J. Spiegel et al., and Use of Nonaqueous Solvents in Parenteral Products, Journal Of Pharmaceutical Sciences, Vol. 52, No. 10, pp. 917-927 (1963).

In some embodiments, the present teachings include methods of treating, ameliorating, mitigating, slowing, arresting, preventing or reversing age-associated obesity in a subject. In some embodiments, the present teachings include methods of treating, ameliorating, mitigating, slowing, arresting, preventing or reversing age-associated increases in blood lipid levels in a subject. In some embodiments, the present teachings include methods of treating, ameliorating, mitigating, slowing, arresting, preventing or reversing age-associated loss of insulin sensitivity in a subject. In some embodiments, the present teachings include methods of treating, ameliorating, mitigating, slowing, arresting, preventing or reversing age-associated impairment of memory function in a subject. In some embodiments, the present teachings include methods of treating, ameliorating, mitigating, slowing, arresting, preventing or reversing age-associated decline in eye function in a subject. In some embodiments, the present teachings include methods of treating, ameliorating, mitigating, slowing, arresting, preventing or reversing age-associated retinal degeneration in a subject. In some embodiments, the present teachings include methods of treating, ameliorating, mitigating, slowing, arresting, preventing or reversing dry eye. In some embodiments, the present teachings include methods of treating, ameliorating, mitigating, slowing, arresting, preventing or reversing age-associated dry eye.

In various embodiments, these methods can each independently comprise, consist essentially of, or consist of administering to a subject a pharmaceutically effective amount of nicotinamide mononucleotide (NMN). In some embodiments, NMN can be administered at a dosage rate of about 100 mg per day, from 100 mg per day to 2000 mg per day, or about 2000 mg per day. In some embodiments, NMN can be administered at a dosage rate of 0.5 mg, about 0.5 mg, 1 mg, about 1 mg, 5 mg, about 5 mg, 10 mg, about 10 mg, 20 mg, about 20 mg, mg, about 30 mg, 40 mg, about 40 mg, 50 mg, about 50 mg, 60 mg, about 60 mg, 70 mg, about 70 mg, 80 mg, about 80 mg, 90 mg, about 90 mg, about 100 mg per day, 100 mg per day, 150 mg, about 150 mg, about 200 mg per day, 200 mg per day, about 300 mg per day, 300 mg per day, about 400 mg per day, 400 mg per day, about 500 mg per day, 500 mg per day, about 600 mg per day, 600 mg per day, about 700 mg per day, 700 mg per day, about 800 mg per day, 800 mg per day, about 900 mg per day, 900 mg per day, about 1000 mg per day, 1000 mg per day, about 1100 mg per day, 1100 mg per day, about 1200 mg per day, 1200 mg per day, about 1300 mg per day, 1300 mg per day, 1350 mg, about 1350 mg, about 1400 mg per day, 1400 mg per day, about 1500 mg per day, 1500 mg per day, about 1600 mg per day, 1600 mg per day, about 1700 mg per day, 1700 mg per day, about 1800 mg per day, 1800 mg per day, about 1900 mg per day, 1900 mg per day, about 2000 mg per day, 2000 mg per day, 2040 mg, about 2040 mg, 2250 mg, about 2250 mg, 2260 mg, about 2260 mg, 2700 mg, about 2700 mg, 2720 mg, about 2720 mg, 3400 mg, about 3400 mg, 3390 mg, about 3390 mg, 3400 mg, about 3400 mg, 3600 mg, about 3600 mg, 4080 mg, about 4080 mg, 4500 mg, about 4500 mg, 4520 mg, about 4520 mg, 5440 mg, about 5440 mg, 5650 mg, about 5650 mg, 6800 mg, about 6800 mg, or an alternation or combination thereof. In some embodiments, NMN can be administered at a dosage rate of about 100 mg/kg body weight/day, from 100 mg/kg body weight/day to 500 mg/kg body weight/day, or about 500 mg/kg body weight/day. In some embodiments, NMN can be administered at a dosage rate of about 100 mg/kg body weight/day, from 100 mg/kg body weight/day to 300 mg/kg body weight/day, or about 300 mg/kg body weight/day. In some embodiments, these methods can comprise administering to a subject any of the pharmaceutically acceptable compositions of the present teachings. In some embodiments, these methods can comprise, consist essentially of or consist of administering a formulation once per day. In some embodiments, these methods can comprise, consist essentially of or consist of administering a formulation twice per day.

In some embodiments, the present teachings include methods of increasing NAD+ levels in a subject through administration of NMN. In some embodiments, the present teachings include methods of treating age-associated defects in neural stem/progenitor cell (NSPC) functionality in a subject through administration of NMN. In some embodiments, the present teachings include methods of reducing age-associated decrease in a NSPC population in a subject through administration of NMN. In some embodiments, the present teachings include methods of maintaining at least one NSPC in a subject through administration of NMN. In some embodiments, the present teachings include methods of enhancing NAD biosynthesis in a subject through administration of NMN. In some embodiments, the present teachings include methods of promoting NSPC proliferation in a subject, in which the methods comprise administration of NMN to the subject. The methods of each of these embodiments can comprise, consist essentially of, or consist of administration of a therapeutically effective amount of NMN.

In some embodiments, the present teachings include methods of increasing bone density levels in a subject. In some embodiments, the present teachings include methods of treating aberrantly low bone density levels in a subject. In some embodiments, the present teachings include methods of treating an age-associated bone density decrease in a subject. In some embodiments, the present teachings include methods of treating osteoporosis in a subject. In some embodiments, the present teachings include methods of preventing an age-associated bone density decrease in a subject. The methods of each of these embodiments can comprise, consist essentially of, or consist of administration of a therapeutically effective amount of NMN.

In various embodiments, the inventors disclose that photoreceptor neuronal cell death and vision can be rescued by NMN administration. In various embodiments, the present inventors demonstrate that nicotinamide phosphoribosyl transferase (NAMPT)-mediated NAD biosynthesis can play a role in for rod and/or cone PR neuron survival. In various embodiments, the present inventors demonstrate that decreased NAD levels can cause impaired mitochondrial function in PR neurons, alterations in TCA cycle metabolites, and can lead to cell death and blindness.

In some embodiments, the inventors have demonstrated that deleting NAMPT can lead to photoreceptor death, loss of normal retinal structure and function, and vision loss. In some embodiments, the inventors have demonstrated that such damage to photoreceptor neurons and their function can be reversed with supplementation of nicotinamide mononucleotide (NMN), an NAMPT enzymatic reaction product. In some embodiments, the present teachings include NMN administration to restore NAD levels in the retina. In some embodiments, NMN supplementation can be an effective therapeutic intervention for many retinal degenerative diseases. Without being limited by theory, NMN supplementation can restore retinal NAD levels.

In some embodiments, the present inventors have demonstrated in vivo using mouse models and in vitro using cell lines that photoreceptor death can be prevented by NMN supplementation. In some embodiments, methods of NMN supplementation for the prevention/treatment of many retinal degenerative diseases are disclosed.

Accordingly, in various embodiments, the inventors disclose methods of preventing, methods of reducing risk of, and methods of treating various diseases associated with photoreceptor dysfunction, including, without limitation, age-related macular degeneration (AMD), inherited and acquired retinal diseases such as, without limitation, retinitis pigmentosa (RP), rod and cone dystrophism, and Leber's congenital amaurosis (LCA) by administration of NMN. In various embodiments, NMN administration can be an effective intervention for the prevention and/or treatment of orphan retinal degenerative diseases including but not limited to rod dystrophy, cone dystrophy, retinitis pigmentosa, other inherited retinal degenerations, Leber's congenital amaurosis (LCA) and acquired retinal degenerations such as, but not limited to, age-related macular degeneration photoreceptor degeneration following retinal detachment.

In various embodiments, NMN can be administered by any administration route known to skilled artisans, such as, without limitation, oral, parenteral, intraocular, intraperitoneal, intravenous or intramuscular routes. In various embodiments, NMN can be administered with or without an excipient.

In some embodiments, the present teachings include methods of treating macular degeneration in a subject. In some embodiments, the present teachings include methods of treating aberrant retinal NAD levels in a subject, including aberrantly low retinal NAD levels. In some embodiments, the present teachings include methods of treating retinal degeneration in a subject. In some embodiments, the present teachings include methods of treating photoreceptor damage in a subject. In some embodiments, the present teachings include methods of treating photoreceptor degeneration in a subject. In some embodiments, the present teachings include methods of treating vision loss associated with retinal degeneration in a subject. In some embodiments, the present teachings include methods of treating vision loss in a subject. In some embodiments, the present teachings include methods of treating aberrant retinal structure in a subject. In some embodiments, the present teachings include methods of treating aberrant retinal function in a subject. In some embodiments, the present teachings include methods of treating aberrant retinal function in a subject. In some embodiments, the present teachings include methods of treating aberrant retinal function in a subject. In some embodiments, the present teachings include methods of increasing retinal NAD levels in a subject. In some embodiments, the present teachings include methods of reducing risk of developing macular degeneration in a subject. In some embodiments, the present teachings include methods of reducing risk of developing macular degeneration in a subject. In some embodiments, the present teachings include methods of reducing risk of developing aberrant retinal NAD levels in a subject. In some embodiments, the present teachings include methods of reducing risk of developing retinal degeneration in a subject. In some embodiments, the present teachings include methods of reducing risk of developing photoreceptor damage/degeneration in a subject. In some embodiments, the present teachings include methods of reducing risk of developing vision loss associated with retinal degeneration in a subject. In some embodiments, the present teachings include methods of reducing risk of developing vision loss in a subject. In some embodiments, the present teachings include methods of reducing risk of developing aberrant retinal structure in a subject. In some embodiments, the present teachings include methods of reducing risk of developing aberrant retinal structure in a subject. In some embodiments, the present teachings include methods of reducing risk of developing aberrant retinal function in a subject. In some embodiments, the present teachings include methods of reducing risk of developing aberrant retinal function in a subject. In some embodiments, the present teachings include methods of treating a photoreceptor dysfunction in a subject. In some embodiments, the present teachings include methods of treating a retina disease in a subject. In various embodiments, these methods can comprise, consist essentially of, or consist of administering to a subject a pharmaceutically effective amount of nicotinamide mononucleotide (NMN). In some embodiments, a pharmaceutically effective amount of nicotinamide mononucleotide (NMN) can be an amount effective for increasing retinal NAD levels. In some embodiments a retina disease that can be treated by administration of NMN can be retinitis pigmentosa (RP), Leber's congenital amaurosis (LCA), rod dystrophy, cone dystrophy, rod-cone dystrophy, cone-rod dystrophy, age-related macular degeneration, photoreceptor degeneration following retinal detachments, or a combination thereof.

In various embodiments, these methods can each independently comprise, consist essentially of, or consist of administering to a subject a pharmaceutically effective amount of nicotinamide mononucleotide (NMN). In some embodiments, NMN can be administered at a dosage rate of about 100 mg per day, from 100 mg per day to 2000 mg per day, or about 2000 mg per day. In some embodiments, NMN can be administered at a dosage rate of 0.5 mg, about 0.5 mg, 1 mg, about 1 mg, 5 mg, about 5 mg, 10 mg, about 10 mg, 20 mg, about 20 mg, mg, about 30 mg, 40 mg, about 40 mg, 50 mg, about 50 mg, 60 mg, about 60 mg, 70 mg, about 70 mg, 80 mg, about 80 mg, 90 mg, about 90 mg, about 100 mg per day, 100 mg per day, 150 mg, about 150 mg, about 200 mg per day, 200 mg per day, about 300 mg per day, 300 mg per day, about 400 mg per day, 400 mg per day, about 500 mg per day, 500 mg per day, about 600 mg per day, 600 mg per day, about 700 mg per day, 700 mg per day, about 800 mg per day, 800 mg per day, about 900 mg per day, 900 mg per day, about 1000 mg per day, 1000 mg per day, about 1100 mg per day, 1100 mg per day, about 1200 mg per day, 1200 mg per day, about 1300 mg per day, 1300 mg per day, 1350 mg, about 1350 mg, about 1400 mg per day, 1400 mg per day, about 1500 mg per day, 1500 mg per day, about 1600 mg per day, 1600 mg per day, about 1700 mg per day, 1700 mg per day, about 1800 mg per day, 1800 mg per day, about 1900 mg per day, 1900 mg per day, about 2000 mg per day, 2000 mg per day, 2040 mg, about 2040 mg, 2250 mg, about 2250 mg, 2260 mg, about 2260 mg, 2700 mg, about 2700 mg, 2720 mg, about 2720 mg, 3400 mg, about 3400 mg, 3390 mg, about 3390 mg, 3400 mg, about 3400 mg, 3600 mg, about 3600 mg, 4080 mg, about 4080 mg, 4500 mg, about 4500 mg, 4520 mg, about 4520 mg, 5440 mg, about 5440 mg, 5650 mg, about 5650 mg, 6800 mg, about 6800 mg, or an alternation or combination thereof. In some embodiments, NMN can be administered at a dosage rate of about 100 mg/kg body weight/day, from 100 mg/kg body weight/day to 500 mg/kg body weight/day, or about 500 mg/kg body weight/day. In some embodiments, NMN can be administered at a dosage rate of about 100 mg/kg body weight/day, from 100 mg/kg body weight/day to 300 mg/kg body weight/day, or about 300 mg/kg body weight/day. In some embodiments, these methods can comprise administering to a subject any of the pharmaceutically acceptable compositions of the present teachings. In some embodiments, these methods can comprise, consist essentially of or consist of administering a formulation once per day. In some embodiments, these methods can comprise, consist essentially of or consist of administering a formulation twice per day, three times per day, or four times per day. In some embodiments, these methods can comprise, consist essentially of or consist of administering a sustained-release formulation once, or at long intervals such as, without limitation, once per week, semi-weekly, or once per month.

In various embodiments, these methods can each independently comprise, consist essentially of, or consist of administering to a subject a pharmaceutically effective amount of a formulation comprising nicotinamide mononucleotide (NMN) such as, without limitation, a pill, a tablet, a caplet, a capsule, a chewable tablet, a quick dissolve tablet, a powder, an effervescent tablet, a hard gelatin capsule, a soft gelatin capsule, a non-aqueous liquid, an aqueous liquid, a granule, a capsule, a suspension, a solution, an emulsion, a syrup, a sterilized aqueous suspension or solution, a non-aqueous suspension or solution, a lyophilized formulation, a suppository or a food product. In various embodiments, these methods can each independently comprise, consist essentially of, or consist of administering to a subject a pharmaceutically effective amount of nicotinamide mononucleotide by oral administration, sublingual administration, parenteral administration, administration by injection, subcutaneous injection, intramuscular injection, intraperitoneal injection, intra-ocular injection, direct ocular contact (eye drops) or a combination thereof.

In various embodiments, a subject can be a mammal. In various embodiments, a subject can be a vertebrate, such as a mammal, a fish, a bird or a reptile. A mammal can be, without limitation, a human, a rodent, a canine, a feline, a bovine, an ovine, an equine or a porcine. In some embodiments, a subject can be a bird such as a chicken, a reptile, a fish, or other aquatic organism.

In some embodiments, the present teachings include methods of augmentation of NAD+ levels during aging with NMN administration to maintain an NSPC pool, through administration of NMN. In some embodiments, the present teachings include methods of enhancing NAD+ levels in NSPCs in a subject through administration of NMN, to preserve an endogenous NSPC population for the repair of aged, diseased, or damaged brain.

The present teachings include the following non-limiting aspects.

1. A pharmaceutically acceptable composition comprising, consisting essentially of, or consisting of: nicotinamide mononucleotide (NMN), a salt thereof and/or a prodrug thereof; and at least one pharmaceutically acceptable excipient.

2. A pharmaceutically acceptable composition in accordance with aspect 1, comprising, consisting essentially of, or consisting of a single dosage formulation.

3. A pharmaceutically acceptable composition in accordance with aspect 2, wherein the single dosage formulation is selected from the group consisting of a pill, a tablet, a caplet, a capsule, a chewable tablet, a quick dissolve tablet, a powder, an effervescent tablet, a hard gelatin capsule, a soft gelatin capsule, a non-aqueous liquid, an aqueous liquid and an emulsion.

4. A pharmaceutically acceptable composition in accordance with aspect 2, wherein the single dosage formulation comprises an enteric coating.

5. A pharmaceutically acceptable composition in accordance with aspect 2, wherein the single dosage formulation comprises, consists essentially of, or consists of NMN, a salt thereof and/or a prodrug thereof in an amount of about 100 mg, from 100 mg to 2000 mg, or about 2000 mg.

6. A pharmaceutically acceptable composition in accordance with aspect 2, wherein the single dosage formulation comprises, consists essentially of, or consists of NMN, a salt thereof and/or a prodrug thereof in an amount selected from the group consisting of about 100 mg, about 200 mg, about 300 mg, about 400 mg, about 500 mg, about 600 mg, about 700 mg, about 800 mg, about 900 mg, about 1000 mg, about 1100 mg, about 1200 mg, about 1300 mg, about 1400 mg, about 1500 mg, about 1600 mg, about 1700 mg, about 1800 mg, about 1900 mg and about 2000 mg.

7. A pharmaceutically acceptable composition in accordance with aspect 2, wherein the single dosage formulation comprises, consists essentially of, or consists of NMN, a salt thereof and/or the prodrug thereof in an amount selected from the group consisting of 50-150 mg, 151-250 mg, 251-350 mg, 351-450 mg, 451-550 mg, 561-650 mg, 651-750 mg, 751-860 mg, 861-950 mg, 951-1050 mg, 1051-1150 mg, 1151-1250 mg, 1251-1350 mg, 1351-1450 mg, 1451-1550 mg, 1551-1650 mg, 1651-1750 mg, 1751-1850 mg, 1851-1950 mg and 1951-2000 mg.

8. A pharmaceutically acceptable composition in accordance with aspect 2, wherein the single dosage formulation comprises nicotinamide mononucleotide (NIVIN), a salt thereof and/or a prodrug thereof in an amount selected from the group consisting of 0.5 mg, about 0.5 mg, 1 mg, about 1 mg, 5 mg, about 5 mg, 10 mg, about 10 mg, 20 mg, about 20 mg, 30 mg, about 30 mg, 40 mg, about 40 mg, 50 mg, about 50 mg, 60 mg, about 60 mg, 70 mg, about 70 mg, 80 mg, about 80 mg, 90 mg, about 90 mg, 100 mg, about 100 mg, 150 mg, about 150 mg, 200 mg, about 200 mg, 300 mg, about 300 mg, 400 mg, about 400 mg, 450 mg, about 450 mg, 500 mg, about 500 mg, 600 mg, about 600 mg, 680 mg, about 680 mg, 700 mg, about 700 mg, 800 mg, about 800 mg, 900 mg, about 900 mg, 1000 mg, about 1000 mg, 1100 mg, about 1100 mg, 1130 mg, about 1130 mg, 1200 mg, about 1200 mg, 1300 mg, about 1300 mg, 1350 mg, about 1350 mg, 1360 mg, about 1360 mg, 1400 mg, about 1400 mg, 1500 mg, about 1500 mg, 1600 mg, about 1600 mg, 1700 mg, about 1700 mg, 1800 mg, about 1800 mg, 2040 mg, about 2040 mg, 2250 mg, about 2250 mg, 2260 mg, about 2260 mg, 2700 mg, about 2700 mg, 2720 mg, about 2720 mg, 3400 mg, about 3400 mg, 3390 mg, about 3390 mg, 3400 mg, about 3400 mg, 3600 mg, about 3600 mg, 4080 mg, about 4080 mg, 4500 mg, about 4500 mg, 4520 mg, about 4520 mg, 5440 mg, about 5440 mg, 5650 mg, about 5650 mg, 6800 mg, and about 6800 mg.

9. A pharmaceutically acceptable composition in accordance with aspect 2, wherein the single dosage formulation comprises a liquid solution, an emulsion or a suspension.

10. A pharmaceutically acceptable composition in accordance with aspect 2, wherein the single dosage formulation is a liquid solution, an emulsion or a suspension.

11. A pharmaceutically acceptable composition in accordance with aspect 2, wherein the single dosage formulation comprises a food product.

12. A pharmaceutically acceptable composition in accordance with aspect 2, wherein the single dosage formulation is a food product.

13. A pharmaceutically acceptable composition in accordance with aspect 1, wherein the composition is suitable for oral administration.

14. A pharmaceutically acceptable composition in accordance with aspect 1, wherein the composition is suitable for sublingual administration.

15. A pharmaceutically acceptable composition in accordance with aspect 1, wherein the composition is suitable for parenteral administration.

16. A pharmaceutically acceptable composition in accordance with aspect 1, wherein the composition is suitable for administration by injection.

17. A pharmaceutically acceptable composition in accordance with aspect 1, wherein the composition is suitable for administration by subcutaneous injection.

18. A pharmaceutically acceptable composition in accordance with aspect 1, wherein the composition is suitable for administration by intramuscular injection.

19. A pharmaceutically acceptable composition in accordance with aspect 1, wherein the composition is suitable for administration by intraperitoneal injection.

20. pharmaceutically acceptable composition in accordance with aspect 1, wherein the composition is suitable for administration by intra-ocular injection or topically to the eye (eye drops).

21. A pharmaceutically acceptable composition in accordance with aspect 1, wherein the composition is selected from the group consisting of a tablet, a pill, powder, granules, a capsule, a suspension, a solution, an emulsion, a syrup, a sterilized aqueous suspension or solution, a non-aqueous suspension or solution, a lyophilized formulation, and a suppository.

22. A pharmaceutically acceptable composition in accordance with aspect 1, wherein the at least one excipient is selected from the group consisting of a bulking agent, a tableting agent, a dissolution agent, a wetting agent, a lubricant, a coloring, a flavoring, a disintegrant, a coating, a binder, an antioxidant, a taste masking agent and a sweetener.

23. A pharmaceutically acceptable composition in accordance with aspect 22, wherein the bulking agent is selected from the group consisting of mannitol, sorbitol, sucrose and trehalose.

24. A pharmaceutically acceptable composition in accordance with aspect 1, wherein the composition is formulated as an orally disintegrating capsule, tablet, pill or wafer.

25. A pharmaceutically acceptable composition in accordance with aspect 1, wherein the composition is formulated as a liquid, syrup, or spray.

26. A pharmaceutically acceptable composition in accordance with aspect 1, further comprising at least one vitamin or nutrient selected from the group consisting of vitamin C, vitamin D3, vitamin E, vitamin B1, vitamin B2, niacin, vitamin B6, folic acid, vitamin B12, pantothenic acid, biotin, magnesium, zinc, copper, selenium, chromium, alpha lipoic acid, b co-enzyme Q-10, lutein and lycopene.

27. A pharmaceutically acceptable composition in accordance with aspect 1, further comprising at least one vitamin or nutrient selected from the group consisting of from about 150 mg to about 750 mg of vitamin C, from about 315 IUs to about 1800 IUs of vitamin D3, from about 75 IUs to about 150 IUs of vitamin E, from about 15 mg to about 35 mg of vitamin B1, from about 1.7 mg to about 5.1 mg of vitamin B2, from about 20 mg to about 50 mg of niacin, from about 20 mg to about 50 mg of vitamin B6, from about 0.5 mg to about 2.5 mg of folic acid, from about 35 mcg to about 105 mcg of vitamin B12, from about 2.5 mg to about 7.5 mg of pantothenic acid, from about 50 mcg to about 450 mcg of biotin, from about 15 mg to about 55 mg of magnesium, from about 15 mg to about 55 mg of zinc, from about 0.5 to about 1.5 mg of copper, from about 75 mcg to about 175 mcg of selenium, from about 75 mcg to about 225 mcg of chromium, from about 10 mg to about 40 mg of alpha lipoic acid, from about 20 mg to about 50 mg of co-enzyme Q-10, from about 350 mcg to about 3 mg of lutein and from about 100 mcg to about 750 mcg of lycopene.

28. A pharmaceutically acceptable composition in accordance with aspect 1, further comprising at least one vitamin or nutrient selected from the group consisting of about 500 mg of ascorbic acid; about 400 IUs of cholecalciferol; about 125 IUs of d-alpha tocopherol succinate; about 35 mg of thiamine mononitrate; about 5.1 mg of riboflavin; about 50 mg of niacinamide; about 50 mg of pyridoxine HCl; about 2.5 mg of folic acid; about 105 mcg of cyanocobalamin; about 7.5 mg of d-calcium pantothenate; about 75 mcg of d-biotin; about 55 mg of dimagnesium malate; about 55 mg of zinc bisglycinate chelate; about 1.5 mg of copper amino acid chelate; about 175 mcg of selenium amino acid chelate; about 225 mcg of chromium amino acid chelate; about 10 mg of alpha lipoic acid; about 50 mg of co-enzyme Q-10; about 400 mcg of lutein; about 125 mcg of lycopene.

29. A pharmaceutically acceptable composition in accordance with aspect 1, wherein the at least one excipient is selected from the group consisting of dicalcium phosphate, microcrystalline cellulose, stearic acid, croscarmellose sodium, magnesium trisilicate, magnesium stearate, hydroxypropyl methylcellulose, hypromellose, titanium dioxide, tripotassium citrate, polyvinyl alcohol, fumed silica, citric acid, polyethylene glycol, talc, and any combination thereof.

30. A pharmaceutically acceptable composition in accordance with aspect 1, wherein the at least one excipient is selected from the group consisting of from about 100 mg to about 300 mg of dicalcium phosphate; from about 25 mg to about 75 mg of microcrystalline cellulose; from about 10 mg to about 30 mg of stearic acid; from about 10 mg to about 30 mg of croscarmellose sodium; from about 5 mg to about 15 mg of magnesium trisilicate; from about 5 mg to about 15 mg of magnesium stearate; and from about 5 mg to about 15 mg of hydroxypropyl methylcellulose.

31. A pharmaceutically acceptable composition in accordance with aspect 1, wherein the at least one excipient is selected from the group consisting of about 200 mg of dicalcium phosphate; about 50 mg of microcrystalline cellulose; about 20 mg of stearic acid; about 20 mg of croscarmellose sodium; about 10 mg of magnesium trisilicate;

about 10 mg of magnesium stearate; and about 10 mg of hydroxypropyl methylcellulose.

32. A sustained release formulation of nicotinamide mononucleotide for oral administration to a subject, comprising nicotinamide mononucleotide as an active ingredient that is released from the formulation along a pre-determined release profile, wherein the formulation comprises an extended release component and an immediate release component, wherein the extended release component is contained in at least one population of beads and releases nicotinamide mononucleotide in a continuous manner and each bead population is coated with its own release controlling coating and characterized by its own rate of release.

33. The formulation of aspect 32, wherein the extended release component releases the nicotinamide mononucleotide in vivo in a continuous manner, and 80% of the nicotinamide mononucleotide is released in vitro in a period of time selected from not more than 24 hours, not more than 16 hours, not more than 12 hours, not more than 8 hours and not more than 4 hours.

34. The formulation of aspect 32, wherein the immediate release component is an enhanced immediate release (EIR) composition comprising a complexing agent, an enhancing agent, or both.

35. The formulation of aspect 34, wherein the EIR composition exhibits an in vitro release profile such that 80% of the active ingredient is dissolved in not more than 30 min.

36. The formulation of aspect 35, wherein the EIR composition exhibits an in vitro release profile selected from a group consisting of: a) a dissolution of at least 50% of the active compound in not more than 10 minutes; b) a dissolution of at least 70% of the active compound in not more than 10 minutes; c) a dissolution of at least 25% of the active compound in not more than 5 minutes; d) a dissolution of at least 40% of the active compound in not more than 5 minutes; and e) a dissolution of at least 55% of the active compound in not more than 5 minutes.

37. The formulation of aspect 34, wherein the complexing agent is a cyclodextrin selected from a group consisting of hydroxypropyl-beta-cyclodextrin, beta-cyclodextrin, gamma-cyclodextrin, alpha-cyclodextrin, and derivatives thereof.

38. The formulation of aspect 34, wherein the enhancing agent is selected from a group comprising solubility enhancing agents, dissolution enhancing agents, absorption enhancing agents, penetration enhancing agents, surface active agents, stabilizers, enzyme inhibitors, p-glycoprotein inhibitors, multidrug resistance protein inhibitors and combinations thereof.

39. The formulation of aspect 38, wherein the enhancing agent is selected from a group consisting of Vitamin E TPGS, glutamic acid, glycine, sorbitol, mannose, amylose, maltose, mannitol, lactose, sucrose, glucose, xylitose, dextrins, glycerolpolyethylene glycol oxystearate, PEG-32 glyceryl palmitostearate, sodium lauryl sulfate, polyoxyethylene sorbitan monooleate, benzyl alcohol, sorbitan monolaurate, Poloxamer 407, PEG3350, PVP K25, oleic acid, glyceryl monooleate, sodium benzoate, cetyl alcohol, sucrose stearate, crospovidone, sodium starch glycolate, croscarmellose sodium, carboxymethylcellulose, starch, pregelatinized starch, HPMC, substituted hydroxypropylcellulose, microcrystalline cellulose sodium bicarbonate, calcium citrate, sodium docusate, menthol and any combination thereof.

40. The formulation of aspect 32, wherein at least a part of the active ingredient is in a form of micronized particles.

41. The formulation of aspect 40, wherein the particles have an average size of from about 2 µm to about 100 µm.

42. The formulation of aspect 32, wherein a specific amount of each component is determined according to the purpose of administration and the pre-determined release profile, and the total amount of NMN in the formulation is from 0.5 to 3000 mg.

43. The formulation of aspect 32, wherein the beads comprise an inert carrier, NMN, an optional enhancer, and a release controlling coating that comprises a coating material and optionally a pore former and other excipients.

44. The formulation of aspect 43, wherein the inert carrier is selected from a group consisting of cellulose spheres, silicon dioxide, starch and sugar spheres.

45. The formulation of aspect 43, wherein the enhancer is selected from a group consisting of solubility enhancers, dissolution enhancers, permeability enhancers, stabilizers, complexing agents, enzyme inhibitors, p-glycoprotein inhibitors, multidrug resistance protein inhibitors and combinations thereof.

46. The formulation of aspect 43, wherein the coating material is selected from a group consisting of ethylcellulose, methylcellulose, hydroxypropyl cellulose, hydroxypropylmethyl cellulose, cellulose acetate, cellulose acetate phthalate, polyvinyl alcohol, polyacrylates, polymethacrylates and copolymers thereof; and/or the pore former is selected from a group consisting of glucose, fructose, mannitol, mannose, galactose, sorbitol, pullulan, dextran, water-soluble hydrophilic polymers, hydroxyalkylcelluloses, carboxyalkylcelluloses, hydroxypropylmethylcellulose, cellulose ethers, acrylic resins, polyvinylpyrrolidone, cross-linked polyvinylpyrrolidone, polyethylene oxide, Carbowaxes, Carbopol, diols, polyols, polyhydric alcohols, polyalkylene glycols, polyethylene glycols, polypropylene glycols or block polymers thereof, polyglycols, poly(a-w) alkylenediols; inorganic compounds selected from a group consisting of alkali metal salts and alkaline earth metal salts, and combinations thereof.

47. The formulation of aspect 32, wherein an amount of each bead population is determined according to a pre-determined release profile.

48. The formulation of aspect 32, wherein the pre-determined release profile comprises a sustained rate of release after an initial immediate release.

49. The formulation of aspect 32, suitable for once a day oral administration.

50. The formulation of aspect 32, wherein at least one population of beads consists of extended release NMN beads additionally comprising an immediate release component coated on top of the release controlling coating.

51. The formulation of aspect 43, wherein the enhancer is contained in a layer separate from the release controlling coating.

52. The formulation of aspect 32, additionally comprising at least one enhancing agent, wherein the enhancing agent is incorporated into the formulation in the form of a powder or of a population of beads that are optionally characterized by a controlled rate of release, and wherein the enhancing agent is separated from the active ingredient.

53. A method of treating, ameliorating, mitigating, slowing, arresting, preventing or reversing age-associated obesity in a subject, comprising: administering to a subject a pharmaceutically effective amount of nicotinamide mononucleotide (NMN).

54. A method in accordance with aspect 53, wherein the NMN is administered at a dosage rate of about 100 mg per day, from 100 mg per day to 2000 mg per day, or about 2000 mg per day.

55. A method in accordance with aspect 53, wherein the NMN is administered at a dosage rate of about 100 mg per day, or 100 mg per day.

56. A method in accordance with aspect 53, wherein the NMN is administered at a dosage rate of about 200 mg per day, or 200 mg per day.

57. A method in accordance with aspect 53, wherein the NMN is administered at a dosage rate of about 300 mg per day, or 300 mg per day.

58. A method in accordance with aspect 53, wherein the NMN is administered at a dosage rate of about 400 mg per day, or 400 mg per day.

59. A method in accordance with aspect 53, wherein the NMN is administered at a dosage rate of about 500 mg per day, or 500 mg per day.

60. A method in accordance with aspect 53, wherein the NMN is administered at a dosage rate of about 600 mg per day, or 600 mg per day.

61. A method in accordance with aspect 53, wherein the NMN is administered at a dosage rate of about 700 mg per day, or 700 mg per day.

62. A method in accordance with aspect 53, wherein the NMN is administered at a dosage rate of about 800 mg per day, or 800 mg per day.

63. A method in accordance with aspect 53, wherein the NMN is administered at a dosage rate of about 900 mg per day, or 900 mg per day.

64. A method in accordance with aspect 53, wherein the NMN is administered at a dosage rate of about 1,000 mg per day, or 1,000 mg per day.

65. A method in accordance with aspect 53, wherein the NMN is administered at a dosage rate of about 1,100 mg per day, or 1,100 mg per day.

66. A method in accordance with aspect 53, wherein the NMN is administered at a dosage rate of about 1,200 mg per day, or 1,200 mg per day.

67. A method in accordance with aspect 53, wherein the NMN is administered at a dosage rate of about 1,300 mg per day, or 1,300 mg per day.

68. A method in accordance with aspect 53, wherein the NMN is administered at a dosage rate of about 1,400 mg per day, or 1,400 mg per day.

69. A method in accordance with aspect 53, wherein the NMN is administered at a dosage rate of about 1,500 mg per day, or 1,500 mg per day.

70. A method in accordance with aspect 53, wherein the NMN is administered at a dosage rate of about 1,600 mg per day, or 1,600 mg per day.

71. A method in accordance with aspect 53, wherein the NMN is administered at a dosage rate of about 1,700 mg per day, or 1,700 mg per day.

72. A method in accordance with aspect 53, wherein the NMN is administered at a dosage rate of about 1,800 mg per day, or 1,800 mg per day.

73. A method in accordance with aspect 53, wherein the NMN is administered at a dosage rate of about 1,900 mg per day, or 1,900 mg per day.

74. A method in accordance with aspect 53, wherein the NMN is administered at a dosage rate of about 2,000 mg per day, or 2,000 mg per day.

75. A method in accordance with aspect 53, wherein the NMN is administered at a dosage rate of about 100 mg/kg body weight/day, from 100 mg/kg body weight/day to 300 mg/kg body weight/day, or about 300 mg/kg body weight/day.

76. A method in accordance with aspect 53, comprising administering to a subject a formulation of any one of aspects 1-52.

77. A method in accordance with aspect 76, wherein the administering a formulation comprises, consists essentially of or consists of administering the formulation once per day.

78. A method in accordance with aspect 76, wherein the administering a formulation comprises, consists essentially of or consists of administering the formulation twice per day.

79. A method of treating, ameliorating, mitigating, slowing, arresting, preventing or reversing age-associated increases in blood lipid levels in a subject, comprising: administering to a subject a pharmaceutically effective amount of nicotinamide mononucleotide (NMN).

80. A method in accordance with aspect 79, wherein the NMN is administered at a dosage rate of about 100 mg per day, from 100 mg per day to 2000 mg per day, or about 2000 mg per day.

81. A method in accordance with aspect 79, wherein the NMN is administered at a dosage rate of about 100 mg per day, or 100 mg per day.

82. A method in accordance with aspect 79, wherein the NMN is administered at a dosage rate of about 200 mg per day, or 200 mg per day.

83. A method in accordance with aspect 79, wherein the NMN is administered at a dosage rate of about 300 mg per day, or 300 mg per day.

84. A method in accordance with aspect 79, wherein the NMN is administered at a dosage rate of about 400 mg per day, or 400 mg per day.

85. A method in accordance with aspect 79, wherein the NMN is administered at a dosage rate of about 500 mg per day, or 500 mg per day.

86. A method in accordance with aspect 79, wherein the NMN is administered at a dosage rate of about 600 mg per day, or 600 mg per day.

87. A method in accordance with aspect 79, wherein the NMN is administered at a dosage rate of about 700 mg per day, or 700 mg per day.

88. A method in accordance with aspect 79, wherein the NMN is administered at a dosage rate of about 800 mg per day, or 800 mg per day.

89. A method in accordance with aspect 79, wherein the NMN is administered at a dosage rate of about 900 mg per day, or 900 mg per day.

90. A method in accordance with aspect 79, wherein the NMN is administered at a dosage rate of about 1,000 mg per day, or 1,000 mg per day.

91. A method in accordance with aspect 79, wherein the NMN is administered at a dosage rate of about 1,100 mg per day, or 1,100 mg per day.

92. A method in accordance with aspect 79, wherein the NMN is administered at a dosage rate of about 1,200 mg per day, or 1,200 mg per day.

93. A method in accordance with aspect 79, wherein the NMN is administered at a dosage rate of about 1,300 mg per day, or 1,300 mg per day.

94. A method in accordance with aspect 79, wherein the NMN is administered at a dosage rate of about 1,400 mg per day, or 1,400 mg per day.

95. A method in accordance with aspect 79, wherein the NMN is administered at a dosage rate of about 1,500 mg per day, or 1,500 mg per day.

96. A method in accordance with aspect 79, wherein the NMN is administered at a dosage rate of about 1,600 mg per day, or 1,600 mg per day.

97. A method in accordance with aspect 79, wherein the NMN is administered at a dosage rate of about 1,700 mg per day, or 1,700 mg per day.

98. A method in accordance with aspect 79, wherein the NMN is administered at a dosage rate of about 1,800 mg per day, or 1,800 mg per day.

99. A method in accordance with aspect 79, wherein the NMN is administered at a dosage rate of about 1,900 mg per day, or 1,900 mg per day.

100. A method in accordance with aspect 79, wherein the NMN is administered at a dosage rate of about 2,000 mg per day, or 2,000 mg per day.

101. A method in accordance with aspect 79, wherein the NMN is administered at a dosage rate of about 100 mg/kg body weight/day, from 100 mg/kg body weight/day to 300 mg/kg body weight/day, or about 300 mg/kg body weight/day.

102. A method in accordance with aspect 79, comprising administering to a subject a formulation of any one of aspects 1-51.

103. A method in accordance with aspect 102, wherein the administering a formulation comprises, consists essentially of or consists of administering the formulation once per day.

104. A method in accordance with aspect 102, wherein the administering a formulation comprises, consists essentially of or consists of administering the formulation twice per day.

105. A method of treating, ameliorating, mitigating, slowing, arresting, preventing or reversing age-associated loss of insulin sensitivity in a subject, comprising: administering to a subject a pharmaceutically effective amount of nicotinamide mononucleotide (NMN).

106. A method in accordance with aspect 105, wherein the NMN is administered at a dosage rate of about 100 mg per day, from 100 mg per day to 2000 mg per day, or about 2000 mg per day.

107. A method in accordance with aspect 105, wherein the NMN is administered at a dosage rate of about 100 mg per day, or 100 mg per day.

108. A method in accordance with aspect 105, wherein the NMN is administered at a dosage rate of about 200 mg per day, or 200 mg per day.

109. A method in accordance with aspect 105, wherein the NMN is administered at a dosage rate of about 300 mg per day, or 300 mg per day.

110. A method in accordance with aspect 105, wherein the NMN is administered at a dosage rate of about 400 mg per day, or 400 mg per day.

111. A method in accordance with aspect 105, wherein the NMN is administered at a dosage rate of about 500 mg per day, or 500 mg per day.

112. A method in accordance with aspect 105, wherein the NMN is administered at a dosage rate of about 600 mg per day, or 600 mg per day.

113. A method in accordance with aspect 105, wherein the NMN is administered at a dosage rate of about 700 mg per day, or 700 mg per day.

114. A method in accordance with aspect 105, wherein the NMN is administered at a dosage rate of about 800 mg per day, or 800 mg per day.

115. A method in accordance with aspect 105, wherein the NMN is administered at a dosage rate of about 900 mg per day, or 900 mg per day.

116. A method in accordance with aspect 105, wherein the NMN is administered at a dosage rate of about 1,000 mg per day, or 1,000 mg per day.

117. A method in accordance with aspect 105, wherein the NMN is administered at a dosage rate of about 1,100 mg per day, or 1,100 mg per day.

118. A method in accordance with aspect 105, wherein the NMN is administered at a dosage rate of about 1,200 mg per day, or 1,200 mg per day.

119. A method in accordance with aspect 105, wherein the NMN is administered at a dosage rate of about 1,300 mg per day, or 1,300 mg per day.

120. A method in accordance with aspect 105, wherein the NMN is administered at a dosage rate of about 1,400 mg per day, or 1,400 mg per day.

121. A method in accordance with aspect 105, wherein the NMN is administered at a dosage rate of about 1,500 mg per day, or 1,500 mg per day.

122. A method in accordance with aspect 105, wherein the NMN is administered at a dosage rate of about 1,600 mg per day, or 1,600 mg per day.

123. A method in accordance with aspect 105, wherein the NMN is administered at a dosage rate of about 1,700 mg per day, or 1,700 mg per day.

124. A method in accordance with aspect 105, wherein the NMN is administered at a dosage rate of about 1,800 mg per day, or 1,800 mg per day.

125. A method in accordance with aspect 105, wherein the NMN is administered at a dosage rate of about 1,900 mg per day, or 1,900 mg per day.

125. A method in accordance with aspect 105, wherein the NMN is administered at a dosage rate of about 2,000 mg per day, or 2,000 mg per day.

127. A method in accordance with aspect 105, wherein the NMN is administered at a dosage rate of about 100 mg/kg body weight/day, from 100 mg/kg body weight/day to 300 mg/kg body weight/day, or about 300 mg/kg body weight/day.

128. A method in accordance with aspect 105, comprising administering to a subject a formulation of any one of aspects 1-51.

129. A method in accordance with aspect 128, wherein the administering a formulation comprises, consists essentially of or consists of administering the formulation once per day.

130. A method in accordance with aspect 128, wherein the administering a formulation comprises, consists essentially of or consists of administering the formulation twice per day.

131. A method of treating, ameliorating, mitigating, slowing, arresting, preventing or reversing age-associated impairment of memory function in a subject, comprising: administering to a subject a pharmaceutically effective amount of nicotinamide mononucleotide (NMN).

131. A method in accordance with aspect 130, wherein the NMN is administered at a dosage rate of about 100 mg per day, from 100 mg per day to 2000 mg per day, or about 2000 mg per day.

133. A method in accordance with aspect 131, wherein the NMN is administered at a dosage rate of about 100 mg per day, or 100 mg per day.

134. A method in accordance with aspect 131, wherein the NMN is administered at a dosage rate of about 200 mg per day, or 200 mg per day.

135. A method in accordance with aspect 131, wherein the NMN is administered at a dosage rate of about 300 mg per day, or 300 mg per day.

136. A method in accordance with aspect 131, wherein the NMN is administered at a dosage rate of about 400 mg per day, or 400 mg per day.

137. A method in accordance with aspect 131, wherein the NMN is administered at a dosage rate of about 500 mg per day, or 500 mg per day.

138. A method in accordance with aspect 131, wherein the NMN is administered at a dosage rate of about 600 mg per day, or 600 mg per day.

139. A method in accordance with aspect 131, wherein the NMN is administered at a dosage rate of about 700 mg per day, or 700 mg per day.

140. A method in accordance with aspect 131, wherein the NMN is administered at a dosage rate of about 800 mg per day, or 800 mg per day.

141. A method in accordance with aspect 131, wherein the NMN is administered at a dosage rate of about 900 mg per day, or 900 mg per day.

142. A method in accordance with aspect 131, wherein the NMN is administered at a dosage rate of about 1,000 mg per day, or 1,000 mg per day.

143. A method in accordance with aspect 131, wherein the NMN is administered at a dosage rate of about 1,100 mg per day, or 1,100 mg per day.

144. A method in accordance with aspect 131, wherein the NMN is administered at a dosage rate of about 1,200 mg per day, or 1,200 mg per day.

145. A method in accordance with aspect 131, wherein the NMN is administered at a dosage rate of about 1,300 mg per day, or 1,300 mg per day.

146. A method in accordance with aspect 131, wherein the NMN is administered at a dosage rate of about 1,400 mg per day, or 1,400 mg per day.

147. A method in accordance with aspect 131, wherein the NMN is administered at a dosage rate of about 1,500 mg per day, or 1,500 mg per day.

148. A method in accordance with aspect 131, wherein the NMN is administered at a dosage rate of about 1,600 mg per day, or 1,600 mg per day.

149. A method in accordance with aspect 131, wherein the NMN is administered at a dosage rate of about 1,700 mg per day, or 1,700 mg per day.

150. A method in accordance with aspect 131, wherein the NMN is administered at a dosage rate of about 1,800 mg per day, or 1,800 mg per day.

151. A method in accordance with aspect 131, wherein the NMN is administered at a dosage rate of about 1,900 mg per day, or 1,900 mg per day.

152. A method in accordance with aspect 131, wherein the NMN is administered at a dosage rate of about 2,000 mg per day, or 2,000 mg per day.

153. A method in accordance with aspect 131, wherein the NMN is administered at a dosage rate of about 100 mg/kg body weight/day, from 100 mg/kg body weight/day to 300 mg/kg body weight/day, or about 300 mg/kg body weight/day.

154. A method in accordance with aspect 131, comprising administering to a subject a formulation of any one of aspects 1-51.

155. A method in accordance with aspect 154, wherein the administering a formulation comprises, consists essentially of or consists of administering the formulation once per day.

156. A method in accordance with aspect 154, wherein the administering a formulation comprises, consists essentially of or consists of administering the formulation twice per day.

157. A method of treating, ameliorating, mitigating, slowing, arresting, preventing or reversing age-associated decline in eye function in a subject, comprising: administering to a subject a pharmaceutically effective amount of nicotinamide mononucleotide (NMN).

158. A method in accordance with aspect 157, wherein the NMN is administered at a dosage rate of about 100 mg per day, from 100 mg per day to 2000 mg per day, or about 2000 mg per day.

159. A method in accordance with aspect 157, wherein the NMN is administered at a dosage rate of about 100 mg per day, or 100 mg per day.

160. A method in accordance with aspect 157, wherein the NMN is administered at a dosage rate of about 200 mg per day, or 200 mg per day.

161. A method in accordance with aspect 157, wherein the NMN is administered at a dosage rate of about 300 mg per day, or 300 mg per day.

162. A method in accordance with aspect 157, wherein the NMN is administered at a dosage rate of about 400 mg per day, or 400 mg per day.

163. A method in accordance with aspect 157, wherein the NMN is administered at a dosage rate of about 500 mg per day, or 500 mg per day.

164. A method in accordance with aspect 157, wherein the NMN is administered at a dosage rate of about 600 mg per day, or 600 mg per day.

165. A method in accordance with aspect 157, wherein the NMN is administered at a dosage rate of about 700 mg per day, or 700 mg per day.

166. A method in accordance with aspect 157, wherein the NMN is administered at a dosage rate of about 800 mg per day, or 800 mg per day.

167. A method in accordance with aspect 157, wherein the NMN is administered at a dosage rate of about 900 mg per day, or 900 mg per day.

168. A method in accordance with aspect 157, wherein the NMN is administered at a dosage rate of about 1,000 mg per day, or 1,000 mg per day.

169. A method in accordance with aspect 157, wherein the NMN is administered at a dosage rate of about 1,100 mg per day, or 1,100 mg per day.

170. A method in accordance with aspect 157, wherein the NMN is administered at a dosage rate of about 1,200 mg per day, or 1,200 mg per day.

171. A method in accordance with aspect 157, wherein the NMN is administered at a dosage rate of about 1,300 mg per day, or 1,300 mg per day.

172. A method in accordance with aspect 157, wherein the NMN is administered at a dosage rate of about 1,400 mg per day, or 1,400 mg per day.

173. A method in accordance with aspect 157, wherein the NMN is administered at a dosage rate of about 1,500 mg per day, or 1,500 mg per day.

174. A method in accordance with aspect 157, wherein the NMN is administered at a dosage rate of about 1,600 mg per day, or 1,600 mg per day.

175. A method in accordance with aspect 157, wherein the NMN is administered at a dosage rate of about 1,700 mg per day, or 1,700 mg per day.

176. A method in accordance with aspect 157, wherein the NMN is administered at a dosage rate of about 1,800 mg per day, or 1,800 mg per day.

177. A method in accordance with aspect 157, wherein the NMN is administered at a dosage rate of about 1,900 mg per day, or 1,900 mg per day.

178. A method in accordance with aspect 157, wherein the NMN is administered at a dosage rate of about 2,000 mg per day, or 2,000 mg per day.

179. A method in accordance with aspect 157, wherein the NMN is administered at a dosage rate of about 100 mg/kg body weight/day, from 100 mg/kg body weight/day to 300 mg/kg body weight/day, or about 300 mg/kg body weight/day.

180. A method in accordance with aspect 157, comprising administering to a subject a formulation of any one of aspects 1-51.

181. A method in accordance with aspect 180, wherein the administering a formulation comprises, consists essentially of or consists of administering the formulation once per day.

182. A method in accordance with aspect 180, wherein the administering a formulation comprises, consists essentially of or consists of administering the formulation twice per day.

183. A method of treating, ameliorating, mitigating, slowing, arresting, preventing or reversing age-associated retinal degeneration in a subject, comprising: administering to a subject a pharmaceutically effective amount of nicotinamide mononucleotide (NMN).

184. A method in accordance with aspect 183, wherein the NMN is administered at a dosage rate of about 100 mg per day, from 100 mg per day to 2000 mg per day, or about 2000 mg per day.

185. A method in accordance with aspect 183, wherein the NMN is administered at a dosage rate of about 100 mg per day, or 100 mg per day.

186. A method in accordance with aspect 183, wherein the NMN is administered at a dosage rate of about 200 mg per day, or 200 mg per day.

187. A method in accordance with aspect 183, wherein the NMN is administered at a dosage rate of about 300 mg per day, or 300 mg per day.

188. A method in accordance with aspect 183, wherein the NMN is administered at a dosage rate of about 400 mg per day, or 400 mg per day.

189. A method in accordance with aspect 183, wherein the NMN is administered at a dosage rate of about 500 mg per day, or 500 mg per day.

190. A method in accordance with aspect 183, wherein the NMN is administered at a dosage rate of about 600 mg per day, or 600 mg per day.

191. A method in accordance with aspect 183, wherein the NMN is administered at a dosage rate of about 700 mg per day, or 700 mg per day.

192. A method in accordance with aspect 183, wherein the NMN is administered at a dosage rate of about 800 mg per day, or 800 mg per day.

193. A method in accordance with aspect 183, wherein the NMN is administered at a dosage rate of about 900 mg per day, or 900 mg per day.

194. A method in accordance with aspect 183, wherein the NMN is administered at a dosage rate of about 1,000 mg per day, or 1,000 mg per day.

195. A method in accordance with aspect 183, wherein the NMN is administered at a dosage rate of about 1,100 mg per day, or 1,100 mg per day.

196. A method in accordance with aspect 183, wherein the NMN is administered at a dosage rate of about 1,200 mg per day, or 1,200 mg per day.

197. A method in accordance with aspect 183, wherein the NMN is administered at a dosage rate of about 1,300 mg per day, or 1,300 mg per day.

198. A method in accordance with aspect 183, wherein the NMN is administered at a dosage rate of about 1,400 mg per day, or 1,400 mg per day.

199. A method in accordance with aspect 183, wherein the NMN is administered at a dosage rate of about 1,500 mg per day, or 1,500 mg per day.

200. A method in accordance with aspect 183, wherein the NMN is administered at a dosage rate of about 1,600 mg per day, or 1,600 mg per day.

201. A method in accordance with aspect 183, wherein the NMN is administered at a dosage rate of about 1,700 mg per day, or 1,700 mg per day.

202. A method in accordance with aspect 183, wherein the NMN is administered at a dosage rate of about 1,800 mg per day, or 1,800 mg per day.

203. A method in accordance with aspect 183, wherein the NMN is administered at a dosage rate of about 1,900 mg per day, or 1,900 mg per day.

204. A method in accordance with aspect 183, wherein the NMN is administered at a dosage rate of about 2,000 mg per day, or 2,000 mg per day.

205. A method in accordance with aspect 183, wherein the NMN is administered at a dosage rate of about 100 mg/kg body weight/day, from 100 mg/kg body weight/day to 300 mg/kg body weight/day, or about 300 mg/kg body weight/day.

206. A method in accordance with aspect 183, comprising administering to a subject a formulation of any one of aspects 1-52.

207. A method in accordance with aspect 206, wherein the administering a formulation comprises, consists essentially of or consists of administering the formulation once per day.

208. A method in accordance with aspect 206, wherein the administering a formulation comprises, consists essentially of or consists of administering the formulation twice per day.

209. A method of treating, ameliorating, mitigating, slowing, arresting, preventing or reversing dry eye, comprising administering to a subject a pharmaceutically effective amount of nicotinamide mononucleotide (NMN).

210. A method in accordance with aspect 209, wherein the NMN is administered at a dosage rate of about 100 mg per day, from 100 mg per day to 2000 mg per day, or about 2000 mg per day.

211. A method in accordance with aspect 209, wherein the NMN is administered at a dosage rate of about 100 mg per day, or 100 mg per day.

212. A method in accordance with aspect 209, wherein the NMN is administered at a dosage rate of about 200 mg per day, or 200 mg per day.

213. A method in accordance with aspect 209, wherein the NMN is administered at a dosage rate of about 300 mg per day, or 300 mg per day.

214. A method in accordance with aspect 209, wherein the NMN is administered at a dosage rate of about 400 mg per day, or 400 mg per day.

215. A method in accordance with aspect 209, wherein the NMN is administered at a dosage rate of about 500 mg per day, or 500 mg per day.

216. A method in accordance with aspect 209, wherein the NMN is administered at a dosage rate of about 600 mg per day, or 600 mg per day.

217. A method in accordance with aspect 209, wherein the NMN is administered at a dosage rate of about 700 mg per day, or 700 mg per day.

216. A method in accordance with aspect 209, wherein the NMN is administered at a dosage rate of about 800 mg per day, or 800 mg per day.

219. A method in accordance with aspect 209, wherein the NMN is administered at a dosage rate of about 900 mg per day, or 900 mg per day.

220. A method in accordance with aspect 209, wherein the NMN is administered at a dosage rate of about 1,000 mg per day, or 1,000 mg per day.

221. A method in accordance with aspect 209, wherein the NMN is administered at a dosage rate of about 1,100 mg per day, or 1,100 mg per day.

222. A method in accordance with aspect 209, wherein the NMN is administered at a dosage rate of about 1,200 mg per day, or 1,200 mg per day.

223. A method in accordance with aspect 209, wherein the NMN is administered at a dosage rate of about 1,300 mg per day, or 1,300 mg per day.

224. A method in accordance with aspect 209, wherein the NMN is administered at a dosage rate of about 1,400 mg per day, or 1,400 mg per day.

225. A method in accordance with aspect 209, wherein the NMN is administered at a dosage rate of about 1,500 mg per day, or 1,500 mg per day.

226. A method in accordance with aspect 209, wherein the NMN is administered at a dosage rate of about 1,600 mg per day, or 1,600 mg per day.

227. A method in accordance with aspect 209, wherein the NMN is administered at a dosage rate of about 1,700 mg per day, or 1,700 mg per day.

228. A method in accordance with aspect 209, wherein the NMN is administered at a dosage rate of about 1,800 mg per day, or 1,800 mg per day.

229. A method in accordance with aspect 209, wherein the NMN is administered at a dosage rate of about 1,900 mg per day, or 1,900 mg per day.

230. A method in accordance with aspect 209, wherein the NMN is administered at a dosage rate of about 2,000 mg per day, or 2,000 mg per day.

231. A method in accordance with aspect 209, wherein the NMN is administered at a dosage rate of about 100 mg/kg body weight/day, from 100 mg/kg body weight/day to 300 mg/kg body weight/day, or about 300 mg/kg body weight/day.

232. A method in accordance with aspect 209, comprising administering to a subject a formulation of any one of aspects 1-52.

233. A method in accordance with aspect 232, wherein the administering a formulation comprises, consists essentially of or consists of administering the formulation once per day.

234. A method in accordance with aspect 232, wherein the administering a formulation comprises, consists essentially of or consists of administering the formulation twice per day.

235. A method of increasing NAD+ levels in a subject, comprising: administering to a subject a pharmaceutically effective amount of nicotinamide mononucleotide (NMN).

236. A method of treating age-associated defects in NSPC functionality in a subject, comprising: administering to a subject a pharmaceutically effective amount of nicotinamide mononucleotide (NMN).

237. A method of maintaining at least one NSPC in a subject, comprising: administering to a subject a pharmaceutically effective amount of nicotinamide mononucleotide (NMN).

238. A method of enhancing NAD biosynthesis in a subject, comprising: administering to a subject a pharmaceutically effective amount of nicotinamide mononucleotide (NMN).

239. A method of promoting NSPC proliferation in a subject, comprising: administering to a subject a pharmaceutically effective amount of nicotinamide mononucleotide (NMN).

240. A method in accordance with any of aspects 235-239, wherein the NMN is administered at a dosage rate of about 100 mg per day, from 100 mg per day to 2000 mg per day, or about 2000 mg per day.

241. A method in accordance with any of aspects 235-239, wherein the NMN is administered at a dosage rate of 0.5 mg, about 0.5 mg, 1 mg, about 1 mg, 5 mg, about 5 mg, mg, about 10 mg, 20 mg, about 20 mg, 30 mg, about 30 mg, 40 mg, about 40 mg, 50 mg, about 50 mg, 60 mg, about 60 mg, 70 mg, about 70 mg, 80 mg, about 80 mg, 90 mg, about 90 mg, 100 mg, about 100 mg, 150 mg, about 150 mg, 200 mg, about 200 mg, 300 mg, about 300 mg, 400 mg, about 400 mg, 450 mg, about 450 mg, 500 mg, about 500 mg, 600 mg, about 600 mg, 680 mg, about 680 mg, 700 mg, about 700 mg, 800 mg, about 800 mg, 900 mg, about 900 mg, 1000 mg, about 1000 mg, 1100 mg, about 1100 mg, 1130 mg, about 1130 mg, 1200 mg, about 1200 mg, 1300 mg, about 1300 mg, 1350 mg, about 1350 mg, 1360 mg, about 1360 mg, 1400 mg, about 1400 mg, 1500 mg, about 1500 mg, 1600 mg, about 1600 mg, 1700 mg, about 1700 mg, 1800 mg, about 1800 mg, 2040 mg, about 2040 mg, 2250 mg, about 2250 mg, 2260 mg, about 2260 mg, 2700 mg, about 2700 mg, 2720 mg, about 2720 mg, 3400 mg, about 3400 mg, 3390 mg, about 3390 mg, 3400 mg, about 3400 mg, 3600 mg, about 3600 mg, 4080 mg, about 4080 mg, 4500 mg, about 4500 mg, 4520 mg, about 4520 mg, 5440 mg, about 5440 mg, 5650 mg, about 5650 mg, 6800 mg, and about 6800 mg.

242. A method in accordance with any of aspects 235-239, wherein the NMN is administered at a dosage rate of about 100 mg/kg body weight/day, from 100 mg/kg body weight/day to 300 mg/kg body weight/day, or about 300 mg/kg body weight/day.

243. A method in accordance with any of aspects 235-239, comprising administering to a subject a formulation of any one of aspects 1-52.

244. A method in accordance with aspect 243, wherein the administering a formulation comprises, consists essentially of or consists of administering the formulation once per day.

245. A method in accordance with aspect 243, wherein the administering a formulation comprises, consists essentially of or consists of administering the formulation twice per day.

246. A method of increasing bone density levels in a subject, comprising: administering to a subject a pharmaceutically effective amount of nicotinamide mononucleotide (NMN).

247. A method of treating aberrantly low bone density levels in a subject, comprising: administering to a subject a pharmaceutically effective amount of nicotinamide mononucleotide (NMN).

248. A method of treating an age-associated bone disorder in a subject, comprising: administering to a subject a pharmaceutically effective amount of nicotinamide mononucleotide (NMN).

249. A method in accordance with claim 284, wherein the age-associated bone disorder is osteoporosis.

250. A method in accordance with any of aspects 246-249, wherein the NMN is administered at a dosage rate of about 100 mg per day, from 100 mg per day to 2000 mg per day, or about 2000 mg per day.

251. A method in accordance with any of aspects 246-249, wherein the NMN is administered at a dosage rate of 0.5 mg, about 0.5 mg, 1 mg, about 1 mg, 5 mg, about 5 mg, mg, about 10 mg, 20 mg, about 20 mg, 30 mg, about 30 mg, 40 mg, about 40 mg, 50 mg, about 50 mg, 60 mg, about 60 mg, 70 mg, about 70 mg, 80 mg, about 80 mg, 90 mg, about 90 mg, 100 mg, about 100 mg, 150 mg, about 150 mg, 200 mg, about 200 mg, 300 mg, about 300 mg, 400 mg, about 400 mg, 450 mg, about 450 mg, 500 mg, about 500 mg, 600 mg, about 600 mg, 680 mg, about 680 mg, 700 mg, about 700 mg, 800 mg, about 800 mg, 900 mg, about 900 mg, 1000 mg, about 1000 mg, 1100 mg, about 1100 mg, 1130 mg, about 1130 mg, 1200 mg, about 1200 mg, 1300 mg, about 1300 mg, 1350 mg, about 1350 mg, 1360 mg, about 1360 mg, 1400 mg, about 1400 mg, 1500 mg, about 1500 mg, 1600 mg, about 1600 mg, 1700 mg, about 1700 mg, 1800 mg, about 1800 mg, 2040 mg, about 2040 mg, 2250 mg, about 2250 mg, 2260 mg, about 2260 mg, 2700 mg, about 2700 mg, 2720 mg, about 2720 mg, 3400 mg, about 3400 mg, 3390 mg, about 3390 mg, 3400 mg, about 3400 mg, 3600 mg, about 3600 mg, 4080 mg, about 4080 mg, 4500 mg, about 4500 mg, 4520 mg, about 4520 mg, 5440 mg, about 5440 mg, 5650 mg, about 5650 mg, 6800 mg, and about 6800 mg.

252. A method in accordance with any of aspects 246-249, wherein the NMN is administered at a dosage rate of about 100 mg/kg body weight/day, from 100 mg/kg body weight/day to 300 mg/kg body weight/day, or about 300 mg/kg body weight/day.

253. A method in accordance with any of aspects 246-249, comprising administering to a subject a formulation of any one of aspects 1-52.

254. A method in accordance with aspect 253, wherein the administering a formulation comprises, consists essentially of or consists of administering the formulation once per day.

255. A method in accordance with aspect 253, wherein the administering a formulation comprises, consists essentially of or consists of administering the formulation twice per day.

256. A method of treating macular degeneration in a subject, comprising administering to a subject a therapeutically effective amount of NMN.

257. A method of treating macular degeneration in a subject, comprising: administering to a subject NMN in an amount effective for increasing retinal NAD levels.

258. A method of treating aberrant retinal NAD levels in a subject, comprising administering to a subject NMN in an amount effective for increasing retinal NAD levels.

259. A method of treating retinal degeneration in a subject, comprising administering to a subject NMN in an amount effective for increasing retinal NAD levels.

260. A method of treating retinal degeneration in a subject, comprising administering to a subject a therapeutically effective amount of NMN.

261. A method of treating photoreceptor damage/degeneration in a subject, comprising administering to a subject a therapeutically effective amount of NMN.

262. A method of treating photoreceptor damage/degeneration in a subject, comprising administering to a subject NMN in an amount effective for increasing retinal NAD levels.

263. A method of treating vision loss associated with retinal degeneration in a subject, comprising: administering to a subject a therapeutically effective amount of NMN.

264. A method of treating vision loss in a subject, comprising: administering to a subject NMN in an amount effective for increasing retinal NAD levels.

265. A method of treating aberrant retinal structure in a subject, comprising: administering to a subject a therapeutically effective amount of NMN.

266. A method of treating aberrant retinal structure in a subject, comprising: administering to a subject NMN in an amount effective for increasing retinal NAD levels.

267. A method of treating aberrant retinal function in a subject, comprising: administering to a subject a therapeutically effective amount of NMN.

268. A method of treating aberrant retinal function in a subject, comprising: administering to a subject NMN in an amount effective for increasing retinal NAD levels.

269. A method of increasing retinal NAD levels in a subject, comprising: administering to a subject NMN in an amount effective for increasing retinal NAD levels.

270. A method of reducing risk of developing macular degeneration in a subject, comprising: administering to a subject NMN in an amount effective for preventing macular degeneration.

271. A method of reducing risk of developing macular degeneration in a subject, comprising: administering to a subject NMN in an amount effective for increasing retinal NAD levels.

272. A method of reducing risk of developing aberrant retinal NAD levels in a subject, comprising: administering to a subject NMN in an amount effective for increasing retinal NAD levels.

273. A method of reducing risk of developing retinal degeneration in a subject, comprising: administering to a subject NMN in an amount effective for increasing retinal NAD levels.

274. A method of reducing risk of developing photoreceptor damage/degeneration in a subject, comprising: administering to a subject NMN in an amount effective for preventing photoreceptor damage/degeneration.

275. A method of reducing risk of developing photoreceptor damage/degeneration in a subject, comprising: administering to a subject NMN in an amount effective for increasing retinal NAD levels.

276. A method of reducing risk of developing vision loss associated with retinal degeneration in a subject, comprising: administering to a subject NMN in an amount effective for reducing risk of developing vision loss associated with retinal degeneration.

277. A method of reducing risk of developing vision loss in a subject, comprising: administering to a subject NMN in an amount effective for increasing retinal NAD levels.

278. A method of reducing risk of developing aberrant retinal structure in a subject, comprising: administering to a subject NMN in an amount effective for preventing development of aberrant retinal structure.

279. A method of reducing risk of developing aberrant retinal structure in a subject, comprising: administering to a subject NMN in an amount effective for increasing retinal NAD levels.

280. A method of reducing risk of developing aberrant retinal function in a subject, comprising: administering to a subject NMN in an amount effective for preventing development of aberrant retinal function.

281. A method of reducing risk of developing aberrant retinal function in a subject, comprising: administering to a subject NMN in an amount effective for increasing retinal NAD levels.

282. A method of treating a retina disease in a subject, comprising: administering to a subject a therapeutically effective amount of NMN.

283. A method in accordance with aspect 282, wherein the retina disease is selected from the group consisting of retinitis pigmentosa (RP), Leber's congenital amaurosis (LCA), rod dystrophy, cone dystrophy, rod-cone dystrophy, cone-rod dystrophy, age-related macular degeneration and photoreceptor degeneration following retinal detachment.

284. A method in accordance with any of aspects 256-283, wherein the NMN is administered at a dosage rate of about 100 mg per day, from 100 mg per day to 2000 mg per day, or about 2000 mg per day.

285. A method in accordance with any of aspects 256-283, wherein the NMN is administered at a dosage rate of 0.5 mg, about 0.5 mg, 1 mg, about 1 mg, 5 mg, about 5 mg, about 10 mg, 20 mg, about 20 mg, 30 mg, about 30 mg, 40 mg, about 40 mg, 50 mg, about 50 mg, 60 mg, about 60 mg, 70 mg, about 70 mg, 80 mg, about 80 mg, 90 mg, about 90 mg, 100 mg, about 100 mg, 150 mg, about 150 mg, 200 mg, about 200 mg, 300 mg, about 300 mg, 400 mg, about 400 mg, 450 mg, about 450 mg, 500 mg, about 500 mg, 600 mg, about 600 mg, 680 mg, about 680 mg, 700 mg, about 700 mg, 800 mg, about 800 mg, 900 mg, about 900 mg, 1000 mg, about 1000 mg, 1100 mg, about 1100 mg, 1130 mg, about 1130 mg, 1200 mg, about 1200 mg, 1300 mg, about 1300 mg, 1350 mg, about 1350 mg, 1360 mg, about 1360 mg, 1400 mg, about 1400 mg, 1500 mg, about 1500 mg, 1600 mg, about 1600 mg, 1700 mg, about 1700 mg, 1800 mg, about 1800 mg, 2040 mg, about 2040 mg, 2250 mg, about 2250 mg, 2260 mg, about 2260 mg, 2700 mg, about 2700 mg, 2720 mg, about 2720 mg, 3400 mg, about 3400 mg, 3390 mg, about 3390 mg, 3400 mg, about 3400 mg, 3600 mg, about 3600 mg, 4080 mg, about 4080 mg, 4500 mg, about 4500 mg, 4520 mg, about 4520 mg, 5440 mg, about 5440 mg, 5650 mg, about 5650 mg, 6800 mg, and about 6800 mg.

286. A method in accordance with any of aspects 256-283, wherein the NMN is administered at a dosage rate of about 100 mg/kg body weight/day, from 100 mg/kg body weight/day to 300 mg/kg body weight/day, or about 300 mg/kg body weight/day.

287. A method in accordance with any of aspects 256-283, comprising administering to a subject a formulation of any one of aspects 1-52.

288. A method in accordance with aspect 283, wherein the administering a formulation comprises, consists essentially of or consists of administering the formulation once per day.

289. A method in accordance with aspect 283, wherein the administering a formulation comprises, consists essentially of or consists of administering the formulation twice per day.

290. A method in accordance with any of aspects 32 or 53-289, wherein the subject is a mammal.

291. A method in accordance with any of aspects 32 or 53-289, wherein the subject is a human.

292. A method in accordance with any of aspects 32 or 53-289, wherein the subject is a vertebrate.

BRIEF DESCRIPTION OF THE DRAWINGS

FIG. 3 illustrates age-associated body weight gain.

FIG. 4 illustrates oxygen consumption in control, 100 and 300 mg/kg NMN-administered mice.

FIG. 5 illustrates energy expenditure in control, 100 and 300 mg/kg NMN-administered mice.

FIG. 6 illustrates respiratory quotient in control, 100 and 300 mg/kg NMN-administered mice.

FIG. 7A-C illustrates blood levels of (A) cholesterol, (B) triglycerides and (C) free fatty acids shown over 12 months in the control and the 100 and 300 mg/kg NMN-administered cohorts.

FIG. 8A-C illustrates body weight-matched blood levels of (A) cholesterol, (B) triglycerides and (C) free fatty acids shown over 12 months in the control and the 100 and 300 mg/kg NMN-administered cohorts.

Figure 1:
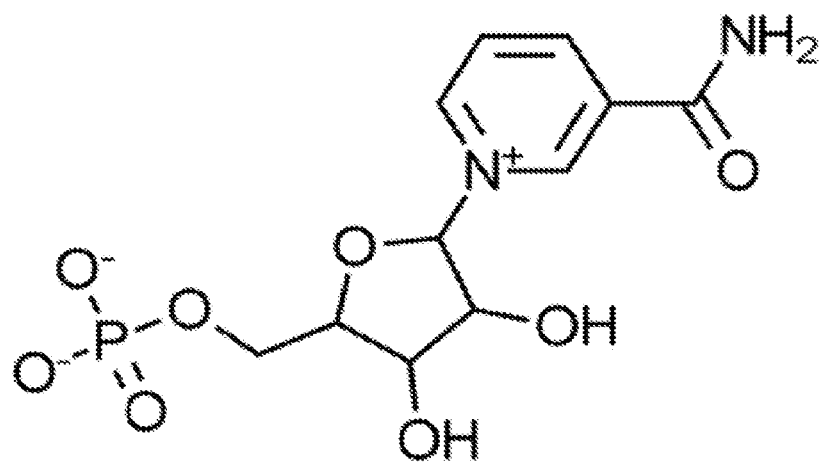
FIG. 1 illustrates structure of nicotinamide mononucleotide (NMN).

FIG. 18A-L illustrates that genetic ablation of Nampt in NSPCs in vitro impairs NAD+ biosynthesis, proliferation, and differentiation. Neurospheres were isolated from Nampt$^{flox/flox}$ mice and infected with a Cre-recombinase expressing adenovirus (Nampt AD-Cre) or a control adenovirus expressing LacZ (Nampt AD-LacZ). A) HPLC analysis of NAD+ levels with and without NMN (100 μM, 48 hours) (n=10-22). B-C) Quantification of the fold increase in cell number (n=13-50) and neurosphere diameter (n=9 independent samples, 57-96 neurospheres). D) Representative images of neurospheres 7 days after dissociation. Scale bars denote 10 μm. E) The number of neurospheres formed 7 days after plating dissociated cells at 100 cells/ml, 0.5 ml/well in 24-well plates (n=8 independent samples, 48-84 wells). F-G) Nampt Ad-Cre and Nampt AD-LacZ infected neurospheres were cultured without NMN until Nampt Ad-Cre infected neurospheres exhibited a growth defect. Cultures were then passaged and plated at equal density with or without NMN (200 μM). Fold increases in cell number (F) (n=6), and the percentages of total Dapi+ cells that express Ki67+ cells were quantified (G) (n=3 independent samples, 9 fields of view). H-L) The percentages of total Dapi+ cells that express the indicated cell type-specific markers (H) by immunofluorescence after 6-7 days of differentiation: O4 (I), Gfap (J), and B-III-tubulin (K) (n=3-6 independent samples, 23-43 fields of view). The effect of NMN was also examined for O4, S100β, TUNEL, and Nestin (L) (n=3-6 independent samples, 10-26 fields of view). *, ˆ, and #indicate statistical significance between Nampt AD-LacZ and Nampt AD-Cre, Nampt AD-LacZ and Nampt AD-LacZ+ NMN, and Nampt AD-Cre and Nampt AD-Cre+ NMN, respectively. Data are presented as mean±s.e.m. *P<0.05. P<0.01. *P<0.001.

FIG. 19A-G illustrates that genetic ablation of Nampt in vitro impairs OPC formation. A) A scheme for oligodendrocyte differentiation with stage-specific markers. B-C) Neurospheres were infected with a Cre recombinase-expressing adenovirus (Nampt AD-Cre) or a control adenovirus expressing LacZ (Nampt AD-LacZ). To assess oligodendrocyte formation, dissociated neurospheres were harvested after 6-7 days of differentiation (B). To assess OPC formation, dissociated neurospheres were examined after 2 days of differentiation (C). Markers of NSPCs (Gfap, Nestin), OPCs (Pdgfra+), and oligodendrocyte lineage cells (Olig2+, O4+) were assessed (n=3-9 independent samples, 6-51 fields of view). D) Treatment of dissociated neurospheres with the selective inhibitor of Sirt1, EX527 (80 μM) or the selective inhibitor of Sirt2, AGK2 (10 μM). The formation of oligodendrocytes was evaluated after 6-7 days of differentiation (n=6-11 independent samples, 21-32 fields of view). E-G) Knockout and control neurospheres were formed by infecting with a Cre-recombinase expressing adenovirus or a control adenovirus expressing LacZ, respectively. E) Neurospheres were isolated from Sirt1$^{flox/flox}$ mice and Sirt1$^{flox/flox}$; Sirt2−/− mice. The formation of oligodendrocytes was evaluated after 6-7 days of differentiation (n=3-11 independent samples, 12-28 fields of view). F-G) Neurospheres were isolated from Nampt$^{flox/flox}$ mice (F, n=8-9) or Sirt1$^{flox/flox}$; Sirt2−/− mice (G, n=3-7) and differentiated for 2 days. Quantitative RT-PCR results for mRNA expression of oligodendrocyte lineage genes. Data are presented as mean±s.e.m. *P<0.05. P<0.01. *P<0.001.

FIG. 20A-J illustrates adult NSPC-specific deletion of Nampt impairs NSPC self-renewal and differentiation in response to insult-induced demyelination in vivo. A) Quantification of the percentage of NestinGFP-positive cells in the SVZ that also express Olig2 in iNSPC-GFP (n=7) and iNSPC-Nampt-KO (n=8) mice 7 days post initial TAM injection. B) 6- to 9-week-old iNSPC-GFP control and iNSPC-Nampt-KO mice were fed a diet containing 0.2% cuprizone for 4-5 weeks. Deletion of Nampt in the adult Nestin+ population was induced by 5 tamoxifen (TAM) injections at 180 mg/kg body weight per day the week before starting the cuprizone diet. C) A scheme of a coronal mouse brain section. Original red boxed areas indicate regions used for quantification. Original red dotted line indicates the SGZ. CC, corpus callosum; DHC, dorsal hippocampal commissure; DG, dentate gyrus; HPF, hippocampal formation; SCZ, subcallosal zone; SGZ, subgranular zone; V3, third ventricle. D) Quantification of the number of NestinGFP+ cells per unit area in the CC. E) A scheme for the specificity of the markers assessed. F-I) Quantification of the percentages of NestinGFP+ cells that express NSPC markers (Nestin, Gfap) or oligodendrocyte markers (Sox10, Apc) in the CC (n=2-11 mice). * and ˆ indicate statistical significance between iNSPC-GFP control littermates and iNSPC-Nampt-KO mice and between regular chow- and cuprizone-fed iNSPC-GFP mice, respectively. J) Representative images of immunofluorescence for Dapi (blue), Nampt (red), and Olig2 (green) in the CC. Arrows indicate examples of colocalization. Scale bars denote 20 μm. Data are presented as mean±s.e.m. *P<0.05.  ,ˆˆP<0.01. * ,ˆˆˆP<0.001.

Figure 21:
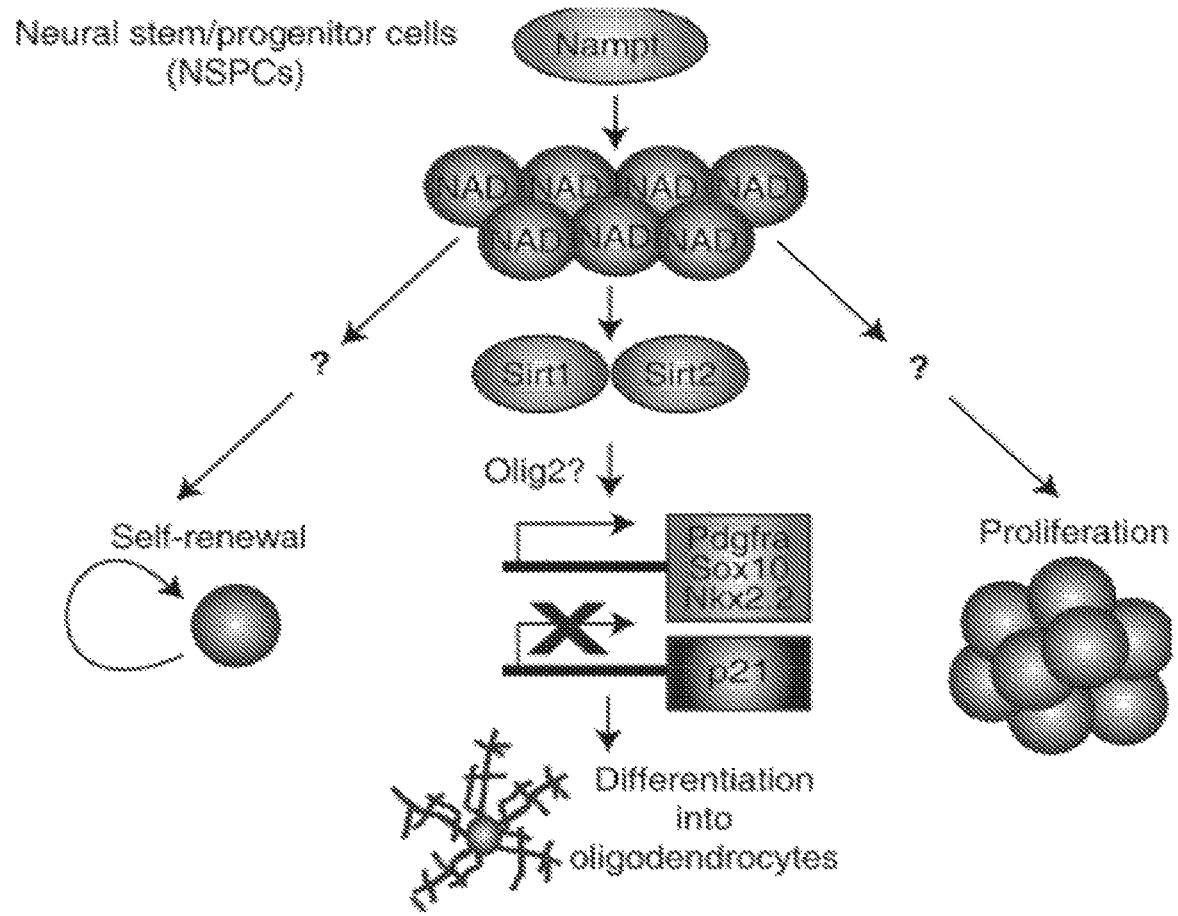

FIG. 21 illustrates a model for the role of Nampt-mediated NAD biosynthesis in NSPCs. Nampt-mediated NAD+ biosynthesis promotes NSPC self-renewal, proliferation and differentiation into oligodendrocytes. While the mechanism by which Nampt promotes self-renewal and proliferation remains unidentified, Nampt-mediated NAD+ biosynthesis activates Sirt1 and Sirt2 to promote NSPC oligodendrocyte lineage fate decisions by a mechanism involving transcriptional downregulation of Pdgfra, Sox10, and Nkx2.2 and transcriptional upregulation of p21 (cdkn1a). Sirt1 and Sirt2 may act via an effect on Olig2 activity. See text for a detailed discussion.

FIG. 22A-I illustrates Nampt expressed in a subpopulation of SGZ NSPCs. A-C, H-I) Representative images of immunofluorescence for Dapi (blue), Nampt (red), and cell type specific markers (NeuN: mature neurons, S100β: mature astrocytes, Ki67: proliferating cells, Olig2: oligodendrocyte lineage cells; green) in the subgranular zone (SGZ). Dotted lines denote the SGZ. Single arrowheads indicate examples of colocalization. Double arrowheads indicate examples of non-colocalization. Scale bars denote 10 μm. B) Zoom of boxed region shown in A). D) A scheme for the specificity of the markers assessed. E) Percentage of Dapi+ cells that express the neuronal marker NeuN in the SGZ (n=5). F) Percentage of Dapi+ cells that express the NSPC marker Sox2 in the SGZ (n=5). G) Quantification of the percentages of marker-positive cells that also express Nampt in the SGZ (Ki67: n=304 cells from 13 mice; Olig2: n=122 cells from 10 mice).

FIG. 23A-I illustrates that adult NSPC-specific deletion of Nampt impairs NSPC proliferation and self-renewal in vivo. A-F) iNSPC-Nampt-KO and littermate control (iNSPC-GFP) mice were injected with tamoxifen (TAM) or vehicle (5 total injections, 1 injection per day). A-B) Representative images of immunofluorescence for Dapi (blue), activated caspase 3 (red), and NestinGFP (green) in the indicated brain regions at 28 (A) or 3 (B) days post TAM injection. Arrows highlight the rare activated caspase 3+ cells observed. Scale bars denote 50 µm. A) Control iNSPC-GFP mice were treated with oil or TAM to ensure that there was no leaky NestinGFP reporter expression. B) iNSPC-Nampt-KO or iNSPC-GFP mice were treated with TAM. C) Recombination-confirmatory PCR performed on hippocampal DNA from TAM treated iNSPC-Nampt-KO (KO) and control mice (n=7-8). D) Quantification of the percentages of NestinGFP-positive cells in the SGZ that also express NSPC (Sox2: n=190 cells from 7 mice; Gfap: n=208 cells from 7 mice) or neuronal (Dcx, NeuN, n=473 cells from 7 mice) markers in 3 to 6 month old iNSPC-GFP mice 7 days post initial TAM injection. E) Quantification of the percentages of NestinGFP-positive cells that also express Nampt in iNSPC-Nampt-KO and iNSPC-GFP mice in the DG at the indicated days post initial TAM injection (n=more than 350 cells from 7 mice). F) Newborn neurons (Dcx+, n=12-16) were categorized by the length of their projection per unit area of the dentate gyrus (DG). G) Mice were injected with NMN (500 mg/kg body weight, IP), and hippocampal NAD+ levels were measured by HPLC at the indicated time points post injection (n=3-9). H-I) Mice were administered NMN (100 or 300 mg/kg body weight) in their drinking water from 6 to 18 months of age.

FIG. 24A-E illustrates that inhibition of Nampt in NSPCs impairs NAD+ biosynthesis and proliferation in vitro. Neurospheres were cultured with the Nampt-specific inhibitor FK866 (10 nM) with or without NMN (100 µM) for 24 (A-B) or 48 hours (C-G). A) HPLC analysis of NAD+ levels (n=6). B) Quantification of the fold increase of cell number in neurospheres under each condition indicated (n=5-11). C) A representative immunoblot of FK866-treated neurospheres. D-E) Quantification of immunoblots for Ki67 (D) and Pcna (E) normalized by actin in neurospheres (n=6). F-G) Top 50 biological pathways downregulated (F) or upregulated (G) by FK866.

FIG. 25A-G illustrates genetic ablation of Nampt in NSPCs in vitro impairs NAD+ biosynthesis, proliferation, and differentiation. A-G) Neurospheres were isolated from Namptflox/flox mice and infected with a Cre-recombinase expressing adenovirus (Nampt AD-Cre) or a control adenovirus expressing LacZ (Nampt ADLacZ). A) Quantitative RT-PCR results for mRNA expression of Nampt in AD-LacZ and Nampt Ad-Cre infected neurospheres (n=3-33). B) Representative immunoblots for Nampt and Gapdh. C) Quantification of immunoblots for Nampt in neurospheres normalized by Gapdh (n=4-13). D) HPLC analysis of NAD+ levels. NAD+ levels in Nampt Ad-Cre infected neurospheres were normalized by NAD+ levels in Nampt Ad-LacZ infected neurospheres (n=4-9). E) Representative immunoblots of Nampt Ad-Cre or Nampt AD-LacZ infected neurospheres 8 days post infection for markers of cell death (activated caspase 3) and proliferation (Ki67, Pcna). Neurospheres were grown under proliferation conditions (left blot) or differentiated for 2 days (right blot). F) Immunofluorescence analysis of dissociated neurospheres cultured in proliferation media. Histogram shows the percentages of activated caspase 3+(n=3 independent samples, 6 fields of view) or TUNEL+ cells (n=9 independent samples, 14-21 fields of view) relative to the total number of Dapi+ cells. G) A scheme for the non-directed lineage differentiation protocol used.

FIG. 26A-J illustrates A) A scheme for the oligodendrocytic lineage differentiation protocol used. B) Histogram shows the percentages of Dapi+ cells that express markers of NSPCs (Gfap, Nestin), OPCs (Pdgfra+, Olig2+), and astrocytes (S100β) (n=3-12 independent samples, 6-30 fields of view). C) A representative immunoblot for Sirt2 in neurospheres cultured as NSPCs (with EGF, FGF) or OPCs (with EGF, FGF, PDGFaa) before and after differentiation. D) Immunofluorescence for Dapi (original blue), Nampt (original red), and Sirt2 (original green) along the SGZ. Dotted lines denote the SGZ. Single arrowheads indicate examples of colocalization of cell immunoreactivity. Scale bar denotes 10 µm. E-F) Immunofluorescence for Dapi (blue), Sirt2 (red), and NestinGFP (original green, 3 days post TAM) along the SGZ. Dotted lines denote the SGZ. E) Scale bar denotes 50 µm. F) Scale bar denotes 20 µm. G-H) Neurospheres were isolated from Sirt1 flox/flox mice and infected with a Cre recombinase-expressing adenovirus (Sirt1 AD-Cre) or a control adenovirus expressing LacZ (Sirt1 AD-LacZ). G) Quantitative RT-PCR results for mRNA expression of Sirt1 (n=17-24). H-J) Quantification of the fold increase in cell number (n=5-20). Neurospheres were derived from full body Sirt1 KO mice (I), Sirt2 KO (J) mice, and their respective littermate controls.

FIG. 27A-H illustrates adult NSPC specific deletion of Nampt impairs NSPC self-renewal in response to insult-induced demyelination in vivo. A) Representative images of immunofluorescence for Dapi (blue), Nestin (red), and NestinGFP (green), and in regular chow (RC) and cuprizone fed (CUPR) mice in the indicated regions of the brain: SGZ, subgranular zone; SVZ, subventricular zone; CC, corpus callosum. Scale bars denote 20 µm. B) Representative images of immunofluorescence for Dapi (blue), MBP (red), and NestinGFP (green) in regular chow- and cuprizone-fed mice before and after 1 week of recovery in the SGZ. Scale bars denote 20 µm. C-G) Quantification of the number of NestinGFP+ cells per unit area of the dentate gyrus (C) and percentages of NestinGFP+ cells that express NSPC markers (Nestin, Gfap) or oligodendrocyte markers (Sox10, Apc) in the SGZ (D-G) (n=5-12 mice). * and ˆindicate statistical significance between iNSPC-GFP control littermates and iNSPC-Nampt-KO mice and between regular chow- and cuprizone-fed iNSPCGFP mice, respectively. H) Representative images of immunofluorescence for Dapi (blue), Nampt (red), and Sox2 (green) in the CC. Arrows indicate examples of colocalization of immunoreactivity. Scale bars denote 20 µm.

Figure 28A:
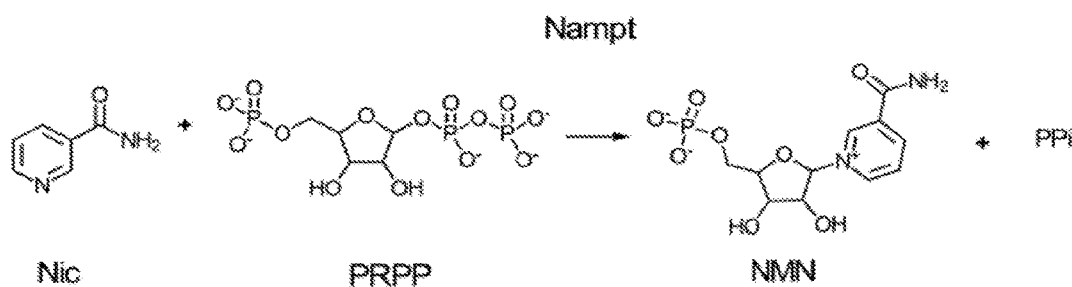
Figure 28B:
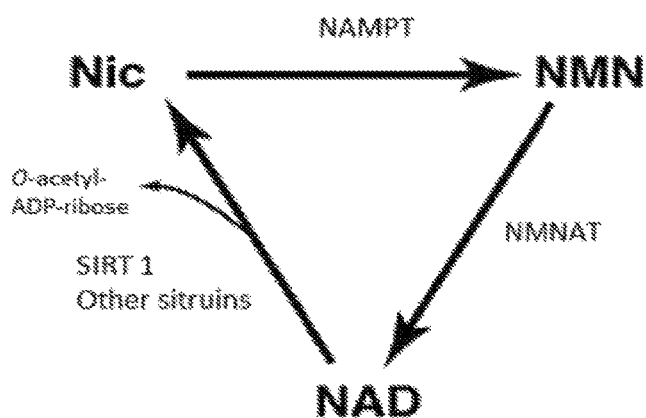

FIG. 28A-B illustrates the NAD biosynthetic pathway from nicotinamide. (A) The rate-limiting step catalyzed by nicotinamide phosphoribosyltransferase (NAMPT). Nic, nicotinamide; PRPP, 5'-phosphoribosyl-1-pyrophosphate; NMN, nicotinamide mononucleotide; PPi, pyrophosphate. (B) The NAD biosynthetic pathway from nicotinamide.

FIG. 29A-L illustrates (A-B) retinas from NAMPT rod-CKO mice showed a significant reduction of NAMPT within rods by PCR, immunohistochemistry and immunoblotting. (C) Neurosensory retinal degeneration was associated with secondary atrophy and pallor of the optic nerve. (D-F) Electroretinography (ERG) was performed to measure PR neuron and retinal function. (G) Photopic visual acuity measurements confirmed vision loss in rod-CKO mice. (H) Histopathologic examination of eyes from NAMPT rod-CKO mice. (I) Normalized NAD measurements obtained from NAMPT rod-cko whole retinas. (J-L) CKO mice treated with NMN showed significant rescue of photopic and scotopic function.

FIG. 30A-L illustrates (A) NAMPT cone-CKO mice (B-D) ERG demonstrated progressive decline in cone function. (E) Significant decrease in visual acuity in cone-CKO mice. (F-H) ERG function compared to PBS treated cone-CKO mice. (I-J) FK866 treatment of cone cells in vitro causes decrease in intracellular NAD levels and significant cell death after the 4 hours of treatment. (I-K) NMN (100 µM) was able to completely rescue cells. (L) depicts histopathologic examination of eyes from NAMPT rod-CKO mice.

Figure 31A:
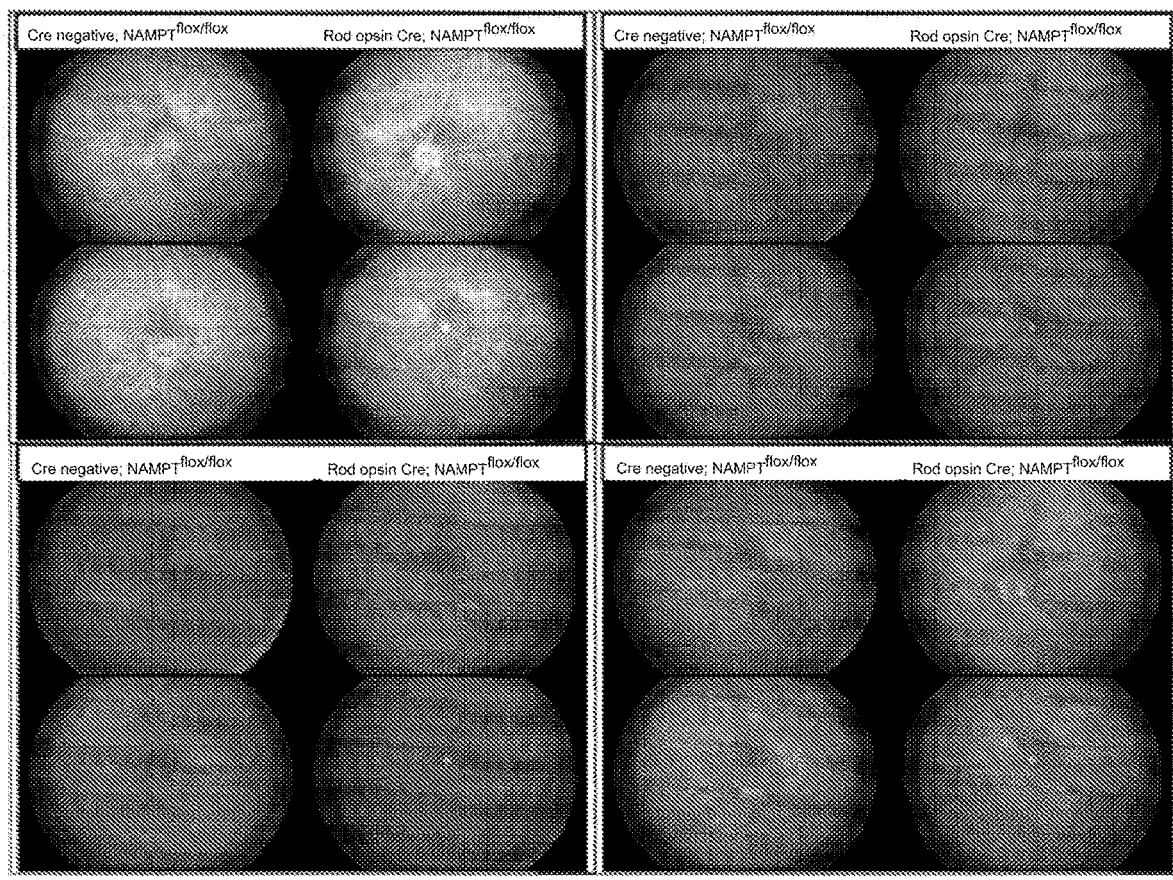
Figure 31B:
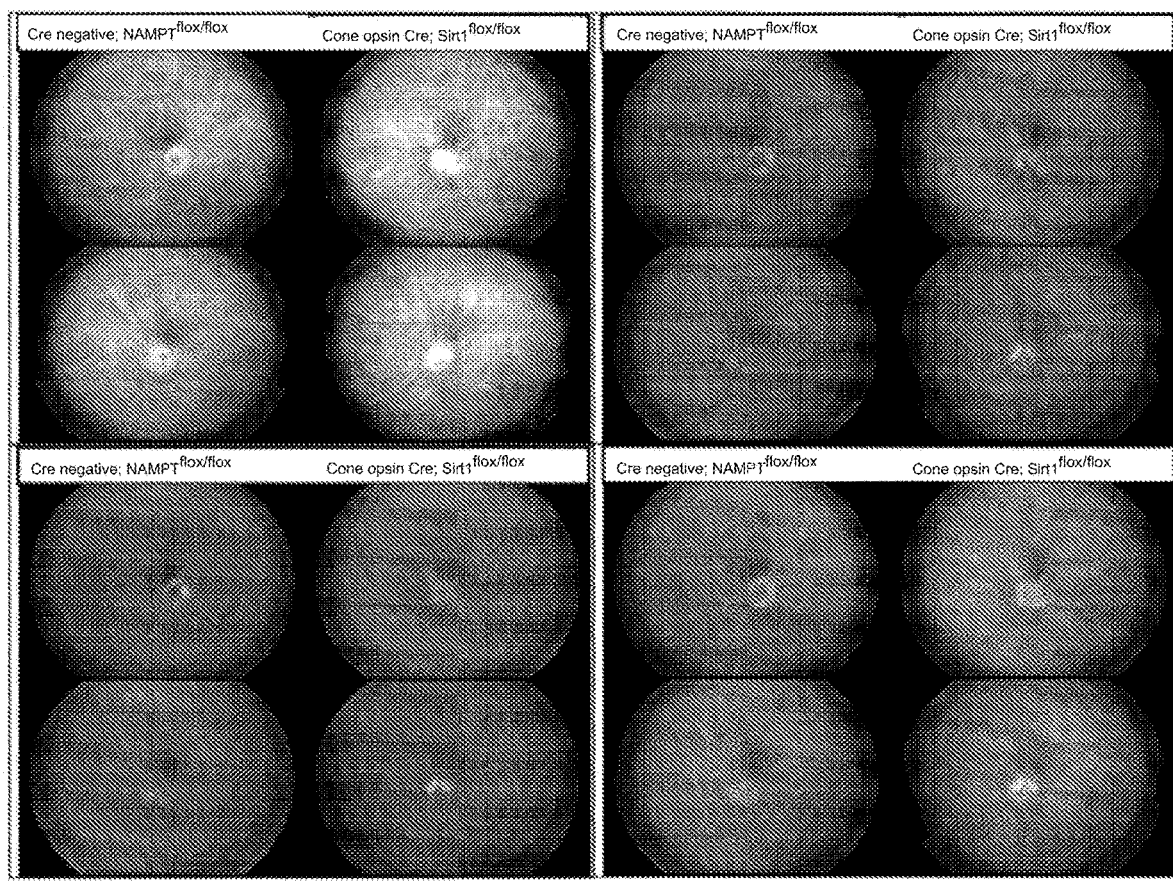
Figure 31C:
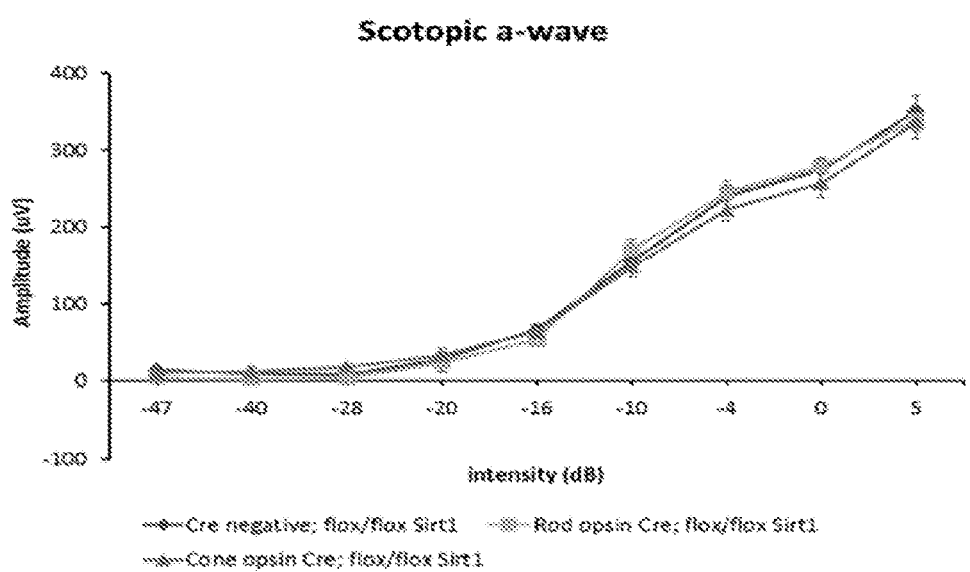
Figure 31D:
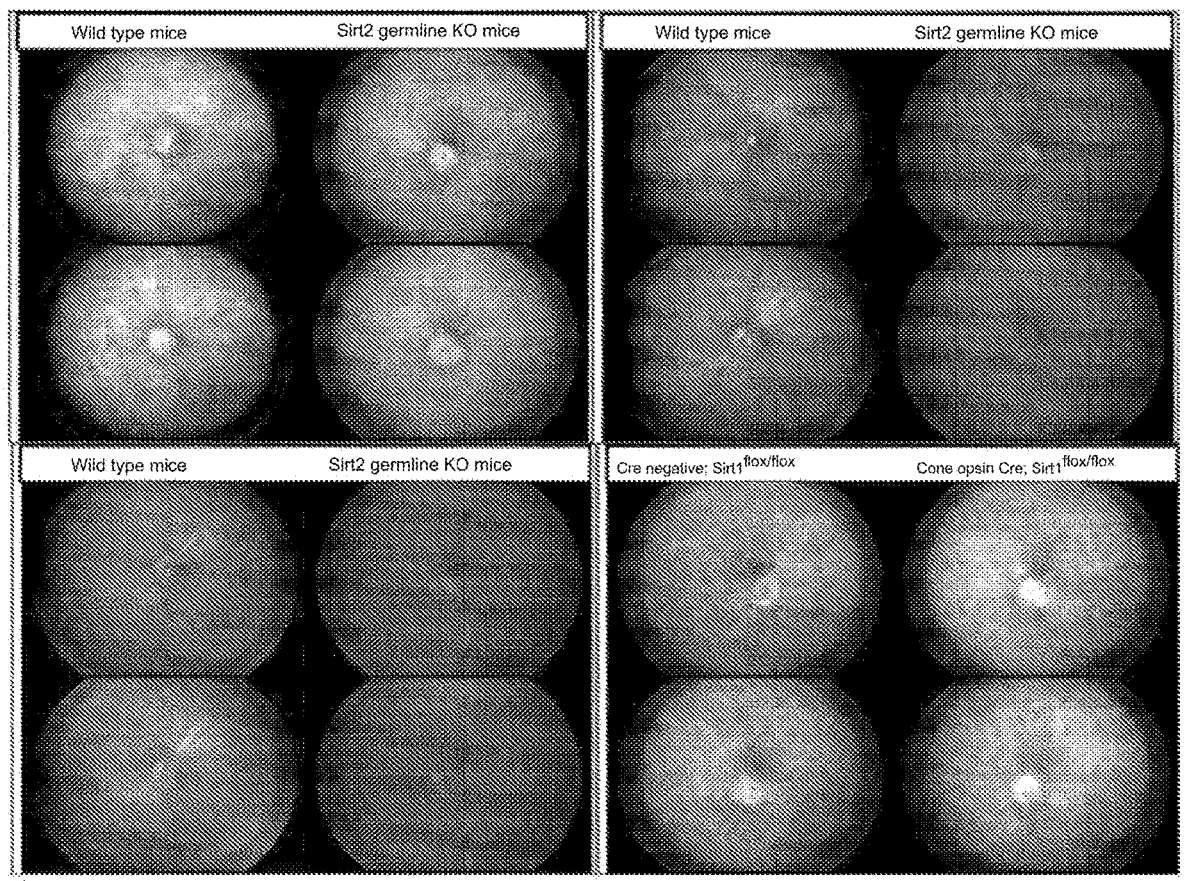
Figure 31E:
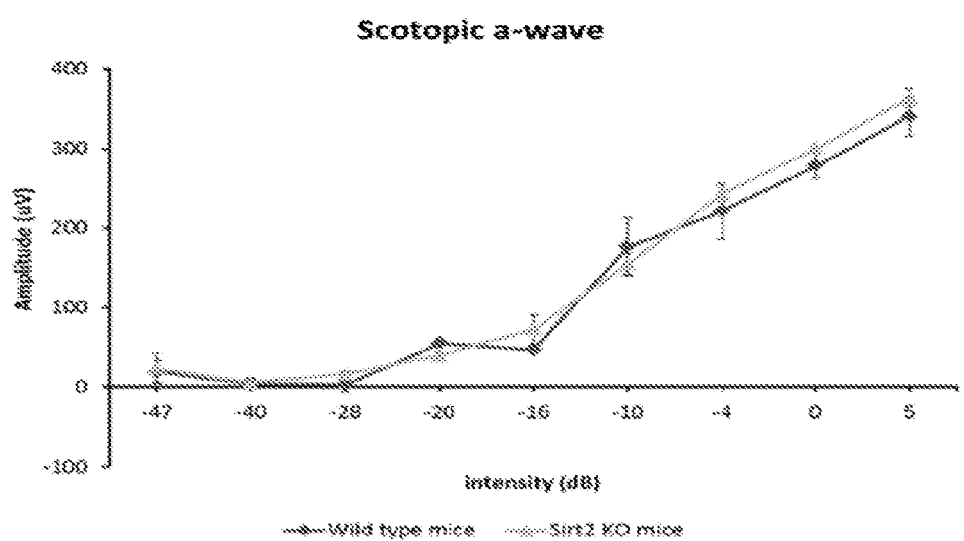
Figure 31F:
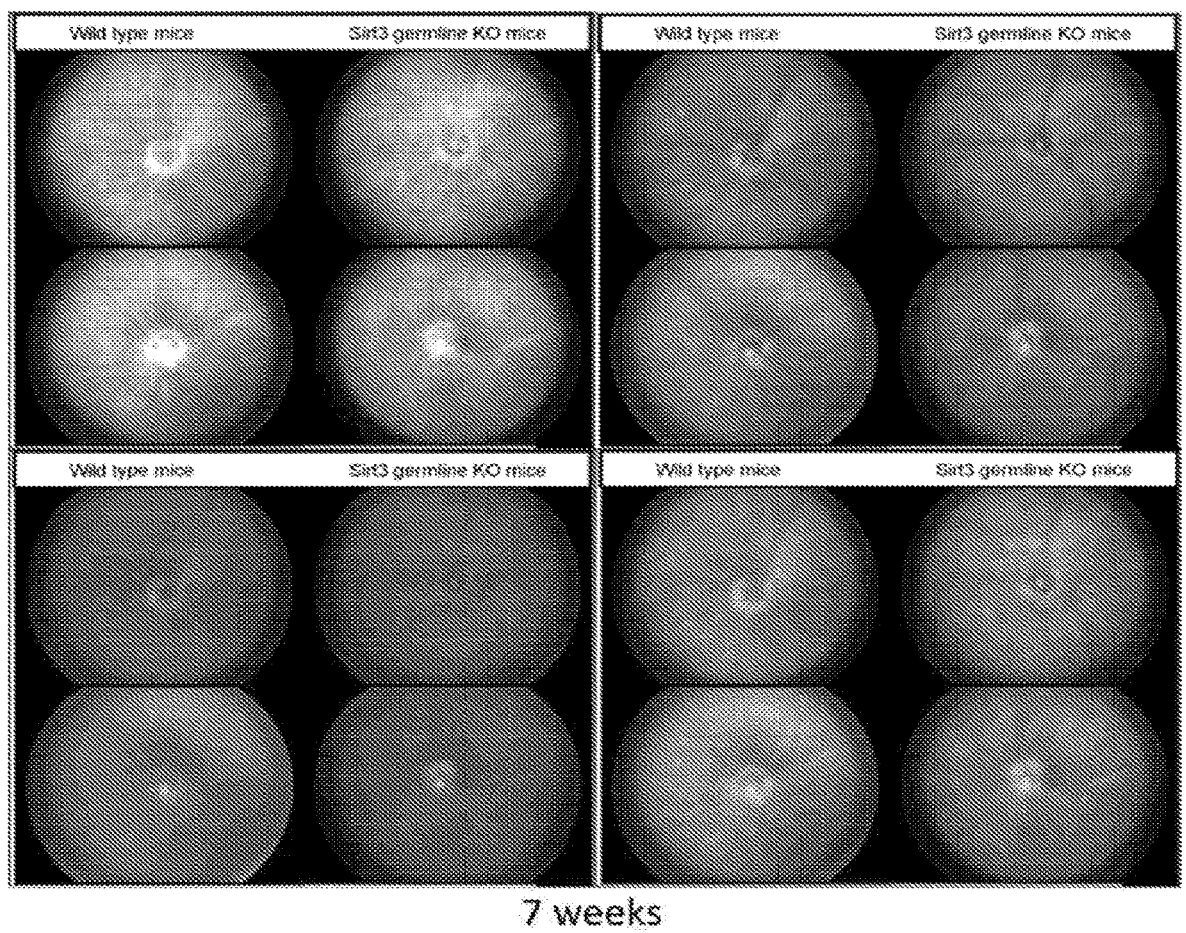
Figure 31G:
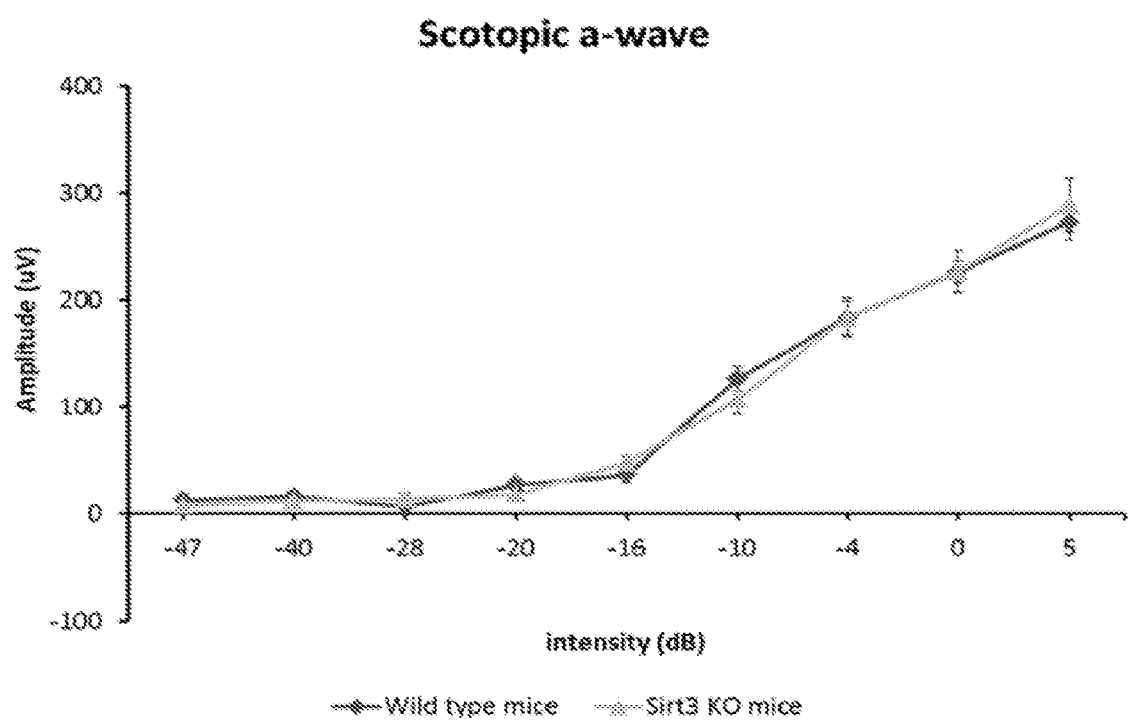
Figure 31H:
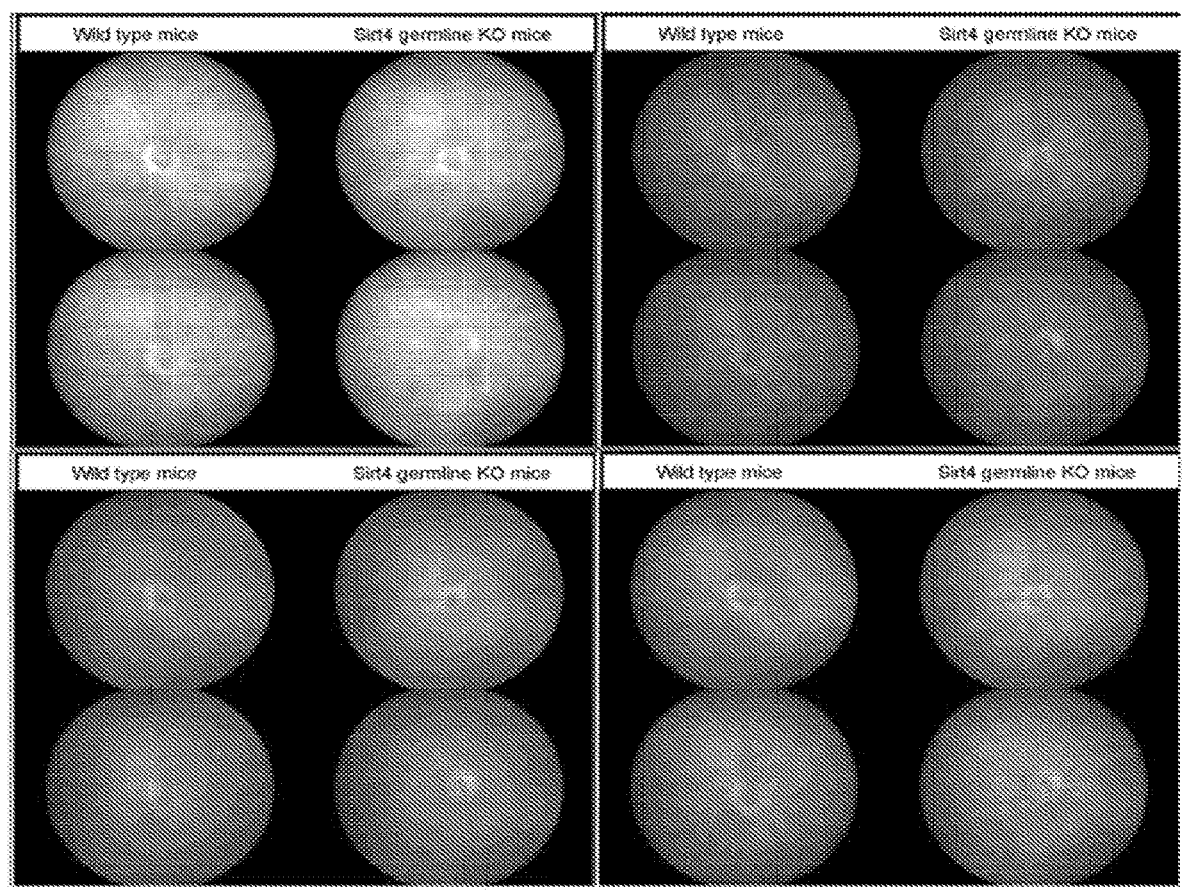

FIG. 31A-N illustrates (A-J) Retinal and PR neuron structure and function. (K-M) Examination of mice that had normal retinal structure and function.

FIG. 32A-E illustrates (A-D) Electron microscopic examination. (E) Role of NAD in NAMPT-mediated effects on PR neurons.

Figure 33B:
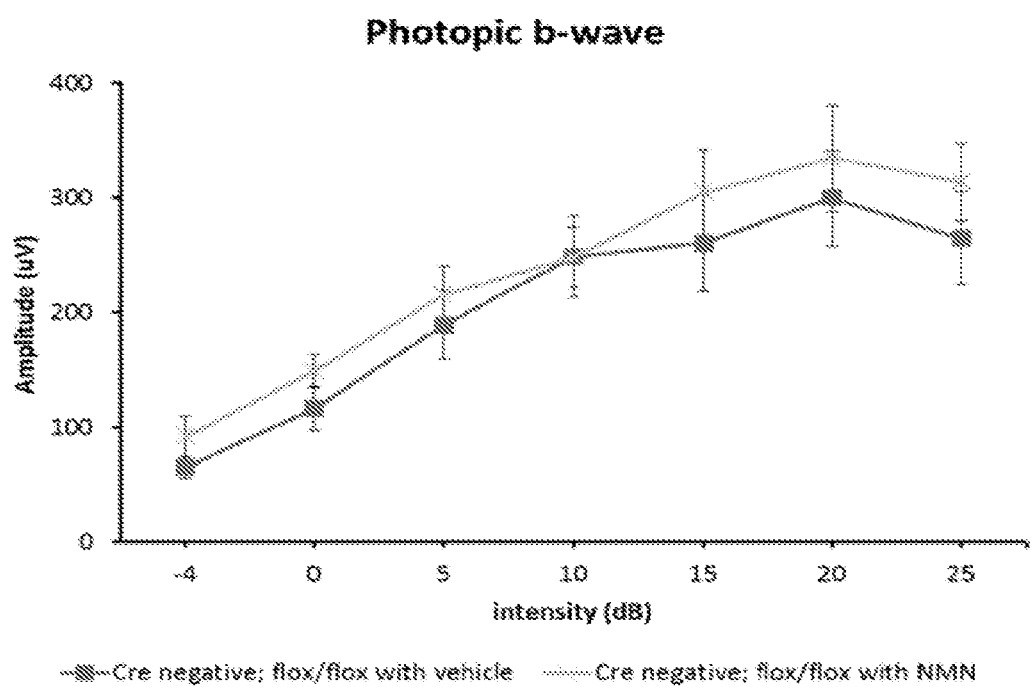
Figure 34A:
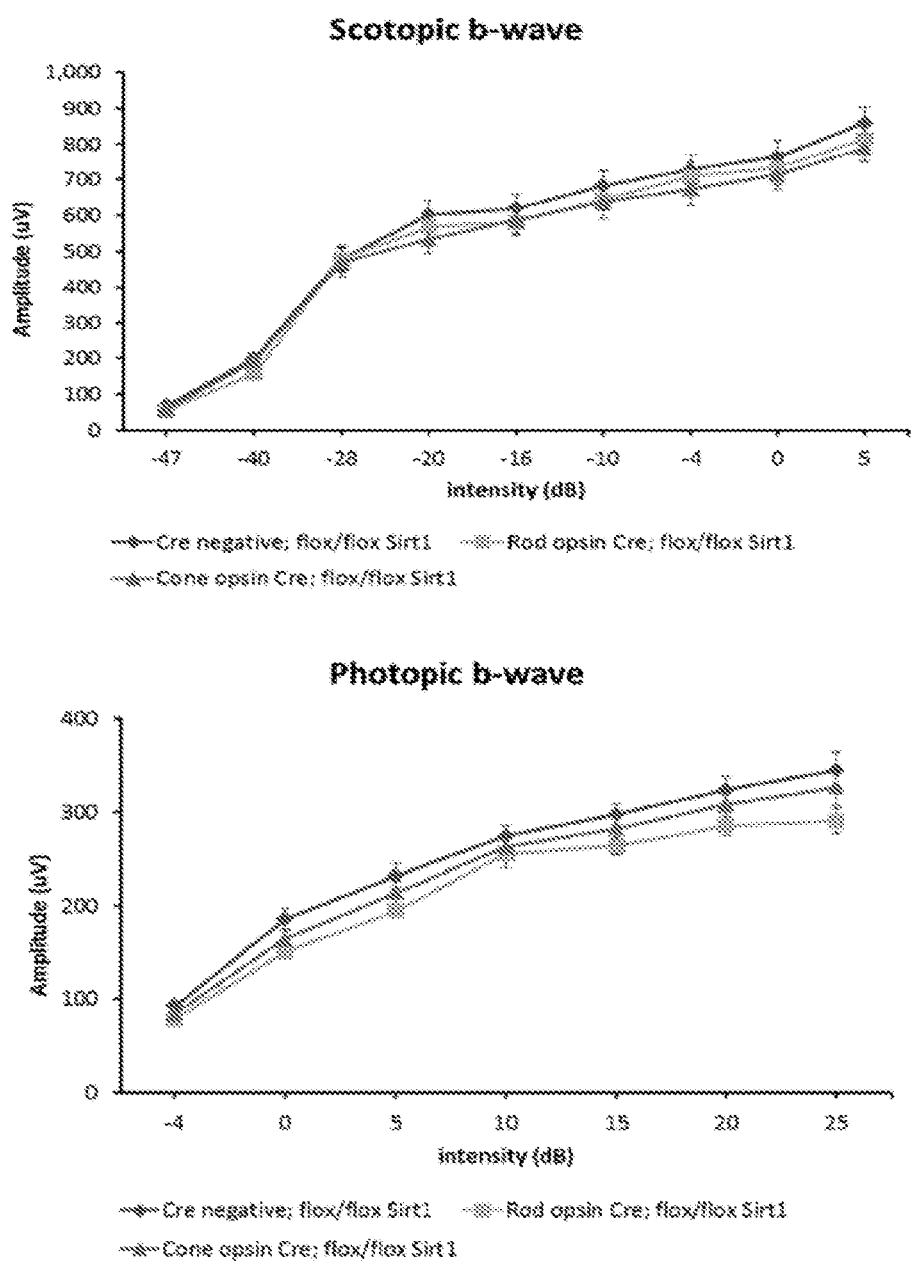
Figure 34B:
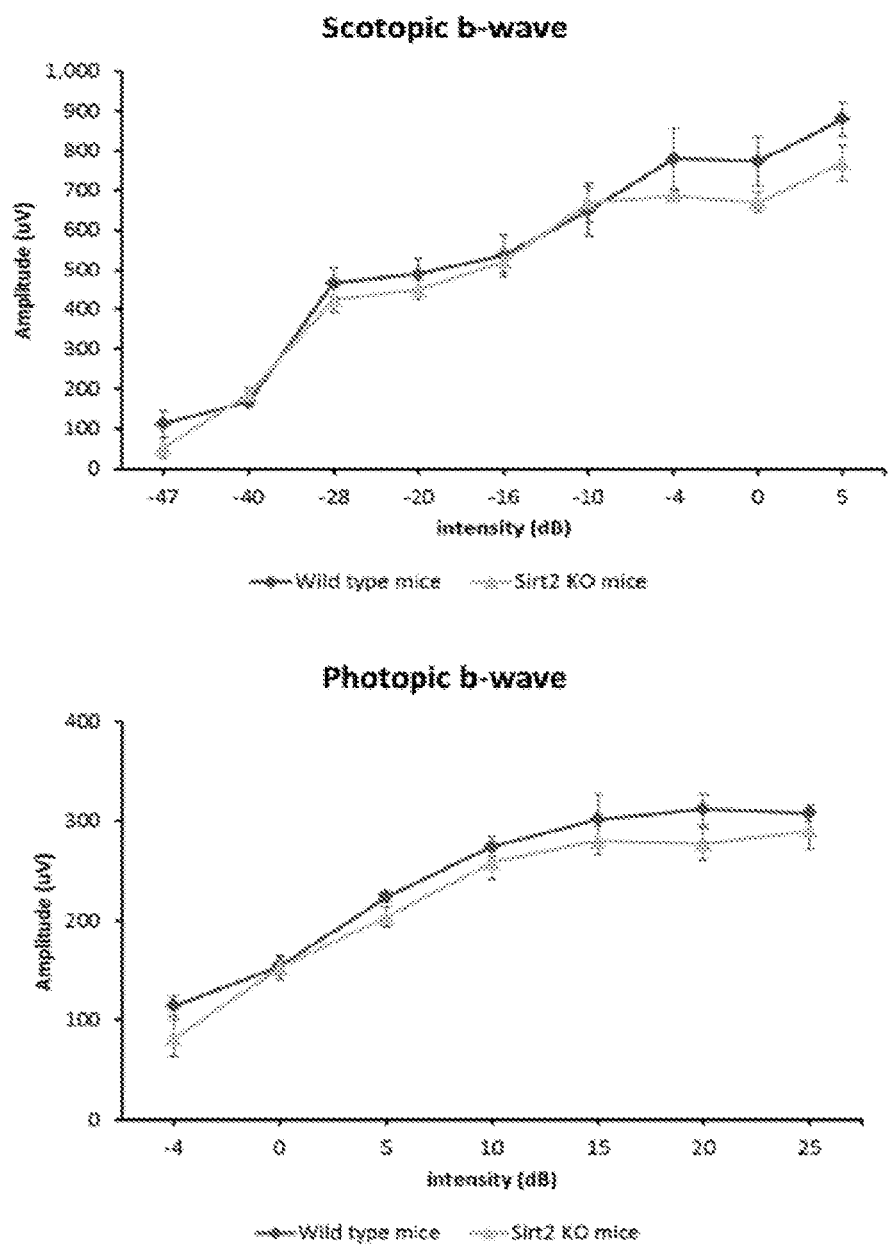
Figure 34F:
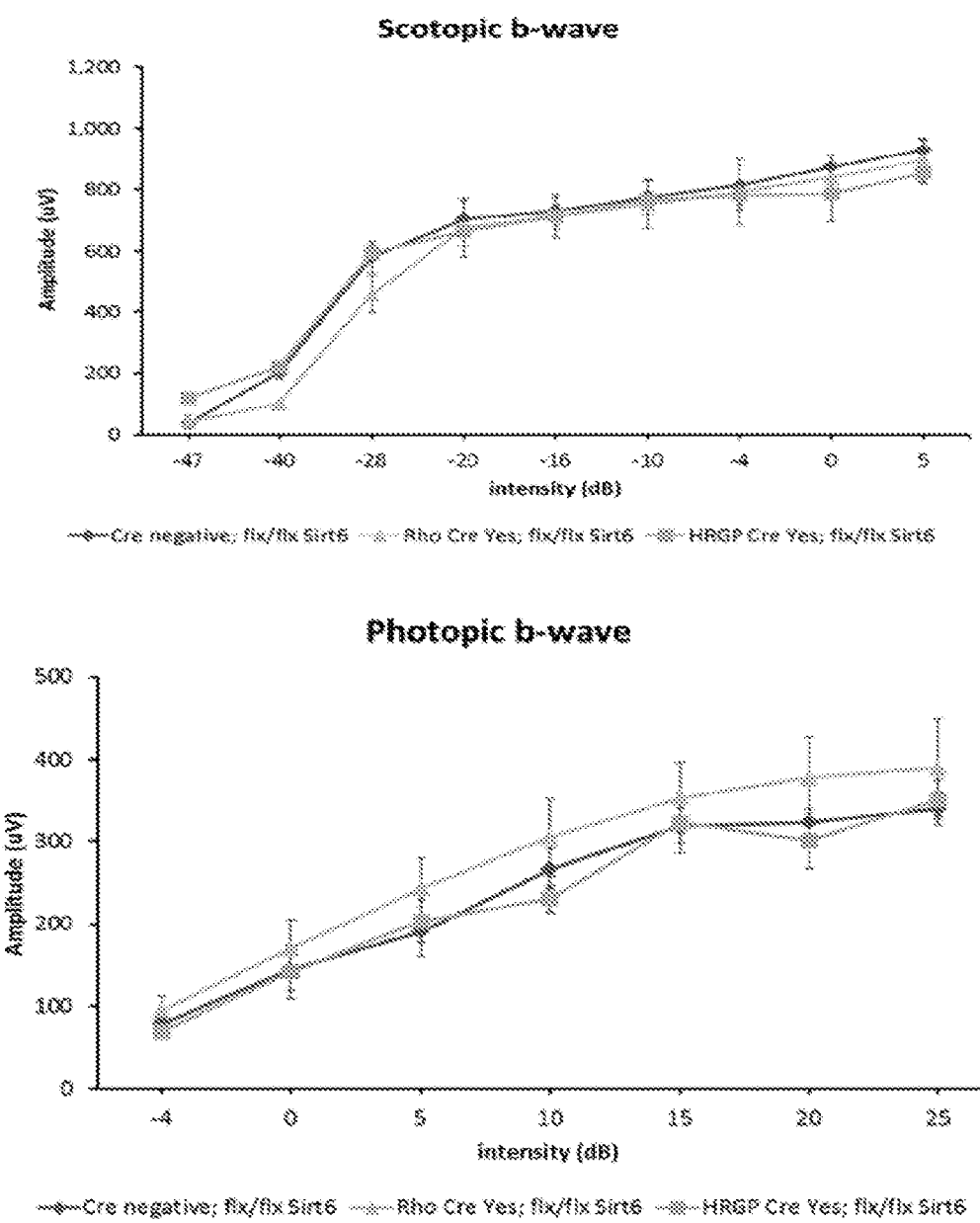

FIG. 33A-B illustrates NMN treatment effect on littermate controls.

FIG. 34A-F illustrates retinal and PR neuron structure and function.

Figure 35:
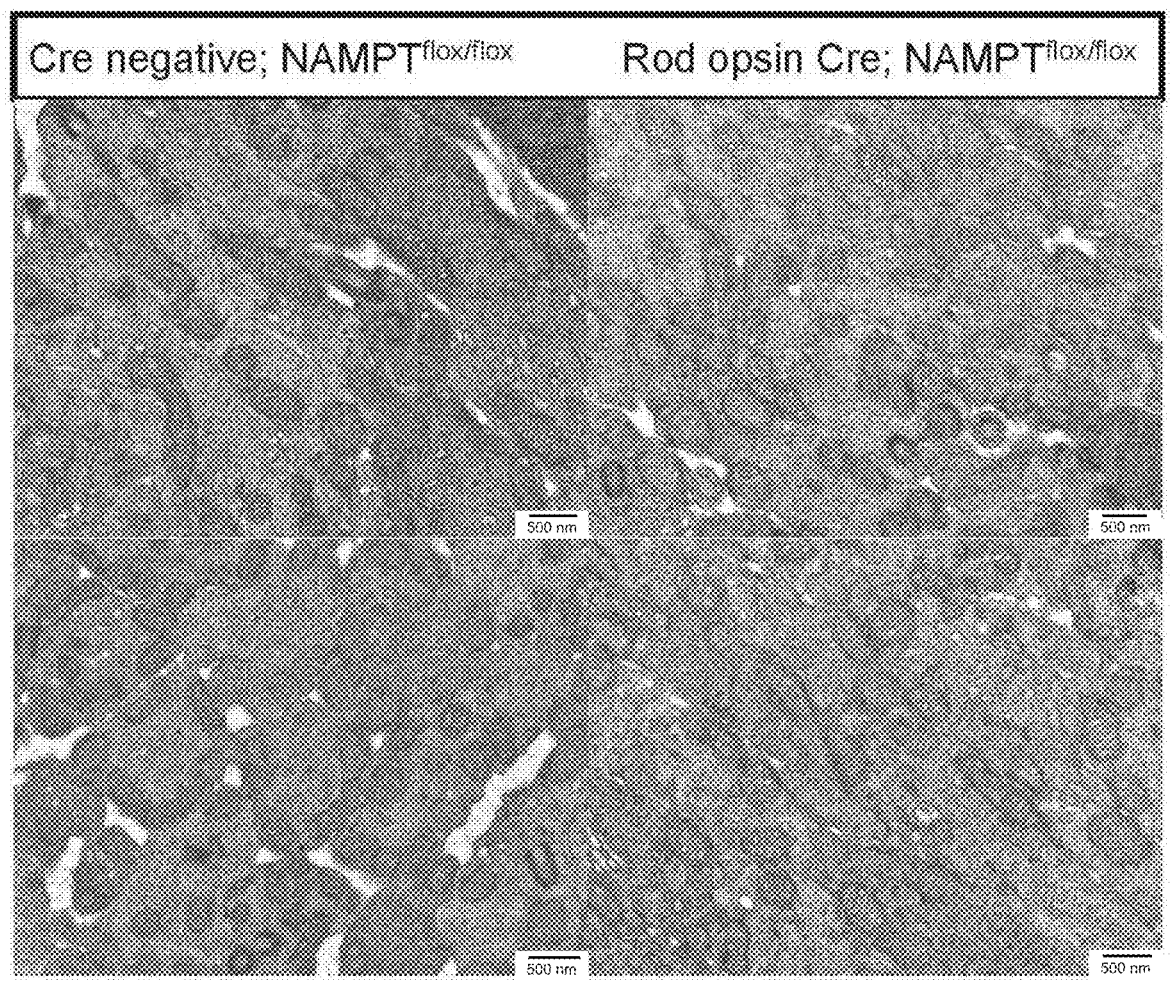

FIG. 35 illustrates changes in inner segments could be identified in rod-CKO mice.

DETAILED DESCRIPTION

Abbreviations

BMD: Bone mineral density
CC: Corpus callosum
DG: Dentate gyms
DXA: Dual-energy X-ray absorptiometry
EIR: Enhanced immediate release
ERG: Electroretinography
FFA: Free fatty acid
HFD: High fat diet
NMN: Nicotinamide mononucleotide
OPC: Oligodendrocyte precursor cells
PR: Photoreceptor
SGZ: Subgranular zone
SVZ: Subventricular zone Methods The methods and compositions described herein utilize laboratory techniques well known to skilled artisans, and can be found in laboratory manuals such as Sambrook, J., et al., Molecular Cloning: A Laboratory Manual, 3rd ed. Cold Spring Harbor Laboratory Press, Cold Spring Harbor, N Y, 2001; Spector, D. L. et al., Cells: A Laboratory Manual, Cold Spring Harbor Laboratory Press, Cold Spring Harbor, N Y, 1998; Nagy, A., Manipulating the Mouse Embryo: A Laboratory Manual (Third Edition), Cold Spring Harbor, N Y, 2003 and Harlow, E., Using Antibodies: A Laboratory Manual, Cold Spring Harbor Laboratory Press, Cold Spring Harbor, N Y, 1999. Methods of administration of pharmaceuticals and dosage regimes, can be determined according to standard principles of pharmacology well known skilled artisans, using methods provided by standard reference texts such as Remington: the Science and Practice of Pharmacy (Alfonso R. Gennaro ed. 19th ed. 1995); Hardman, J. G., et al., Goodman & Gilman's The Pharmacological Basis of Therapeutics, Ninth Edition, McGraw-Hill, 1996; and Rowe, R. C., et al., Handbook of Pharmaceutical Excipients, Fourth Edition, Pharmaceutical Press, 2003. As used in the present description and the appended claims, the singular forms "a", "an" and "the" are intended to include the plural forms as well, unless the context indicates otherwise.

The following Methods are applicable to Examples 1-7
Administration of NMN through Drinking Water and Determination of NMN Stability and Toxicity A 12 month-long NMN administration study using wild-type mice under a regular chow-fed condition was conducted. NMN was administered through drinking water, and two doses of NMN, 100 and 300 mg/kg body weight/day, were tested. The stability of NMN was examined in drinking water and found that NMN was stable in solution. No significant degradation was observed at room temperature. Water intake was also monitored very carefully, and the water intake did not change significantly through the experimental period. To assess beneficial and possible adverse effects of NMN, a variety of physiological parameters were periodically monitored, including body weight, body temperature, food and water intake, fed and fasted blood glucose levels, fed and fasted plasma lipid panels, and glucose and insulin tolerance, in NMN-administered and control mice. Blood chemistry, blood cell counts, urine strip test, and other physiological tests including physical activity test were also checked. Based on all these assessments, no adverse effects, such as malnutrition, or signs of toxicity were observed in either of the 100 mg/kg or 300 mg/kg groups.

Memory Function Study

Two groups of wild-type C57BL/6 mice at ~2 months of age were fed a high fat diet (HFD) containing 42% of the total calories from fat (TD88137; Harlan Taklad). NMN at a dose of 300 mg/kg/day began to be administered through drinking water to one of the HFD-fed groups after 4 months of HFD feeding. The control group was fed a regular chow. After 8 months of HFD feeding with or without 4 months of NMN treatment, the contextual fear conditioning test, a sensitive test to examine the memory function that involves the hippocampus, was conducted for mice in these three groups.

The Following Methods are Applicable to Examples 8-15

Mice

Figures 23A, 23B:
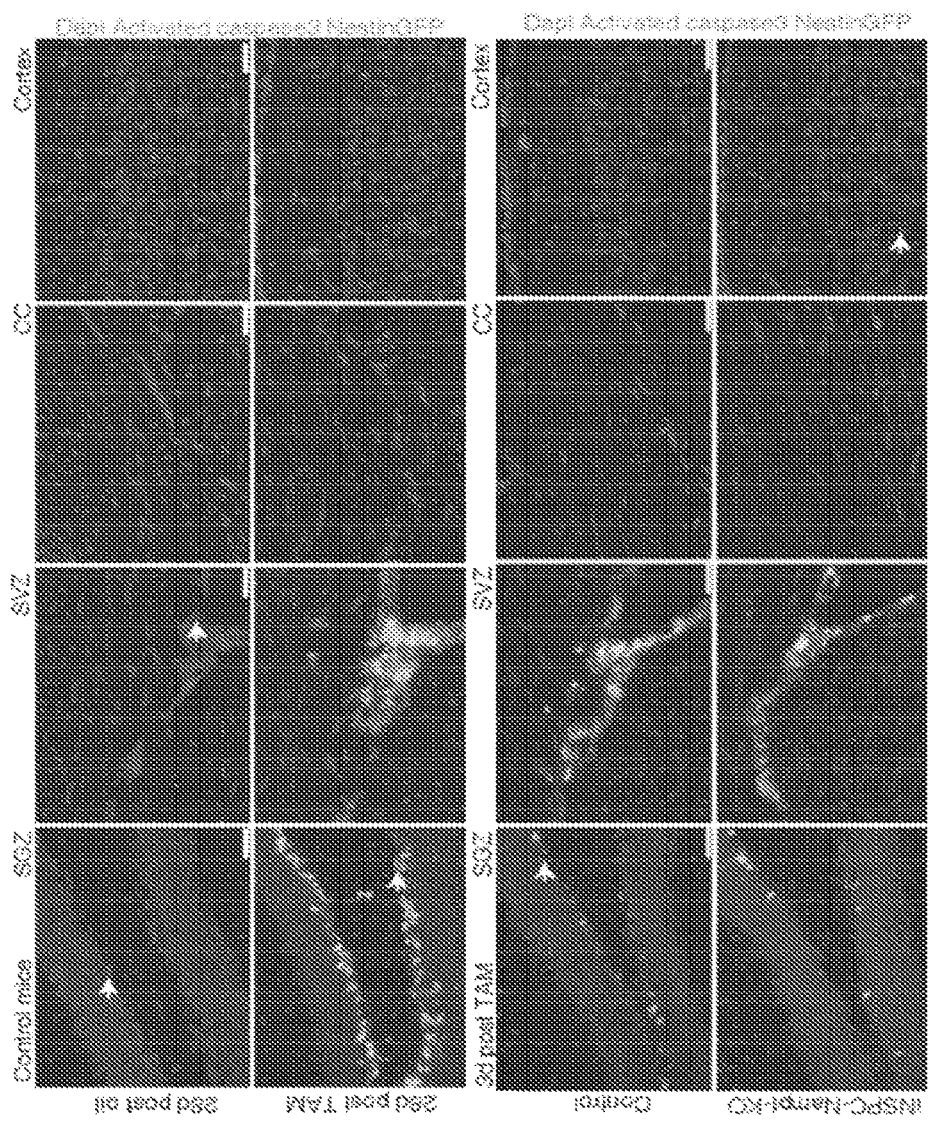
Figure 23C:
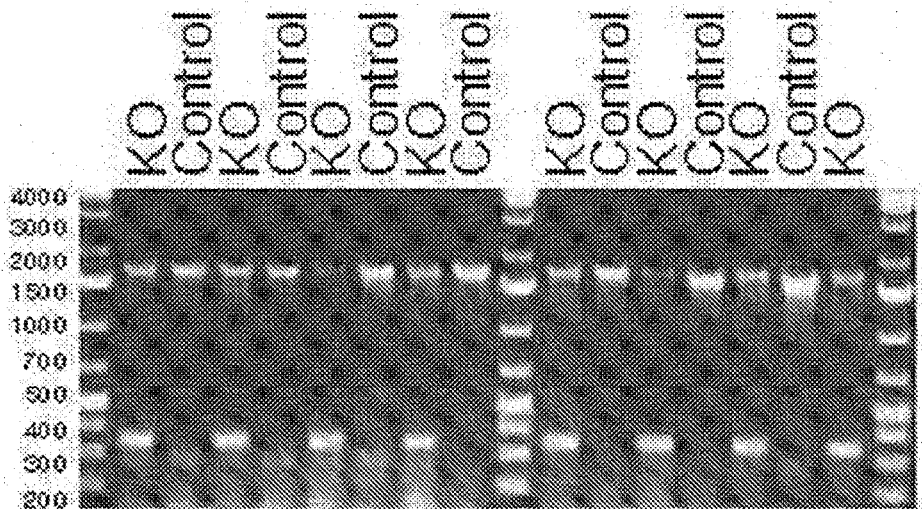

Mice were maintained on a regular chow ad libitum on a 12 hr light/dark cycle (lights on from 6 am to 6 pm). Namptflox/flox mice (Rongvaux et al, 2008), in which exons 5 and 6 of the Nampt gene are flanked by loxP sites, were crossed to Nestin-CreERT2 mice (Lagace et al, 2007) to generate Nampt flox/+; Cre double heterozygous mice. Double heterozygous mice were bred to Namptflox/flox mice to obtain Namptflox/flox; Cre mutant mice (iNSPC-Nampt-KO mice) in the expected Mendelian ratio. To trace the progeny of adult NSPCs and to confirm the specificity and magnitude of the recombination induced by tamoxifen injection, iNSPC-Nampt-KO and Nestin-CreERT2 mice were crossed to a reporter mouse strain that expresses a loxP-flanked STOP cassette that prevents transcription of the downstream enhanced green fluorescent protein [ZsGreen1; Jackson laboratories #7906 (Madisen et al, 2010)]. Recombination PCR on hippocampal extracts of tamoxifen or vehicle treated mice showed successful deletion upon treatment with tamoxifen (FIG. 23C)

Induction of Nampt Deletion

Tamoxifen injections were performed as described previously (Lagace et al, 2007). Briefly, iNSPC-Nampt-KO mice (5-7 weeks old) were administered tamoxifen (TAM, Sigma T5648) at 180 mg/kg/d for 5 days (d, intraperitoneally; dissolved in 10% EtOH/90% sunflower oil), a protocol that produces maximal recombination with minimal lethality (5%) (Lagace et al, 2007).

BrdU Incorporation (BrdU, Sigma, B9285) was diluted in sterile saline and administered by intraperitoneal injections (100 mg/kg body weight). For analysis of the cumulative effects of loss of Nampt, mice were given BrdU twice a day for 2 days and sacrificed the following day or 28 days later. For analysis of the effect of loss of Nampt on adult NSC differentiation and postnatal oligodendrocyte differentiation, mice were given BrdU twice a day for 1 day and sacrificed 2 days later.

Cuprizone

Demyelination was induced by feeding 6 to 8-week-old mice a diet containing cuprizone (bis-cyclohexanone oxaldihydrazone; Sigma C9012) mixed into a ground standard rodent chow for 4 to 5 weeks (Harlan Laboratories, TD.01453). To allow recovery from cuprizone treatment, food was replaced with standard chow for an additional 1 week. This protocol has been shown to successfully demyelinate and remyelinate the hippocampus (Skripuletz et al, 2011).

Immunofluorescence

All tissue sections were and cells incubated in blocking/permeabilization solution containing 10% normal goat serum, 1% BSA, and 0.3% Triton-X in PBS for 45 to 60 min prior to 24 or 48 h of incubation with primary antibodies in 5% normal goat serum and 0.1% Triton-X in PBS at 4° C. at the concentrations listed below. Alexa627, Alexa488, or Cy3 conjugated-secondary antibodies diluted in 2% normal goat serum, 1% BSA, and 0.1% Triton-X in PBS were added for 2 h at room temperature. Nuclei were stained with 4,6-diamidino-2-phenylindole (Sigma) for 10 min at room temperature.

Cells were harvested by fixation with 4% paraformaldehyde in PBS (15 min). Mice were anesthetized by i.p. injection of ketamine and xylazine, and perfused transcardially through left ventricle with cold 0.1 M phosphate buffer at pH 7.4 followed by a phosphate-buffered solution of 4% paraformaldehyde (PFA). Brains were postfixed with 4% PFA overnight and placed into 15% sucrose followed by 30% sucrose, frozen, and stored at −80° C. until use. Coronal sections (30 μm) were made by cryostat in a 1 in 8 series and stored at −30° C. in cryoprotectant until use. To remove any endogenous peroxidase activity, all sections were incubated with 3% H2O2 for 10 min. Tissue sections used to assess BrdU incorporation were treated before the immunostaining procedure with 50% formamide in 2× saline/sodium citrate (SSC) at 65° C. for 2 h, 2N HCl for 30 min at 37° C., 0.1 M borate pH 8.5, and then washed twice with PBS before proceeding with the staining protocol. Tissue sections not used to assess BrdU incorporation were either incubated in 50% formamide in 2× saline/sodium citrate (SSC) at 65° C. for 2 h or 10 mM citrate buffer at 65° C. for 1 h before proceeding with the staining protocol. Detection of Dcx, Nestin, Nampt, and APC was performed using the TSA-Plus fluorescein kit (PerkinElmer).

Quantification

For tissue sections, high-magnification (20×, 0.8DICII or 40× oil 1.3DICII) microscopic imaging was performed using a Zeiss Axioimage.Z1. Images were taken in z-stacks of 1 μm steps through the range of tissue section immunoreactivity. For the dorsolateral corner of the SVZ, images were taken from bregma 1.10 to −0.10 mm. For the corpus callosum, images were taken from bregma −1.06 to −2.54 mm. For the dentate gyrus, images were taken from bregma −1.34 to −3.64 mm. Quantification was performed blinded to genotype on 3–8 tissue sections per animal. Cell densities were estimated by the number of immunoreactive cells divided by the area of the structure, measured with ImageJ.

Verification of colocalization was achieved by importing stacks of Z images into ImageJ and performing 3D rendering. For cells, 10 or 20× microscopic imaging was performed using a Zeiss Axioimage.Z1. Quantification was performed blinded to genotype on 2 to 3 fields of view per sample and treatment, from 3 to 9 independent samples.

NAD+ Measurement

NAD+ Levels were Determined Using an HPLC System (Shimadzu) with a Supelco LC-18-T column (15 cm×4.6 cm; Sigma), as described previously (Yoshino et al, 2011).

Microarrays and Bioinformatic Analyses

For individual genes, raw microarray data were subjected to Z score transformation, and Z ratios were calculated as described previously (Cheadle et al, 2003). Subsequent analysis and Parametric Analysis of Gene Set Enrichment (PAGE) analysis was performed as previously described (Yoshino et al, 2011). The microarray data used in this study has been deposited into the NCBI GEO database (GEO accession number GSE49784).

Western Blotting

Protein extracts (15-50 μg) from mouse hippocampi or neurospheres were prepared as previously described (Yoshino et al, 2011).

Quantitative Real-Time RT-PCR

Total RNA was extracted from the hippocampus using an RNeasy kit (Qiagen) and reverse-transcribed into cDNA with a High Capacity cDNA Reverse Transcription kit (Applied Biosystems). Quantitative real-time RT-PCR was conducted with the TaqMan Fast Universal PCR Master mix and appropriate TaqMan primers for each gene with the GeneAmp 7500 fast sequence detection system (Applied Biosystems). Relative expression levels were calculated for each gene by normalizing to Gapdh levels and then to a control.

Reagents

The following primary and secondary antibodies were used:

Primary antibodies and their uses or cell type specificities (See von Bohlen and Halbach, 2011): Actin: normalization, WB 1:4000 CPO1, Sigma; Gapdh: normalization, WB 1:4000 6C5 Millipore CB1001; Nampt: IHC 1:1000; WB 1:3000 Alexis Biochemicals ALX-804-717-C100; Pdgfrα: oligodendrocyte precursor cells, IF 1:500 APAS BD Biosciences; Olig2: all oligodendrocyte lineage cells, IHC 1:500, IF 1:1000; Millipore; 04: immature oligodendrocytes, IF 1:1000 Millipore, MAB345; APC: oligodendrocytes, IHC 1:1000 Millipore CC-1 OP80; MBP: mature oligodendrocytes, IHC 1:1000 Millipore MAB386; Ki67: proliferating cells, IHC, IF 1:500; WB 1:3000 Abcam ab66155; Pcna: proliferating cells, WB 1:2000; PC10 Cell signaling #2586; 5-bromo-2'-deoxyuridine (BrdU): a thymine analog that incorporates into the DNA of cells in S phase, IHC 1:500; OBT0030 Accurate; Activated caspase 3: apoptosis, IHC, IF 1:500; Cell Signaling #9661; LC3B: autophagy, WB 1:1000; Novus NB600-1384; TUNEL: cell death, Roche In Situ Cell Death Detection Kit 11 684 795 910; Dcx: newly born neurons, IHC 1:1000; Cell Signaling #4604; NeuN: mature neurons, IHC, 1:500, Millipore, MAB377; Nestin: NSPCs, IHC, IF 1:1000, Millipore MAB353; Sox2: NSPCs, IHC, IF 1:500; WB 1:2000; Millipore AB5603; Gfap: NSPCs and astrocytes, IHC, IF 1:1000; Millipore MAB360;

Secondary antibodies: Jackson ImmunoResearch anti-rat, anti-rabbit, anti-mouse Cy3 (1:400), Alexa Fluor488 (1:200), and Alexa Fluor647 (1:200). Anti-rabbit, anti-mouse horseradish peroxidase (Invitrogen).

FK866 (Hasmann & Schemainda, 2003) (Sigma F8557), EX527 (Peck et al, 2010) (Cayman Chemical 10009798), and AGK2 (Outeiro et al, 2007) (Sigma A8231) were dissolved in DMSO and used to inhibit Nampt, Sirt1, and Sirt2 respectively.

Neurosphere Culture

Neurosphere cultures and culture media were prepared as described by Dasgupta & Gutmann, 2005 and Lu & Ramanan, 2012 with the following minor modifications. Briefly, postnatal hippocampi were dissected in HibernateA (Invitrogen, A12475-01) and trypsinized at 37° C. for 7 m. Cells were mechanically dissociated by pipetting and pelleted by centrifugation (1700 rpm, 7 min). Dissociation medium (0.1% sodium bicarbonate, 15 mM HEPES, 0.5% glucose in HBSS) was used to wash the cells before they were resuspended in growth medium. Growth medium consisted of DMEM:F12 (1:1, Invitrogen 11966-025 and 21700-075, respectively), B27 (Invitrogen, 17504-044), N2 (Invitrogen, 17502-048), Pen/Strep (Invitrogen), epidermal growth factor (EGF, 20 ng/ml, Sigma, E4127), fibroblast growth factor (FGF, 10 ng/mL, R&D Systems, 233-fb), and heparin (Sigma). Cultures were maintained at 37° C. with 5% CO2, and passaged twice before use in experiments. Three to nine independent samples, each in 1 to 3 replicates, from at least two different litters, were used in all experiments. Neurospheres were cultured in the physiological glucose level of 5 mM (Dienel & Cruz, 2006), which has been previously shown to have no negative consequences on NSPC proliferation, differentiation, or death (Fu et al, 2006; Gao & Gao, 2007).

Neurosphere Infection

Neurospheres derived from $Nampt^{flox/flox}$ mice were infected with Ad5 Cre recombinase- or b-galactosidase-expressing (LacZ, control) adenoviruses at an MOI of 100. All assessments were performed at least 6 days post infection.

Neurosphere Proliferation Analysis

Neurospheres derived from $Nampt^{flox/flox}$ mice were dissociated by trypsin digestion and seeded at similar cell densities in 24-well plates with fresh growth medium. Every 24 hours, neurospheres from triplicate wells were collected, dissociated, and counted on a hemocytometer using 0.2% trypan blue exclusion to distinguish viable cells. For analysis of neurosphere diameter, the largest neurosphere in each well was imaged (20× objective) and the diameter was calculated using ImageJ. For secondary neurosphere analysis, the total number of neurospheres in each well was counted at 7 days post-plating.

Neurosphere Differentiation

Three to five days after their first passage, neurospheres were trypsinized, washed with dissociation medium, and plated at 150,000 cells per well in 24-well plates in differentiation medium [growth medium without FGF and EGF and with BDNF (5 ng/mL, Peprotech, 450-02) on glass coverslips coated with poly-D-lysine (50 ug/mL; Sigma) and laminin (20 ug/mL; BD Biosciences)]. 6-well plates were coated with poly-D-lysine (20 ug/mL) and laminin (10 ug/mL). To enrich for oligodendrocytes, PDGFαα (10 ng/ml, Peprotech 100-13A) was added to neurospheres at passage 2 and PDGFαα (2.5 ng/ml) and 3,3-,5-triiodo-L-thyronine (T3, 40 ng/ml, Sigma T4397) were added to differentiation medium. The percentage of oligodendrocyte precursor cells (OPCs) generated was analyzed after 2 d of differentiation, and the percentage of differentiated oligodendrocytes was analyzed after 6-7 d of differentiation.

Statistical Analyses

Differences between two groups were assessed using the Student's unpaired t-test. Comparisons among several groups were performed using one-way ANOVA with the Tukey-Kramer post hoc test except for FIG. 16J and FIG. 24D-E, in which the Games-Howell post-hoc test and the Fisher LSD posthoc test were used, respectively. P values <0.050 were considered statistically significant.

The Following Methods are Applicable to Example 15

Administration of NMN Through Drinking Water and Determination of NMN Stability and Toxicity A 12 month-long NMN administration study using wild-type mice under a regular chow-fed condition was conducted. NMN was administered through drinking water, and two doses of NMN, 100 and 300 mg/kg body weight/day, were tested. The stability of NMN was examined in drinking water and found that NMN was stable in solution. No significant degradation was observed at room temperature. Water intake was also monitored very carefully, and the water intake did not change significantly through the experimental period. To assess beneficial and possible adverse effects of NMN, a variety of physiological parameters were periodically monitored, including body weight, body temperature, food and water intake, fed and fasted blood glucose levels, fed and fasted plasma lipid panels, and glucose and insulin tolerance, in NMN-administered and control mice. Blood chemistry, blood cell counts, urine strip test, and other physiological tests including physical activity test were also checked. Based on all these assessments, no adverse effects, such as malnutrition, or signs of toxicity were observed in either of the 100 mg/kg or 300 mg/kg groups.

EXAMPLES

The present teachings including descriptions provided in the Examples that are not intended to limit the scope of any claim or aspect. Unless specifically presented in the past tense, an example can be a prophetic or an actual example. The following non-limiting examples are provided to further illustrate the present teachings. Those of skill in the art, in light of the present disclosure, will appreciate that many changes can be made in the specific embodiments that are disclosed and still obtain a like or similar result without departing from the spirit and scope of the present teachings.

Example 1

This example illustrates a suppressive effect of NMN on age-associated body weight increase.

Figure 2:
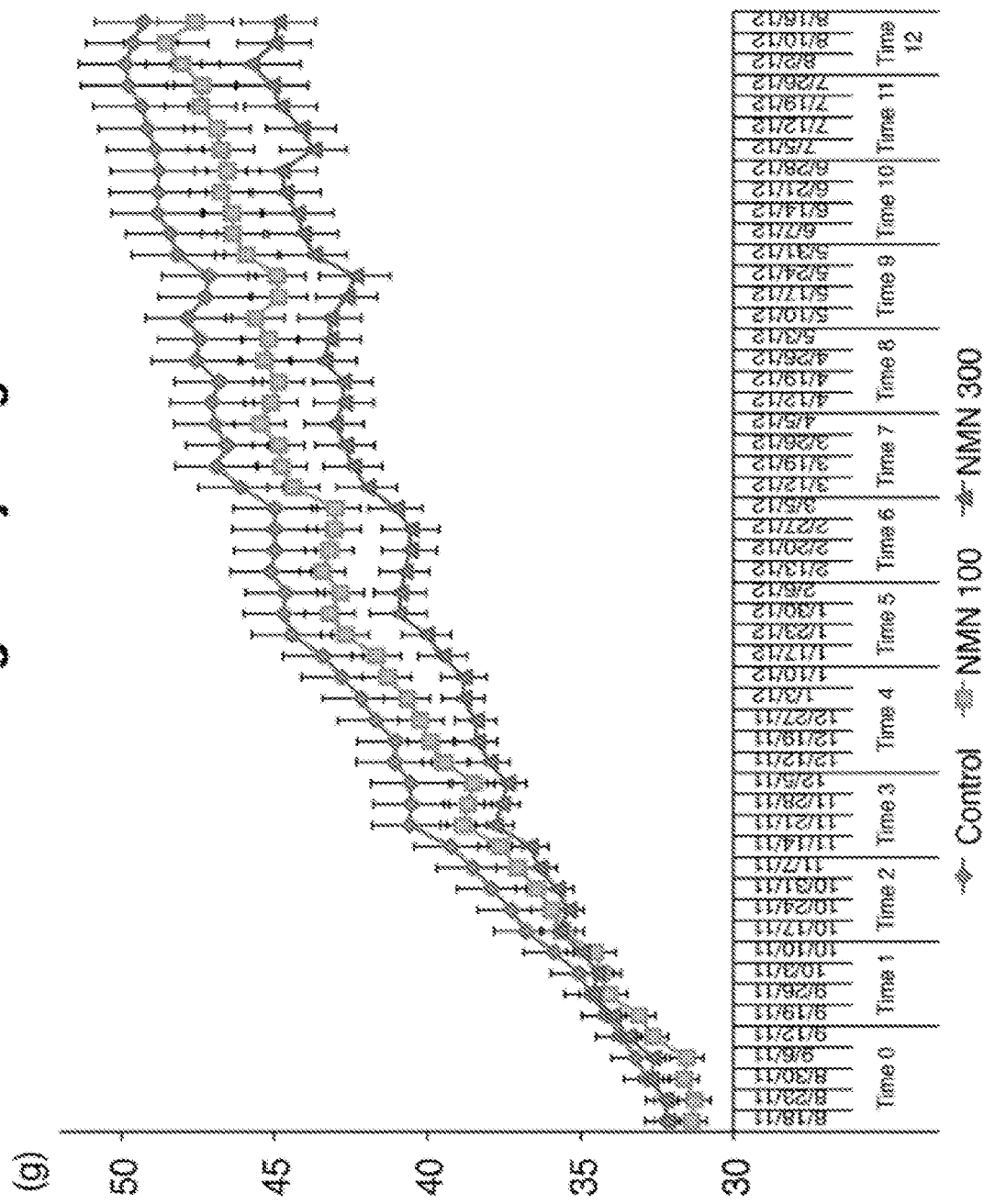
FIG. 2 illustrates age-associated body weight increase.

In these experiments, NMN was administered to mice at a dosage rate of 100 mg/kg per day or 300 mg/kg per day. NMN demonstrated a suppressive effect on age-associated body weight increase in a 12 month-long NMN administration study. (See Methods; Administration of NMN through Drinking Water and Determination of NMN Stability and Toxicity) In these experiments, NMN demonstrated a suppressive effect on age-associated body weight increase (FIG. 2). The results were analyzed with two-way RANOVA and one-way RANOVA with the unweighted linear term. All values are presented as mean±SEM (n=15, 14, and 14 for control, 100, and 300 mg/kg NMN-administered groups).

Average body weights in each group are shown through 0-12 months. There was a statistically highly significant interaction between time and group (P<0.001 from the two-way RANOVA), and linear dose-dependent effects were statistically significant at all time points through 4-12 months (P<0.05 from one-way RANOVA with the unweighted linear term). The average percent body weight reduction normalized to control mice were 4% and 9% in 100 and 300 mg/kg groups, respectively.

This suppressive effect of NMN on age-associated body weight increase was further recognized by calculating body weight gains in each group (FIG. 3 0569) In FIG. 3, average body weight gains in each group are shown through 0-12 months. The results were analyzed with two-way RANOVA and one-way RANOVA with the unweighted linear term. All values are presented as mean±SEM (n=15, 14, and 14 for control, 100, and 300 mg/kg NMN-administered groups). The interaction between time and group was statistically highly significant (P<0.001 from the two-way RANOVA), and the linear dose-dependent effects were significant at all points through 2-12 months (P<0.01 from the one-way RANOVA with the unweighted linear term). The average numbers of percent body weight gain suppression normalized to control mice were 12% and 30% in 100 and 300 mg/kg groups, respectively.

Taken together, these results from this 12 month-long NMN administration study demonstrate that NMN can suppress age-associated body weight increase in a dose-dependent manner, without showing any serious side effects during the entire experimental period. These results demonstrate that NMN can be used for the treatment, reduction or prevention of age-associated obesity.

Example 2

This example illustrates an enhancement of energy metabolism over age with NMN administration.

In this long-term NMN administration study (See Methods; Administration of NMN through Drinking Water and Determination of NMN Stability and Toxicity), the inventors measured oxygen consumption, energy expenditure, and respiratory quotient for control, mice administered 100 mg/kg NMN per day and mice administered 300 mg/kg NMN per day at the 12 month time point by using the Oxymax Lab Animal Monitoring System (Columbus Instruments, Columbus, OH).

FIG. 4 shows oxygen consumption in control, 100 and 300 mg/kg NMN-administered mice. The data were analyzed by Wilcoxon signed ranks test. All values are presented as mean±SEM (n=5 in each group). *P<0.001. As illustrated in FIG. 4**, oxygen consumption significantly increased in both 100 mg/kg and 300 mg/kg groups when examined at times 0 through 27 (P<0.001, Wilcoxon signed ranks test).

Energy expenditure measurements also showed significant increases in both 100 mg/kg and 300 mg/kg groups through 24 hours (P<0.001, Wilcoxon signed ranks test) (FIG. 5). Energy expenditure in control, 100 and 300 mg/kg NMN-administered mice is presented in FIG. 5. The data were analyzed by Wilcoxon signed ranks test. All values are presented as mean±SEM (n=5 in each group). ***P<0.001.

Respiratory quotient in control, 100 and 300 mg/kg NMN-administered mice are presented in FIG. 6. The data were analyzed by Wilcoxon signed ranks test. All values are presented as mean±SEM (n=5 in each group). *P<0.001. Respiratory quotient significantly decreased in both groups (P<0.001, Wilcoxon signed ranks test) (FIG. 6 0569**). Without being limited by theory, these results suggest that NMN increases energy expenditure by switching their main energy source from glucose to fatty acids, thereby increasing fatty acid oxidation. Without being limited by theory, this phenomenon could provide an explanation for the suppressive effect of NMN on age-associated body weight increase.

Example 3

This example illustrates a suppressive effect of NMN on age-associated increases in blood lipid levels.

Blood levels of cholesterol, triglycerides, and free fatty acids are shown over 12 months in the control and the 100 and 300 mg/kg NMN-administered cohorts in FIG. 7. The results were analyzed with two-way RANOVA and one-way RANOVA. All values are presented as mean±SEM (n=25 for each group).

Blood levels of cholesterol, triglycerides, and free fatty acids are shown over 12 months in the control and the 100 and 300 mg/kg NMN-administered cohorts. The results were analyzed with two-way RANOVA and one-way RANOVA. All values are presented as mean±SEM (n=25 for each group).

In the control cohort of a long-term NMN study (See Methods; Administration of NMN through Drinking Water and Determination of NMN Stability and Toxicity), blood levels of cholesterol showed steady increases over time, whereas blood levels of triglycerides and free fatty acids (FFAs) peaked at the 6-month time point and then decreased. However, in both 100 and 300 mg/kg groups, these age-associated increases in cholesterol and free fatty acids tended to be suppressed (FIG. 7A-C). In particular, the interaction between time and group was statistically highly significant for FFAs (P=0.003 from the two-way RANOVA), and the 300 mg/kg group did not show any statistically significant increase over time, whereas the control and the 100 mg/kg groups did show statistically significant increases over 12 months and the first 6 months, respectively (P<0.05 from tests of within-subjects effects in the one-way RANOVA). All values are presented as mean±SEM (n=25 for each group). Although the average level of free fatty acids at the 0-month time point in the 300 mg/kg group was significantly higher than those in the other two groups, NMN at the dose of 300 mg/kg suppressed age-associated increases in blood levels of FFAs, particularly at the 6-month time point (P<0.05 from the one-way ANOVA with the Dunnett T3 post-hoc test). Therefore, NMN is capable of suppressing age-associated increases in blood lipid levels, particularly blood FFA levels.

Without being limited by theory, since NMN has an effect of suppressing age-associated body weight increase, it was hypothesized that NMN's effect on blood lipid levels could be due to the reduction in body weight. To address this possibility, lipid levels were compared among individual mice whose average body weights were matched through control and experimental cohorts. Body weight-matched blood levels of cholesterol, triglycerides, and free fatty acids are shown over 12 months in the control and the 100 and 300 mg/kg NMN-administered cohorts in FIG. 8. The results were analyzed with two-way RANOVA and one-way RANOVA. All values are presented as mean±SEM (n=10-15 for each group). After matching body weight, blood cholesterol levels became very similar through control and experimental groups, whereas FFA levels were still lower in 100 and 300 mg/kg groups compared to those in the control group (FIG. 8A-C). Even after body weight match, the interaction between time and group was still statistically highly significant for FFAs (P=0.007 from the two-way RANOVA), and again, the 300 mg/kg group did not show any statistically significant increases over time, whereas the control and the 100 mg/kg groups showed significant increases over time (P<0.01 from tests of within-subjects effects in the one-way RANOVA). Blood FFA levels tended to be lower in the 100 mg/kg and 300 mg/kg groups compared to those in the control group after the 6-month time point, although the differences did not reach statistical significance (FIG. 8C). All values are presented as mean±SEM (n=10-15 for each group). These findings indicate that NMN has the effect of suppressing the age-associated increase in blood FFA levels, independent of the reduction in body weight. Without being limited by theory, the effect of NMN on blood cholesterol levels may be secondary to the effect of suppressing age-associated body weight increase.

It has been reported that chronic treatment with nicotinic acid tends to increase blood FFA levels, whereas it lowers total cholesterol and triglyceride levels (Wang, W., et al. Am. J. Phyisol. Endocrinol. Metab. 279: E50-E59, 2000). As shown herein, NMN has a capability of suppressing the age-associated increase in blood FFA levels, which distinguishes NMN from nicotinic acid. NMN is also able to reduce cholesterol levels through the suppression of age-associated body weight increase. Whereas chronic administration of nicotinic acid can cause skeletal muscle insulin resistance (Fraterrigo, G., et al. Cardiorenal. Med. 2: 211-7, 2012), NMN does not show any adverse effect on glucose metabolism. Therefore, NMN administration can be an effective intervention to suppress age-associated increases in blood lipid levels.

Example 4

This example illustrates that administration of NMN enhances insulin sensitivity in old individuals.

Figure 9A:
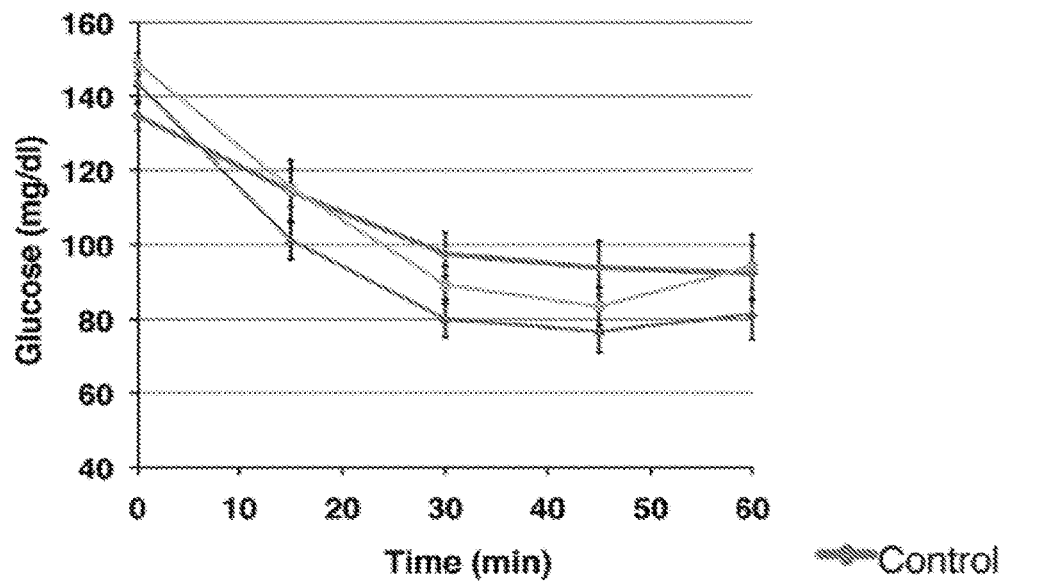
FIG. 9A-B illustrates insulin tolerance shown in (A) blood glucose levels and (B) percent glucose changes in control and the 100 mg/kg and 300 mg/kg NMN-administered groups at the 12-month time point.
Figure 9B:
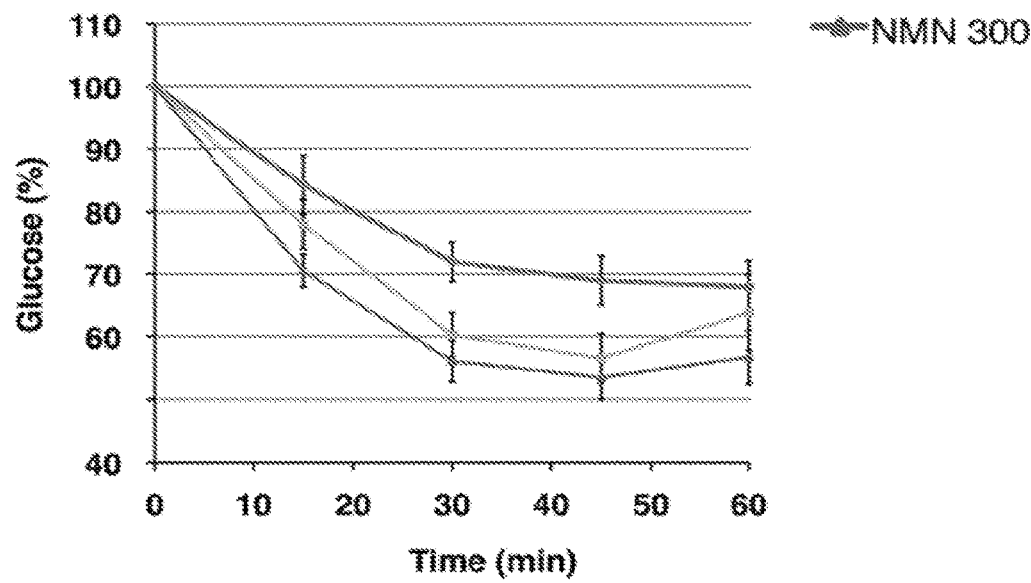

In these investigations, insulin sensitivity, assessed by the insulin tolerance test, showed significant differences among the control and the 100 mg/kg and 300 mg/kg NMN-administered groups after the 12-month time point. (See Methods; Administration of NMN through Drinking Water and Determination of NMN Stability and Toxicity). As illustrated in FIG. 9A-B, insulin tolerance results from body weight-matched mice in the control and the 100 and 300 mg/kg NMN-administered groups at the 12-month time point are presented. Blood glucose levels (FIG. 9A) and percent glucose changes (FIG. 9B) after insulin injection are shown. The results were analyzed with two-way RANOVA and one-way ANOVA. All values are presented as mean±SEM (n=10-15 for each group).

In these experiments, the last measured time point when mice reached 17 month-old, the NMN-administered, body weight-matched mice showed significantly enhanced insulin sensitivity compared to the body weight-matched control group (FIG. 9A). There was a statistically significant interaction between time and group (P=0.023 from the Greenhouse-Geisser test in two-way RANOVA), and the linear dose-dependent effects were statistically significant or close to significance at the 30-min and 45-min time points, respectively (P=0.026 and P=0.061 in the one-way ANOVA with unweighted linear term). The results were analyzed with two-way RANOVA and one-way ANOVA. All values are presented as mean±SEM (n=10-15 for each group). This enhanced insulin sensitivity in the 100 mg/kg and 300 mg/kg groups was recognized further when plotting percent glucose changes (FIG. 9B), although the interaction between time and group did not reach statistical significance in this assessment (P=0.091 from the Greenhouse-Geisser test in two-way RANOVA). Long-term NMN administration can enhance insulin sensitivity in old mice, indicating that NMN administration is an effective anti-aging intervention to maintain better insulin sensitivity in the elderly.

Example 5

This example illustrates improvement of memory function under a high-fat diet (HFD) by administration of NMN. (See Methods; Memory Function Study)

Figure 10:
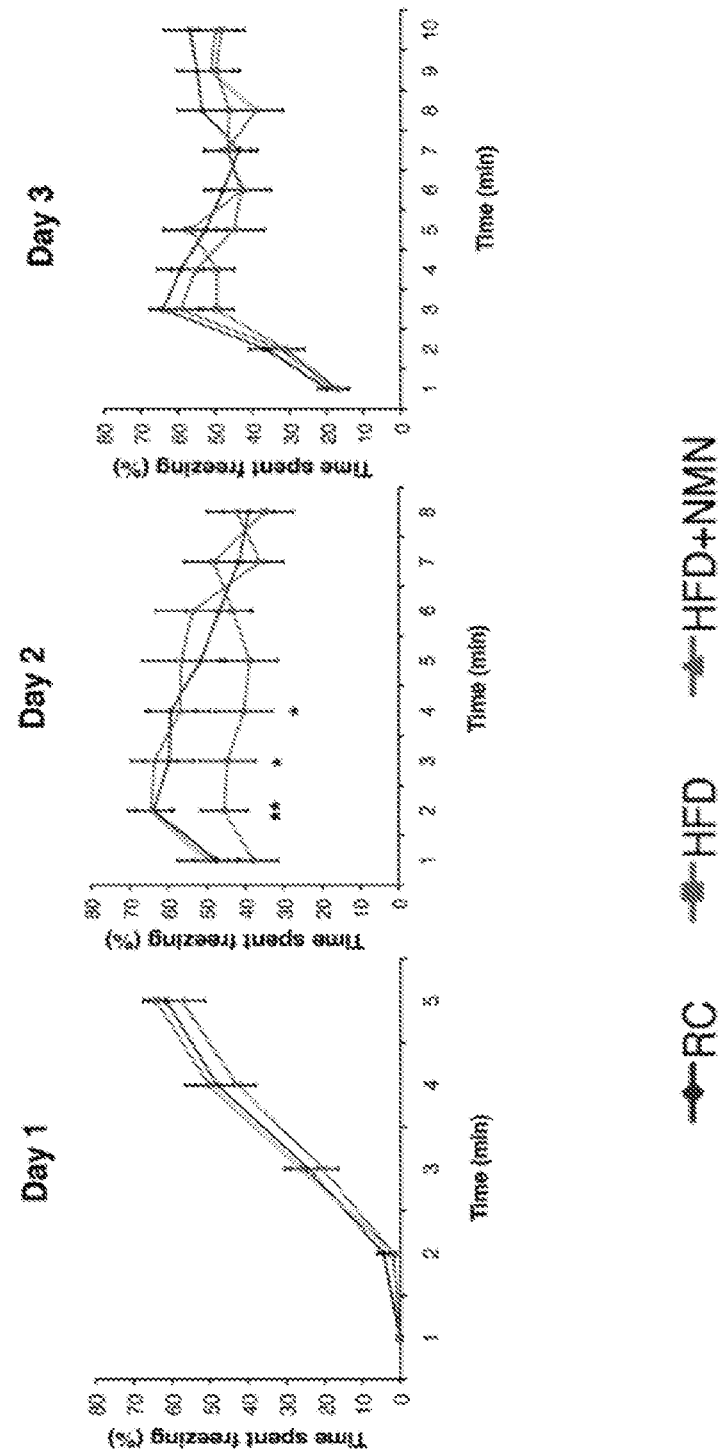
FIG. 10 illustrates freezing responses of regular chow-fed control, HFD-fed, and HFD-fed, NMN-treated mice in contextual and cued fear conditioning tests on Day 1, Day 2 and Day3.

FIG. 10 illustrates freezing responses of regular chow-fed control, HFD-fed, and HFD-fed, NMN-treated mice in contextual and cued fear conditioning tests on Day 1, Day 2 and Day3. NMN was administered at the dose of 300 mg/kg/day for 4 months. On Day 1 of the study, mice were given an auditory cue and then a mild electric foot shock, and a time of freezing was analyzed individually. On Day 2, the trained mice were placed into a training chamber with no tone cues, and their freezing responses were evaluated. On Day 3, cued fear conditioning, which does not involve the hippocampus, was tested by giving the same tone cue used in the conditioning session (Day 1) and analyzing their freezing responses. HFD-fed mice showed an impairment of contextual fear conditioning on Day 2 compared to regular chow-fed control mice but did not show any defect in the conditioning session on Day 1 and the cued fear conditioning test on Day 3 (FIG. 10), demonstrating that HFD specifically impairs the hippocampus-dependent memory function. NMN-treated, HFD-fed mice demonstrated freezing responses indistinguishable from those of regular chow-fed control mice in the contextual fear conditioning test on Day 2. Their freezing responses did not differ from those of control mice on both Day 1 and Day 3. These results demonstrate that the 4-month administration of NMN in mice can restore the normal hippocampus-dependent memory function even under a HFD-fed condition. NMN was administered at the dose of 300 mg/kg/day for 4 months. The results were analyzed by one-way ANOVA with unweighted quadratic term. All values are presented as mean±SEM (n=17, 15, and 12 for regular chow-fed control, HFD-fed, and HFD-fed, NMN-treated mice, respectively). ** P<0.01; * P<0.05. These results demonstrate that the 4-month administration of NMN in mice can restore the normal hippocampus-dependent memory function even under a HFD-fed condition.

Example 6

This example illustrates the improvement of retinal photoreceptor cell function over age.

Figure 11:
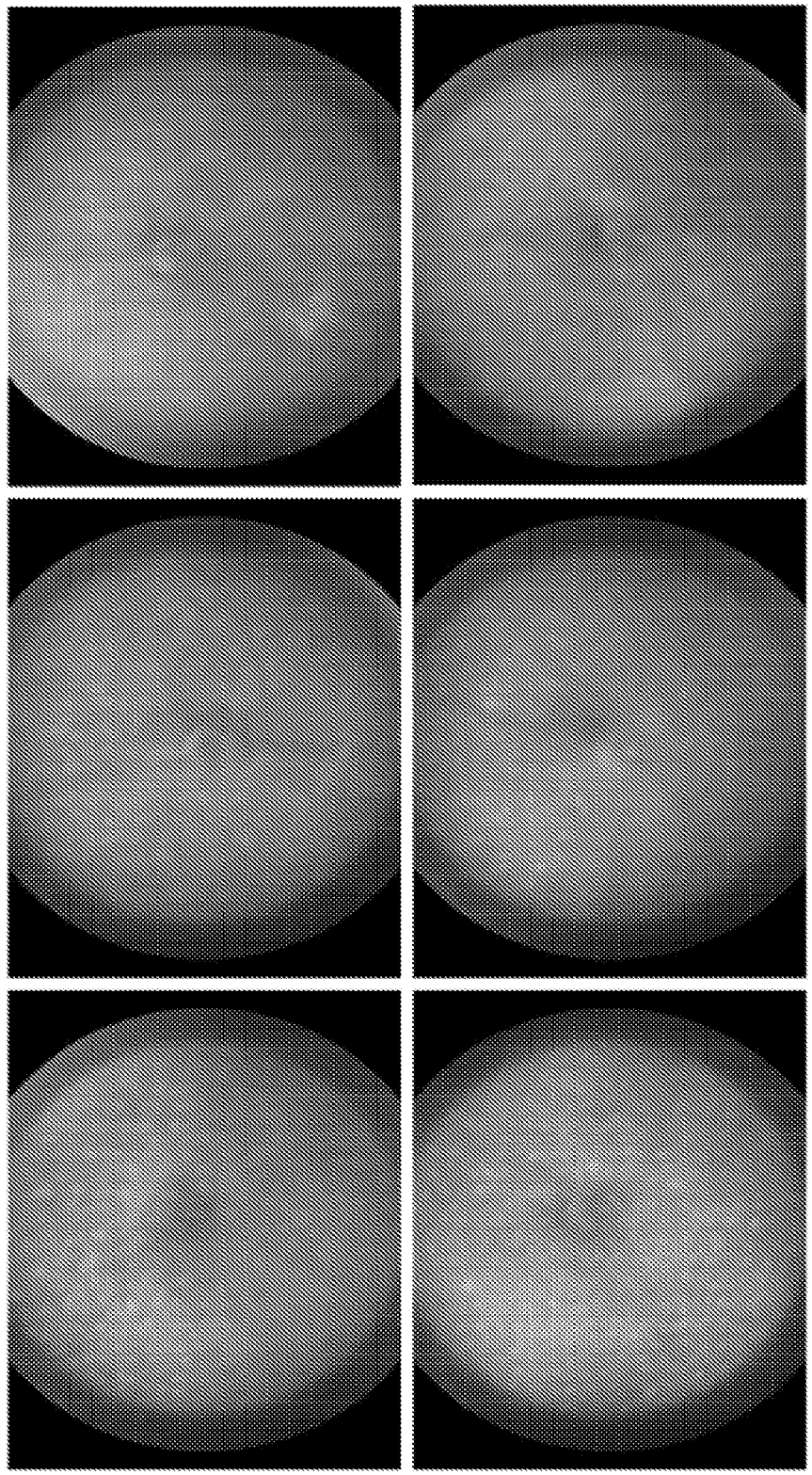
FIG. 11 illustrates fundus biomicroscopy images from control and NMN-administered mice.

In the long-term NMN administration study (See Methods; Administration of NMN through Drinking Water and Determination of NMN Stability and Toxicity), retinal function was evaluated by fundus biomicroscopy and electroretinography (ERG). FIG. 11 illustrates fundus biomicroscopy images from control and NMN-administered mice. For each group, five mice were examined, and two representative images are shown.

Intraretinal whitish deposits were reduced dramatically in NMN-administered mice. On fundus biomicroscopy, all five control mice at 18 months of age showed many intraretinal whitish deposits, whereas two and four each out of five mice at 100 mg/kg and 300 mg/kg doses, respectively, showed dramatic reductions in these deposits, suggesting that age-associated pathological changes in the retina are suppressed by NMN (FIG. 11).

Figure 12A:
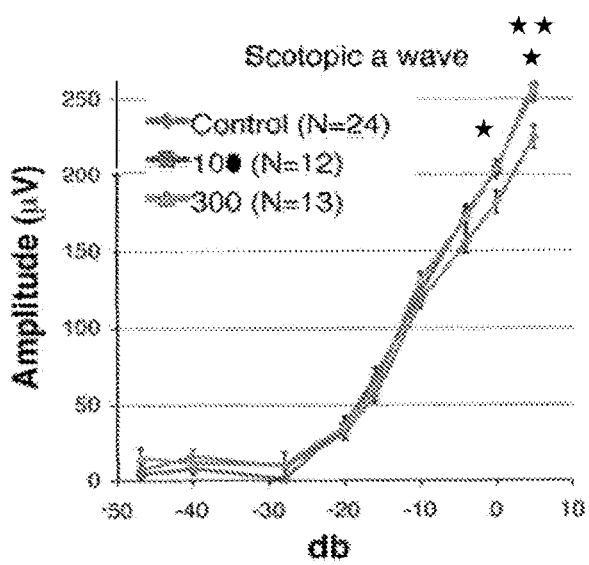
FIG. 12A-C illustrates electroretinograms from control and NMN-administered mice.
Figure 12B:
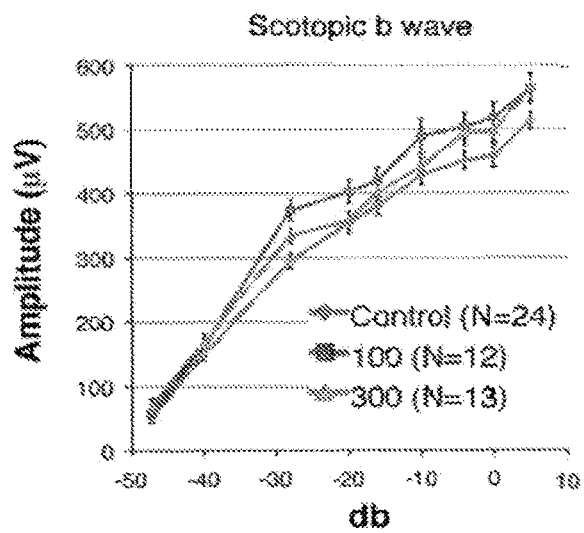
Figure 12C:
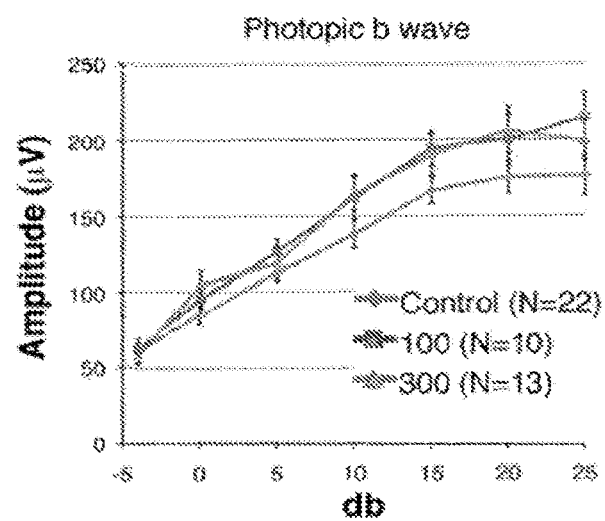

FIG. 12A-C illustrates electroretinograms from control and NMN-administered mice. Amplitudes of scotopic a and b (FIG. 12A, FIG. 12B) and photopic b (FIG. 12C) waves over each stimulus range are shown. Consistently, in the ERG analysis, there was a significant interaction between stimulus and group (P=0.009 from the two-way RANOVA) for the scotopic a wave, and NMN-administered mice showed significantly higher amplitudes at 0 and 5 db (P=0.035 and 0.022 for the 300 mg/kg group at 0 and 5 db, respectively; P=0.009 for the 100 mg/kg group at 5 db from the Dunnett T3 test in the one-way RANOVA within groups), demonstrating that NMN is able to improve rod cell function in aged mice (FIG. 12A). The data were analyzed with the two-way repeated ANOVA. All values are presented as mean±SEM. *p≤0.05; p≤0.01.

Although there were no significant interactions between stimulus and group for the scotopic b and photopic b waves, there appeared to be a trend of improvement for the photopic b wave, which represents cone cell function, through an entire range of stimulus in both 100 and 300 mg/kg groups (FIGS. 12B and 12C). The data were analyzed with the two-way repeated ANOVA. All values are presented as mean±SEM. *p≤0.05; p≤0.01. Taken together, these findings indicate that NMN is able to improve the retinal photoreceptor cell function in aged mice.

The present inventors assessed the physiological importance of NAMPT-mediated NAD biosynthesis in the retina by generating rod cell- and cone cell-specific NAMPT knockout mice. On fundus biomicroscopy, cone cell-specific NAMPT knockout mice had an atrophic appearance at the optic nerve head, intraretinal whitish deposits, and perivascular sheathing, while littermate control animals were normal. ERG demonstrated a significant and dramatic decrease in the scotopic b and photopic b wave amplitudes as compared to the littermate control mice. The scotopic a wave amplitudes in the cone cell-specific NAMPT knockout mice were significantly decreased but to a lesser extent than the photopic b wave responses. Furthermore, rod cell-specific NAMPT knockout mice exhibited total retinal degeneration. Both a and b wave ERG responses were completely depressed as characterized by a total lack of response to all stimuli. Additionally, the treatment of the mouse photoreceptor-derived 661W cone cell line with FK866, a potent NAMPT inhibitor, led them to apoptotic cell death. Adding NMN to the culture media successfully rescued 661W cells from FK866-mediated cell death, suggesting that NAD deficiency causes the observed cell death. These results indicate that inhibition of NAMPT-mediated NAD biosynthesis by genetic and pharmacologic means leads to photoreceptor cell death and eventually retinal degeneration. NMN administration is an effective intervention to treat/prevent retinal degeneration.

Example 7

This example illustrates the improvement of tear production over age using modified Schirmer testing.

Figure 13:
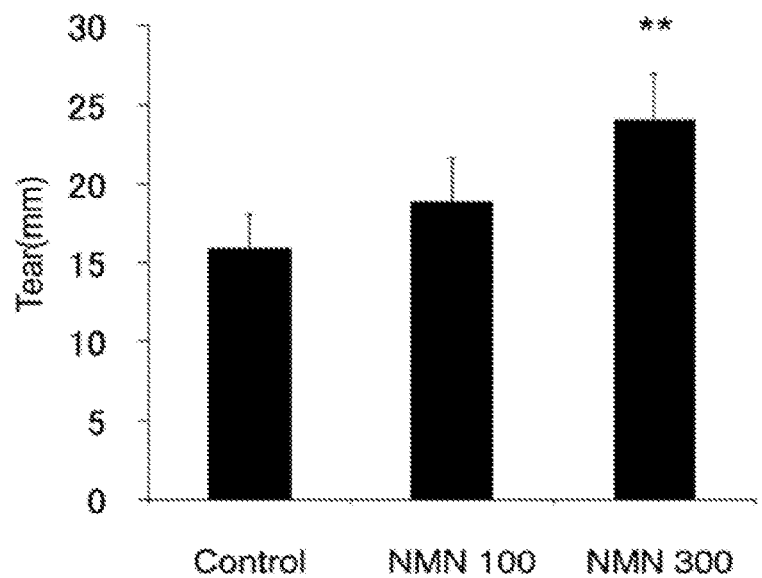
FIG. 13 illustrates tear production in 18 month-old control and NMN-administered mice. All values are presented as mean±SEM. **p<0.01.

In this long-term NMN administration study (See Methods; Administration of NMN through Drinking Water and Determination of NMN Stability and Toxicity), tear production was assessed in control and NMN-administered mice with modified Schirmer's test. All values are presented as mean±SEM. p≤0.01. NMN increased tear production in a dose-dependent manner in 18 month-old mice (FIG. 13**). The tear production observed in the 300 mg/kg group was comparable to the maximal tear production through the mouse lifespan. These findings indicate that NMN administration is able to increase tear production significantly in aged mice, providing an effective intervention to protect eye function from dry eye diseases.

Example 8

This example illustrates that hippocampal NAD+ levels and Nampt expression decline with age.

Figure 14A:
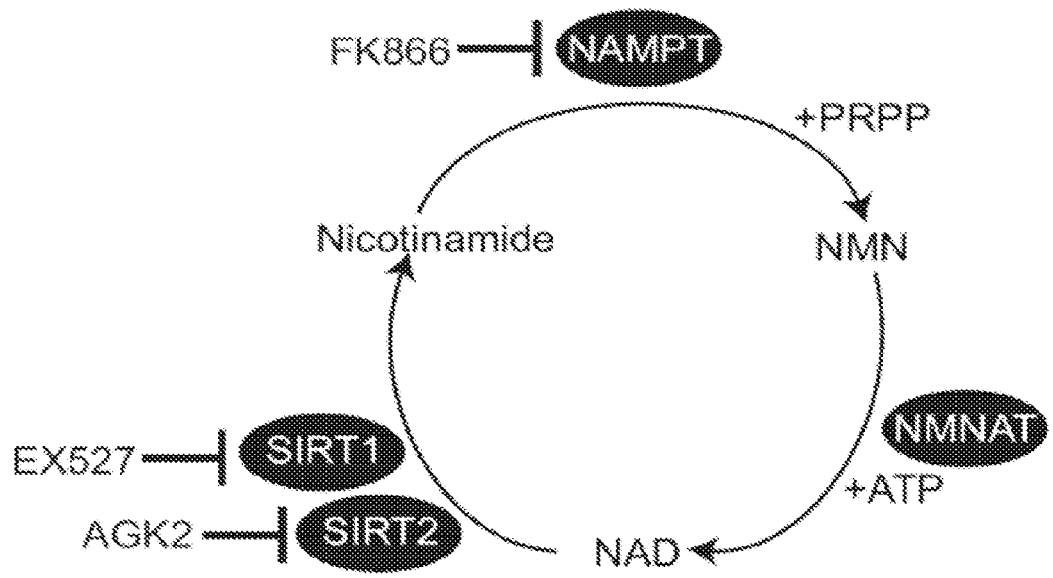
FIG. 14A-E illustrates hippocampal NAD+ levels and Nampt expression declining with age. A) NAD+ biosynthesis from nicotinamide. B) HPLC analysis of NAD+ levels in hippocampal extracts. C-D) Quantification of immunofluorescence for Nampt in the subgranular zone (SGZ). Measurement of thresholded levels of Nampt immunoreactivity (C) and the number of highly immunoreactive Nampt+ cells (D) along the SGZ. E) Representative images of immunofluorescence for Dapi and Nampt in the SGZ in young (6 months old) and old (18 months old) mice.
Figure 14B:
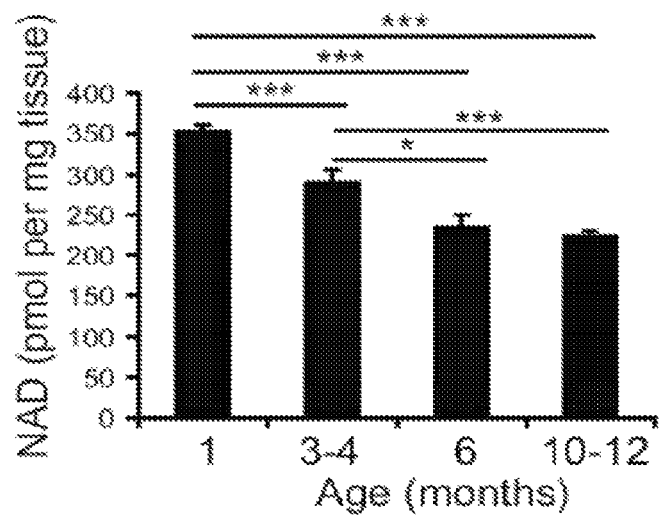
Figure 14C:
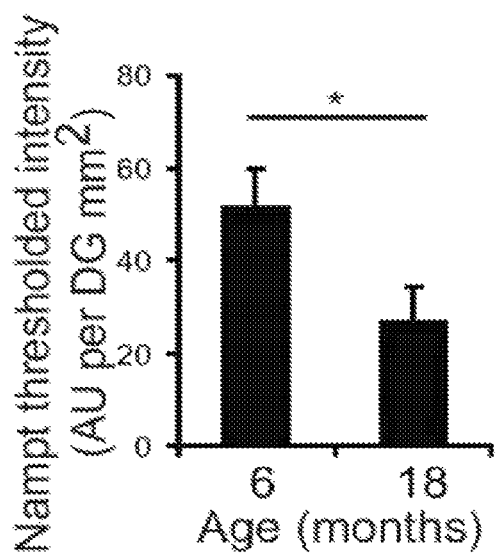
Figure 14D:
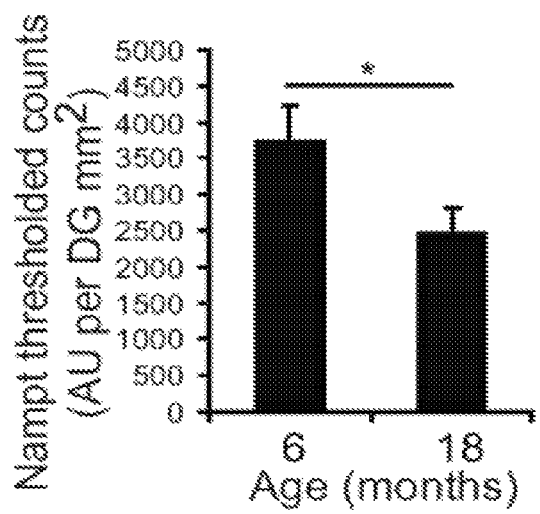
Figure 14:
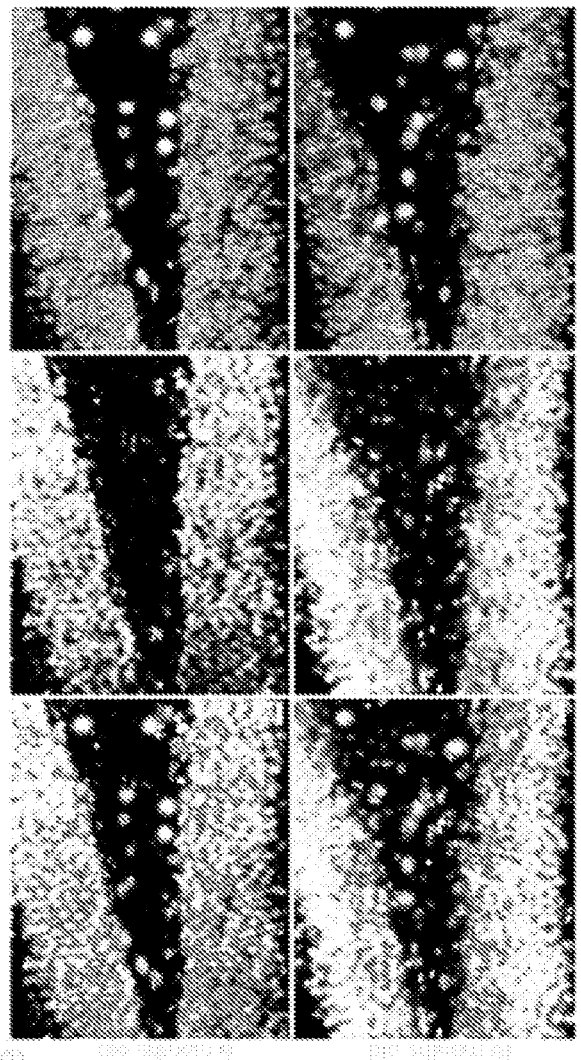

The inventors hypothesized that aging may reduce Nampt-mediated NAD+ biosynthesis in the brain, particularly in the hippocampus, affecting the function of NSPCs. The inventors first measured NAD+ levels in hippocampi isolated from 1, 3-4, 6, and 10-12 month-old C57B16 mice. FIG. 14A-E illustrates hippocampal NAD+ levels and Nampt expression declining with age. FIG. 14A illustrates NAD+ biosynthesis from nicotinamide. Nicotinamide phosphoribosyltransferase (Nampt) converts nicotinamide and 5'-phosphoribosyl-1-pyrophosphate (PRPP) to nicotinamide mononucleotide (NMN). Nicotinamide/nicotinic acid mononucleotide adenylyltransferase (NMNAT) converts NMN and adenosine-5'-triphosphate (ATP) to NAD+. While NAD+ is commonly used in redox reactions, cells primarily require NAD+ as a co-substrate for several families of enzymes, one of which is the sirtuin family of protein deacetylases. The sirtuin family includes Sirt1 and Sirt2, which cleave NAD+ at its glycosidic bond, releasing ADP-ribose (Stein & Imai, 2012). Inhibitors used in subsequent experiments is indicated. FIG. 14B illustrates HPLC analysis of NAD+ levels in hippocampal extracts (1 month, n=5; 3-4 months, n=16; 6 months, n=10; 10-12 months, n=28). FIG. 14C-D illustrates quantification of immunoflourescence for Nampt in the subgranular zone (SGZ). Measurement of thresholded levels of Nampt immunoreactivity (FIG. 14C) and the number of highly immunoreactive Nampt+ cells (FIG. 14D) along the SGZ (n=5). FIG. 14E shows representative images of immunofluorescence for Dapi (original blue) and Nampt (original red) in the SGZ in young (6 months old) and old (18 months old) mice. Scale bars denote 20 μm. Data are presented as mean±s.e.m. *P<0.05. P<0.01. *P<0.001.

NAD+ levels gradually decreased with age, reaching 63% in 10-12 month-old mice compared to that of 1 month-old mice (FIG. 14B). Consistent with this finding, quantifying Nampt immunoreactivity in the SGZ of the DG by both a thresholded level of Nampt intensity as well as a count of the number of thresholded Nampt+ cells demonstrated that 18 month-old mice exhibit 52-66% of the Nampt immunoreactivity present in 6 month-old mice (FIG. 14C-E). Data are presented as mean±s.e.m. *P<0.05. P<0.01. *P<0.001. Without being limited by theory, these results suggest that Nampt-mediated NAD+ biosynthesis in the hippocampus declines with age at a time course similar to that of NSPC proliferation.

Example 9

This example illustrates that Nampt is expressed in a subpopulation of SGZ NSPCs.

Nampt has been reported as predominantly expressed in hippocampal neurons but not in stellate astrocytes (Wang et al, 2011a; Zhang et al, 2010). Consistent with this finding, immunohistochemistry for Nampt and cell type specific markers revealed almost all NeuN+ neurons in the granule layer of the DG expressed Nampt, while almost no S100β+ glial cells did (FIG. 22A-E).

However, the inventors also noticed that many Nampt immunoreactive cells along the SGZ of the DG did not express NeuN (FIG. 22B-22E). The inventors performed co-immunohistochemistry for NSPC markers (Sox2+, radial Gfap+), and found that a significant population of NSPCs expressed Nampt (FIG. 22A-B0). FIG. 22 illustrates that Nampt is expressed in a subpopulation of SGZ NSPCs. A-C) Representative images of immunofluorescence for Dapi (original blue), Nampt (original red), and NSPC markers (Sox2, Gfap, and NestinGFP 3 days post tamoxifen injection; original green) in the SGZ. Dotted lines denote the SGZ. Single arrows indicate examples of colocalization. Double arrows indicate examples of non-colocalization.

Figure 15A:
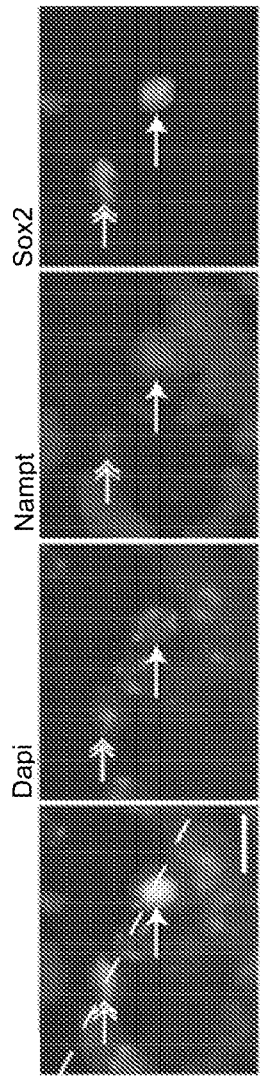
FIG. 15A-F illustrates that Nampt is expressed in a subpopulation of SGZ NSPCs. A-C) Representative fluorescence images for Dapi (original blue), Nampt (original red), and NSPC markers (Sox2, Gfap, and NestinGFP 3 days post tamoxifen injection; original green) in the SGZ. Dotted lines denote the SGZ. D) Quantification of the percentages of NSPC marker-positive cells in the SGZ that also express Nampt in 3 to 6 month old mice.
Figure 15B:
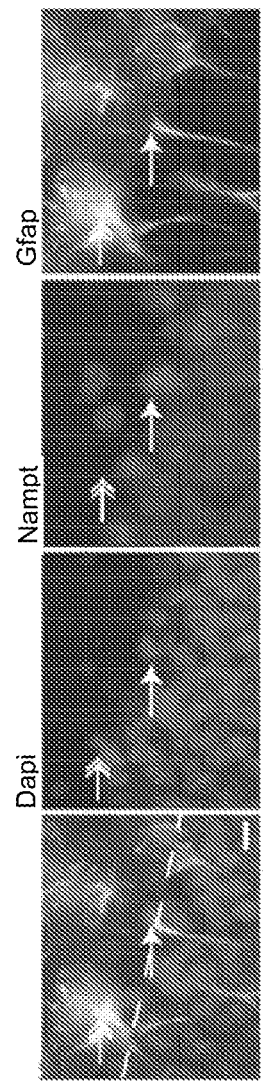
Figure 15:
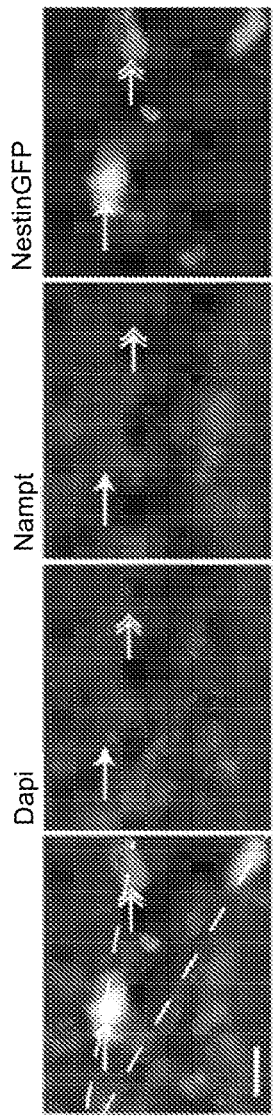

Scale bars denote 10 µm. D) Quantification of the percentages of NSPC marker-positive cells in the SGZ that also express Nampt in 3 to 6 month old mice. At least 350 cells from 7-14 mice were assessed per group. E) A representative immunoblot and quantification of immunoblots for Nampt normalized by actin in neurospheres cultured from postnatal mice (n=6 independent samples, 16 replicates), as well as hippocampal tissue extracts (HC) isolated from either postnatal (n=12) or adult mice (n=12). F) Nampt immunoreactivity was thresholded and the number of highly immunoreactive Nampt+ cells along the SGZ was assessed for colocalization with the neuronal marker NeuN or the NSPC marker Sox2 in the subgranular zone (SGZ, n=5). Data are presented as mean±s.e.m. *$P<0.05$. $P<0.01$. *$P<0.001$ (FIG. 15A-B).

To assess in vivo colocalization between Nampt and Nestin, the inventors crossed mice expressing Cre recombinase under the Nestin promoter (Nestin-CreERT2) to a GFP reporter mouse strain that expresses a loxP-flanked STOP cassette that prevents transcription of the downstream enhanced GFP (see Methods), generating iNSPC-GFP mice. Nampt also colocalized with GFP driven by the Nestin promoter (NestinGFP, FIG. 15C).

Figure 15D:
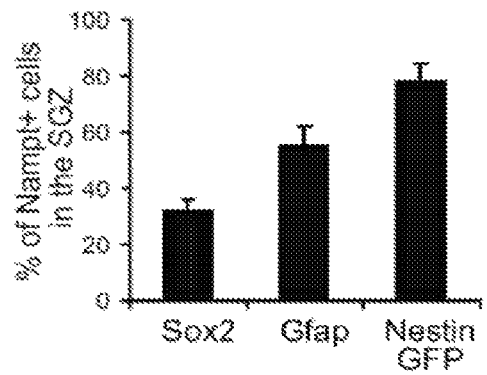

Quantification of these observations revealed that along the SGZ, 32% of Sox2+ cells, 55% of radial Gfap+ cells, and 78% of NestinGFP+ cells expressed Nampt (FIG. 15D, and Table 1). Additionally, Ki67+ and Olig2+ cells along the SGZ also expressed Nampt (Table 2, FIGS. 22H-22I). Separate from SGZ-localized cell populations, 3±1% of NestinGFP+ cells had extremely strong GFP expression, were localized to the granule layer, and expressed NeuN, likely due to residual CreERT2 protein left in the progeny of previously differentiated NSPCs. Data are presented as mean±s.e.m. *$P<0.05$. ***$P<0.001$.

TABLE 1

Top 50 Downregulated Pathways

| Pathway | Members | Changed | Z Ratio | P Value |
|---|---|---|---|---|
| NUCLEAR_PART | 579 | 468 | −7.07 | 0 |
| DNA_METABOLIC_PROCESS | 257 | 226 | −6.49 | 0 |
| DNA_REPLICATION | 102 | 85 | −6.2 | 0 |
| DNA_DEPENDENT_DNA_REPLICATION | 56 | 46 | −6.07 | 0 |
| DNA_REPAIR | 125 | 111 | −5.98 | 0 |
| NUCLEUS | 1433 | 1169 | −5.95 | 0 |
| INTRACELLULAR_ORGANELLE_PART | 1192 | 988 | −5.85 | 0 |
| RESPONSE_TO_DNA_DAMAGE_STIMULUS | 162 | 138 | −5.8 | 0 |
| ORGANELLE_PART | 1197 | 992 | −5.72 | 0 |
| NUCLEOBASE_NUCLEOSIDE_NUCLEOTIDE_AND_NUCLEIC_ACID | 1246 | 1051 | −5.34 | 0 |
| ORGANELLE_LUMEN | 458 | 372 | −5.04 | 0 |
| MEMBRANE_ENCLOSED_LUMEN | 458 | 372 | −5.04 | 0 |
| CHROMOSOME | 124 | 106 | −4.75 | 0 |
| CELL_CYCLE_PROCESS | 193 | 167 | −4.75 | 0 |
| NUCLEAR_LUMEN | 387 | 310 | −4.74 | 0 |
| CELL_CYCLE_GO_0007049 | 315 | 268 | −4.63 | 0 |
| RNA_PROCESSING | 174 | 145 | −4.32 | 0 |
| BASE_EXCISION_REPAIR | 17 | 15 | −4.3 | 0 |
| CELL_CYCLE_PHASE | 170 | 147 | −4.23 | 0 |
| RESPONSE_TO_ENDOGENOUS_STIMULUS | 200 | 168 | −4.18 | 0 |
| MACROMOLECULAR_COMPLEX | 945 | 793 | −4.14 | 0 |
| NUCLEAR_CHROMOSOME | 54 | 45 | −4.11 | 0 |
| STRUCTURE_SPECIFIC_DNA_BINDING | 56 | 45 | −4.08 | 0 |
| DOUBLE_STRANDED_DNA_BINDING | 32 | 26 | −3.95 | 0 |
| CELL_CYCLE_CHECKPOINT_GO_0000075 | 48 | 38 | −3.92 | 0 |
| TRNA_METABOLIC_PROCESS | 19 | 18 | −3.76 | 0 |
| DNA_RECOMBINATION | 47 | 45 | −3.69 | 0 |
| M_PHASE | 114 | 100 | −3.67 | 0 |
| HYDROLASE_ACTIVITY_HYDROLYZING_N_GLYCOSYL_COMPOUNDS | 10 | 10 | −3.63 | 0 |
| NUCLEOPLASM | 279 | 230 | −3.62 | 0 |
| REPLICATION_FORK | 18 | 16 | −3.6 | 0 |
| CONDENSED_CHROMOSOME | 34 | 27 | −3.57 | 0 |
| TRNA_PROCESSING | 10 | 9 | −3.51 | 0 |
| RIBONUCLEOPROTEIN_COMPLEX | 143 | 116 | −3.49 | 0 |
| MITOTIC_CELL_CYCLE | 153 | 133 | −3.48 | 0.001 |
| CHROMOSOMAL_PART | 96 | 83 | −3.48 | 0.001 |
| NUCLEOLUS | 126 | 97 | −3.47 | 0.001 |
| NON_MEMBRANE_BOUND_ORGANELLE | 632 | 513 | −3.46 | 0.001 |
| INTRACELLULAR_NON_MEMBRANE_BOUND_ORGANELLE | 632 | 513 | −3.46 | 0.001 |
| RNA_BINDING | 259 | 211 | −3.44 | 0.001 |
| TRANSFERASE_ACTIVITY_TRANSFERRING_ONE_CARBON_GROUPS | 37 | 34 | −3.37 | 0.001 |
| CONDENSED_NUCLEAR_CHROMOSOME | 18 | 15 | −3.36 | 0.001 |
| NUCLEOBASE_NUCLEOSIDE_AND_NUCLEOTIDE_METABOLIC_PROCESS | 52 | 45 | −3.35 | 0.001 |
| METHYLTRANSFERASE_ACTIVITY | 36 | 33 | −3.3 | 0.001 |
| INTERPHASE | 68 | 57 | −3.28 | 0.001 |
| NUCLEOTIDE_METABOLIC_PROCESS | 42 | 36 | −3.21 | 0.001 |
| DNA_INTEGRITY_CHECKPOINT | 24 | 16 | −3.2 | 0.001 |
| SINGLE_STRANDED_DNA_BINDING | 35 | 27 | −3.17 | 0.002 |

TABLE 1-continued

Top 50 Downregulated Pathways

| Pathway | Members | Changed | Z Ratio | P Value |
|---|---|---|---|---|
| PROTEIN_COMPLEX | 816 | 689 | −3.08 | 0.002 |
| INTERPHASE_OF_MITOTIC_CELL_CYCLE | 62 | 52 | −3.07 | 0.002 |

TABLE 2

Top 50 Upregulated Pathways

| Pathway | Members | Changed | Z Ratio | P Value |
|---|---|---|---|---|
| SYSTEM_DEVELOPMENT | 863 | 759 | 4.69 | 0.000 |
| MULTICELLULAR_ORGANISMAL_DEVELOPMENT | 1051 | 910 | 4.64 | 0.000 |
| SIALYLTRANSFERASE_ACTIVITY | 10 | 10 | 1.61 | 0.000 |
| PHOSPHOINOSITIDE_BINDING | 20 | 13 | 4.49 | 0.000 |
| ANATOMICAL_STRUCTURE_DEVELOPMENT | 1017 | 891 | 4.47 | 0.000 |
| ORGAN_DEVELOPMENT | 572 | 499 | 4.28 | 0.000 |
| RECEPTOR_BINDING | 378 | 321 | 4.25 | 0.000 |
| EXTRACELLULAR_REGION | 448 | 374 | 4.10 | 0.000 |
| ENZYME_LINKED_RECEPTOR_PROTEIN_SIGNALING_PATHWAY | 140 | 126 | 4.05 | 0.000 |
| Growth | 77 | 63 | 3.85 | 0.000 |
| NEGATIVE_REGULATION_OF_GROWTH | 40 | 34 | 3.84 | 0.000 |
| FOCAL_ADHESION_FORMATION | 10 | 9 | 3.83 | 0.000 |
| OLIGOSACCHARIDE_METABOLIC_PROCESS | 11 | 11 | 3.82 | 0.000 |
| EXTRACELLULAR_REGION_PART | 339 | 283 | 3.82 | 0.000 |
| REGULATION_OF_SIGNAL_TRANSDUCTION | 223 | 189 | 3.77 | 0.000 |
| SYSTEM_PROCESS | 563 | 489 | 3.74 | 0.000 |
| EXTRACELLULAR_SPACE | 246 | 204 | 3.66 | 0.000 |
| NEURON_PROJECTION | 21 | 18 | 3.62 | 0.000 |
| INTERMEDIATE_FILAMENT_CYTOSKELETON | 24 | 22 | 3.61 | 0.000 |
| INTERMEDIATE_FILAMENT | 24 | 22 | 3.61 | 0.000 |
| SENSORY_PERCEPTION | 190 | 159 | 3.57 | 0.000 |
| MEMBRANE | 1998 | 1678 | 3.55 | 0.000 |
| POSITIVE_REGULATION_OF_SECRETION | 20 | 15 | 3.51 | 0.000 |
| REGULATION_OF_CELL_GROWTH | 46 | 38 | 3.49 | 0.000 |
| REGULATION_OF_GROWTH | 58 | 49 | 3.48 | 0.000 |
| SIGNAL_TRANSDUCTION | 1637 | 1394 | 3.47 | 0.001 |
| PLASMA_MEMBRANE | 1429 | 1199 | 3.46 | 0.001 |
| MESODERM_DEVELOPMENT | 22 | 17 | 3.45 | 0.001 |
| CELL_DEVELOPMENT | 579 | 512 | 3.44 | 0.001 |
| FOCAL_ADHESION | 13 | 10 | 3.44 | 0.001 |
| ANATOMICAL_STRUCTURE_MORPHOGENESIS | 379 | 335 | 3.39 | 0.001 |
| NERVOUS_SYSTEM_DEVELOPMENT | 386 | 342 | 3.39 | 0.001 |
| EARLY_ENDOSOME | 18 | 15 | 3.37 | 0.001 |
| CYTOSKELETAL_PROTEIN_BINDING | 159 | 137 | 3.36 | 0.001 |
| TASTE_RECEPTOR_ACTIVITY | 15 | 3 | 3.36 | 0.001 |
| AXON_GUIDANCE | 22 | 19 | 3.34 | 0.001 |
| GENERATION_OF_NEURONS | 83 | 76 | 3.34 | 0.001 |
| CELL_JUNCTION | 83 | 67 | 3.29 | 0.001 |
| LIPID_HOMEOSTASIS | 16 | 12 | 3.28 | 0.001 |
| PDZ_DOMAIN_BINDING | 14 | 13 | 3.26 | 0.001 |
| LIGAND_DEPENDENT_NUCLEAR_RECEPTOR_ACTIVITY | 25 | 23 | 3.26 | 0.001 |
| NEUROGENESIS | 93 | 84 | 3.21 | 0.001 |
| CELL_MATRIX_JUNCTION | 18 | 14 | 3.20 | 0.001 |
| VACUOLE | 69 | 56 | 3.19 | 0.001 |
| IDENTICAL_PROTEIN_BINDING | 305 | 253 | 3.19 | 0.001 |
| CELL_MATRIX_ADHESION | 38 | 34 | 3.18 | 0.001 |
| TRANSMEMBRANE_RECEPTOR_PROTEIN_TYROSINE_KINASE_SIGNALING_PATH | 83 | 75 | 3.18 | 0.001 |
| ACTIN_FILAMENT_BASED_PROCESS | 116 | 96 | 3.18 | 0.001 |
| CELL_SURFACE_RECEPTOR_LINKED_SIGNAL_TRANSDUCTION_GO_000166 | 642 | 547 | 3.17 | 0.002 |
| CELL_SUBSTRATE_ADHERENS_JUNCTION | 16 | 13 | 3.17 | 0.002 |

Figure 15E:
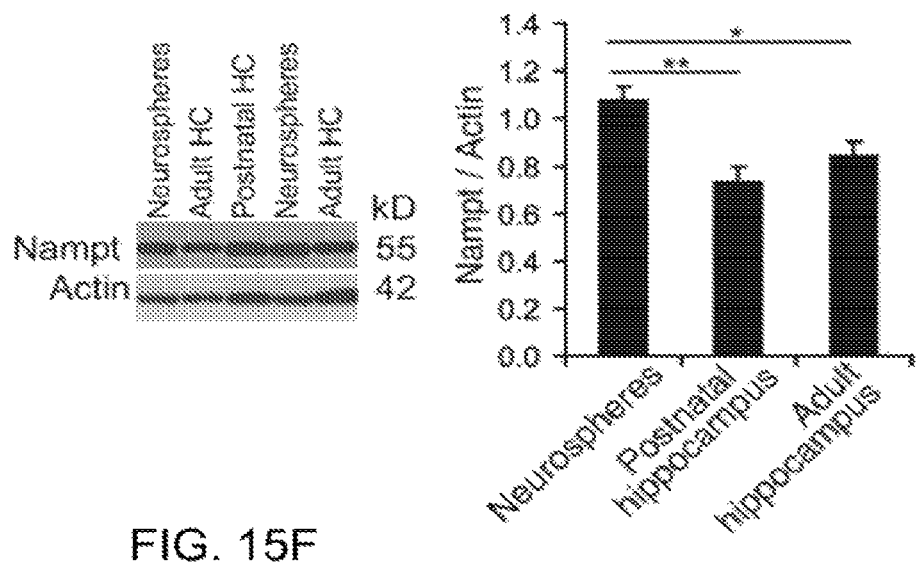

To confirm that Nampt is highly expressed in NSPCs, the inventors cultured NSPCs from the hippocampi of postnatal pups as neurospheres. Neurospheres showed 22 or 32% higher expression levels of Nampt than did whole hippocampal extracts taken from postnatal (P12) or adult mice (2.5-4.5 months), respectively (FIG. 15E), indicating that NSPCs have higher expression levels of Nampt compared to other hippocampal cell types. Without being limited by theory, these results suggest that Nampt is expressed in a large subpopulation of NSPCs.

Figure 15F:
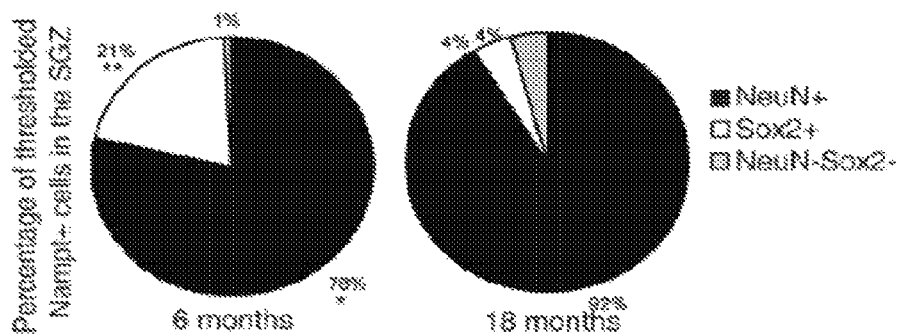
Figure 22D:
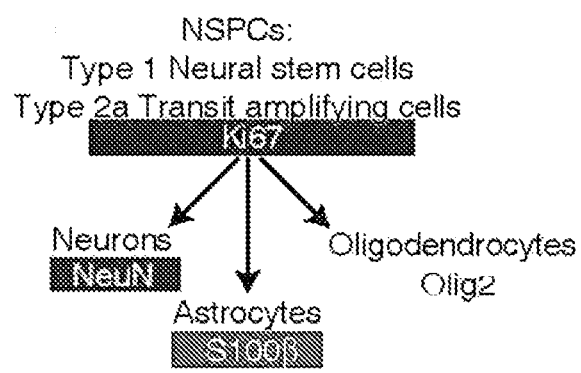
Figure 22E:
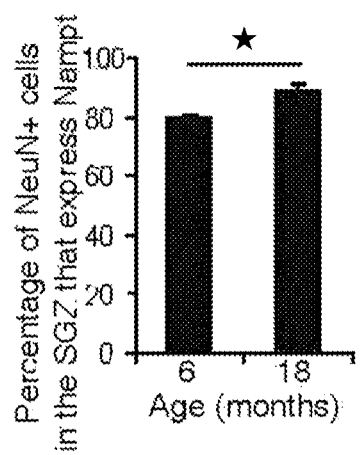
Figure 22F:
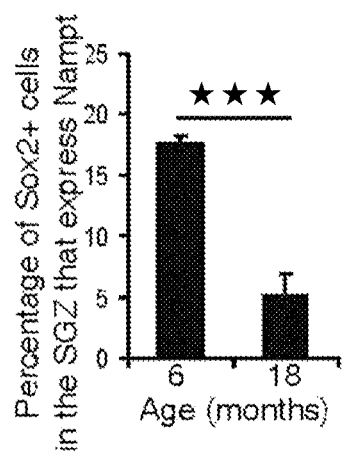
Figure 22G:
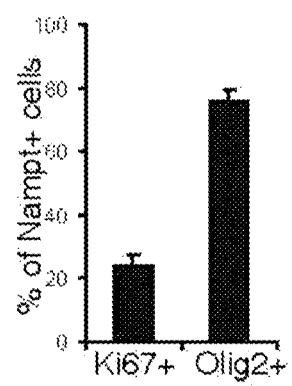
Figures 22H, 22I:
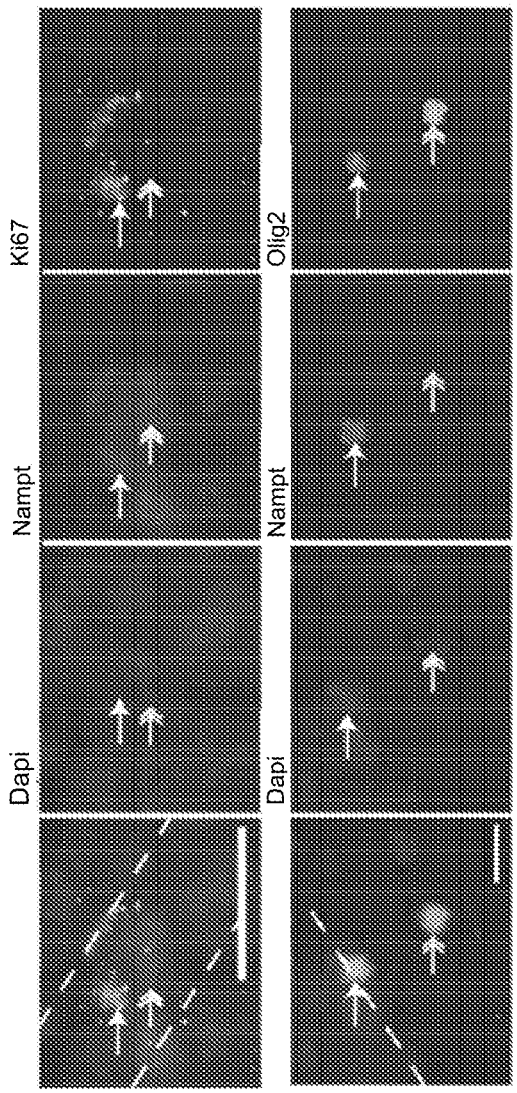

The inventors thresholded Nampt immunoreactivity, and assessed the thresholded Nampt+ cells for colocalization with the neuronal marker NeuN and the NSPC marker Sox2 to determine which cell populations lose Nampt expression with age. With age, the percentage of intensely Nampt immunoreactive cells that colocalized with NeuN increased slightly, whereas the percentage of intensely Nampt immunoreactive cells that colocalized with Sox2 decreased from 21% to 4% (FIG. 15F). Data are presented as mean±s.e.m. *P<0.05. P<0.01. *P<0.001. Similarly, in the SGZ, the percentage of NeuN+ that expressed Nampt increased with age, while the percentage of Sox2+ cells that expressed Nampt decreased (FIG. 22E, table 2). Thus, at least part of the decrease in Nampt expression in the SGZ with age is due to loss of Sox2+ NSPCs.

Example 10

This example illustrates that adult NSPC-specific deletion of Nampt impairs NSPC self-renewal in vivo.

The inventors investigated whether inactivating Nampt specifically in adult NSPCs could recapitulate age-associated phenotypic changes in NSPC functionality in vivo. The inventors generated adult NSPC-specific inducible Nampt knockout mice by crossing Nampt$^{flox/flox}$ mice (Rongvaux et al, 2008) with Nestin-CreERT2 mice (iNSPC-Nampt-KO mice). To trace the progeny of adult NSPCs in which Nampt was inactivated and to confirm the specificity and magnitude of the deletion induced by tamoxifen, the inventors also crossed iNSPC-Nampt-KO mice to the aforementioned iNSPC-GFP mice. After tamoxifen injection, these mice expressed NestinGFP in the SGZ and SVZ but not in non-neurogenic regions of the brain such as the corpus callosum or cortex FIG. 23A-B).

Figure 23D:
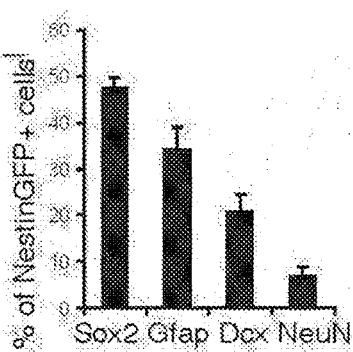
Figure 23E:
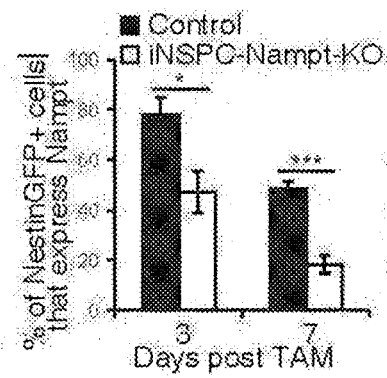

Immunohistochemistry and recombination PCR for NestinGFP confirmed that there was undetectable recombination present in vehicle injected mice. The −350 base pair band confirms the deletion of exons 5 and 6. The 1,800 base pair band corresponds to a Nampt gene with a full-length exon 5 to 6 sequence. (FIGS. 23A, 23C) To verify that the NestinGFP+ population consisted of NSPCs, the inventors co-stained for the NSPC markers Sox2 and Gfap. 61% of Sox2+ cells and 34% of radial Gfap+ cells co-expressed NestinGFP 7 days post tamoxifen (FIG. 23D). The inventors also verified Nampt deletion efficiency by quantifying the percentage of NestinGFP+ cells that expressed Nampt 3 and 7 days post tamoxifen injection. At 3 days post tamoxifen injection, the percentage of NestinGFP+ cells that expressed Nampt in iNSPC-Nampt-KO mice was 40% less than littermate controls, and at 7 days post tamoxifen injection, the percentage of NestinGFP+ cells that expressed Nampt was reduced by 62% (FIG. 23E).

Figure 16:
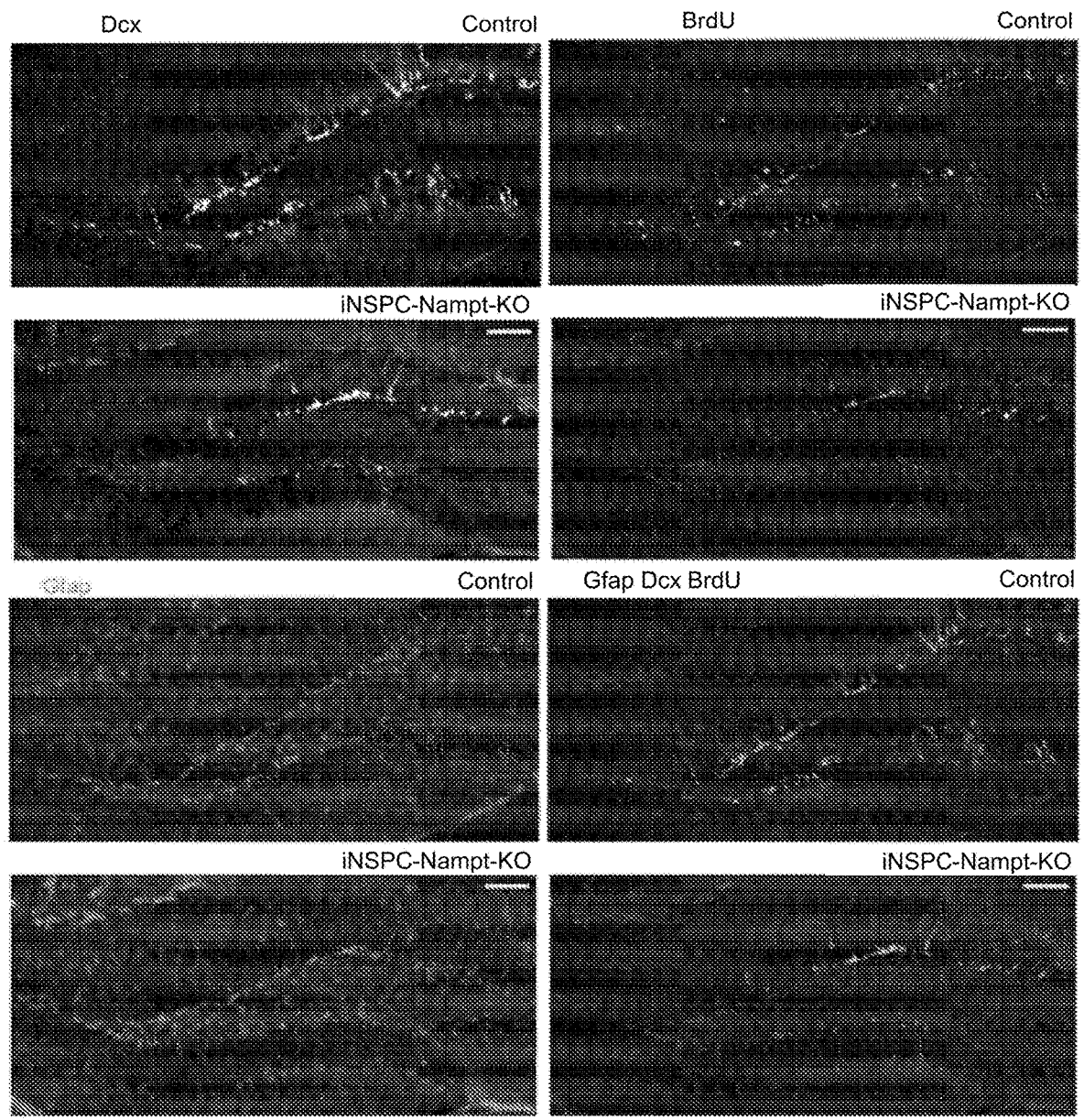
FIG. 16A-J illustrates that adult NSPC-specific deletion of Nampt impairs NSPC proliferation and self-renewal in vivo. A) To assess proliferation, iNSPC-Nampt-KO mice and littermate controls were subjected to three rounds of 5 tamoxifen (TAM) injections (1 injection per day, 6 weeks apart). Sacrifice was performed at 6 months of age. B) A scheme for the specificity of the markers assessed. C-F) Quantification of radial Nestin+ NSPCs (n=15-16 mice) (C), BrdU+ proliferating cells (n=14-16 mice) (D), Ki67+ proliferating cells (n=7 mice) (E), and newborn neurons (Dcx+, n=15-20 mice) (F), per unit area of the dentate gyrus (DG) in control and iNSPC-Nampt-KO mice. For BrdU labeling, 4 injections of BrdU at 100 mg/kg body weight were given intraperitoneally over 48 hours. G) Representative images of immunofluorescence for Gfap (original blue), Dcx (original green), and BrdU (original red) in the subgranular zone (SGZ). Scale bar denotes 200 µm. H) To assess differentiation, control littermates and iNSPC-Nampt-KO mice were subjected to 4 total TAM injections (2 injections on the first day coupled with BrdU at 100 mg/kg body weight as well as 2 total injections on the subsequent 2 days). I) Quantification of the percentage of BrdU+ cells in the DG that also express markers of NSPCs (Gfap+, Nestin+), newborn neurons (Dcx+), and OPCs/oligodendrocytes (Olig2+) (n=6-13 mice). J) Quantification of radial Nestin+ NSPCs in 6 and 18 month-old C57Bl6 mice and 18 month-old C57Bl6 mice treated with 100 or 300 mg/kg body weight NMN in their drinking water for 12 months (n=5 mice). Data are presented as mean±s.e.m. *P<0.05. P<0.01. *P<0.001.
Figure 23F:
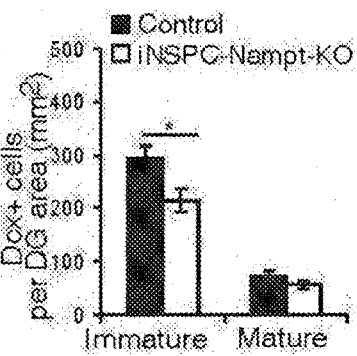

To assess the cumulative effect of loss of Nampt on NSPC proliferation, the inventors deleted Nampt in iNSPC-Nampt-KO mice at 6 weeks of age with 3 rounds of 5 consecutive days of tamoxifen injections, separated by 6 weeks (FIG. 16A). Parametric analysis of gene enrichment (PAGE) was conducted based on microarray analyses. See the Methods section. Data are presented as mean±s.e.m. *P<0.05. P<0.01. *P<0.001. The inventors then assessed control and iNSPC-Nampt-KO mice for the expression of lineage specific markers by immunohistochemistry (FIG. 16C). In iNSPC-Nampt-KO mice, the inventors found that the Nestin+ NSPC pool was decreased by 49% in the DG (FIG. 16C). Incorporation of BrdU and the population of proliferating cells [Ki67+(von Bohlen und Halbach, 2011)] were also decreased by 22% and 35%, respectively (FIG. 16D-16E. Consistent with this defect in the NSPC pool and proliferation, the pool of newborn neurons [doublecortin, Dcx+, (von Bohlen und Halbach, 2011)] was also significantly decreased by 26% (FIG. 16F-16G). In contrast, the inventors did not observe any significant difference in the maturation of newborn neurons (FIG. 23F). Immature cells had no or horizontal projections. Mature cells had vertical projections spanning the granule cell layer. NSPC/daughter cell survival was accessed by immunostaining for activated caspase 3. Only rare activated caspase 3+ cells were observed in both neurogenic and non-neurogenic regions of the brain (FIGS. 23A-23B), and these activated caspase 3+ cells were never observed in GFP+ cells in iNSPC-Nampt-KO DG, without being limited by theory, providing evidence against a potential contribution of cell death to the observed effects.

Figure 16H:

To assess the acute effect of loss of Nampt on NSPC fate decisions, the inventors induced deletion of Nampt at 6 weeks of age with 4 total tamoxifen injections followed by sacrifice 72 hours after the first injection (FIG. 16H). To facilitate assessment of differentiation, dividing cells were labeled by injecting the mice with BrdU concurrently with the first day of tamoxifen treatment. 4 total TAM injections (2 injections on the first day coupled with BrdU at 100 mg/kg body weight as well as 2 total injections on the subsequent 2 days). iNSPC-Nampt-KO mice displayed significantly reduced levels of colocalization of BrdU with radial Nestin+ cells (FIG. 16I), without being limited by theory, suggesting decreased self-renewal decisions. However, iNSPC-Nampt-KO mice exhibited normal levels of BrdU colocalization with neuronal (Dcx+), astrocytic (Gfap+) and oligodendrocytic (Olig2+) markers, indicating that alterations in differentiated cell lineage decisions were undetectable under basal conditions. Without being limited by theory, the lack of increase in colocalization of BrdU with cell type specific markers may imply that a larger percentage of BrdU+ cells have failed to differentiate in iNSPC-Nampt-KO mice. iNSPC-Nampt-KO NSPCs could have stalled during differentiation after losing Nestin expression.

Figure 23G:
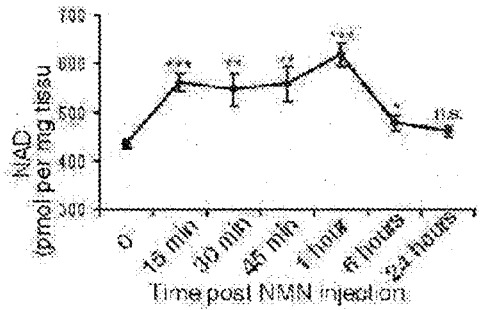
Figure 23H:
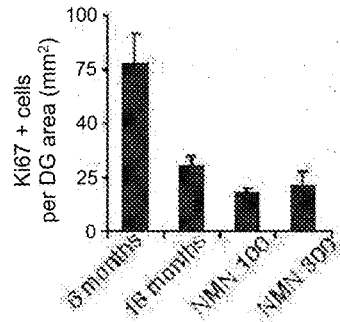
Figure 23I:
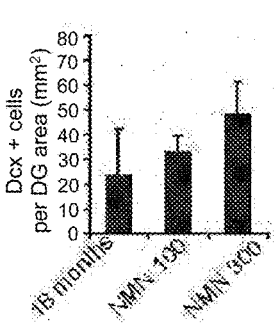

The inventors hypothesized that systemic administration of NMN may be able to correct age-associated defects in NSPC functionality. Intraperitoneal injection of NMN (500 mg/kg body weight) increased hippocampal NAD+ levels 34 to 39% within 15 minutes, suggesting that NMN can cross the blood-brain barrier (FIG. 23G). To see if NMN supplementation can maintain NSPC proliferation and self-renewal with age, the inventors treated 6 month-old mice with NMN at the daily dose of 100 or 300 mg/kg body weight in their drinking water until 18 months of age. The number of Nestin+ cells along the SGZ was significantly lower in the 18 month-old control mice relative to 6 month-old mice, as previously reported (Encinas et al, 2011) (FIG. 16J). Data are presented as mean±s.e.m. *P <0.05. P<0.01. *P<0.001. Mice treated with 300 mg/kg body weight NMN showed improved maintenance of the Type 1 (radial Nestin+) population with age. However, the population of proliferating cells (Ki67+) remained similar to controls (FIG. 23H). The population of newborn neurons (Dcx+) trended to increase (FIG. 23I). Quantification of Ki67+(H) and Dcx+(I) cells in the DG per unit area of the DG (n=5). Data are presented as mean±s.e.m. *P<0.05. P<0.01. *P<0.001. Without being limited by theory, it is possible that NMN administration maintains the NSPC pool by preventing the age-associated increase in terminal fate decisions.

Example 11

This example illustrates that inhibition of Nampt in NSPCs in vitro impairs NAD+ biosynthesis and proliferation.

Figure 17A:
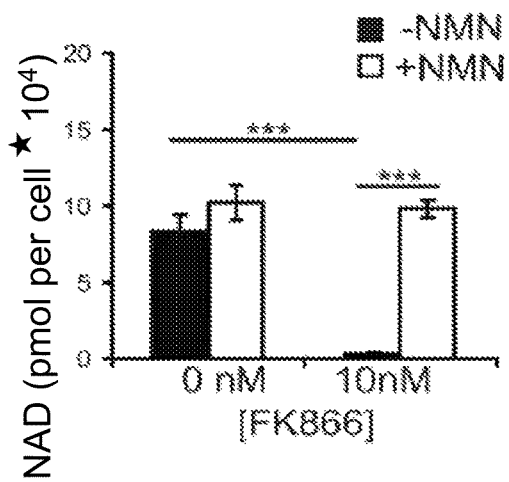
FIG. 17A-E illustrates that inhibition of Nampt in NSPCs in vitro impairs NAD+ biosynthesis and proliferation. Neurospheres were cultured with the Nampt-specific inhibitor FK866 (10 nM) with or without NMN (100 µM) for 48 hours. A) HPLC analysis of NAD+ levels (n=6). B) Quantification of the fold increase of cell number in neurospheres (n=6-30). C) Representative bright-field image of neurospheres. Scale bar denote 10 μm. D) Cell cycle-related pathways among the top 50 biological pathways downregulated by FK866. Parametric analysis of gene enrichment (PAGE) was conducted based on microarray analyses. See the Methods section. E) Quantitative RT-PCR results for mRNA expression of cyclin E2 (Ccne2), cyclin E1 (Ccne 1), cyclin A2 (Ccna2), and E2F1 (n=3). F) FACS analysis of FK866-treated NSPCs (n=8). Data are presented as mean±s.e.m. *P<0.05. P<0.01. *P<0.001.

The inventors hypothesized whether Nampt mediates NSPC-specific NAD+ biosynthesis by using hippocampal neurospheres as the in vitro NSPC culture model. Neurospheres were treated with a highly specific Nampt inhibitor, FK866, at a dosage and duration (10 nM, 48 hours) that has little to no effect on cellular viability (Hasmann & Schemainda, 2003). FK866 reduced NAD+ levels in neurospheres to 4% of controls, a decrease completely rescued by concurrent NMN treatment (FIGS. 17A and 24A), suggesting that, without being limited by theory, Nampt activity is the predominant source of NAD+ biosynthesis in NSPCs.

Figure 17B:
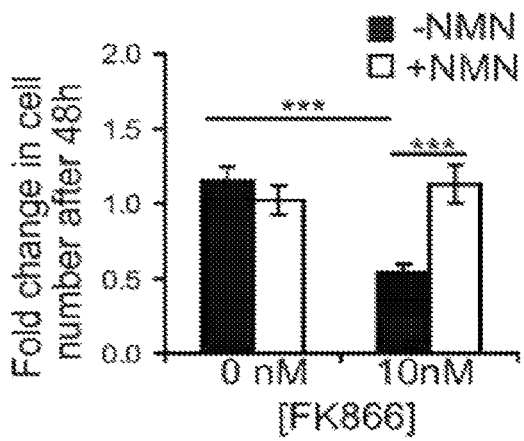
Figure 17:
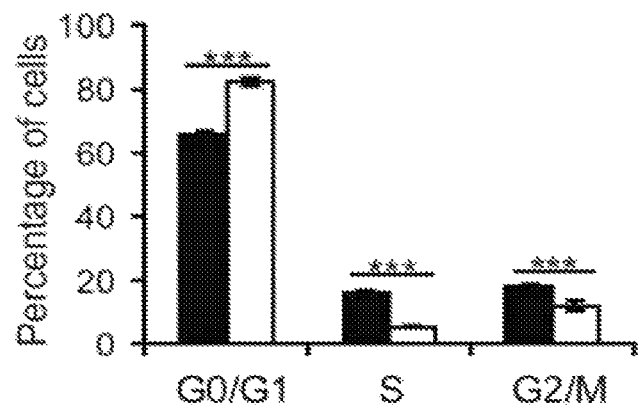
Figure 24A:
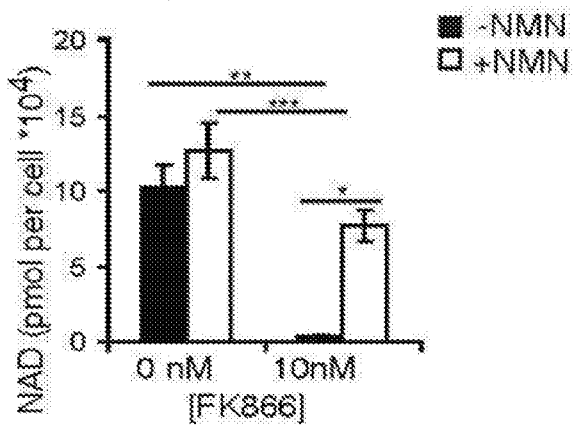
Figure 24B:
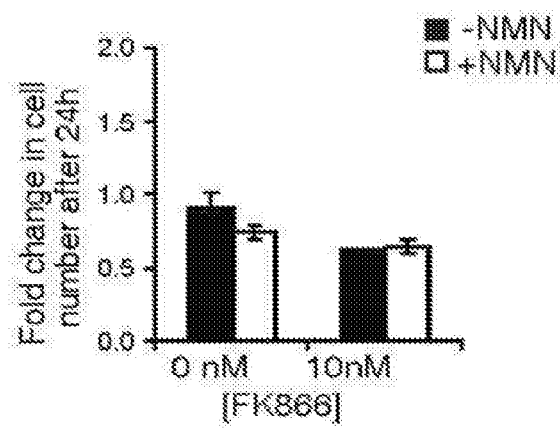
Figure 24C:
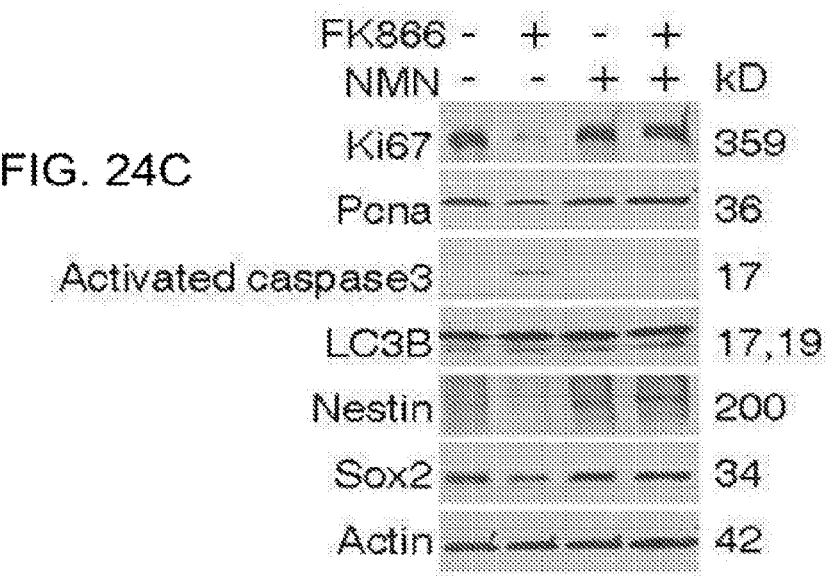
Figure 24D:
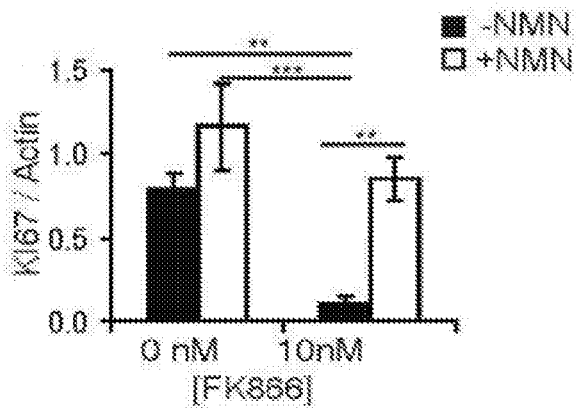
Figure 24E:
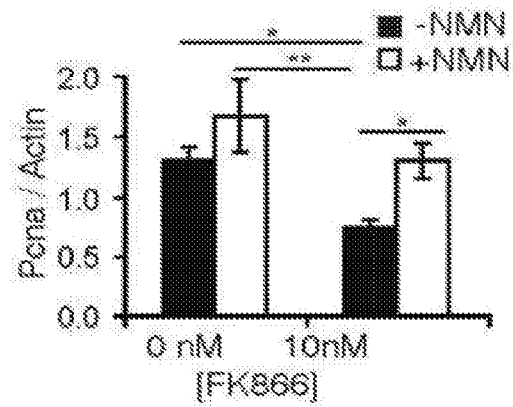

The inventors investigated how inhibition of Nampt affects neurosphere proliferation. Consistent with the decreases in the NSPC pool and in NSPC proliferation in iNSPC-Nampt-KO mice, FK866 reduced NSPC number by 61% after 48 hours, but not 24 hours, of treatment (FIGS. 17B-C and FIG. 24B). To distinguish whether this decrease in cell number was due to an inhibition of proliferation or enhancement of death, the inventors analyzed the protein levels of markers of proliferation, apoptosis, and autophagy. Expression of the proliferation markers Ki67 and PCNA decreased 87% and 43% respectively (FIG. 24C-24E), whereas levels of activated caspase 3 were only slightly increased and levels of the autophagy marker, glycosylated LC3B, were unchanged. Consistent with these observations, parametric analysis of gene set enrichment (PAGE) of a microarray performed on neurospheres treated with FK866 showed that out of the top 50 downregulated pathways, 13 of them were related to the cell cycle, while none of the top 50 upregulated pathways were involved in cell death Table 3, FIGS. 24F-G). Parametric analysis of gene enrichment (PAGE) was conducted based on microarray analyses. See the Methods section. Analysis of specific gene changes by qRT-PCR revealed that cyclins E and A, the two cyclins required for cellular progression from G1 to S, as well as their upstream transcriptional regulator E2F1 (Wong et al, 2011), were the primary cell cycle factors affected by this treatment (FIG. 17E). These alterations in gene expression indicated that reducing Nampt activity stalls NSPCs at G0/G1. Supporting this notion, FACS analysis of neurospheres demonstrated that FK866 treatment increased the proportion of NSPCs in G0/G1 and decreased the proportion in S phase (FIG. 17F). Data are presented as mean±s.e.m. *$P<0.05$. $P<0.01$. *$P<0.001$.

TABLE 3

| Rank | Cell Cycle | Total | Implicated | Z Ration | P Value |
|---|---|---|---|---|---|
| 3 | DNA_REPLICATION | 102 | 85 | −6.20 | 0.000 |
| 4 | DNA_DEPENDENT_DNA_REPLICATION | 56 | 46 | −6.07 | 0.000 |
| 14 | CELL_CYCLE_PROCESS | 193 | 167 | −4.75 | 0.000 |
| 15 | NUCLEAR_LUMEN | 387 | 310 | −4.74 | 0.000 |
| 16 | CELL_CYCLE_GO_0007049 | 315 | 268 | −4.63 | 0.000 |
| 19 | CELL_CYCLE_PHASE | 170 | 147 | −4.23 | 0.000 |
| 25 | CELL_CYCLE_CHECKPOINT_GO_0000075 | 48 | 38 | −3.92 | 0.000 |
| 28 | M_PHASE | 114 | 100 | −3.67 | 0.000 |
| 31 | REPLICATION_FORK | 18 | 16 | −3.60 | 0.000 |
| 32 | CONDENSED_CHROMOSOME | 34 | 27 | −3.57 | 0.000 |
| 35 | MITOTIC_CELL_CYCLE | 153 | 133 | −3.48 | 0.001 |
| 45 | INTERPHASE | 68 | 57 | −3.28 | 0.001 |
| 50 | INTERPHASE_OF_MITOTIC_CELL_CYCLE | 62 | 52 | −3.07 | 0.002 |

Example 12

This example illustrates that genetic ablation of Nampt in NSPCs in vitro impairs NAD+ biosynthesis, proliferation, and differentiation.

Figure 18:
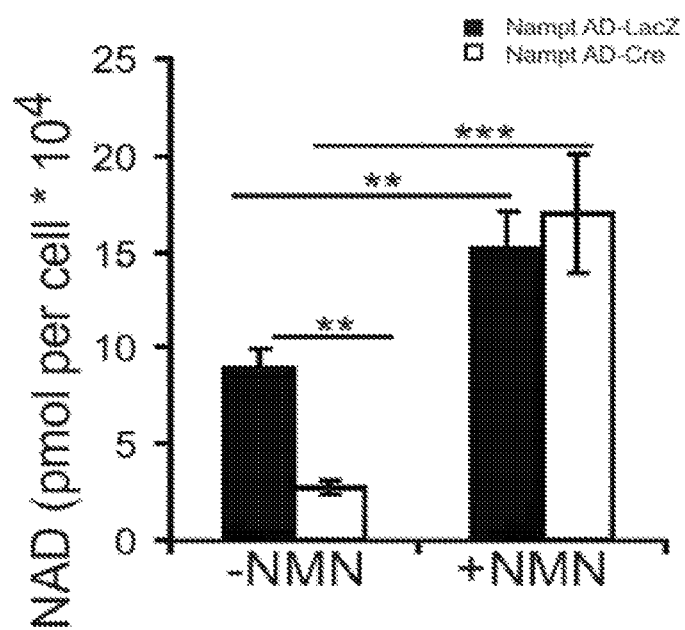

To assess the effect of chronic Nampt ablation on NSPC functionality, the inventors genetically ablated Nampt by infecting neurospheres from Nampt$^{flox/flox}$ mice with Cre recombinase- or LacZ-expressing (control) adenoviruses. Neurospheres infected with Cre recombinase (Nampt Ad-Cre) at passage 1 exhibited a 94% reduction in Nampt mRNA expression 3 days post deletion, and the corresponding decreases in Nampt protein expression and NAD+ levels appeared 6 days post deletion (FIGS. 25A-25E). Analyses were conducted after passage 2, at 6 or more days post infection. Data are presented as mean±s.e.m. *P <0.05. P<0.01. *P<0.001. Eight days post deletion, NSPCs exhibited a 73% reduction in NAD+ levels that was rescued by concurrent NMN administration, and without being limited by theory, further supporting the notion that Nampt activity is the predominant source of NSPCs NAD+ levels (FIG. 18A). Neurospheres were isolated from Namptflox/flox mice and infected with a Cre-recombinase expressing adenovirus (Nampt AD-Cre) or a control adenovirus expressing LacZ (Nampt AD-LacZ).

Figure 18B:
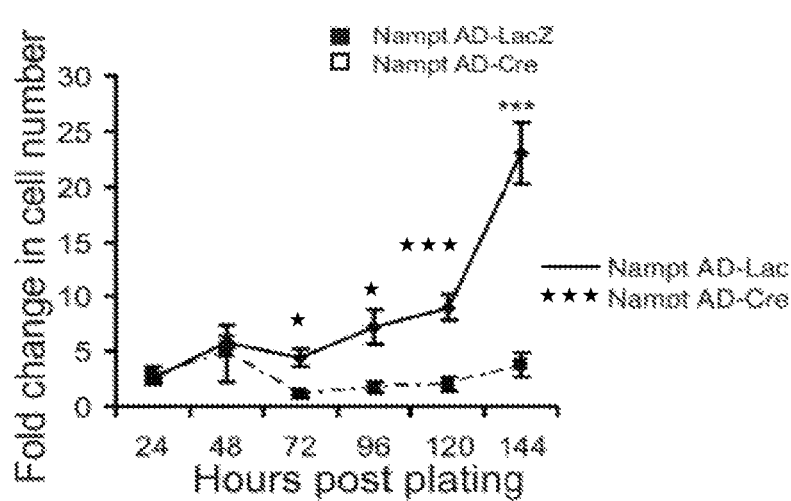
Figure 18C:
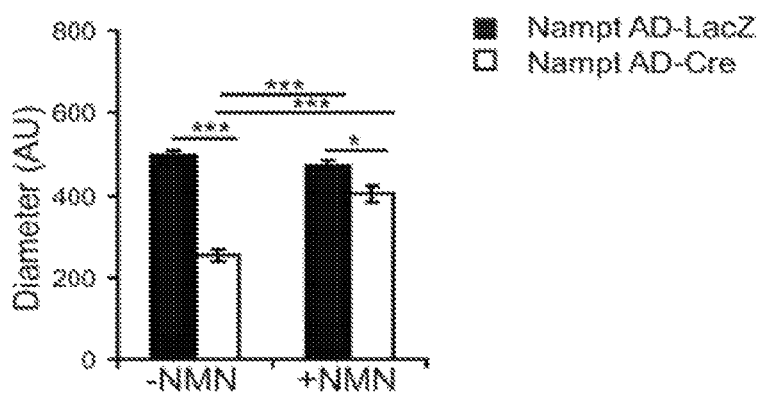
Figure 18:
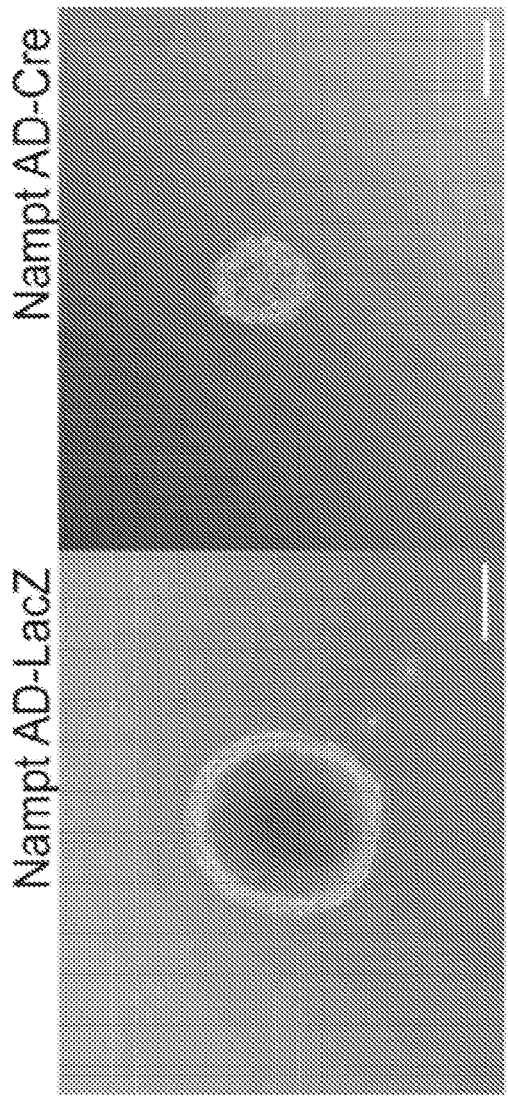
Figure 18E:
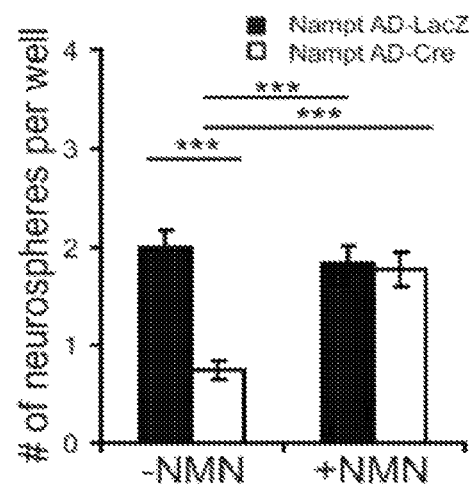
Figure 18F:
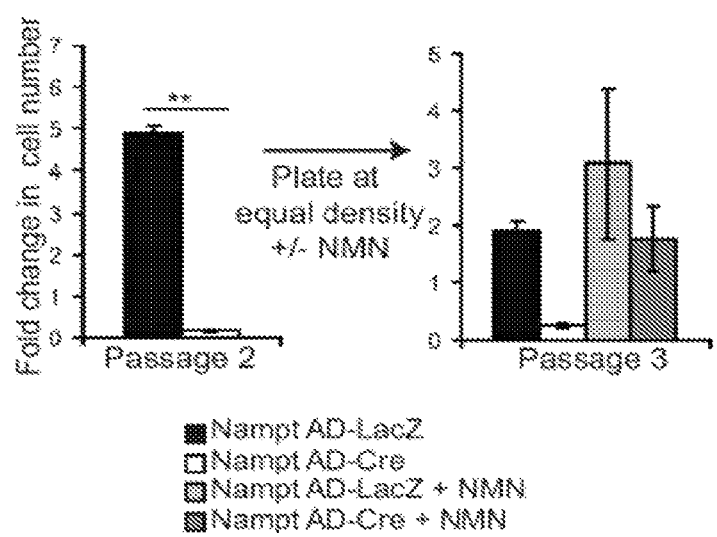
Figure 18G:
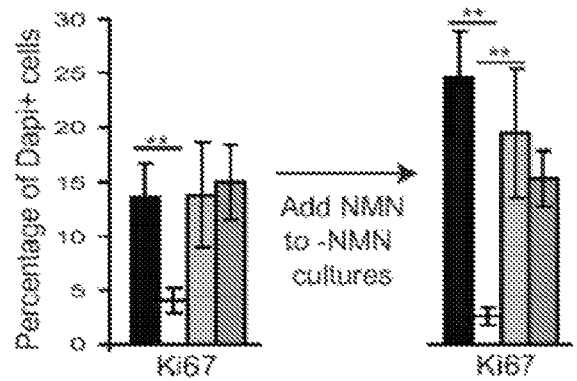
Figure 25A:
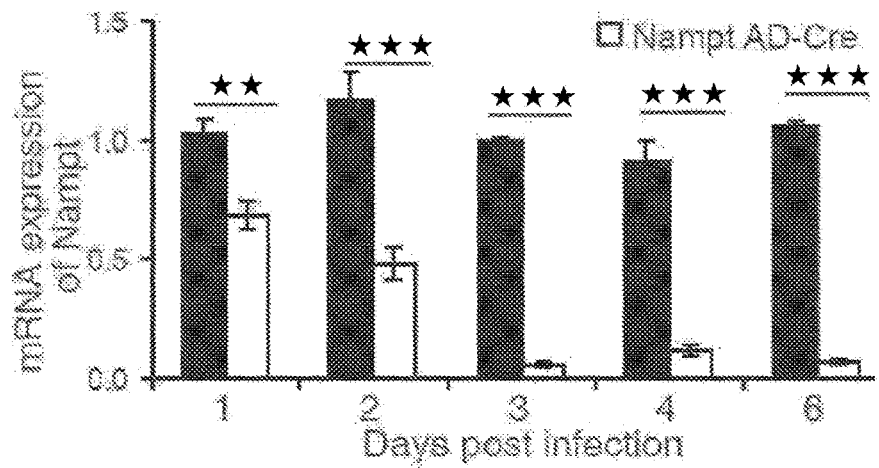
Figure 25B:
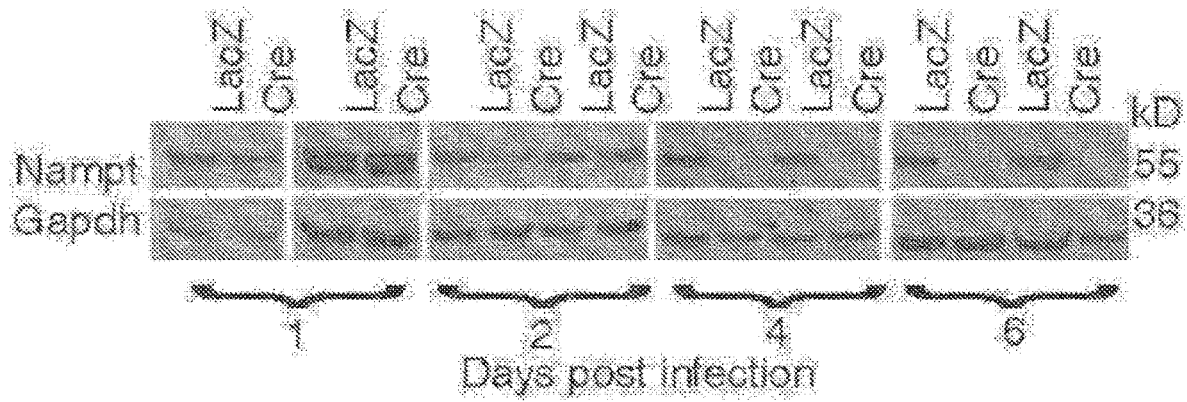
Figure 25C:
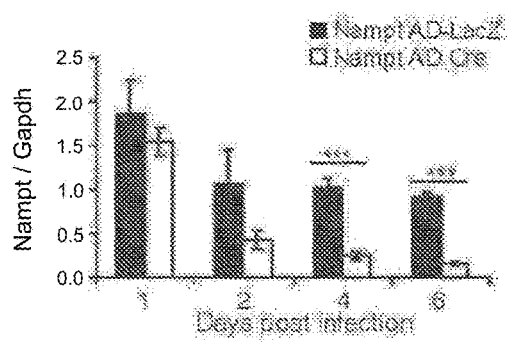
Figure 25D:
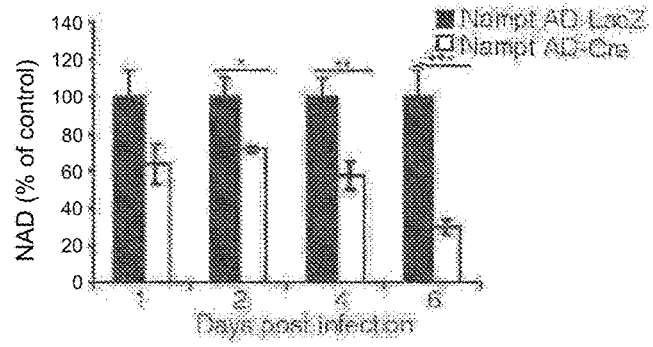
Figure 25E:
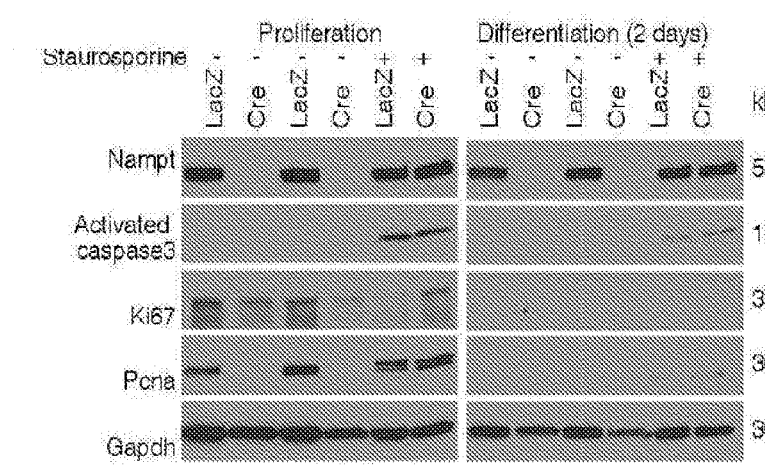
Figure 25F:
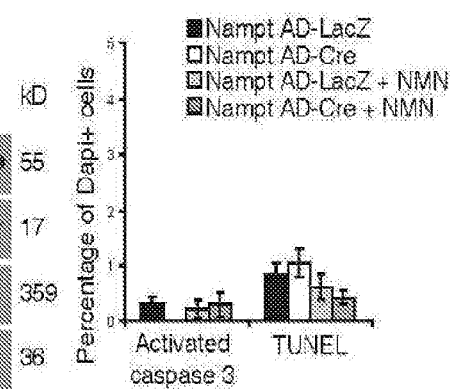

Like FK866-treated cultures, proliferating Nampt Ad-Cre infected NSPCs displayed reduced cell number (FIG. 18B). Nampt Ad-Cre NSPCs were unable to increase their cell number between 24 and 144 hours of culture. In contrast, Nampt AD-LacZ infected cells were able to exponentially increase their cell number over 13-fold in this time frame. Consistent with this finding, Nampt Ad-Cre infected NSPCs also showed a 49% reduction in diameter relative to Nampt AD-LacZ infected NSPCs, indicative of reduced proliferation (FIGS. 18C-D). Since NSPC self-renewal decisions can also contribute to cell number, the inventors assessed secondary neurosphere formation, an assay that quantifies the ability of neurosphere inhabitant cells to reformulate neurospheres upon dissociation. Nampt Ad-Cre infected cells generated 63% fewer secondary neurospheres than did Nampt AD-LacZ infected cells (FIG. 18E). Nampt AD-LacZ and Nampt Ad-Cre NSPCs exhibited no difference in the percentages of TUNEL- or activated caspase 3-positive cells as well as no difference in activated caspase3 immunoreactivity as detected by immunoblotting, without being limited by theory, indicating that the observed phenotypes upon loss of Nampt are not primarily due to cell death (FIG. 25E-F). As a positive control for activated caspase 3 immunoreactivity, indicated samples were treated with stauporine (1 mM) (n=6). To see if Nampt Ad-Cre infected neurospheres could be reactivated to proliferate, the inventors plated equal numbers of Nampt AD-LacZ and Nampt Ad-Cre cells after the second passage and cultured them in the presence or the absence of NMN. NMN treatment was able to fully reactivate the proliferative potential of Nampt Ad-Cre cells (FIG. 18F-G). Collectively, without being limited by theory, these results suggest that Nampt-mediated NAD+ biosynthesis plays a role for NSPCs to successfully progress through the cell cycle.

Figure 18H:
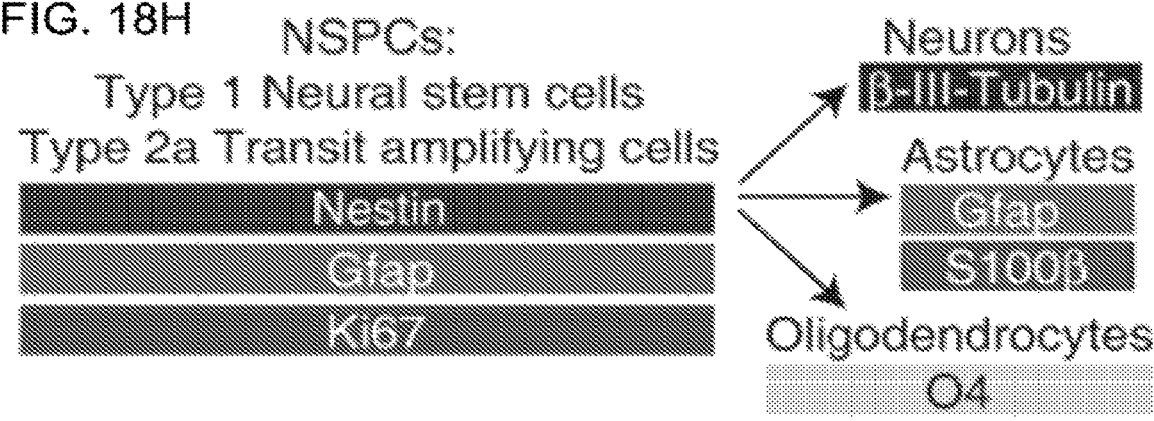
Figure 18I:
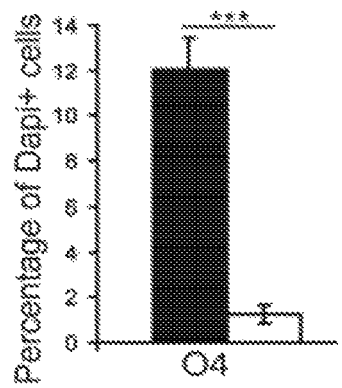
Figure 18J:
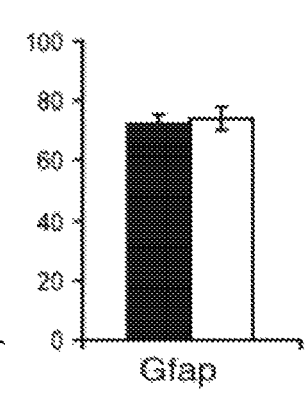
Figure 18K:
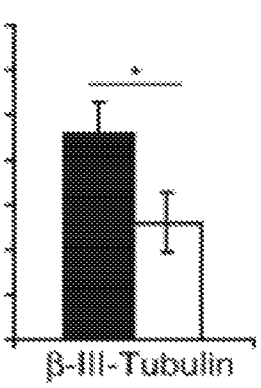
Figure 18:
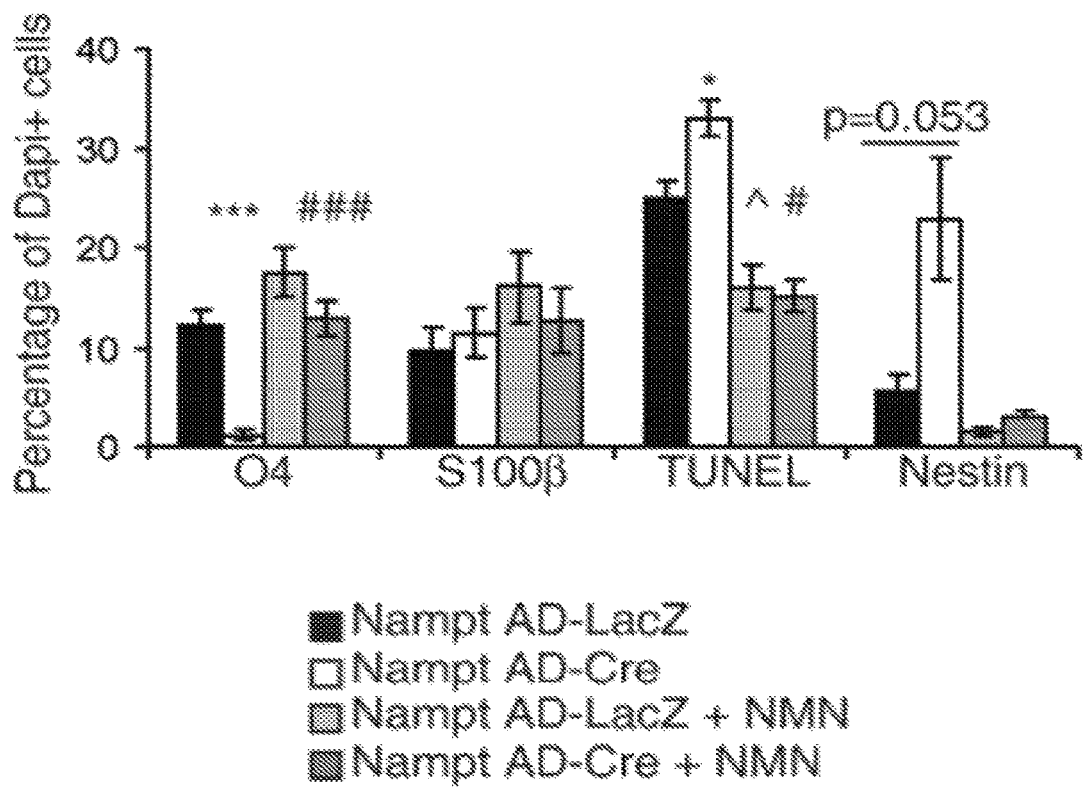
Figure 25G:
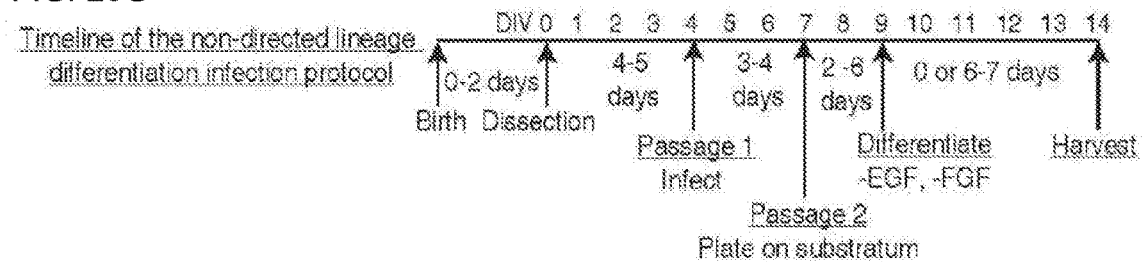

Whereas the inventors did not observe a difference in NSPC fate decisions in the neurogenic environment of the SGZ in vivo, the inventors detected a decrease in self-renewal decisions. To see if this would occur in the absence of the influences of the SGZ niche, the inventors differentiated dissociated neurospheres and assessed the proportion of resulting cell types by immunofluorescence after 6 to 7 days of differentiation induced by removal of growth factors (FIG. 18H, FIG. 25G). Differentiated Nampt Ad-Cre NSPCs exhibited a 90% reduction in oligodendrocytes (FIG. 18I). In contrast, Nampt Ad-Cre infected NSPCs exhibited no change in the generation of Gfap+ cells (FIG. 18J). Genetic knockdown of Nampt also significantly but more mildly decreased the generation of neurons (by 43% β-III-tubulin+, FIG. 18K). Thus, the decrease in oligodendrocytes was not due to an increase in neuronal fate. As Gfap can recognize both NSPCs and mature astrocytes, the inventors employed Nestin and S100β to distinguish whether the decrease in oligodendrocytes we observed upon Nampt knockdown was due to a cell fate choice in these directions. While there was no detectable change in the generation of S100β+ mature astrocytes in Nampt Ad-Cre cultures, there was a 4-fold increase in the percentage of Nestin+ cells (6% in Nampt Ad-LacZ cells; 23% in Nampt Ad-Cre cells), without being limited by theory, suggesting quiescence rather than precocious astrocytic differentiation (FIG. 18L). All of these effects were rescued by treatment with NMN. The inventors also observed a mild increase in TUNEL+ cell death under these conditions (33% increase relative to Nampt Ad-LacZ cells). *, ^, and #indicate statistical significance between Nampt AD-LacZ and Nampt AD-Cre, Nampt AD-LacZ and Nampt AD-LacZ+NMN, and Nampt AD-Cre and Nampt AD-Cre+NMN, respectively. Data are presented as mean±s.e.m. *P<0.05. P<0.01. *P<0.001. (FIGS. 18A-L) Together, without being limited by theory, these data suggest that genetic knockdown of Nampt prevents the successful differentiation of oligodendrocytes from NSPCs, potentially due to quiescence as indicated by a retention of NSPC characteristics.

Example 13

This example illustrates that genetic knockdown of Nampt impairs OPC formation in vitro.

Figure 19:
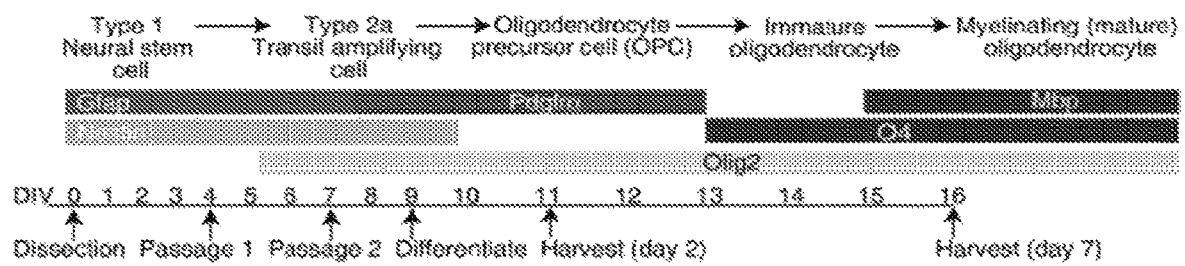
Figure 19B:
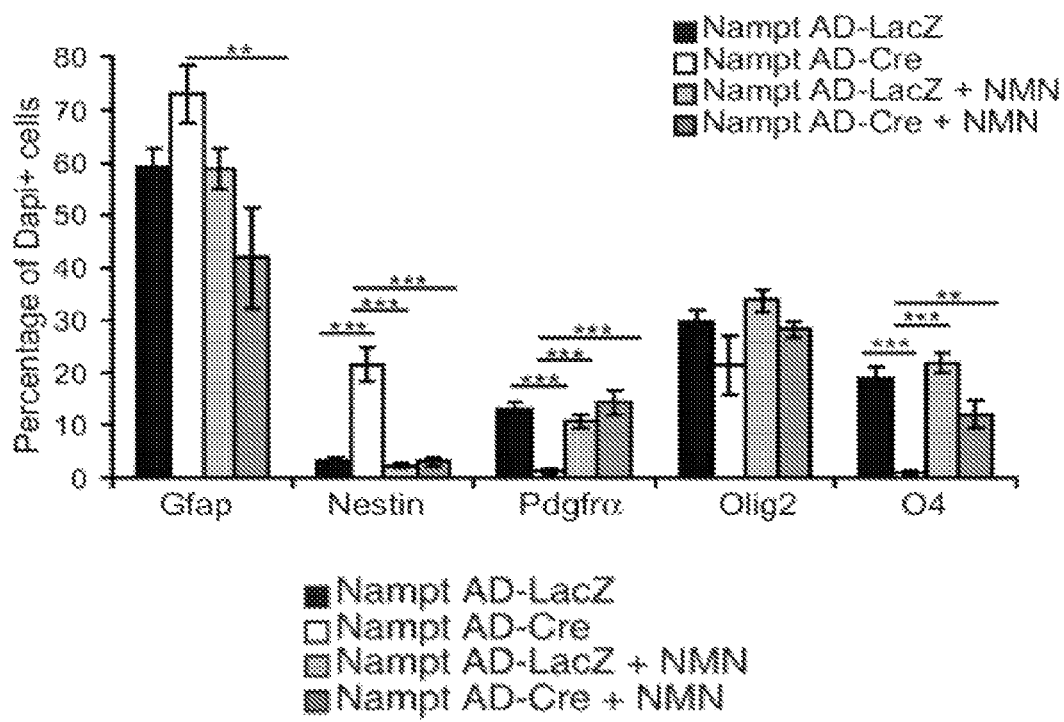
Figure 19C:
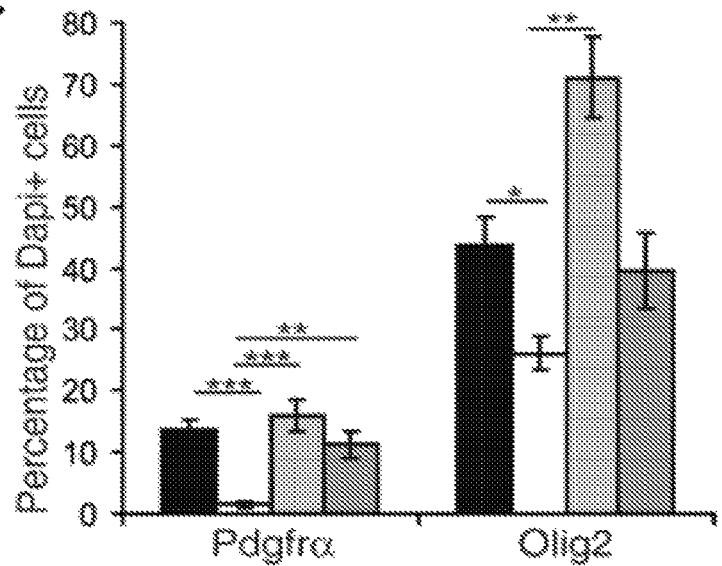
Figure 26A:
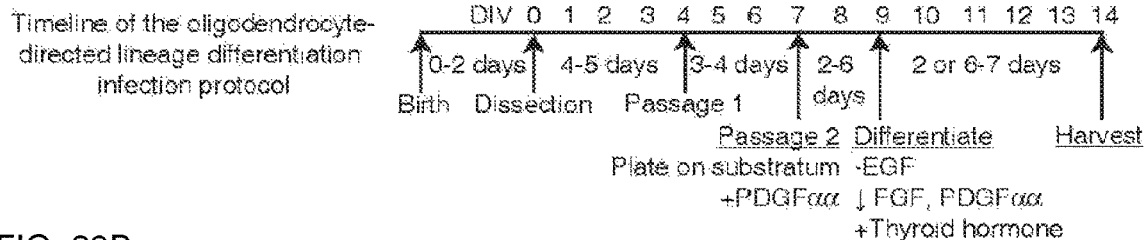
Figure 26B:
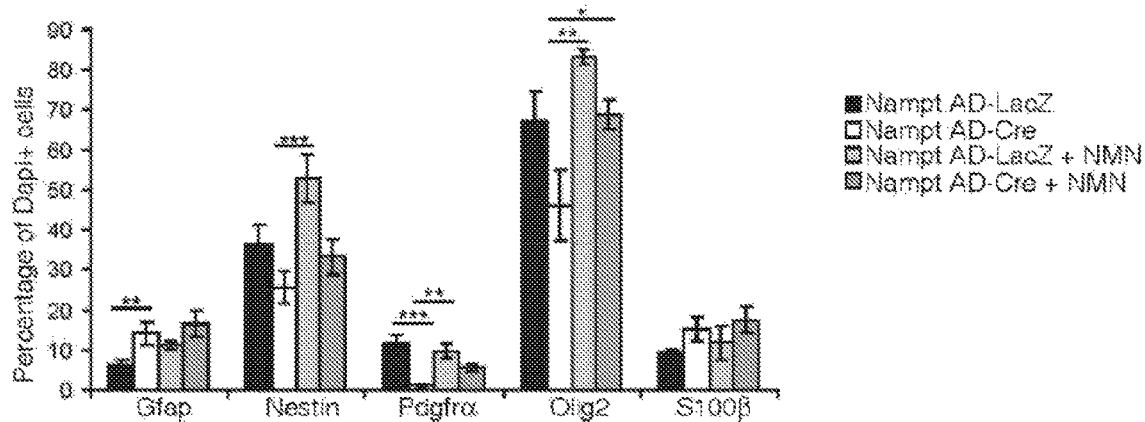

Since differentiation using a nonspecific lineage differentiation protocol (by removal of growth factors) revealed a specific requirement for Nampt in the successful generation of O4+ immature oligodendrocytes, the inventors next asked which stage(s) of NSPC differentiation into oligodendrocytes depends on Nampt by employing a differentiation protocol that promotes the oligodendrocyte lineage (FIG. 19A, FIG. 26A). Neurospheres were isolated from Nampt-flox/flox mice and infected with a Cre-recombinase expressing adenovirus (Nampt AD-Cre) or a control adenovirus expressing LacZ (Nampt AD-LacZ). As previously observed using a nonspecific lineage differentiation protocol, the proportion of O4+ intermediate oligodendrocytes was dramatically decreased in Nampt Ad-Cre cultures at 6-7 days post differentiation (FIG. 19B). The inventors observed that ablation of Nampt resulted in a decreased pool of OPCS (Pdgfrα+), but an increased pool of Nestin+ NSPCs. The proportion of Gfap+ astrocytes/NSPCs also mildly increased. To investigate whether the depletion of the OPC population was preexisting to or induced upon differentiation, the inventors assessed the OPC population present during proliferation. Dissociated neurospheres were cultured in proliferation media containing PDGFaa. (FIG. 26B) and after 2 days of differentiation (FIG. 19C), a time point that enriches for OPCS as assessed by immunofluorescence. Both of these time points also showed loss of OPCS (Pdgfrα+, Olig2+). These results support that, without being limited by theory, Nampt is plays a role for NSPCs to differentiate into OPCS.

Figure 19F:
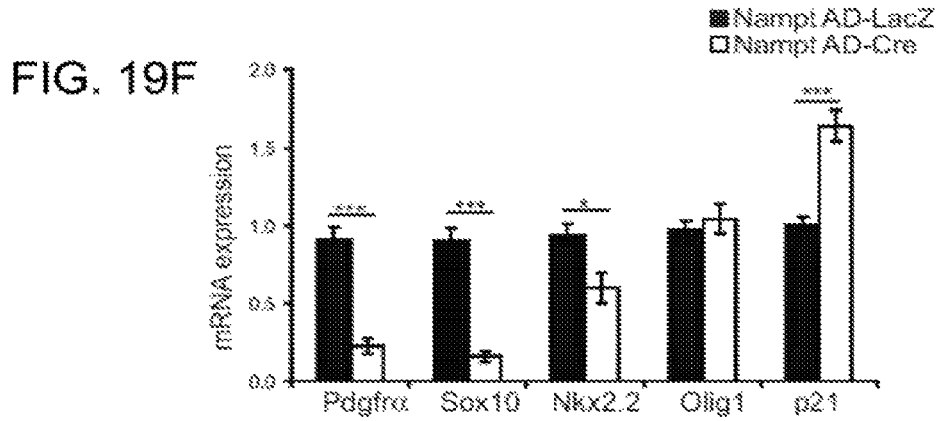
Figure 19G:
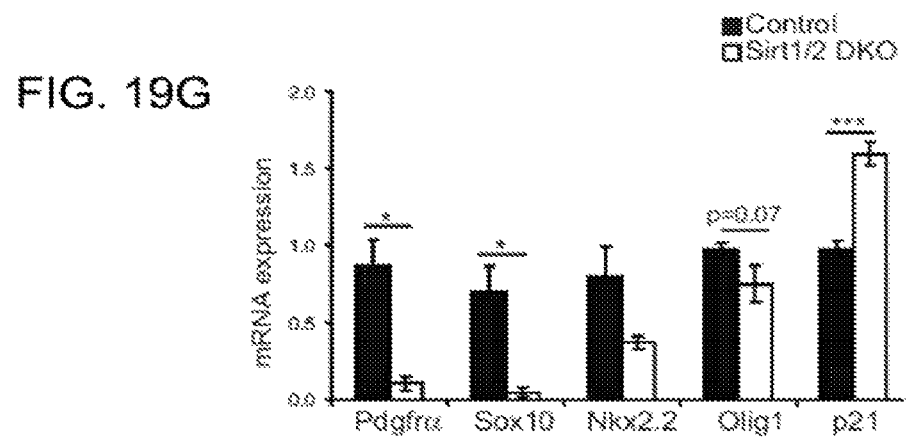
Figure 26C:
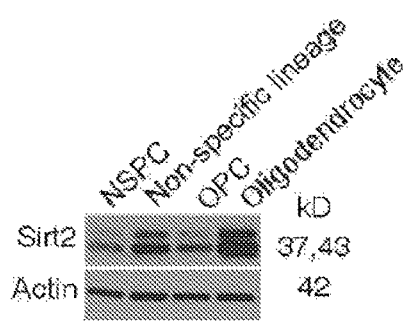
Figure 26D:
Figure 26E:
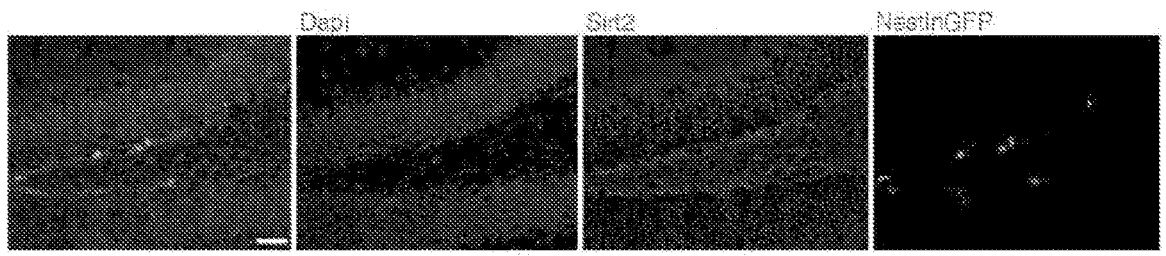
Figure 26F:
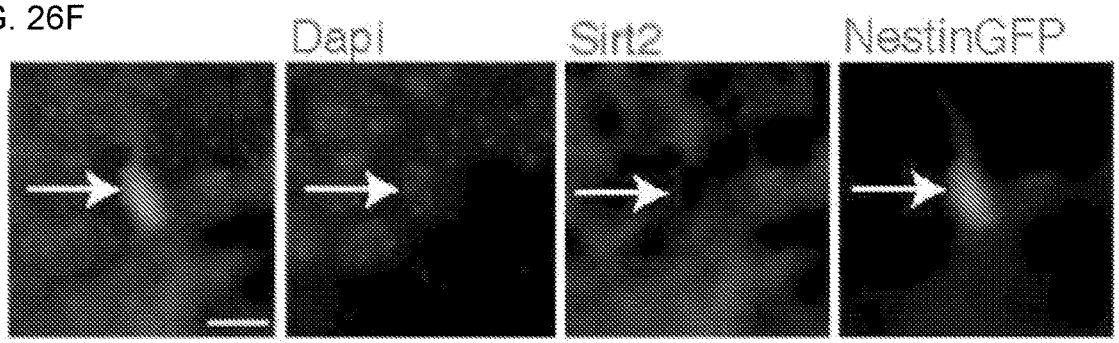
Figure 26G:
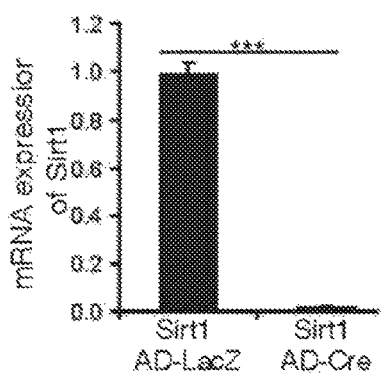
Figure 26H:
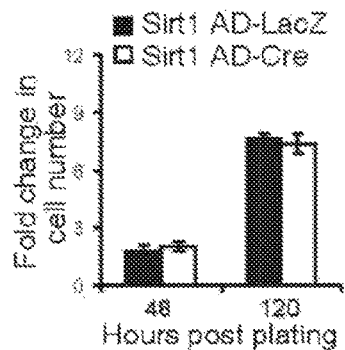
Figure 26I:
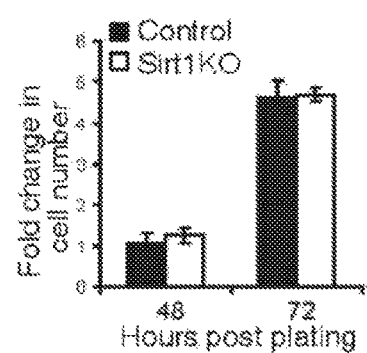
Figure 26J:
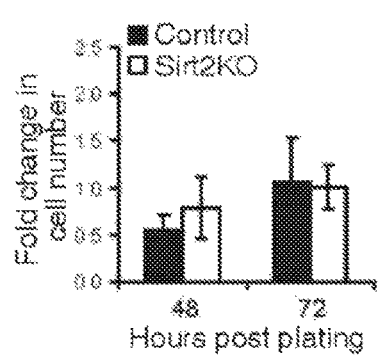

The inventors observed that Sirt2 was upregulated during oligodendrocyte differentiation in vitro and expressed in the SGZ in Nampt+ cells and NestinGFP+ NSPCs (FIG. 26C). The inventors acutely treated NSPCs with the selective inhibitor of Sirt2, AGK2, or the Sirt1 inhibitor, EX527. Whereas both inhibitors acutely suppressed oligodendrocyte formation (O4+, FIG. 19D), neither chronic ablation of Sirt2 in the NSPCs isolated from Sirt2$^{-/-}$ mice nor Cre adenovirus mediated knockdown of Sirt1 in Sirt1$^{flox/flox}$ derived neurospheres affected oligodendrogenesis (Pdgfrα+, Olig2+, O4+), except that Sirt1 deficiency affected the production of O4+ intermediate oligodendrocytes (FIG. 19E). The inventors generated Sirt 1/Sirt2-double knockout (Sirt1/2 DKO) neurospheres. Consistent with the inhibitor studies (FIG. 19D), dissociated Sirt1/2 DKO neurospheres were unable to form oligodendrocyte lineage cells upon differentiation (FIG. 19E). To assess the role of Sirt1 and Sirt2 downstream of Nampt activity, the inventors examined the expression of genes associated with OPC formation in Nampt Ad-Cre neurospheres, Sirt1/2 DKO neurospheres, and their respective controls. Dissociated Nampt Ad-Cre and Sirt1/2 DKO neurospheres showed similar decreases in the mRNA expression of Pdgfrα, Sox10, Nkx2.2 after 2 days of differentiation (FIG. 19F-G). Dissociated Nampt Ad-Cre and Sirt1/2 DKO neurospheres respectively exhibited similar increases in the expression of p21 (cdkn1α). Olig1 expression showed no change or slight reduction by these genetic ablations, potentially due to its lesser expression in NSPCs relative to Olig2 (Ligon et al, 2007) and predominant roles in oligodendrocyte maturation and remyelination rather than specification. Neither Cre mediated knockdown of Sirt1 in neurospheres nor neurospheres cultured from whole-body Sirt1$^{-/-}$ or Sirt2$^{-/-}$ mice exhibited defects in proliferation (FIG. 26G-J). Data are presented as mean±s.e.m. *P<0.05. P<0.01. *P<0.001. The inventors conclude that Sirt1 and Sirt2 can redundantly mediate NSPC differentiation into OPCs.

Example 14

This example illustrates adult NSPC-specific deletion of Nampt impairs NSPC differentiation in response to insult in vivo.

Figure 16I:
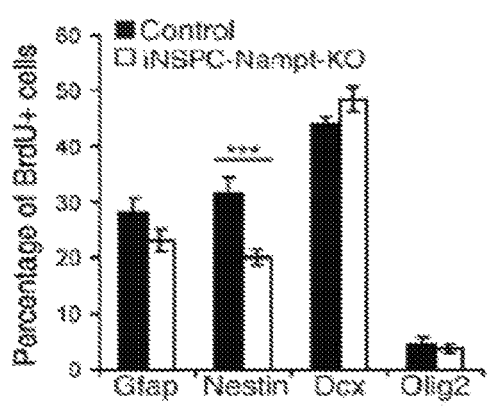
Figure 16J:
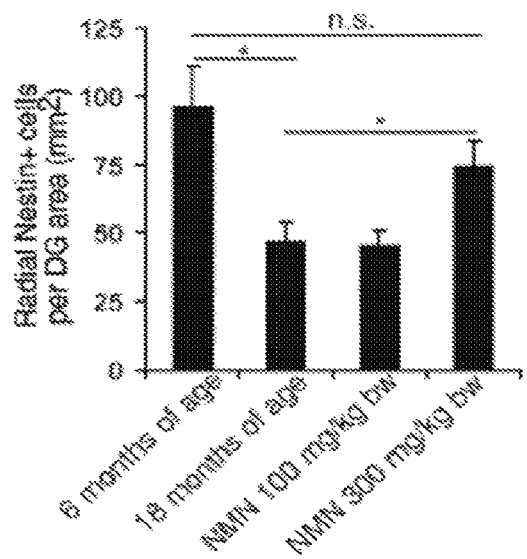

The inventors observed Nampt ablation on NSPC differentiation into OPCs in vitro, but not oligodendrogenesis in the SGZ of iNSPC-Nampt-KO mice in vivo (FIG. 16I). The inventors assessed the percentage of NestinGFP+ cells that expressed Olig2 in the SVZs of iNSPC-GFP and iNSPC-Nampt-KO mice (FIG. 20A). iNSPC-Nampt-KO mice showed a lower percentage of oligodendrocytes generated from adult NSPCs.

The inventors employed the cuprizone model of demyelination and remyelination. Specifically, the inventors fed 6- to 9-week-old iNSPC-Nampt-KO and littermate control mice (iNSPC-GFP) a diet containing 0.2% cuprizone for 4-5 weeks, inducing deletion of Nampt in the adult Nestin+ population the week before starting the cuprizone diet (FIG. 20B) (Skripuletz et al, 2011). To ensure that analysis of progeny of adult Nestin+ cells, all mice in our cohort expressed Cre recombinase under the inducible Nestin promoter (Nestin-CreERT2) (Lagace et al, 2007) and the aforementioned Cre recombinase responsive GFP reporter transgene. The analysis focus was on lineage tracer marked (NestinGFP+) cells.

Cuprizone feeding did not alter the total number of NestinGFP+ cells present in the iNSPC-GFP DG (FIG. 27A-C), suggesting, without being limited by theory, that NSPC proliferation was unaltered. Data are presented as mean±s.e.m. *, ^P<0.05. , ^^P<0.01. *, ^^^P<0.001. Cuprizone fed mice exhibited an increased percentage of NestinGFP+ cells that co-localized with the NSPC markers Nestin+ (from 13 to 35%) and Gfap+ (from 19 to 41%), suggesting that, without being limited by theory, cuprizone treatment prevented SGZ NSPCs from terminally differentiating and instead resulted in their retention of NSPC characteristics, which could occur through increased self-renewal decisions and/or quiescence (FIG. 27D-E). The inventors next assessed colocalization between NestinGFP and oligodendrocyte specific markers, Sox10 and APC. However, the SGZ did not substantially produce oligodendrocytes even in response to demyelination (FIG. 27F-G Therefore, without being limited by theory, SGZ NSPCs do not appear to be the main mediators of short-term remyelination in the hippocampus.

Figure 20:
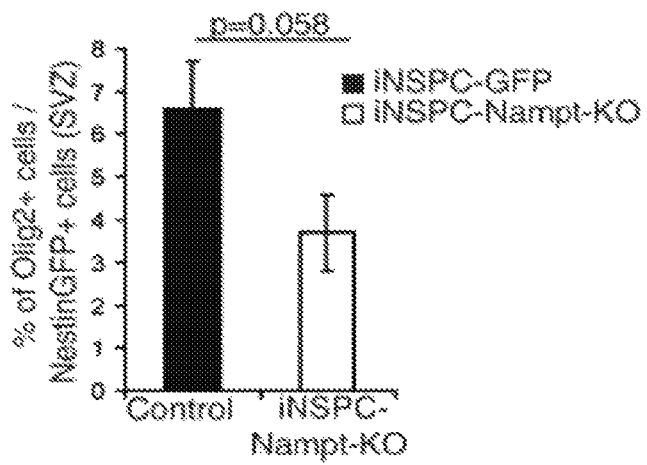
Figure 20D:
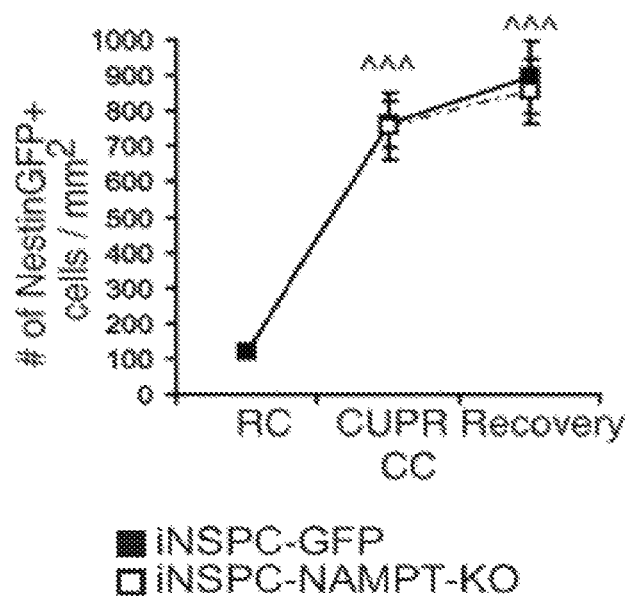
Figure 20E:
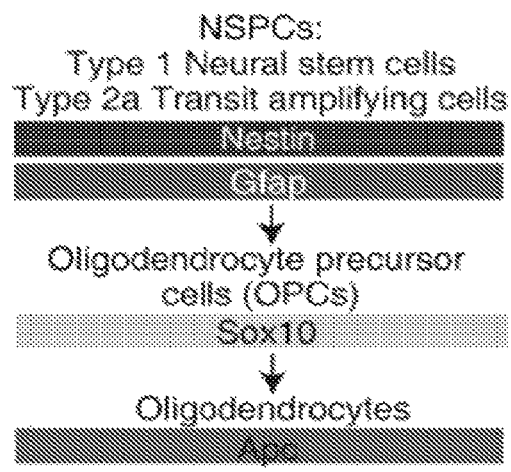
Figure 20F:
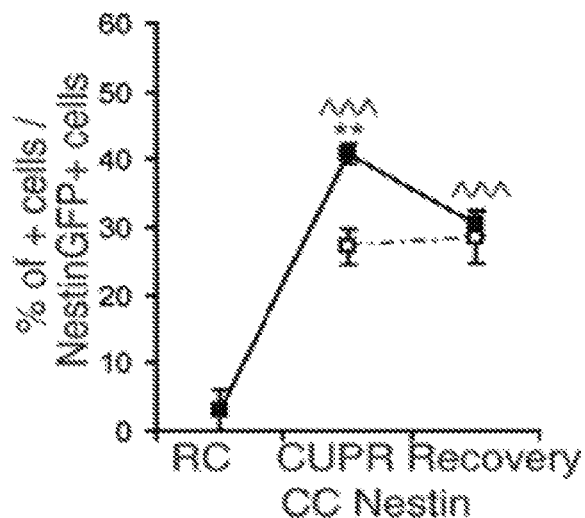
Figure 20G:
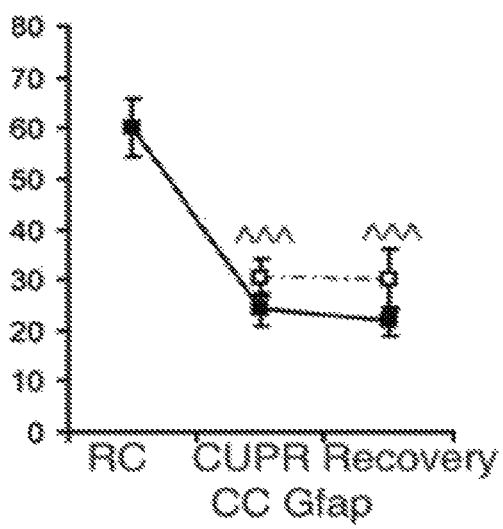
Figure 20H:
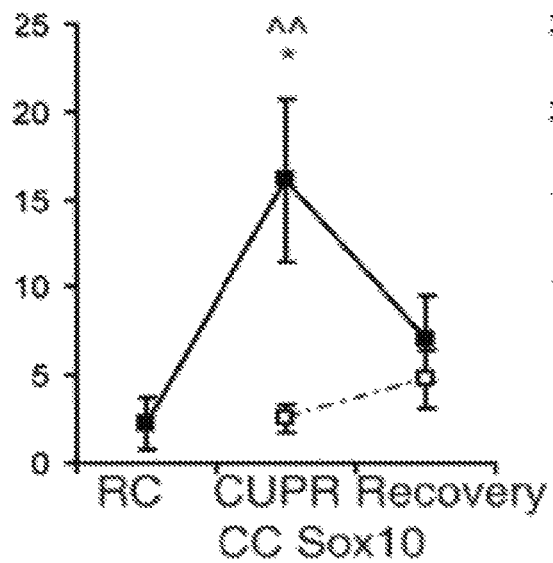
Figure 20I:
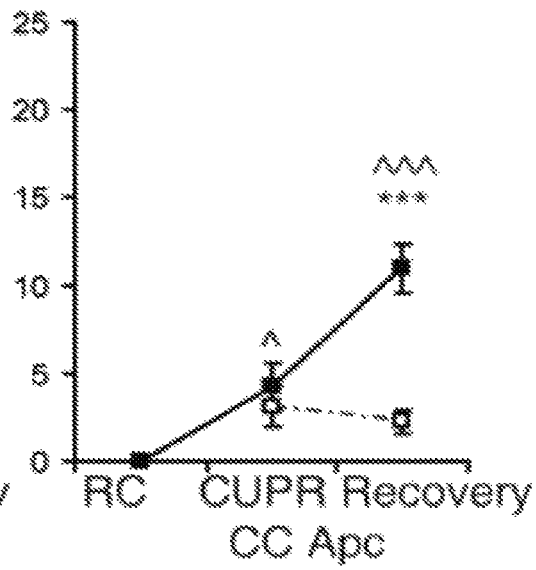
Figure 27A:
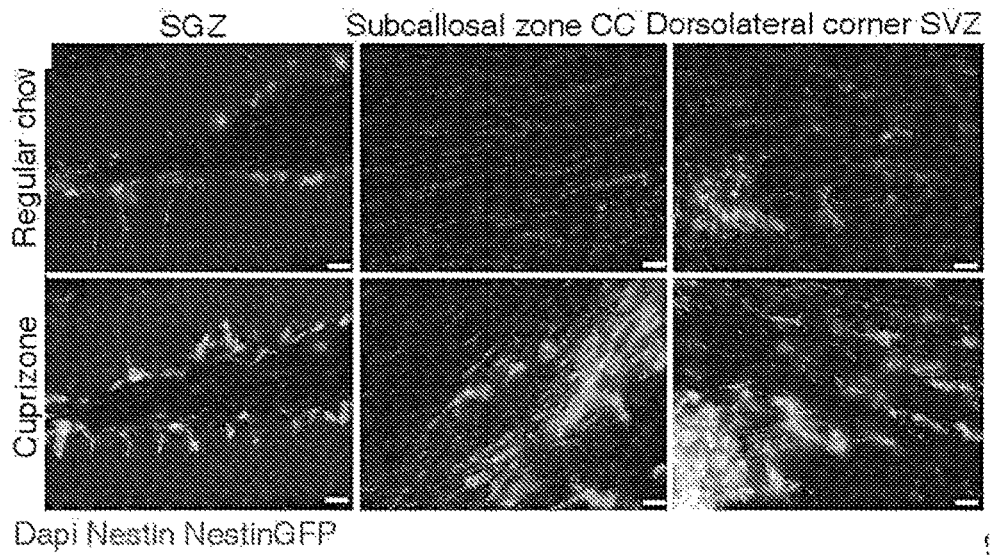
Figure 27B:
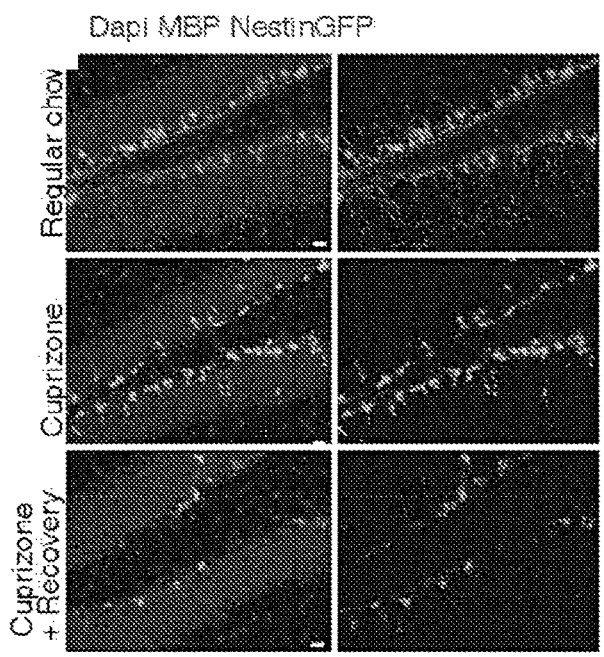
Figure 27C:
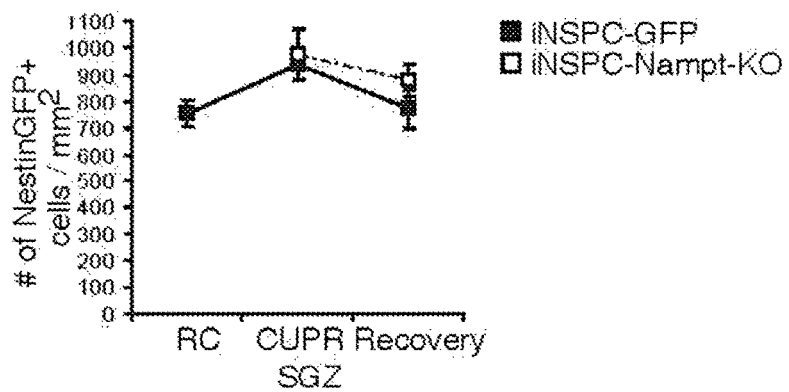
Figure 27D:
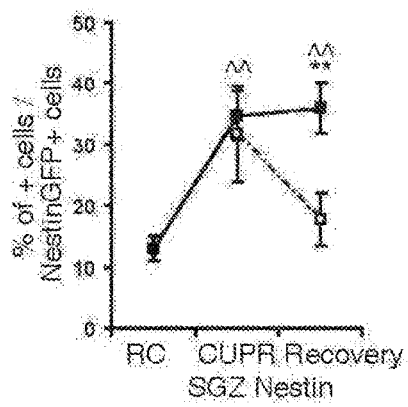
Figure 27E:
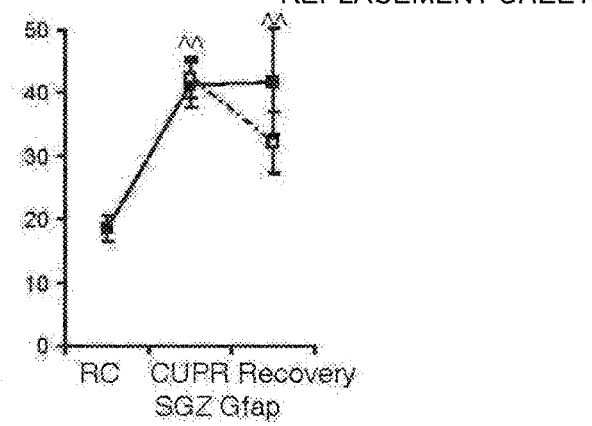
Figure 27F:
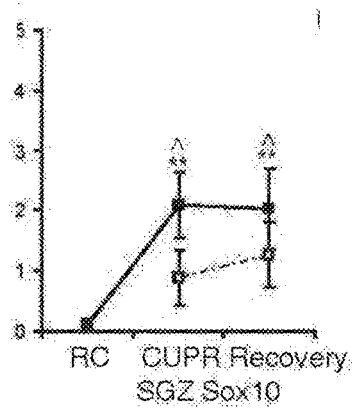
Figure 27G:
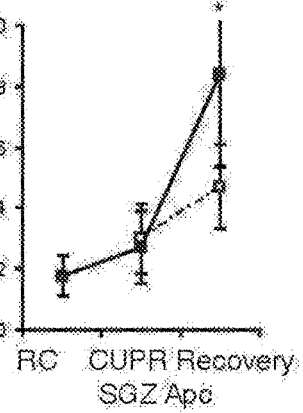

The inventors assessed the fate decisions of migratory cells derived from the adult Nestin+ population in the subcallosal zone of the corpus callosum (FIG. 27A). In the iNSPC-GFP CC, virtually no NestinGFP+ or Nestin+ cells were seen in regular chow fed mice (FIG. FIG. 27A). There were no differences in the number of NestinGFP+ cells in the CC between control and iNSPC-Nampt-KO mice, suggesting, without being limited by theory, that loss of Nampt neither affected insult-induced NSPC proliferation or migration. In the iNSPC-GFP CC, cuprizone feeding significantly increased the percentage of NestinGFP+Nestin+ cells (from 3 to 41%) but decreased the NestinGFP+Gfap+ (from 60 to 24%) double positive cells, suggesting, without being limited by theory, increased self-renewal fate decisions at the expense of astrocytic fate decisions (FIG. 20E-G). In control mice, cuprizone feeding also increased the number of NestinGFP+Sox10+ (from 2 to 16%) and NestinGFP+Apc+ (from 0 to 4%) double positive cells, suggesting increased oligodendrocyte lineage fate decisions (FIG. 20H-I).

Figure 20J:
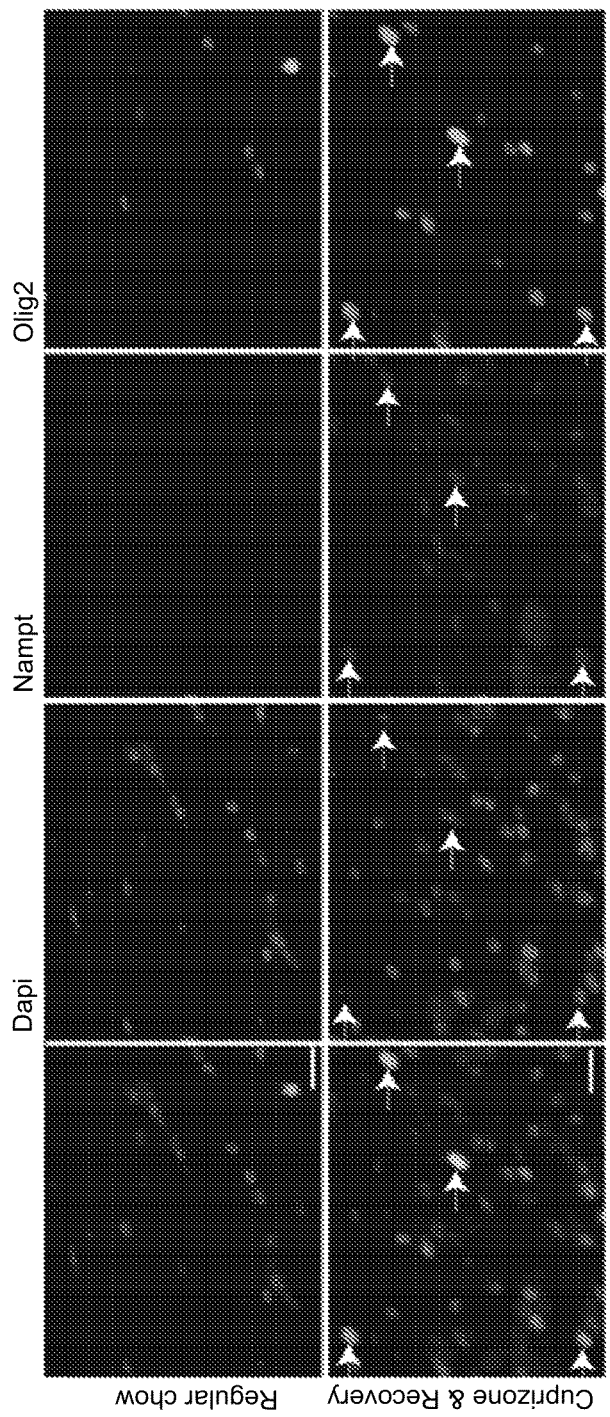
Figure 27H:
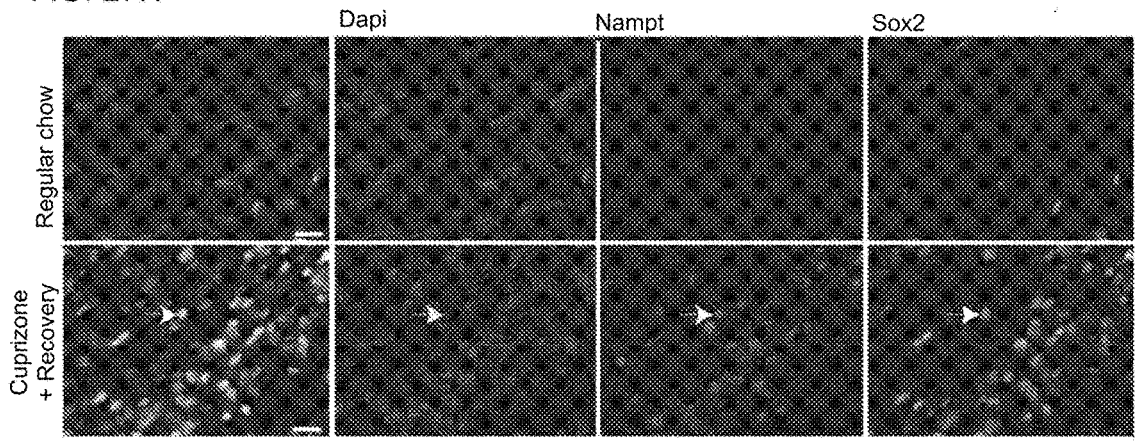

In contrast, the NestinGFP+ cells in the iNSPC-Nampt-KO CC showed significantly less colocalization with Nestin, Sox10, and Apc and more colocalization with Gfap (FIG. 20F-I). Interestingly, Nampt was only expressed in the CC upon insult (FIG. 20J, FIG. 27H). Moreover, Nampt colocalized with markers of NSPCs (Sox2, FIG. 27H) and oligodendrocytes (Olig2, FIG. 20J). These results suggest, without being limited by theory, that Nampt is specifically expressed in SGZ/SVZ derived remyelinating NSPCs and plays a role in oligodendrogenesis in response to insult.

Example 15

This example illustrates a model for the role of Nampt-mediated NAD biosynthesis in NSPCs without being limited by theory.

Nampt-mediated NAD+ biosynthesis promotes NSPC self-renewal, proliferation and differentiation into oligodendrocytes. While the mechanism by which Nampt promotes self-renewal and proliferation remains unidentified, Nampt-mediated NAD+ biosynthesis activates Sirt1 and Sirt2 to promote NSPC oligodendrocyte lineage fate decisions by a mechanism involving transcriptional downregulation of Pdgfrα, Sox10, and Nkx2.2 and transcriptional upregulation of p21 (cdkn1a). Sirt1 and Sirt2 may act via an effect on Olig2 activity. (FIG. 21)

The inventors showed that the NSPC pool decreased with age and that long-term NMN administration was able to maintain the NSPC pool. The inventors assert that a higher dosage of NMN can be used to promote NSPC proliferation. Intraperitoneal injection of NMN substantially increases hippocampal NAD+ levels within 15 minutes (FIG. 23G), without being limited by theory, suggests that NMN can cross the blood-brain barrier.

As E2F1-deficient mice have significantly reduced hippocampal NSPC death (Cooper-Kuhn et al, 2002), without being limited by theory, the observed decrease in E2F1 upon inhibition of Nampt may explain this phenomenon (FIG. 17E). The inventors also observed that loss of Nampt activity specifically downregulated Cyclin E and A expression. E-type cyclins regulate G1 progression. The inventors observed downregulation of E2F1 expression, which transcriptionally regulates Cyclin E, therefore, without being limited by theory, it is likely that the downregulation of E2F1 contributes to the downregulation of Cyclin E. The inventors also observed upregulation of p21 upon loss of Nampt. Thus, the upregulation of p21 that we see upon loss of Nampt, without being limited by theory, may also contribute to the downregulation of E2F/Cyclin E activity. As Cyclin A expression is induced after E2F and Cyclin E (Wong et al, 2011), the changes in Cyclin A levels are likely downstream of both the aforementioned changes. While we have linked Nampt to the E2F/Cyclin E pathway, connecting mediator(s) remain unclear. The inventors found neither Sirt1 nor Sirt2 to be downstream of the effect of Nampt-mediated NAD+ biosynthesis on proliferation. While it is possible that Sirt1/2 function redundantly to mediate NSPC proliferation, the relatively low expression of Sirt2 in NSPCs (FIG. 26G) makes this possibility unlikely, without being limited by theory.

The present inventors revealed that ablation of Nampt specifically reduced the proportion of NSPC-generated Pdgfrα+ OPCs as well as the transcription of Pdgfrα, Sox10, and Nkx2.2 but upregulated the expression of p21. The results showed that in neurospheres, treatment with NMN rescued defects in oligodendrogenesis caused by a reduction in NAD+ levels. Furthermore, systemic NMN administration was able to substantially augment hippocampal NAD+ levels and increase the NSPC pool. Thus, NMN administration could be an efficient intervention to enhance the NSPC pool and promote remyelination by activating endogenous NSPCs during the aging process and/or in neurodegenerative diseases that cause demyelination. The results provide evidence of the therapeutic potential of Nampt-mediated NSPC self-renewal, proliferation, and differentiation into oligodendrocytes.

Example 16

This example illustrates an increase in bone density in aged individuals by NMN administration.

The inventors measured the bone mineral density (BMD) of control and NMN-treated mice at the 12-month time point of a 12 month long NMN administration experiment by dual-energy X-ray absorptiometry (DXA). At this time point, mice were 17-18 month old. The inventors found that NMN-treated mice showed increases in the BMD in a dose-dependent manner, and the difference between control and 300 mg/kg groups is statistically significant (P=0.037, ANOVA, Tukey HSD post hoc test). Mice from 100 and 300 mg/kg groups showed 2.8% and 5.9% increases in the BMD, respectively. Although age-associated BMD loss is extensively varied among mouse strains (http://phenome.jax.org), the extent of these observed BMD increases is significant, indicating that NMN is able to enhance the BMD in aged individuals. These data indicate that NMN administration can be used to treat age-associated osteoporosis in humans.

Example 17

This example illustrates characterization of loss of NAMPT-mediated NAD biosynthesis on PR neuron survival.

Figure 29A:
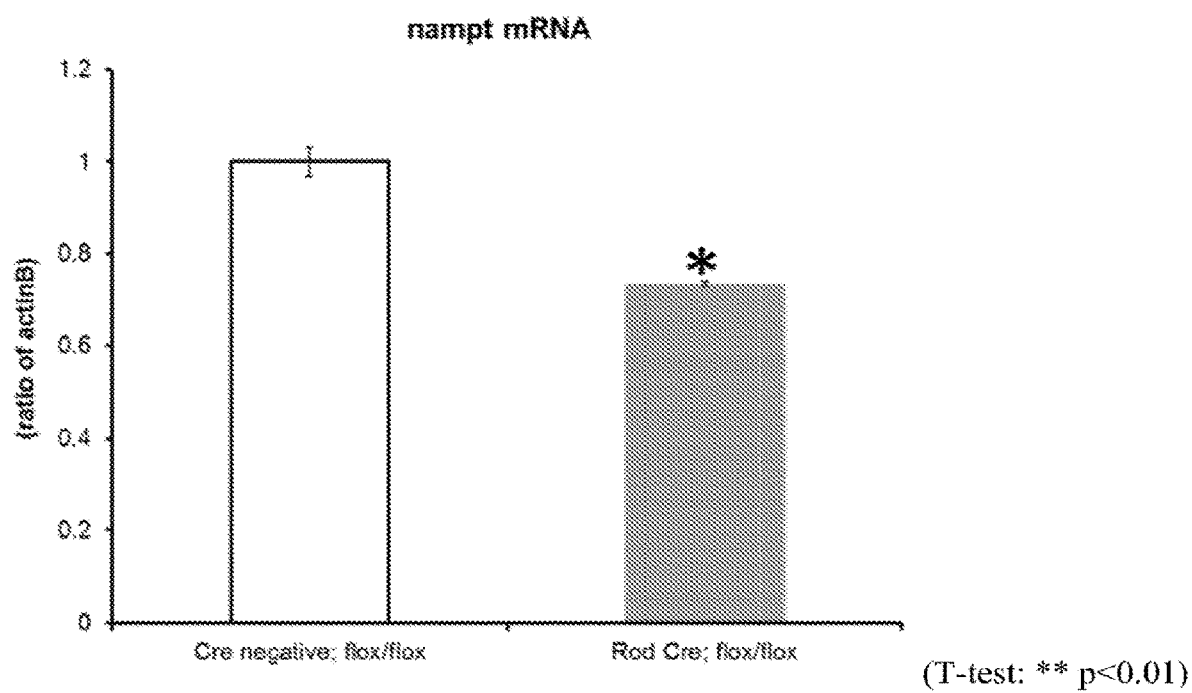
Figure 29B:
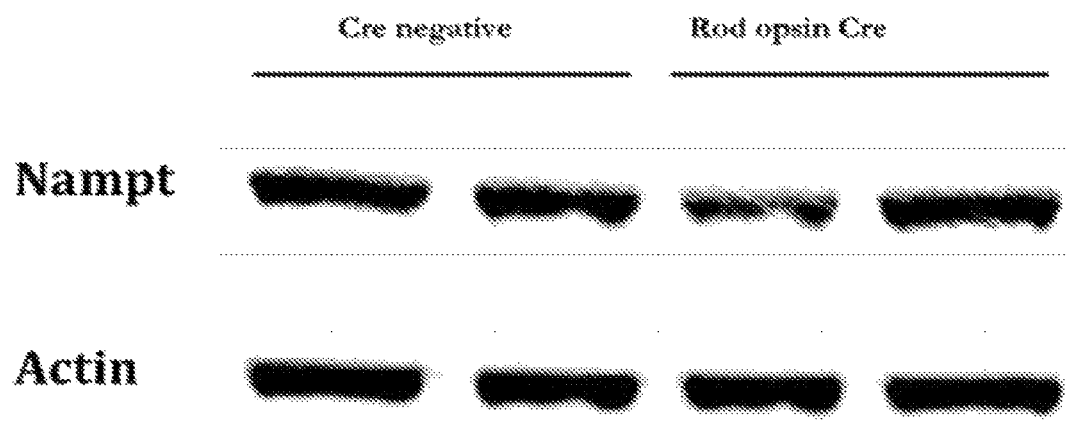
Figure 29C:
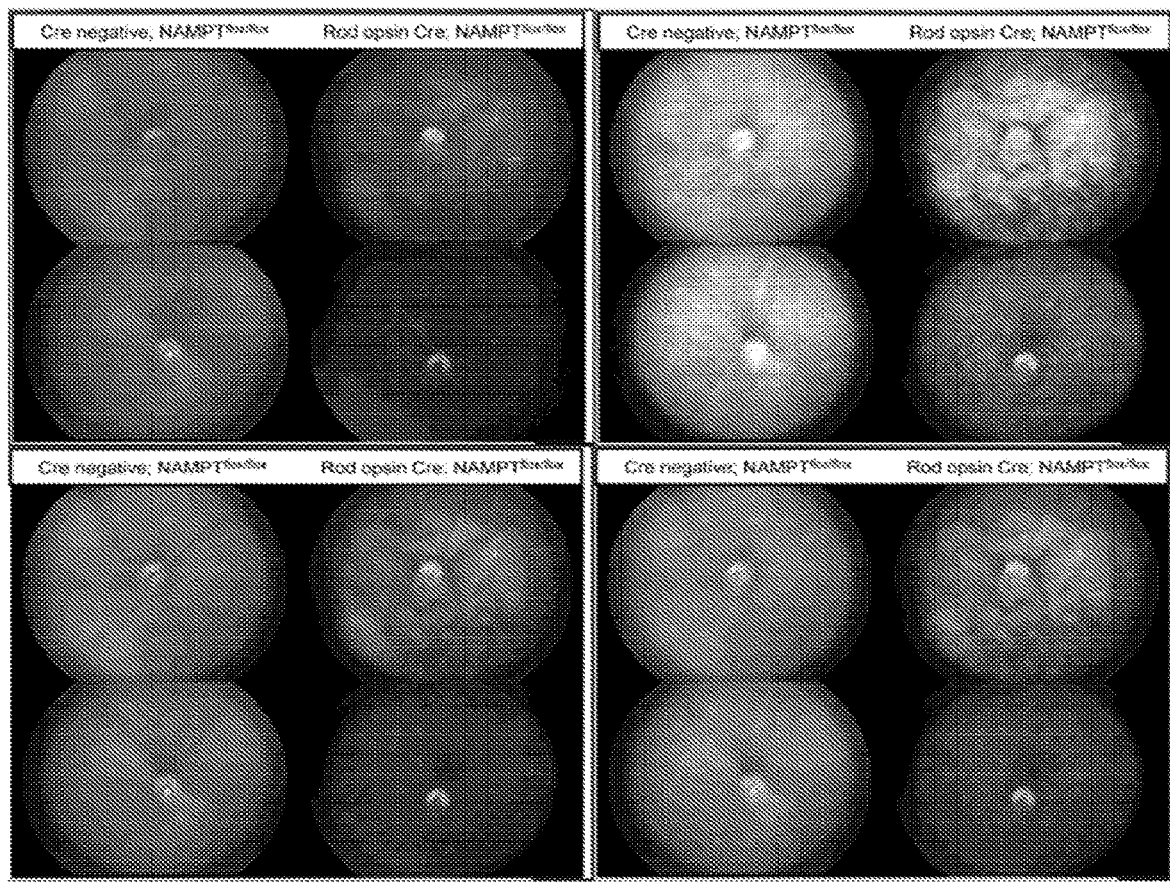
Figure 29D:
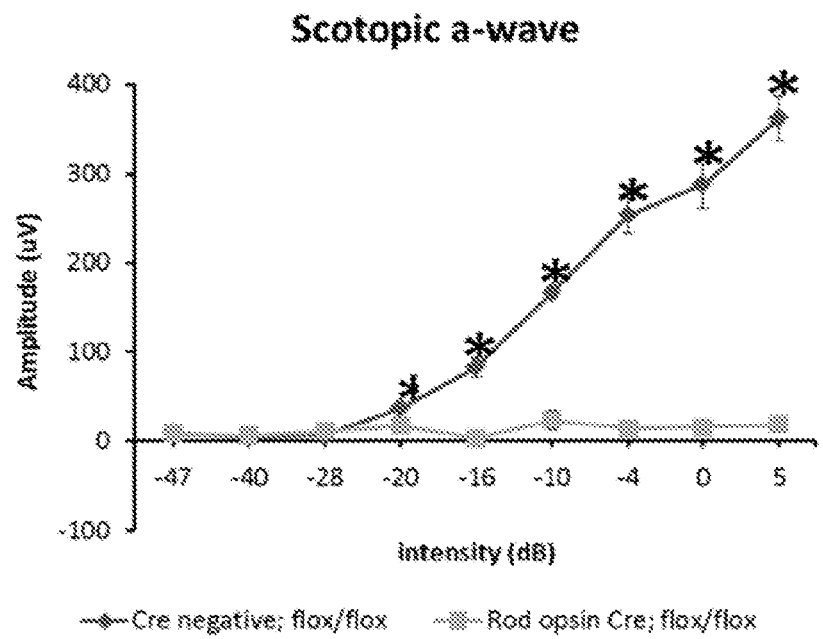
Figure 29E:
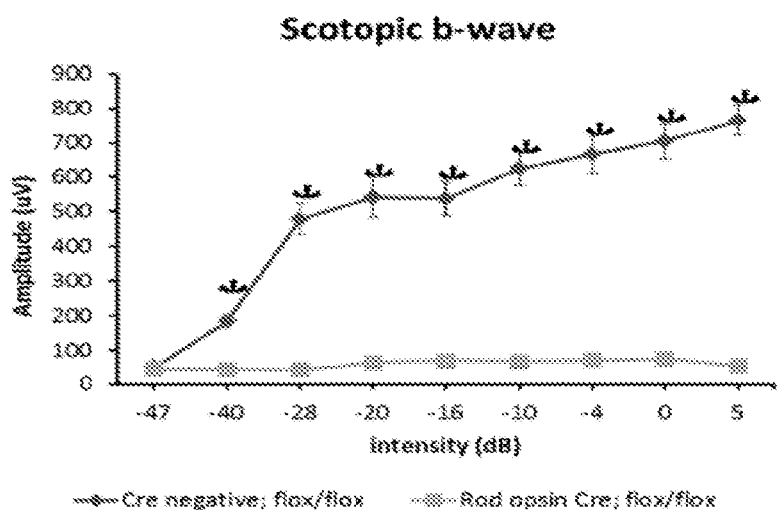
Figure 29F:
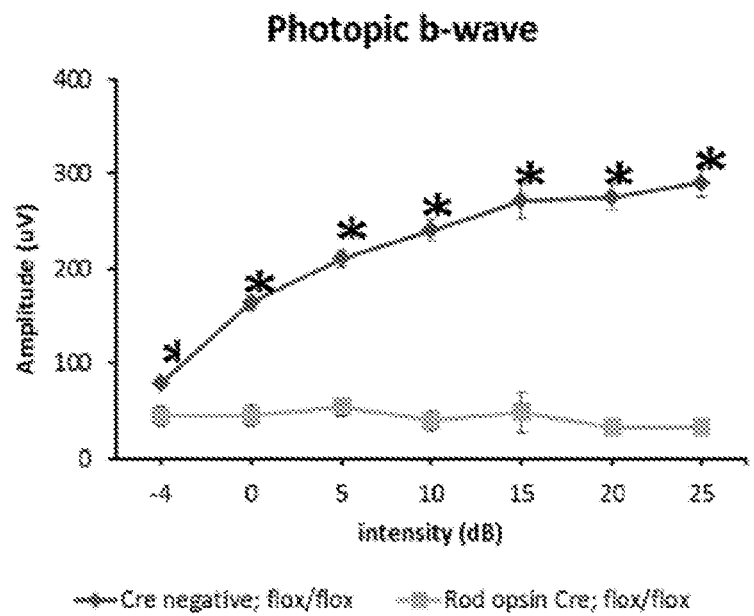

The inventors examined the effect of selectively disrupting NAD biosynthesis within PR. The inventors utilized the cre-lox strategy to generate mice that had NAMPT conditionally deleted from either rods (NAMPT rod-CKO) or cones (NAMPT cone-CKO). The NAMPT fl/fl mice as well as the rhodopsin-cre and cone opsin-cre mice have been previously characterized. Both rod and cone cko mice are generated with normal Mendelian frequencies and are born normal with no observable systemic abnormalities (data not shown). All structural and functional analyses performed in CKO mice are analyzed in comparison to littermate controls. Rods constitute a majority of the PR neurons (97% of all photoreceptors). Retinas from NAMPT rod-CKO mice showed a significant reduction of NAMPT within rods by PCR, immunohistochemistry and immunoblotting (FIG. 29A-B). Biomicroscopic examination of NAMPT rod-cko mice demonstrated a degenerative phenotype characterized by massive atrophy of the neurosensory retina, vascular attenuation with pigment mottling and atrophy of the underlying retinal pigment epithelium. Neurosensory retinal degeneration was associated with secondary atrophy and pallor of the optic nerve (FIG. 29C).

Example 18

This example illustrates electroretinography (ERG) performed to measure PR neuron and retinal function.

Figure 29G:
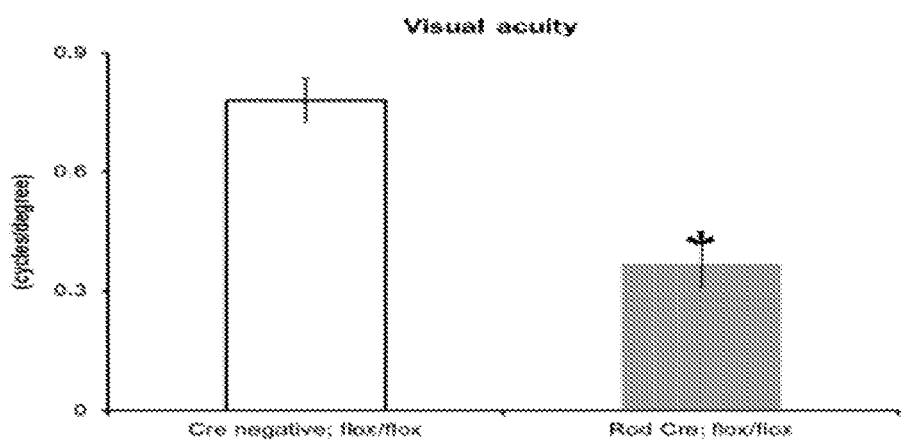
Figure 29I:
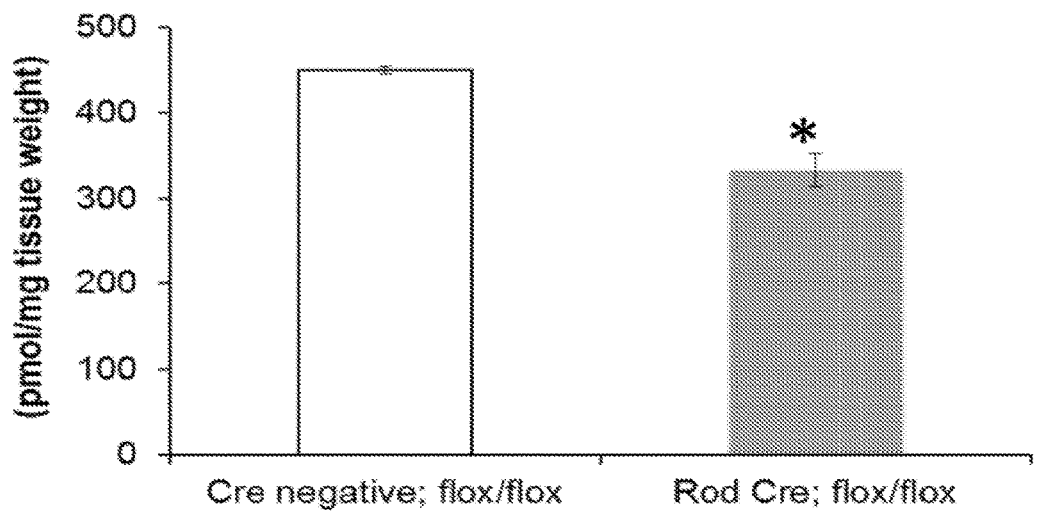

NAMPT rod-CKO mice demonstrated a dramatic reduction in scotopic (rod-associated) and photopic (cone-associated) responses compared to littermate control animals (FIG. 29D-H) Photopic visual acuity measurements confirmed vision loss in rod-CKO mice (FIG. 29G). Histopathologic examination of eyes from NAMPT rod-CKO mice was characterized by retinal degeneration with progressive loss of the outer nuclear layer over time with significant reduction of retinal thickness and subsequent extension of the neurodegeneration to multiple retinal layers (FIG. 29H). Normalized NAD measurements obtained from NAMPT rod-cko whole retinas showed a significant reduction in NAD which is especially important given that NAMPT function is selectively eliminated only from rod PR neurons with other retinal cells being normal (FIG. 29I). These results suggest that, without being limited to theory, if enzymatic activity of NAMPT in NAD biosynthesis in rod PR neurons is necessary for cell survival, intracellular conversion of NAM to NMN by NAMPT can play a role.

Figure 29J:
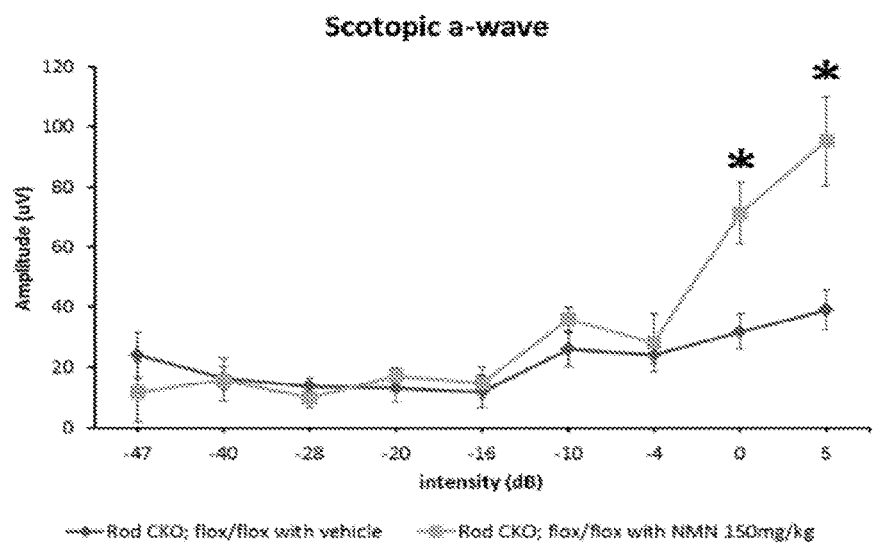
Figure 29K:
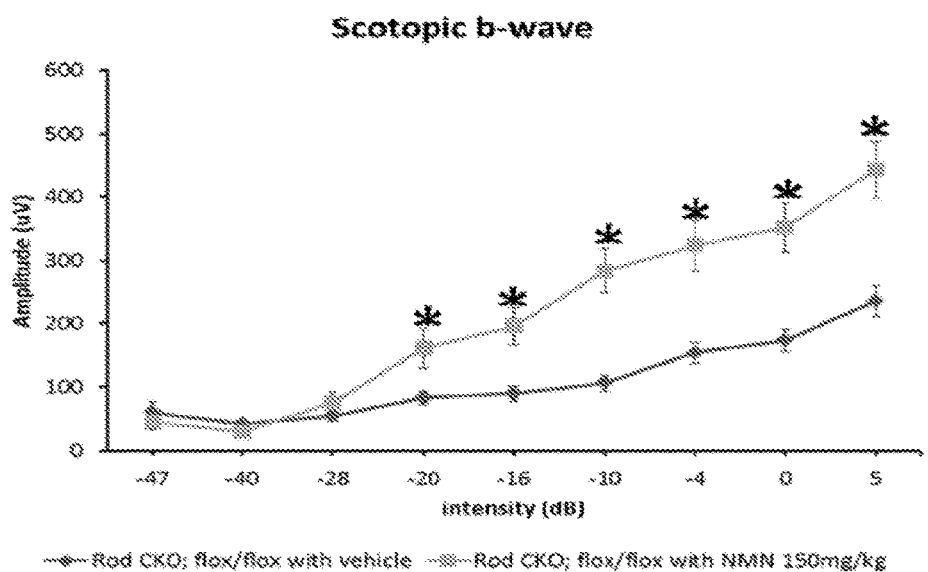
Figure 29L:
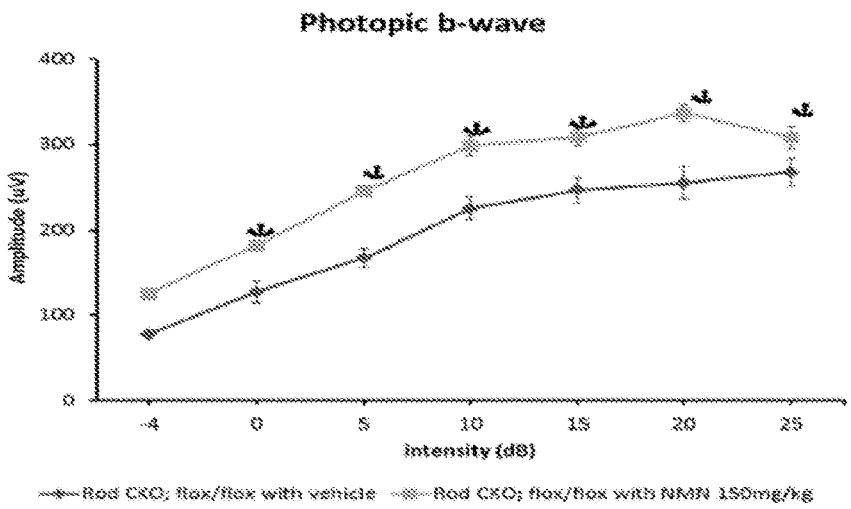

The present inventors determined that exogenous supplementation with NMN is able to rescue PR neurons from cell death in CKO mice. Intraperitoneal (i.p.) delivery was chosen to obtain early and sustained levels of NMN. In these experiments, NAMPT rod-CKO mice were given NMN (150 mg/kg) or PBS i.p. daily starting at day P5. ERG at 4 weeks in CKO mice treated with NMN showed significant rescue of photopic and scotopic function compared to PBS treatment (FIG. 29J-L). There was no effect of NMN on littermate control animals.

Example 19

This example illustrates NMN rescue in NAMPT cone-CKO mice.

Figure 30A:
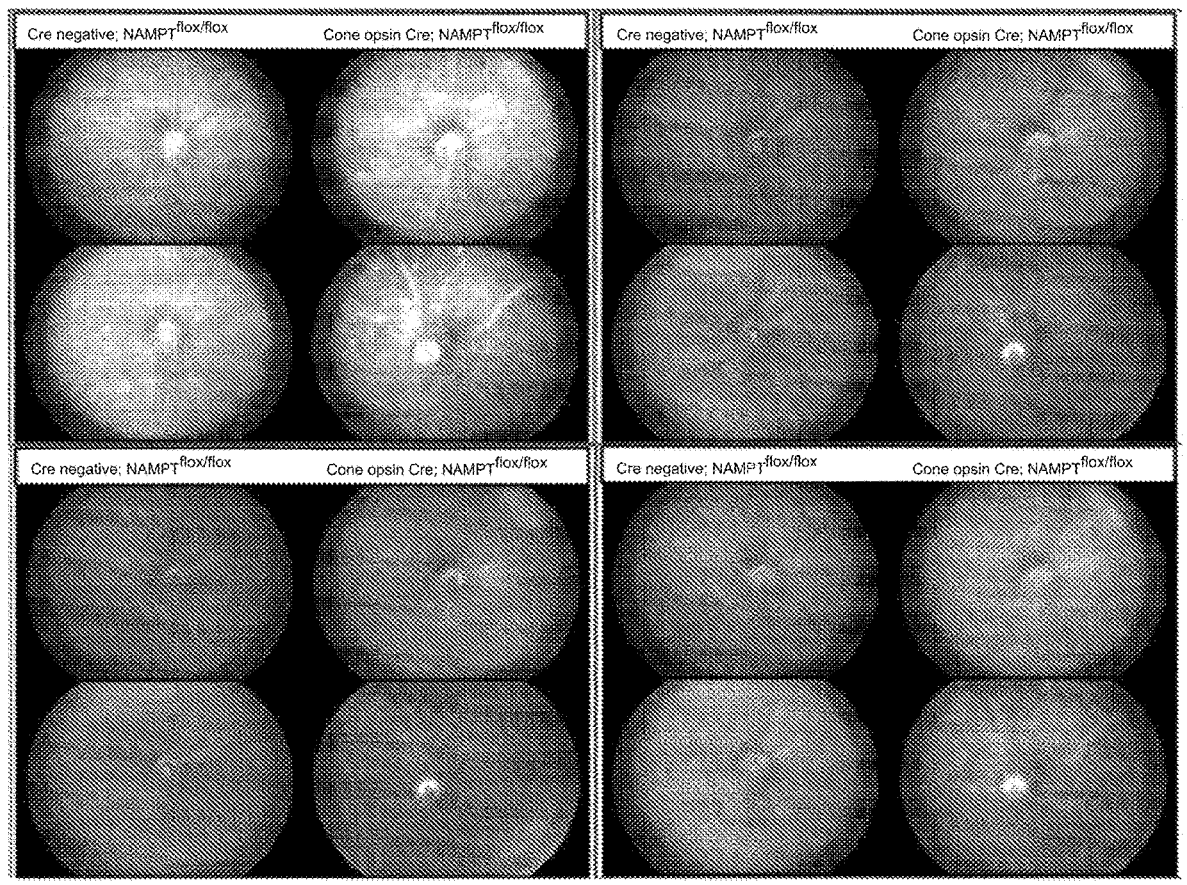
Figure 30B:
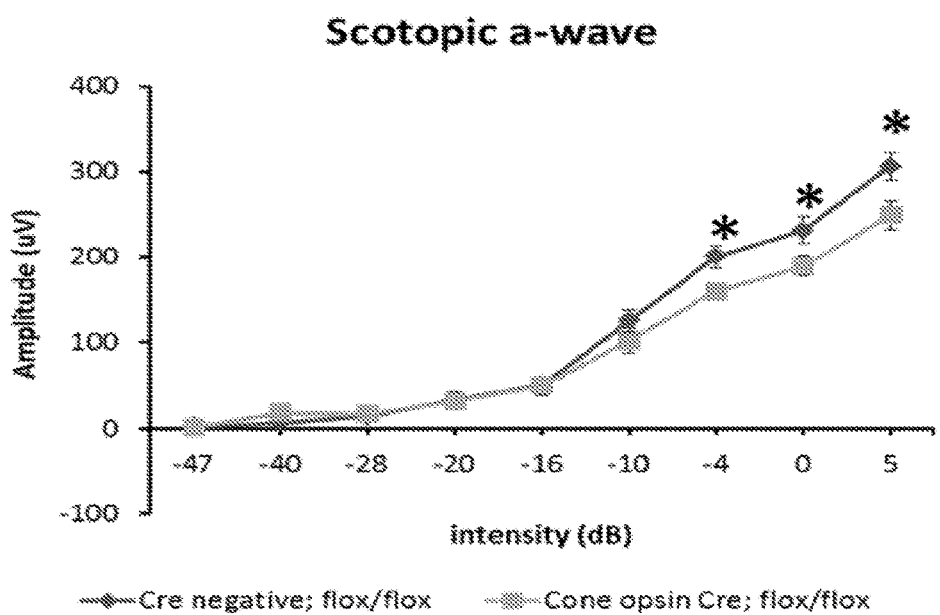
Figure 30C:
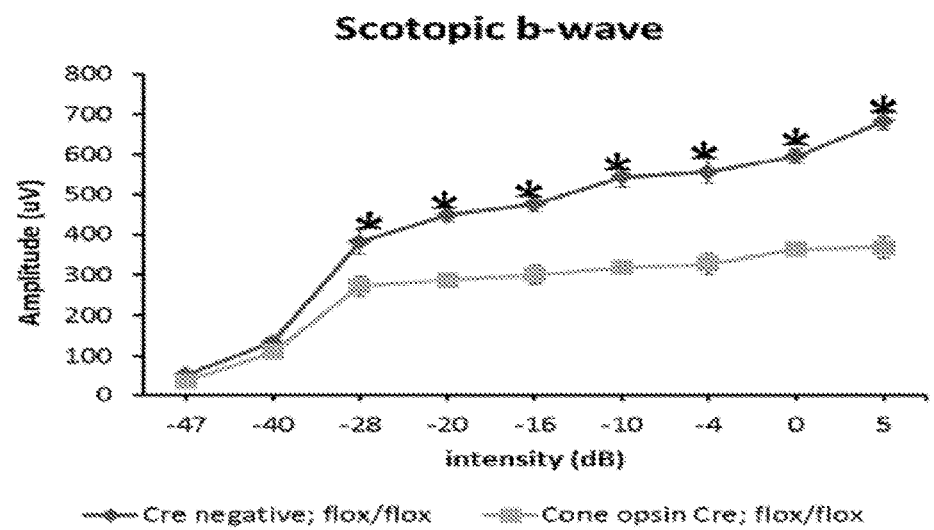
Figure 30D:
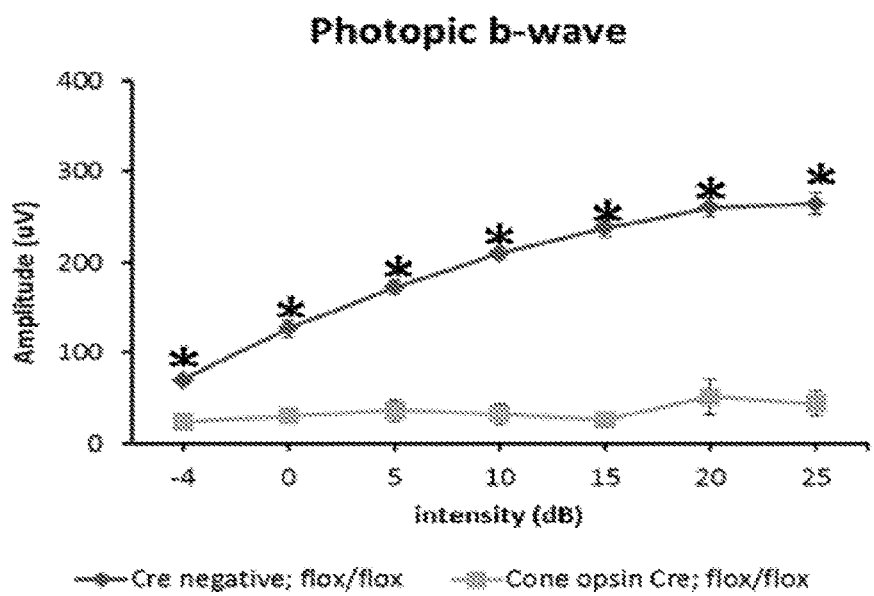
Figure 30E:
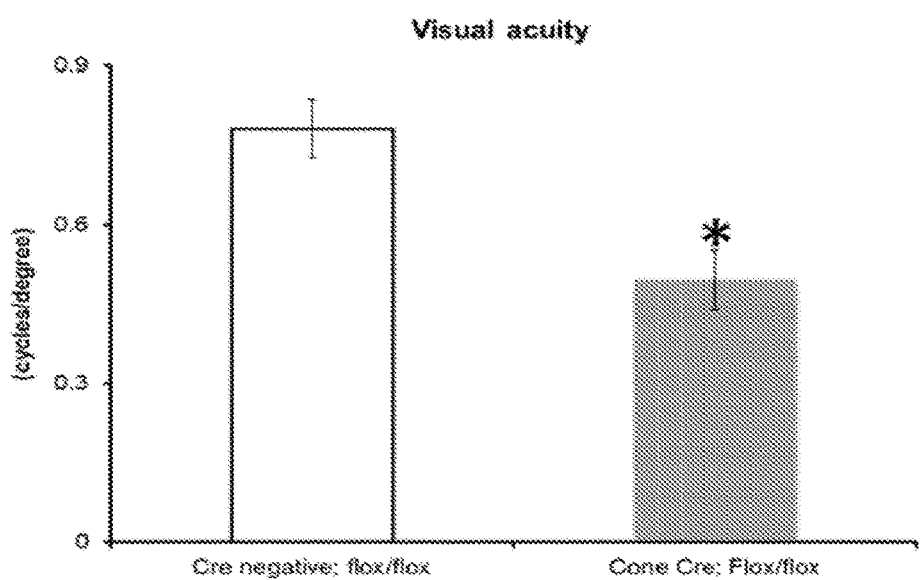
Figure 30F:
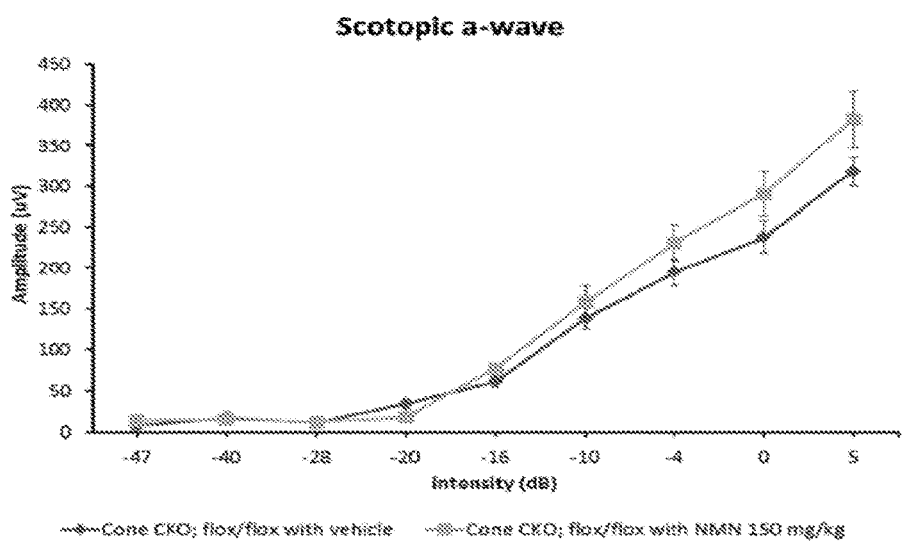
Figure 30G:
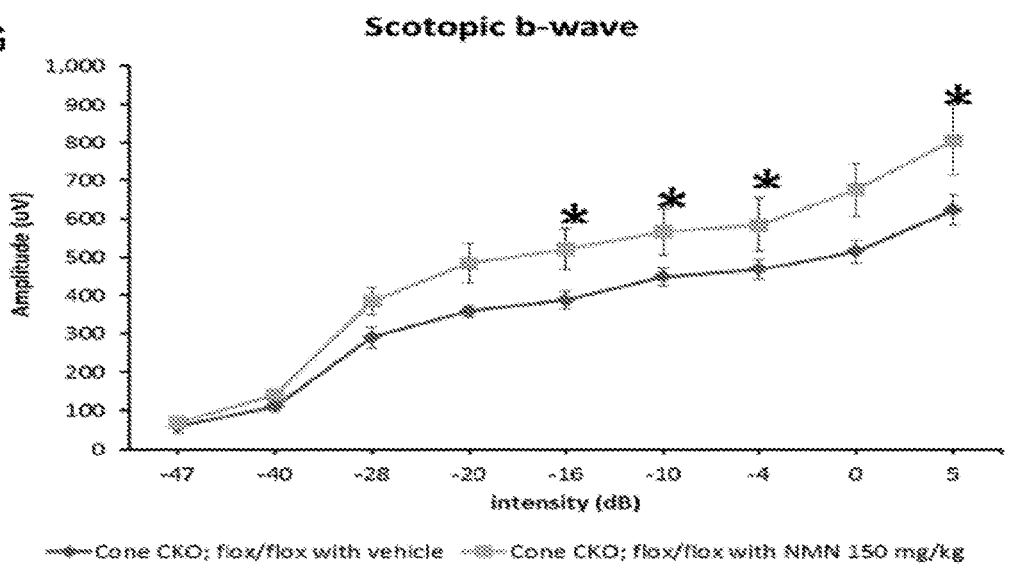
Figure 30H:
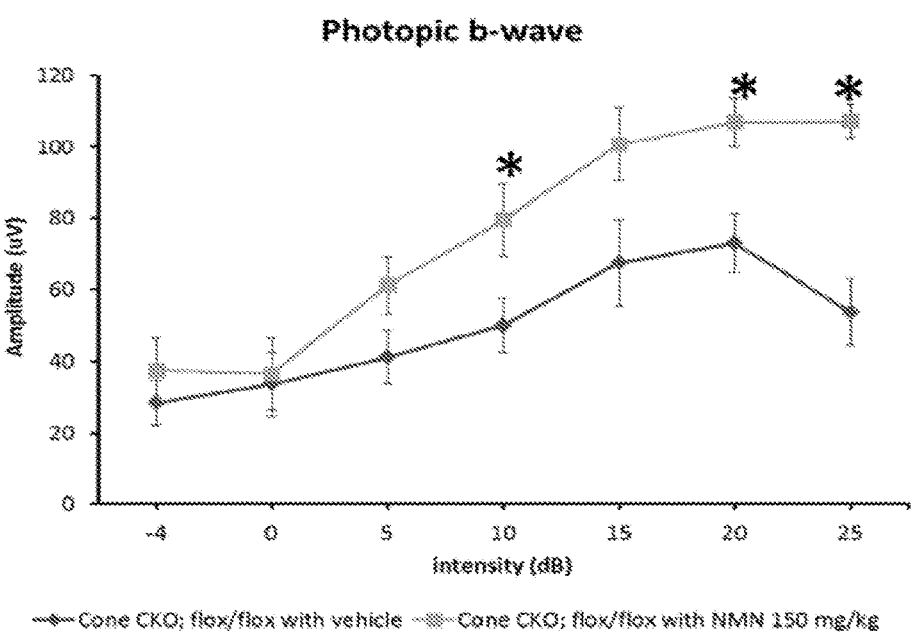
Figure 30I:
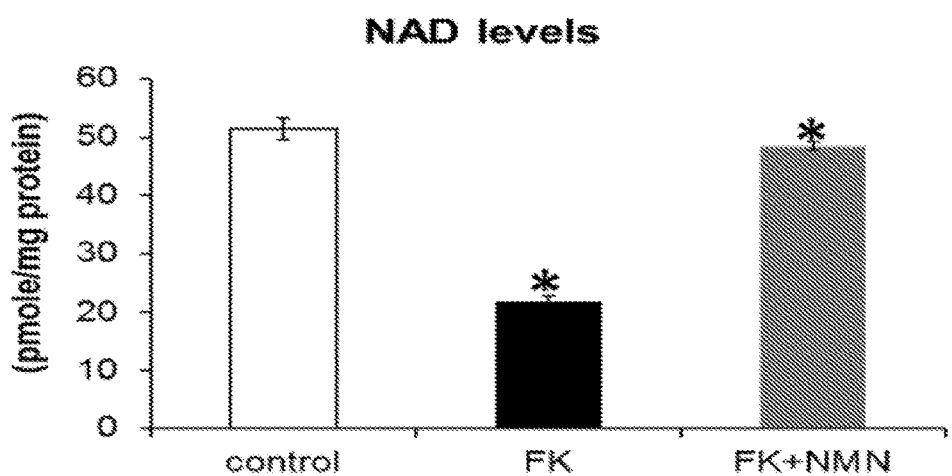
Figure 30J:
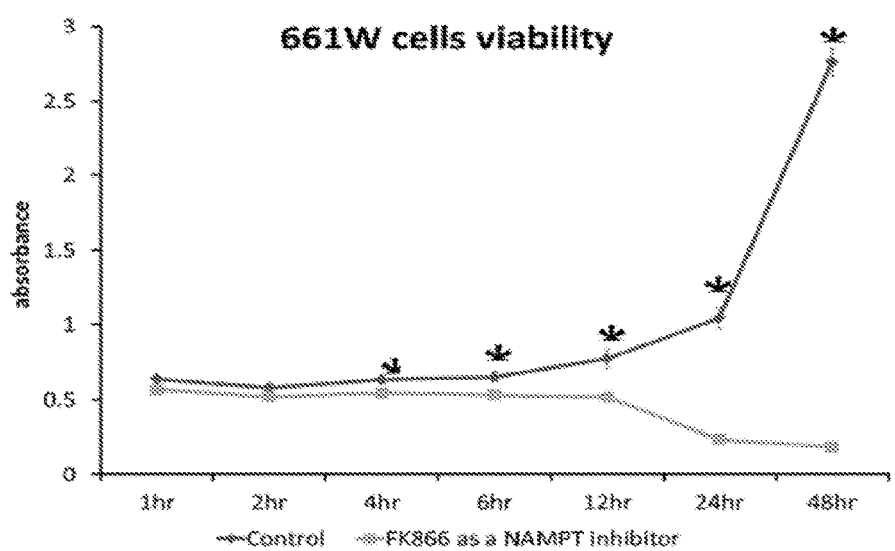
Figure 30K:
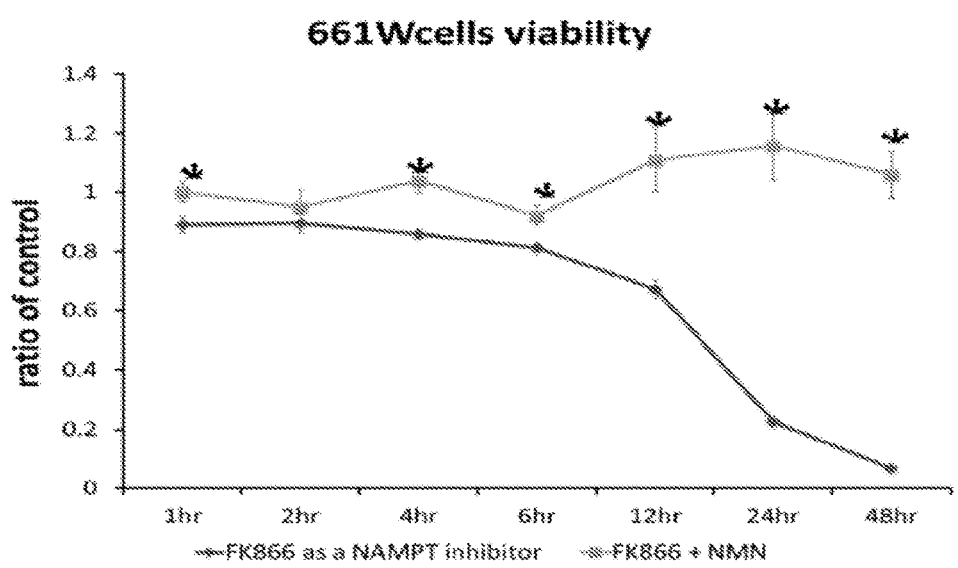

In these experiments, NAMPT cone-CKO mice (without NMN treatment) demonstrated similar but milder changes on biomicroscopy consistent with neuroretinal degeneration as seen in the rod-CKO mice (FIG. 30A). ERG demonstrated significant and progressive decline in cone function as evidenced by reduced photopic responses over time with secondary reduction in scotopic responses (FIG. 30B-D). These quantifiable structural and functional changes were associated with decrease in visual acuity in cone-CKO mice (FIG. 30E). Histopathologic analyses confirmed outer nuclear layer degeneration with subsequent multilayer retinal degeneration and cell death in cone-CKO mice similar to the changes seen above for rod-CKO mice. As with NAMPT rod-CKO mice, delivery of NMN i.p. to NAMPT cone-CKO mice was also able to improve ERG function compared to PBS treated cone-CKO mice (FIG. 30F-H). NMN treatment had no effect on littermate controls (FIG. 33A-B). These data suggest that, without being limited by theory, NAMPT-mediated NAD biosynthesis is necessary for the survival and function of both rod and cone PR neurons. Furthermore, providing NMN treatment is able to rescue PR neurons and vision.

Figure 31I:
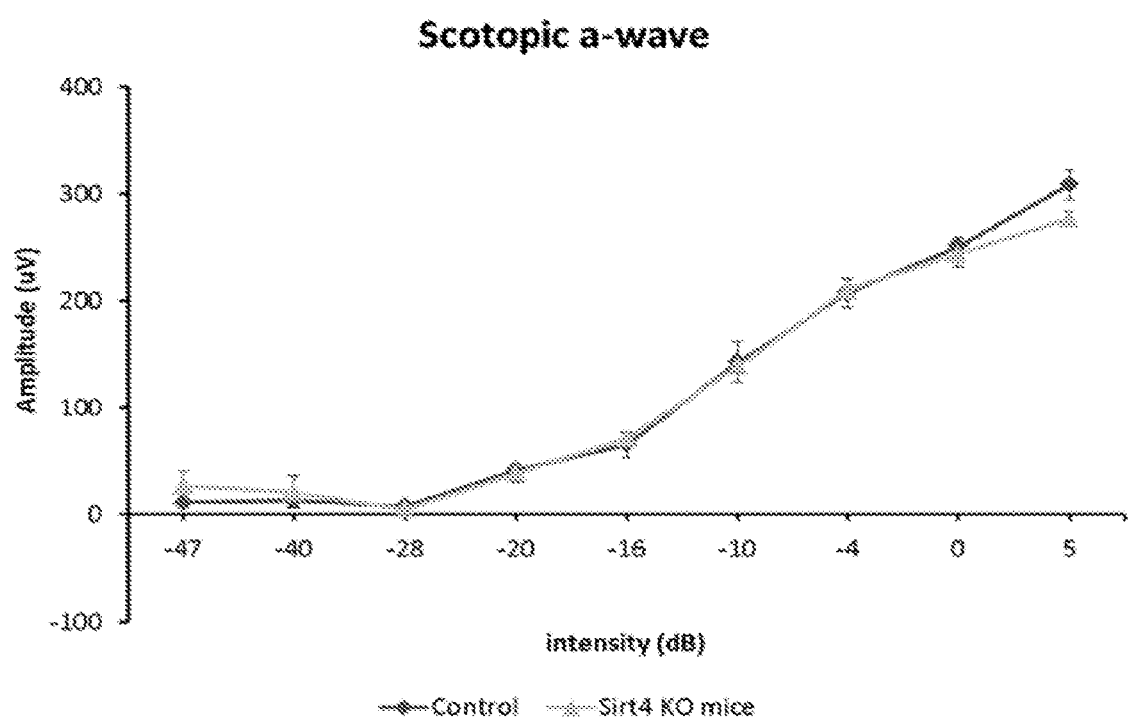
Figure 31J:
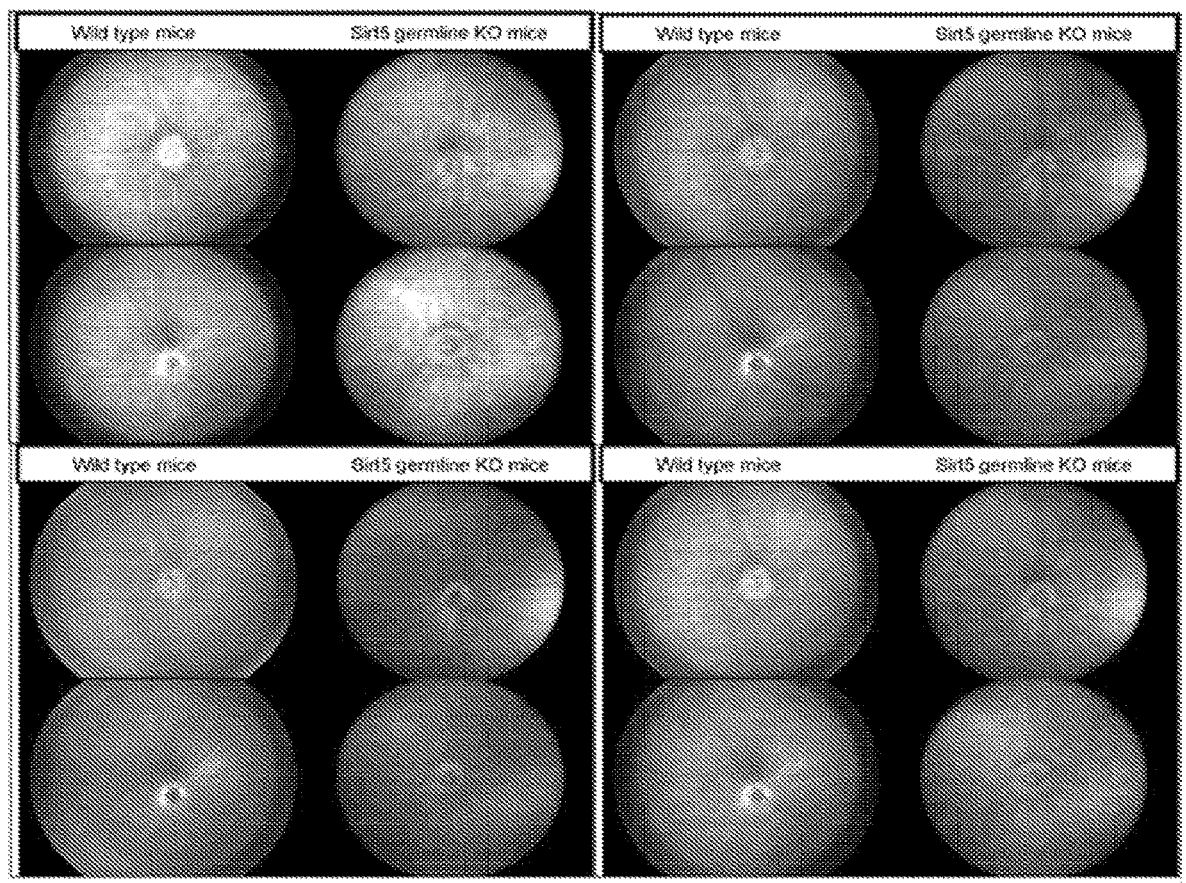
Figure 31K:
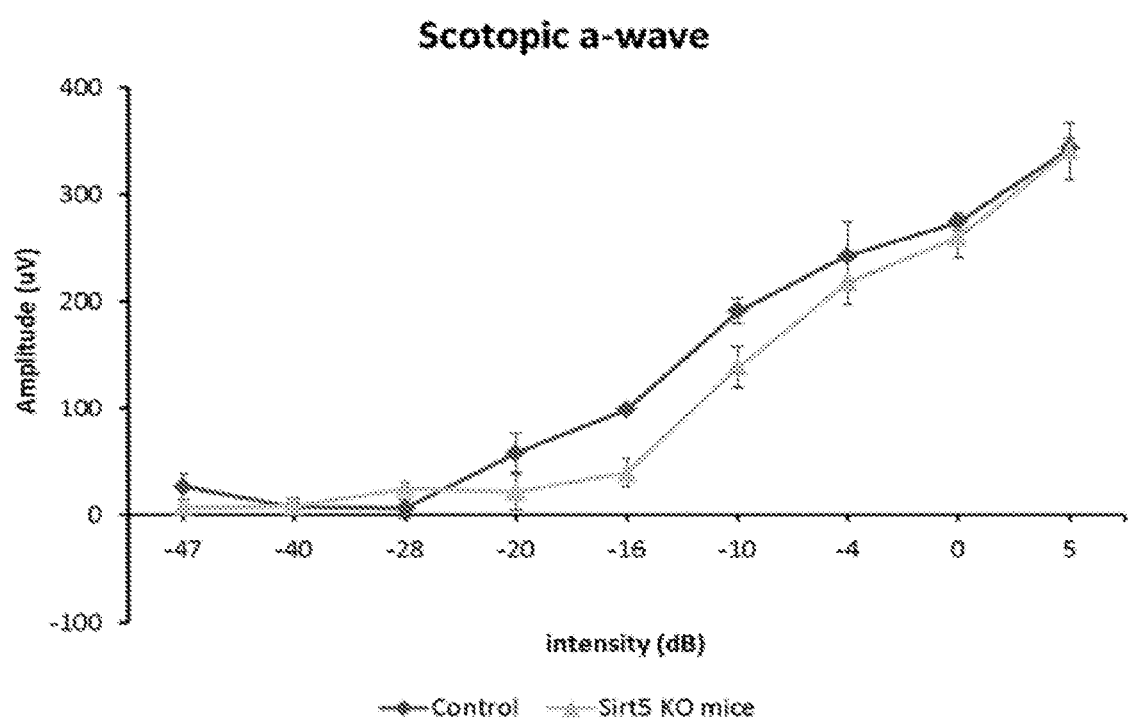
Figure 31L:
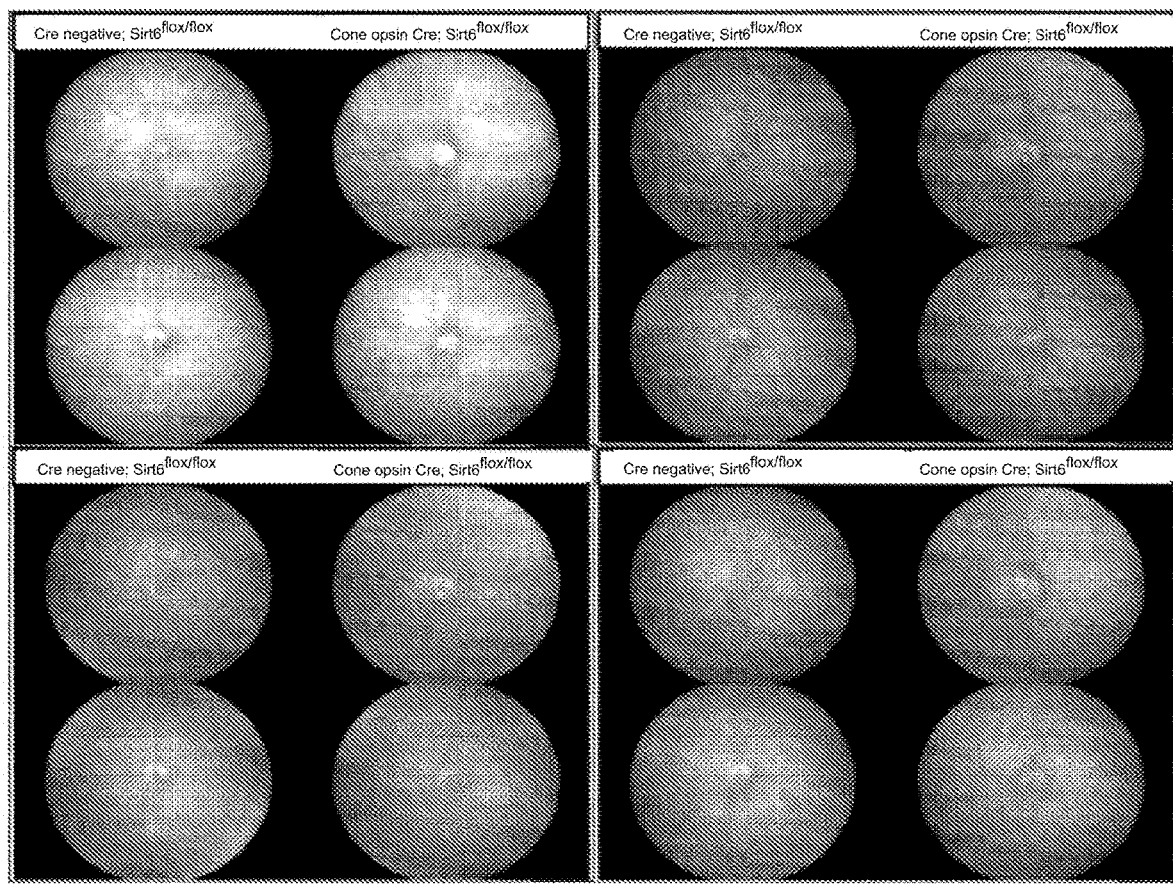
Figure 31M:
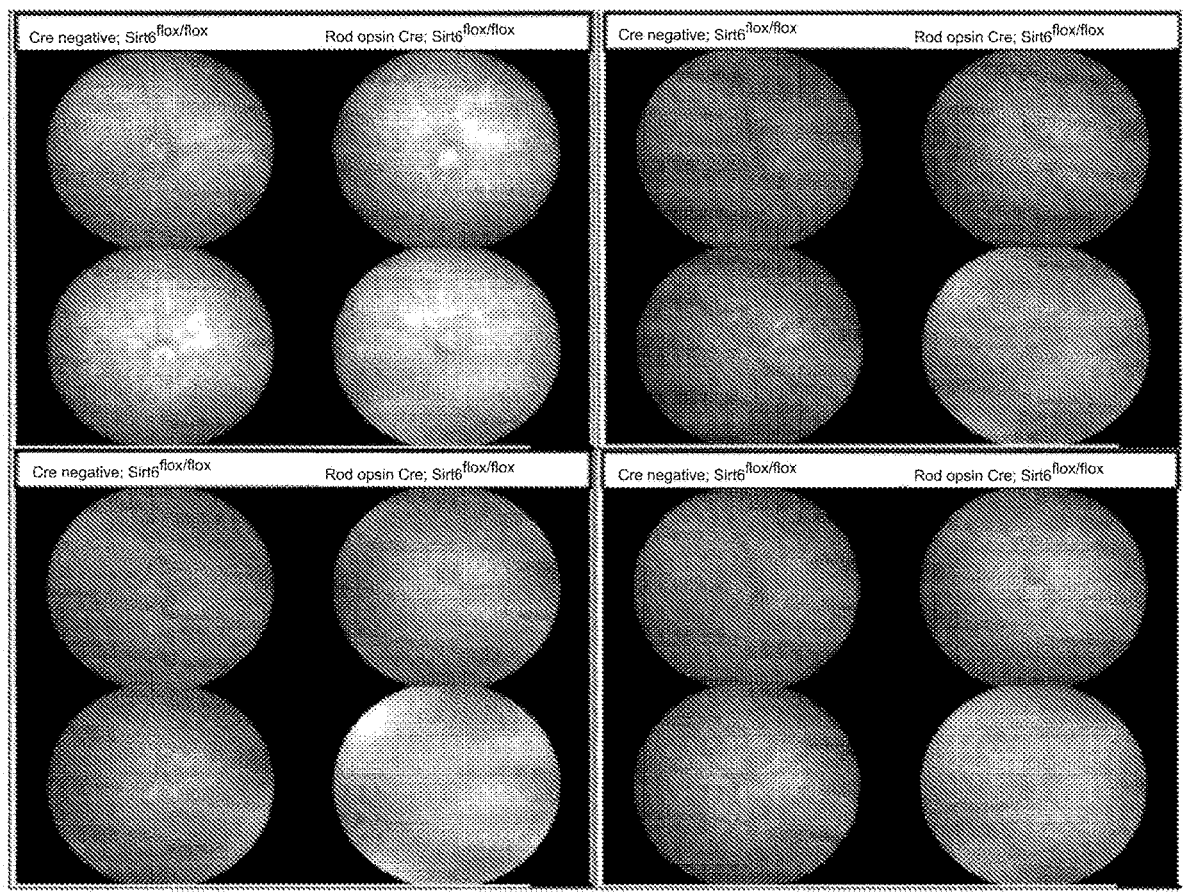

The inventors used a 661W cone PR cell line and treated the cells with the specific pharmacological NAMPT inhibitor FK866 (200 nM). FK866 treatment of cone cells in vitro causes decrease in intracellular NAD levels and significant cell death after the 4 hours of treatment (FIGS. 31I, 31J). Cell death progresses dramatically over the next 20 hours. NMN (100 µM) was able to completely rescue cells from death associated with FK866 treatment and restore NAD to normal levels (FIGS. 31I, 31K). These in vitro results confirm that NMN administration can promote PR neuron survival.

Example 20

This example illustrates that NAD-regulated PR survival is independent of individual sirtuins.

The inventors examined the effect of deletion of several sirtuins on PR survival. Sirt 1 PR CKO mice and Sirt 2-5-/- mice had normal retinal and PR neuron structure and function when examined by fundus biomicroscopy and ERG (FIG. 3a-j and FIG. S2). Sirt6$^{-/-}$ mice have a profound neurodegenerative phenotype and die around 3-4 weeks of age. As such, we examined sirt6 rod and cone conditional knockout mice that also had normal retinal structure and function (FIGS. 31A-N and FIGS. 34A-F). Without being limited by theory, these findings demonstrate that individual sirtuins are not causative of NAMPT-mediated PR degeneration.

Example 21

This example illustrates that photoreceptor loss and blindness is associated with mitochondrial dysfunction.

Figure 32A:
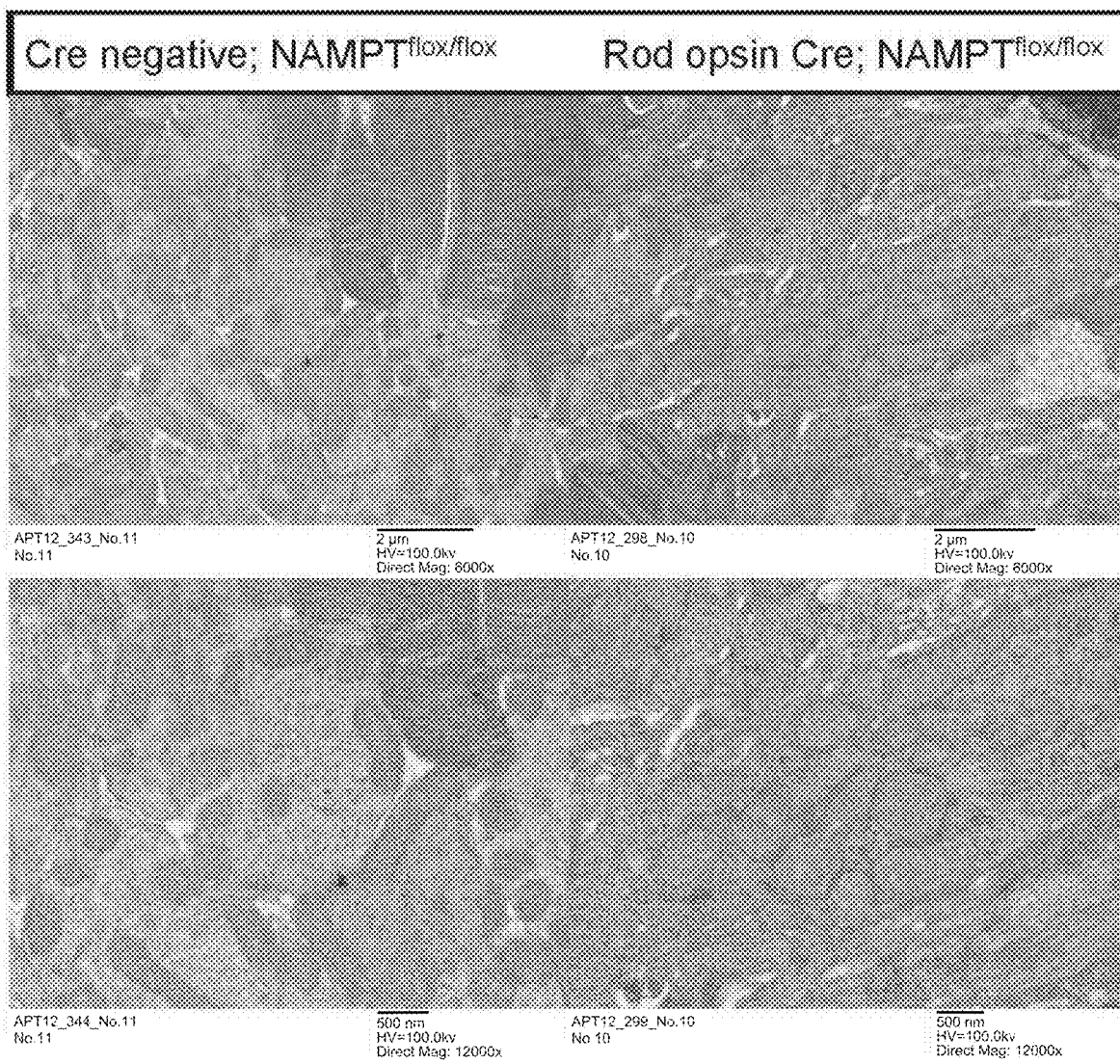
Figure 32B:
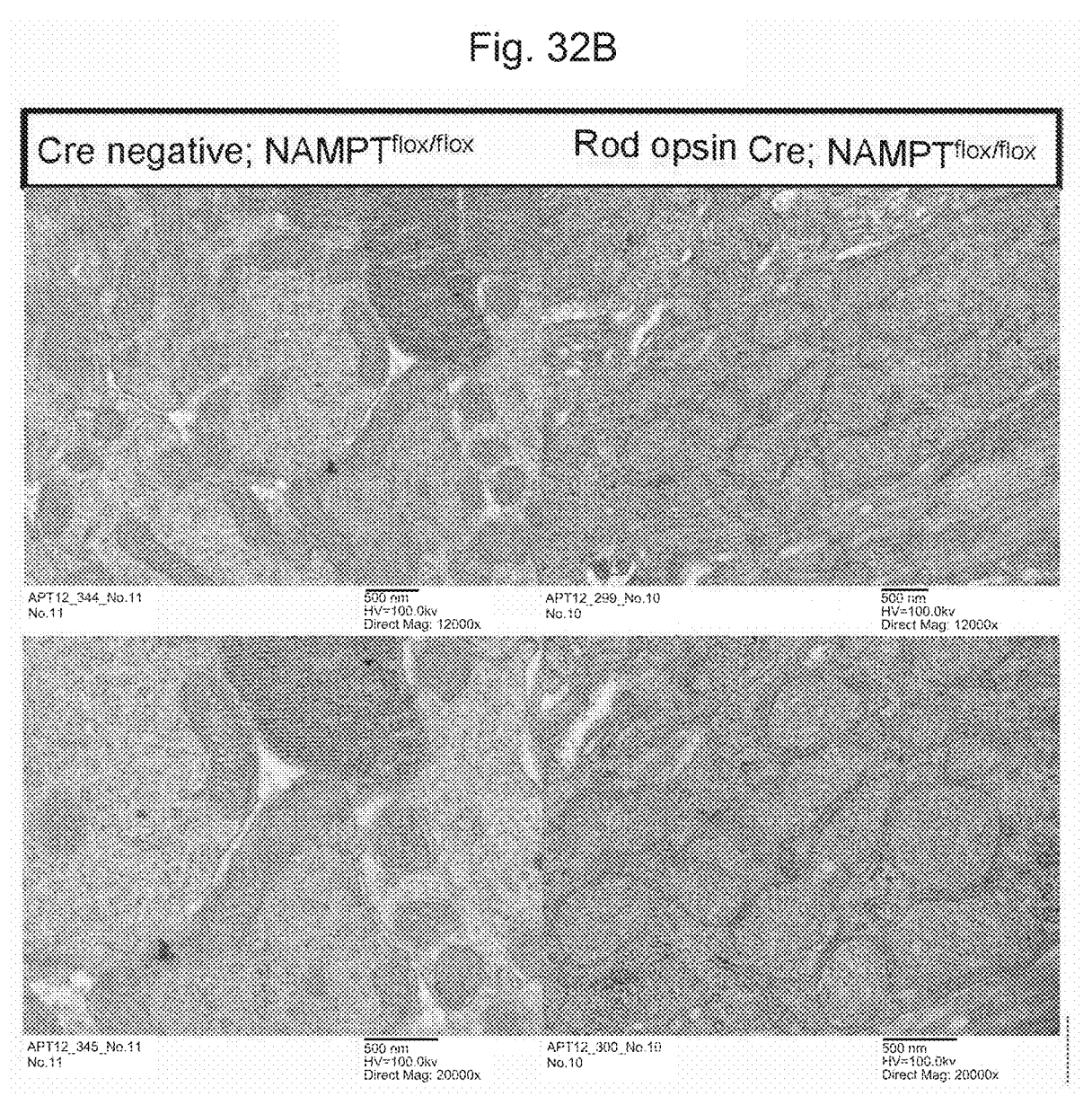
Figure 32C:
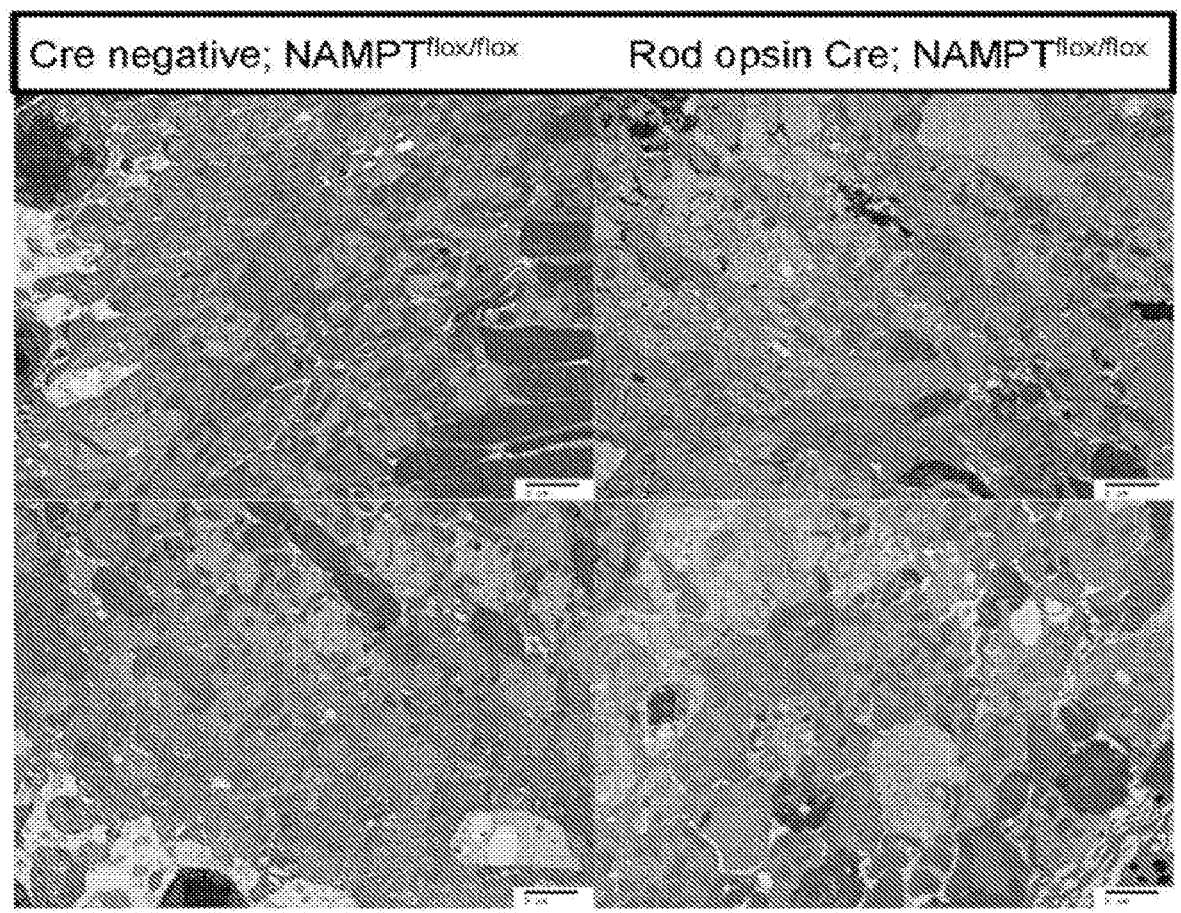
Figure 32D:
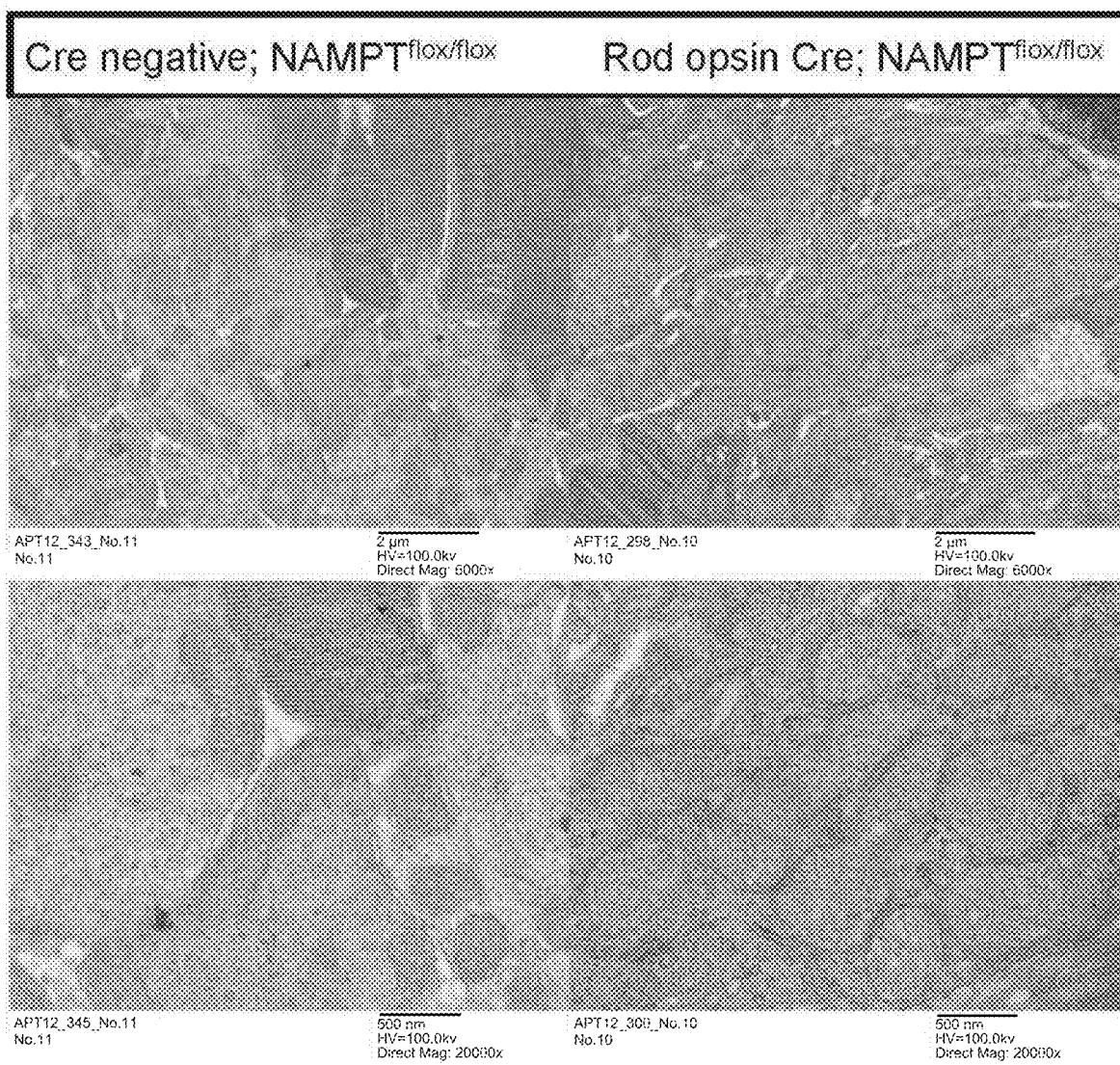
Figure 32E:
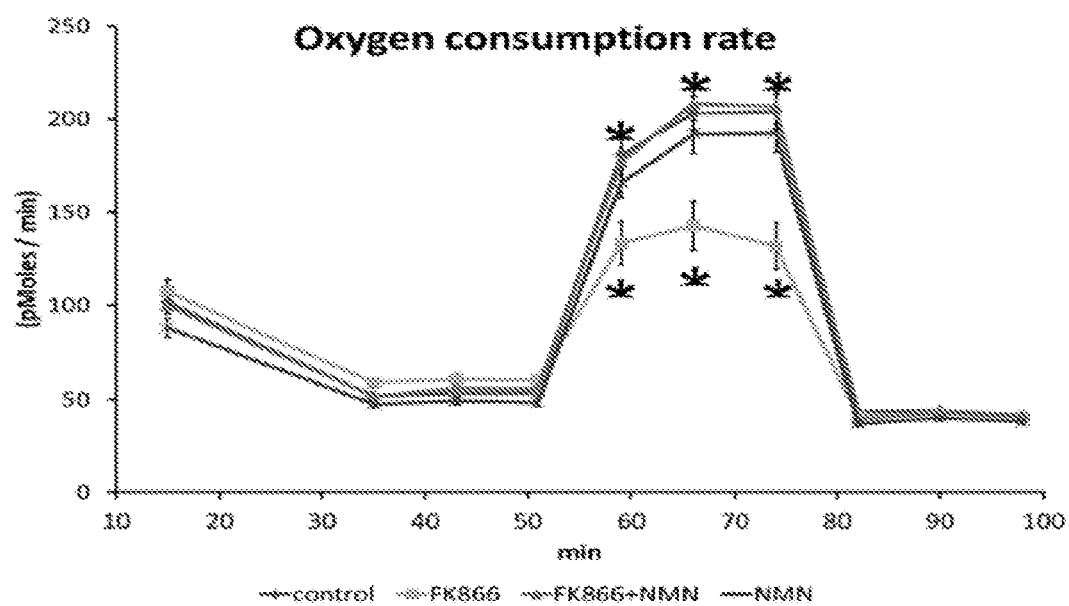

Electron microscopic examination demonstrated dysmorphic changes in the retinal inner segments along with disruption of the outer segments in rod CKO mice but showed normal cellular organization and sub-cellular structures in littermate controls at 4 weeks of age (FIG. 32A-C, 32D). By 4 weeks of age, the mitochondrial numbers in CKO retinas were significantly reduced, the mitochondria were rounded and constricted with loss of cristae as opposed to the normally elongated mitochondria with healthy cristae seen in age-matched littermate control mice (FIG. 32A-D). There was an abundance of degenerative vacuoles with ingested organelles including mitochondria in rod-CKO mice with no such structures identified in littermate wild type controls. At 3 weeks of age, subtle changes in inner segments could be identified in rod-CKO mice although they were not as dramatic as those seen by 4 weeks (FIG. 35). These results suggest that, without being limited by theory, NAD deficiency might impair mitochondrial structure and function. The inventors treated 661W cone cells with NAMPT inhibitor FK866 (200 nM). In the oxygen consumption rate measurement assay, multiple aspects of mitochondrial function were analyzed. As shown in FIG. 32E, maximal respiration was significantly reduced in 661W cone cells after inhibition of NAMPT function (FIG. 32E). NMN treatment was able to completely reverse the effects of FK866 on cone cell photoreceptor mitochondrial function confirming the role of NAD in NAMPT-mediated effects on PR neurons (FIG. 32E).

A non-biased metabolomic analysis using mass spectrophotometry (GC-MS and LC-MS) was performed on retinas isolated from NAMPT rod CKO mice and compared to littermate control retinas. Significant differences were identified in mitochondrial metabolites involved in the TCA cycle.

REFERENCES

Amrnett, H. A., et al., Science 306, 2111-2115, 2004.
Artegiani, B., et al. Aging 4: 176-186, 2012
Ben Abdallah, N. M., et al. Neurobiol Aging 31: 151-161
Bieganowski, P., et al. Cell 117, 495-502 2004.
Bouab, M., et al. Neuroscience 173, 135-149, 2011.
Canto, C., et al. Cell-Metab. 15, 838-847. 2012.
Carlson, L. A. J. Intern. Med. 258, 94-114, 2005.
Cheadle, C., et al. J Mol Diagn 5, 73-81, 2003.
Chen, J., et al. Hepatology (Baltimore, Md 57, 2287-2298, 2013.
Colak, D., et al. J Neurosci 28, 434-446, 2008.
Collins, P. B., et al. Biochem. J. 125, 117P, 1971.
Collins, P. B., et al. J. Biol. Chem. 247, 778-783, 1972.
Cooper-Kuhn, C. M., et al. Molecular and cellular neurosciences 21, 312-323, 2002.
Dasgupta, B., et al. J Neurosci 25, 5584-5594, 2005.
Decker, L., et al. Neurosci Res. 69, 763-771, 2002
Deng, W., et al. Nature reviews 11, 339-350, 2010.
Dienel, G. A., et al. Neurochem Intl, 48, 586-595, 2006.
Di Girolamo, M., et al. FEBS J. 272, 4565-4575, 2005.
Doucette, J. R., et al. Cell. Molec. Neurobiol., 30, 607-629, 2010.
Encinas, J. M., et al. Cell Stem Cell 8, 566-579, 2011
Folmes, C. D., et al. Cell stem cell 11, 596-606, 2012
Franklin, R. J., et al. Nature reviews 9, 839-855, 2008.
Friebe, D., et al. PloS one 6: e19526, 2011.
Fu, J., et al. Diabetologia 49: 1027-1038, 2006.
Gao, Q., et al. Int J Dev Neurosci 25: 349-357, 2007.
Garten, A., et al. Trends Endocrinol. Metab. 20, 130-138, 2009.
Gudi, V., et al. Brain Res., 1283, 127-138, 2009
Guillemin, G. J., et al. J Neurosci 27, 12884-12892, 2007.
Hack, M. A., et al. Nature Neurosci 8, 865-872, 2009
Hack, M. A., et alMolec. Cell. Neurosci. 25: 664-678, 2004.
Hara, N., et al. J Biol Chem 282, 24574-24582, 2007.
Hasmann, M., et al. Cancer Res 63, 7436-7442, 2003.
Higuchi, T. and Sella, V., Pro-drugs as Novel Drug Delivery Systems, A.C.S. Symposium Series 14, 1975.

Hisahara, S., et al. Proc. Nat'l. Acad. Sci. USA 105, 15599-15604, 2008
Houtkooper, R. H., et al. Endocr. Rev. 31, 194-223, 2010.
Husain, J., et al. (1995) Brain Res 698, 86-94, 1995.
Imai, S. FEBS Lett. 585, 1657-1662, 2011.
Imai, S. et al. Trends Pharmacol. Sci. 31, 212-220, 2010.
Imai, S. Curr. Pharm. Des. 15, 20-28, 2009.
Imai, S. Pharmacol. Res. 62, 42-47, 2010.
Ito, K., et al. Nature Med 18, 1350-1358, 2012.
Jablonska, B., et al. Nature Neurosci 13, 541-550, 2010.
Jackson, E. L., et al. Neuron 51, 187-199, 2006.
Jadasz, J. J., et al. Cell Tissue Res. 349, 331-347, 2012.
Ji, S., et al., J. Mol. Cell Biol. 3, 351-359, 2011.
Jin, K., et al. Aging cell 2, 175-183, 2003.
Jin, Y. H., et al. Biochem. Biophys. Res. Comm. 368, 690-695, 2008.
Kakeya, N., et al., Chem Pharm. Bull. 32, 692-698, 1984.
Kim, H. S., et al. Cancer cell 20, 487-499, 2011.
Knobloch, M., et al. Nature 493, 226-230, 2013.
Krogsgaard-Larson, H. and Bundgaard, H., A Textbook of Drug Design and Development, Chapter 5, "Design and Applications of Prodrugs" 113-191, 1991.
Lagace, D C, et al. J Neurosci 27, 12623-12629, 2007.
Lau, C., et al. J. Biol. Chem. 285, 18868-18876, 2010.
Lee, H. C. Sci. China Life Sci. 54, 699-711, 2011.
Li, W., et al. J Neurosci 27, 2606-2616, 2007
Ligon, K. L., et al. Neuron 53, 503-517, 2007.
Liu, A., et al. The EMBO J 25, 4833-4842, 2006
Lu, P. P., et al. J Neurosci 32, 8012-8023, 2012
Lu, Q. R., et al. Cell 109, 75-86, 2002.
Lugert, S., et al. Cell stem cell 6, 445-456, 2010.
Luo, J., et al. Cell 107, 137-148, 2001.
Madisen, L., et al. Nature Neursci 13, 133-140, 2010.
Mehta, S., et al. (2011) Cancer cell 19, 359-371, 2011.
Menn, B., et al. J Neurosci 26, 7907-7918, 2006.
Nait-Oumesmar, B., et al. Euro. J. Neurosci. 11, 4357-4366, 1999.
Nielsen, N. M., and Bundgaard, H., J. Pharm. Sci., 77, 285-298, 2006.
Norkute, A., et al. research Neurosci. Res. 87, 1343-1355, 2009.
Outeiro, T. F., et al. Science 317, 516-519, 2007.
Peck, B., et al. Molec. Cancer Therap. 9, 844-855, 2010.
Picard-Riera, N., et al., Proc. Nat'l. acad. Sci. USA 99, 13211-13216, 2002.
Plassman, B. L., et al. Ann. Internal Med 148, 427-434, 2008.
Polager, S., et al. Nat Rev Cancer 9, 738-748, 2009.
Prozorovski, T., et al. Nature cell Biol 10, 385-394, 2008.
Rafalski, V. A., et al. Nature cell Biol. 15, 614-624, 2013.
Revollo, J. R., et al. chemistry Biol. Chem. 279, 50754-50763, 2004.
Revollo, J. R., et al. Cell metabolism 6, 363-375, 2007.
Rongvaux, A, et al. J Immunol 181, 4685-4695, 2008.
Roche, E. B., Bioreversible Carriers in Drug Design: Theory and Application, Elmsford, N.Y.: Pergamon Press 1987.
Rothgiesser, K. M., et al. science. Cell Sci 123, 4251-4258, 2010.
Saharan, S., et al. research Neurosci. Res. 91, 642-659, 2013.
Saito, K., et al., Proc. Nat'l. Acad. Sci. USA 106, 8350-3355, 2009.
Sanchez-Abarca, L. I., et al. Glia 36, 321-329, 2001.
Sassone-Corsi, P. Endocrinol 153, 1-5, 2012.
Schreiber, V., et al. Nat. Rev. Mol. Cell. Biol. 7, 517-528. 2006.
Sim, F. J., et al. J Neurosci 22, 2451-2459, 2002.
Skripuletz, T., et al. Histol. Histopath. 26, 1585-1597, 2011.
Soundarapandian, M. M., et al. (2011) Scientific reports 1, 2, 2011.
Stein, L. R., et al. (Trends Endocrin. Metabol 23, 420-428, 2012.
Steiner, B., et al. Glia 46, 41-52, 2004.
Stoll, E. A., et al. J Biol. Chem. 286, 38592-38601, 2011.
Sun, Y., et al. Neuron 69, 906-917, 2011.
Takebayashi, H., et alCurr Biol 12, 1157-1163, 2002.
Tyler, W. A., et al. Glia 59, 1754-1769, 2011.
Van Leeuwen, I. M., et al. Molec. Cancer Ther. 12, 471-480, 2013.
Verderio, C., et al. J. Neurochem. 78, 646-657, 2001.
Voloboueva, L. A., et al. J Neurosci 30, 12242-12251, 2010.
von Bohlen and Halbach 0 Cell Tissue Res. 345, 1-19, 2011
Wang, C., et al. Nature cell Biol 8, 1025-1031, 2006.
Wang, P., et al., Ann. Neurol. 69, 360-374, 2011.
Wang, W., et al. J Neurosci 31, 9746-9751, 2011.
Wegner, M., et al. J Mol Neurosci 35, 3-12, 2008.
Wilhelm, F., et al. J Neurosci Res 89, 1956-1964, 2011.
Wong, J. V., et al. Cell cycle 10, 3086-3094, 2011.
Yang, H., et al. Cell 130, 1095-1107, 2007.
Yoshino, J., et al. Cell Metabol 14, 528-536, 2011.
Zhang, J., et al. Cell stem cell 11, 589-595, 2012.
Zhang, W., et al. J Cereb Blood Flow Metab 30, 1962-1971, 2010
Zhang, Y., et al. Biochem. Biophys. Res. Comm. 404, 610-614, 2011.
Zhou, Q., et al. Cell 109, 61-73, 2002.

All publications cited in this application are herein incorporated by reference in their entirety as if each individual publication, patent, patent application or other reference were specifically and individually indicated to be incorporated by reference. Applicant reserves the right to challenge the accuracy and pertinency of the cited references.

What is claimed is:

1. A method of treating age-associated obesity in a subject, comprising: administering to a subject in need of treatment an effective amount for treatment of age-associated obesity of nicotinamide mononucleotide (NMN) or a salt or prodrug thereof.

2. A method of treating age-associated obesity in a subject, comprising: administering to a subject in need of treatment an amount effective for the treatment of age-associated obesity of nicotinamide mononucleotide (NMN).

3. A method in accordance with claim 2, wherein the NMN is administered at a daily dosage of 0.5 mg, about 0.5 mg, 1 mg, about 1 mg, 5 mg, about 5 mg, 10 mg, about 10 mg, 20 mg, about 20 mg, 30 mg, about 30 mg, 40 mg, about 40 mg, 50 mg, about 50 mg, 60 mg, about 60 mg, 70 mg, about 70 mg, 80 mg, about 80 mg, 90 mg, about 90 mg, 100 mg, about 100 mg, 150 mg, about 150 mg, 200 mg, about 200 mg, 250 mg, about 250 mg, 300 mg, about 300 mg, 400 mg, about 400 mg, 450 mg, about 450 mg, 500 mg, about 500 mg, 600 mg, about 600 mg, 700 mg, about 700 mg, 800 mg, about 800 mg, 900 mg, about 900 mg, 1000 mg, about 1000 mg, 1100 mg, about 1100 mg, 1200 mg, about 1200 mg, 1300 mg, about 1300 mg, 1400 mg, about 1400 mg, 1500 mg, about 1500 mg, 1600 mg, about 1600 mg, 1700 mg, about 1700 mg, 1800 mg, about 1800 mg, 1900 mg, about 1900 mg, 2000 mg, about 2000 mg, 2100 mg, about 2100 mg, 2200 mg, about 2200 mg, 2300 mg, about 2300 mg, 2400 mg, about 2400 mg, 2500 mg, about 2500 mg, 2600 mg, about 2600 mg, 2700 mg, about 2700 mg, 2800 mg, about 2800 mg, 2900 mg, about 2900 mg, 3000 mg or about 3000 mg, 3500 mg, about 3500 mg, 4000 mg, about 4000 mg, 4500 mg, about 4500 mg, 5000 mg, about 5000 mg, 5500 mg, about 5500 mg, 6000 mg, about 6000 mg, 6500 mg, about 6500 mg, 6800 mg, or about 6800 mg.

4. A method in accordance with claim 2, wherein the NMN is administered at a dosage rate of from 0.5 mg per day to 6800 mg per day.

5. A method in accordance with claim 2, wherein the NMN is administered at a dosage of 100 mg/kg body weight, about 100 mg kg body weight, from 100 mg/kg body weight to 300 mg kg body weight, 500 mg/kg body weight, or about 500 mg/kg body weight.

6. A method in accordance with claim 2, wherein the NMN is administered orally in an orally acceptable formulation selected from the group consisting of a pill, a tablet, a caplet, a capsule, a chewable tablet, a quick dissolve tablet, a powder, a granule, an effervescent tablet, a hard gelatin capsule, a soft gelatin capsule, a non-aqueous liquid, an aqueous liquid, a suspension, a solution, an emulsion, a syrup, a sterilized aqueous suspension, a sterilized aqueous solution, a non-aqueous suspension, and a non-aqueous solution.

7. A method in accordance with claim 2, wherein the NMN is administered parenterally in an acceptable formulation for injection selected from the group consisting of a non-aqueous liquid, an aqueous liquid, a suspension, a solution, an emulsion, a syrup, a sterilized aqueous suspension, a sterilized aqueous solution, a non-aqueous suspension, a non-aqueous solution, and a reconstituted lyophilized formulation.

8. A method in accordance with claim 2, wherein the NMN is administered intravenously.

9. A method in accordance with claim 2, wherein the NMN is administered enterically.

10. A method in accordance with claim 2, wherein the NMN is administered parenterally.

11. A method in accordance with claim 2, wherein the subject is a mammal.

12. A method in accordance with claim 2, wherein the subject is a human.

13. A method in accordance with claim 2, wherein the NMN is administered at a daily dosage of 200 mg, about 200 mg, 250 mg, about 250 mg, 300 mg, about 300 mg, 400 mg, about 400 mg, 450 mg, about 450 mg, 500 mg, about 500 mg, 600 mg, about 600 mg, 700 mg, about 700 mg, 800 mg, about 800 mg, 900 mg, about 900 mg, 1000 mg, about 1000 mg, 1100 mg, about 1100 mg, 1200 mg, about 1200 mg, 1300 mg, about 1300 mg, 1400 mg, about 1400 mg, 1500 mg, or about 1500 mg.

14. A method in accordance with claim 2, wherein the NMN is administered at a daily dosage of 300 mg, about 300 mg, 400 mg, about 400 mg, 450 mg, about 450 mg, 500 mg, about 500 mg, 600 mg, about 600 mg, 700 mg, about 700 mg, 800 mg, about 800 mg, 900 mg, about 900 mg, 1000 mg, about 1000 mg, 1100 mg, or about 1100 mg.

15. A method in accordance with claim 13, wherein the NMN is administered once per day or twice per day.

16. A method in accordance with claim 13, wherein the NMN is administered buccally or sublingually.

17. A method in accordance with claim 13, wherein the NMN is administered orally in a solid formulation.

18. A method in accordance with claim 13, wherein the subject is human.

19. A method in accordance with claim 1, wherein the subject is canine.

20. A method in accordance with claim 1, wherein the NMN is administered topically.

* * * * *